(12) United States Patent
Kuntz et al.

(10) Patent No.: US 7,615,643 B2
(45) Date of Patent: Nov. 10, 2009

(54) BENZIMIDAZOLE THIOPHENE COMPOUNDS

(75) Inventors: Kevin Kuntz, Durham, NC (US); Kyle Allen Emmitte, Durham, NC (US); Tara Renae Rheault, Durham, NC (US); Stephon Smith, Durham, NC (US); Keith Hornberger, Durham, NC (US); Hamilton Dickson, Durham, NC (US); Mui Cheung, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/754,653

(22) Filed: May 29, 2007

(65) Prior Publication Data

US 2009/0124615 A9      May 14, 2009

Related U.S. Application Data

(60) Provisional application No. 60/810,526, filed on Jun. 2, 2006.

(51) Int. Cl.
*A61K 31/445* (2006.01)
*A61K 31/4184* (2006.01)
*C07D 401/14* (2006.01)
*C07D 409/04* (2006.01)

(52) U.S. Cl. .................. 548/304.7; 514/322; 546/199

(58) Field of Classification Search ............... 548/304.7
See application file for complete search history.

(56) References Cited

U.S. PATENT DOCUMENTS

| 5,990,146 A | 11/1999 | Boschelli et al. |
| 6,162,804 A | 12/2000 | Bilodeau et al. |

| 2007/0219205 A1 | 9/2007 | Brenchley et al. |

FOREIGN PATENT DOCUMENTS

| EP | 1813613 A | 11/2005 |
| WO | 00/12089 A2 | 3/2000 |
| WO | 99/16755 A2 | 3/2000 |
| WO | 2004/014899 A2 | 2/2004 |
| WO | 2005/037827 A2 | 2/2004 |
| WO | 2005/075465 A2 | 8/2005 |
| WO | 2007/030359 A2 | 3/2007 |
| WO | 2007/030361 A2 | 3/2007 |
| WO | 2007/030366 A2 | 3/2007 |
| WO | 2007/087283 A | 8/2007 |

OTHER PUBLICATIONS

Tarasov et al.; Reaction of 1-(ortho-Aminophenyl)-1,2,3-triazole-5-thiols wiht cyclizing reagents; Russian J of Org Chem; 2004; 40/6; 870-873.
C. Corral et al.; Reactions of Methyl 3-Hydroxythiophene-2-carboxylate. Part 4. Synthesis of Methyl 5-Azolyl-3-hydroxythiopene-2-carboxylates; J. Het Chem; Sep. 1987; 24, 1301.
M. Whitfield et al.; Common Markers of Proliferation; Nature Reviews, Cancer; Feb. 2006; 6; 99-106; Nature Publishing Group.
M.M. Donaldson et al.; The Mitotic Roles of Polo-Like Kinase; Journal of Cell Science; 2001; 114(13); 2357-2358.
D.R. Buckle et al.; Novel 1H-Benzimidazol-4-ols with Potent 5-Lipoxygenase Inhibitory Activity; J. Med. Chem.; 1987; 30; 2216-2221.
N. Lee Harris et al.; World Health Organization Classification of Neoplastic Diseases of the Hematopoietic and Lymphoid Tissues: Report of the Clinical Advisory Committee Meeting—Airlie House, VA, Nov. 1997; J. Clin. Oncology; Dec. 1999; 17(12); 3838-3849; American Soc. of Clin. Onc.
J. Chan; The New World Health Organization Classification of Lymphomas: The Past, The Present and The Future; Hematological Oncology; Jul. 2001; 19; 129-150; John Wiley & Sons Ltd.
D.M. Glover et al.; Polo-Like Kinases: A Team That Plays Throughout Mitosis; Genes & Development; 1998; 12; 3777-3787.

*Primary Examiner*—Laura L. Stockton
(74) *Attorney, Agent, or Firm*—Robert H. Brink

(57) ABSTRACT

The present invention provides benzimidazole thiophene compounds pharmaceutical compositions containing the same, processes for preparing the same and their use as pharmaceutical agents.

21 Claims, No Drawings

SEQUENCE LISTING

<160> NUMBER OF SEQ ID NOS: 2

<210> SEQ ID NO 1
<211> LENGTH: 11
<212> TYPE: PRT
<213> ORGANISM: baculovirus infected T.ni cells

<400> SEQUENCE: 1

Met Lys Lys Gly His His His His His His Asp

```
1               5              10

<210> SEQ ID NO 2
<211> LENGTH: 9
<212> TYPE: PRT
<213> ORGANISM: Artificial Sequence
<220> FEATURE:
<223> OTHER INFORMATION: optimized PLK peptide substrate

<400> SEQUENCE: 2

Ser Phe Asn Asp Thr Leu Asp Phe Asp
1               5
```

BENZIMIDAZOLE THIOPHENE COMPOUNDS

CROSS-REFERENCE TO RELATED APPLICATION

The instant application claims priority to U.S. Provisional Patent Application Ser. No. 60/810,526, filed 2 Jun. 2006.

BACKGROUND OF THE INVENTION

The present invention relates to novel benzimidazole thiophene compounds, pharmaceutical formulations comprising these compounds, and the use of these compounds in therapy.

Polo-like kinases ("PLK") are evolutionary conserved serine/threonine kinases that play critical roles in regulating processes in the cell cycle. PLK plays a role in the entry into and the exit from mitosis in diverse organisms from yeast to mammalian cells. PLK includes PLK1, PLK2, PLK3 and PLK4.

Overexpression of PLK1 appears to be strongly associated with neoplastic cells (including cancers). A published study has shown high levels of PLK1 RNA expression in >80% of lung and breast tumors, with little to no expression in adjacent normal tissue. Several studies have shown correlations between PLK expression, histological grade, and prognosis in several types of cancer. Significant correlations were found between percentages of PLK-positive cells and histological grade of ovarian and endometrial cancer (P<0.001). These studies noted that PLK is strongly expressed in invading endometrial carcinoma cells and that this could reflect the degree of malignancy and proliferation in endometrial carcinoma. Using RT-PCR analysis, PLK overexpression was detected in 97% of esophageal carcinomas and 73% of gastric carcinomas as compared to the corresponding normal tissues. Further, patients with high levels of PLK overexpression in esophageal carcinoma represented a significantly poorer prognosis group than those with low levels of PLK overexpression. In head and neck cancers, elevated mRNA expression of PLK1 was observed in most tumors; a Kaplan-Meier analysis showed that those patients with moderate levels of PLK1 expression survived longer than those with high levels of PLK1 expression. Analysis of patients with non-small cell lung carcinoma showed similar outcomes related to PLK1 expression.

PCT Publication No. WO2004/014899 to SmithKline Beecham discloses novel benzimidazole thiophene compounds of formula (I):

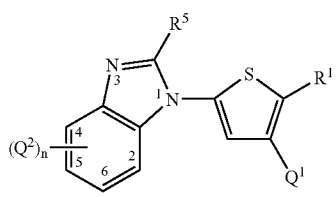

I wherein:
$R^1$ is selected from the group consisting of H, alkyl, alkenyl, alkynyl, —C(O)$R^7$, —CO$_2R^7$, —C(O)N$R^7R^8$, —C(O)N($R^7$)O$R^8$, —C(O)N($R^7$)—$R^2$—O$R^8$, —C(O)N($R^7$)-Ph, —C(O)N($R^7$)—$R^2$-Ph, —C(O)N($R^7$)C(O)$R^8$, —C(O)N($R^7$)CO$_2R^8$; —C(O)N($R^7$)C(O)N$R^7R^8$, —C(O)N($R^7$)S(O)$_2R^8$, —$R^2$—O$R^7$, —$R^2$—O—C(O)$R^7$, —C(S)$R^7$, —C(S)N$R^7R^8$, —C(S)N($R^7$)-Ph, —C(S)N($R^7$)—$R^2$-Ph, —$R^2$—S$R^7$, —C(=N$R^7$)N$R^7R^8$, —C(=N$R^7$)N($R^8$)-Ph, —C(=N$R^7$)N($R^8$)—$R^2$-Ph, —$R^2$—N$R^7R^8$, —CN, —O$R^7$, —S(O)$_fR^7$, —S(O)$_2$N$R^7R^8$, —S(O)$_2$N($R^7$)-Ph, —S(O)$_2$N($R^7$)—$R^2$-Ph, —N$R^7R^8$, N($R^7$)-Ph, —N($R^7$)—$R^2$-Ph, —N($R^7$)—SO$_2R^8$ and Het;

Ph is phenyl optionally substituted from 1 to 3 times with a substituent selected from the group consisting of halo, alkyl, —OH, —$R^2$—OH, —O— alkyl, —$R^2$—O-alkyl, —NH$_2$, —N(H)alkyl, —N(alkyl)$_2$, —CN and —N$_3$;

Het is a 5-7 membered heterocycle having 1, 2, 3 or 4 heteroatoms selected from N, O and S, or a 5-6 membered heteroaryl having 1, 2, 3 or 4 heteroatoms selected from N, O and S, each optionally substituted from 1 to 2 times with a substituent selected from the group consisting of halo, alkyl, oxo, —OH, —$R^2$—OH, —O—alkyl, —$R^2$—O-alkyl, —NH$_2$, —N(H)alkyl, —N(alkyl)$_2$, —CN and —N$_3$;

$Q^1$ is a group of formula: —($R^2$)$_a$—($Y^1$)$_b$—($R^2$)$_c$—$R^3$ a, b and c are the same or different and are each independently 0 or 1 and at least one of a or b is 1;

n is 0, 1, 2, 3 or 4;

$Q^2$ is a group of formula: —($R^2$)$_{aa}$—($Y^2$)$_{bb}$—($R^2$)$_{cc}$—$R^4$ or two adjacent $Q^2$ groups are selected from the group consisting of alkyl, alkenyl, —O$R^7$, —S(O)$_fR^7$ and —N$R^7R^8$ and together with the carbon atoms to which they are bound, they form a $C_{5-6}$cycloalkyl, $C_{5-6}$ cycloalkenyl, phenyl, 5-7 membered heterocycle having 1 or 2 heteroatoms selected from N, O and S, or 5-6 membered heteroaryl having 1 or 2 heteroatoms selected from N, O and S;

aa, bb and cc are the same or different and are each independently 0 or 1;

each $Y^1$ and $Y^2$ is the same or different and is independently selected from the group consisting of —O—, —S(O)$_f$—, —N($R^7$)—, —C(O)—, —OC(O)—, —CO$_2$—, —C(O)N($R^7$)—, —C(O)N($R^7$)S(O)$_2$—, —OC(O)N($R^7$)—, —OS(O)$_2$—, —S(O)$_2$N($R^7$)—, —S(O)$_2$N($R^7$)C(O)—, —N($R^7$)S(O)$_2$—, —N($R^7$)C(O)—, —N($R^7$)CO$_2$— and —N($R^7$)C(O)N($R^7$)—;

each $R^2$ is the same or different and is independently selected from the group consisting of alkylene, alkenylene and alkynylene;

each $R^3$ and $R^4$ is the same or different and is each independently selected from the group consisting of H, halo, alkyl, alkenyl, alkynyl, —C(O)$R^7$, —C(O)N$R^7R^8$, —CO$_2R^7$, —C(S)$R^7$, —C(S)N$R^7R^8$, —C(=N$R^7$)$R^8$, —C(=N$R^7$)N$R^7R^8$, —C$R^7$=N—O$R^7$, —O$R^7$, —S(O)$_fR^7$, —S(O)$_2$N$R^7R^8$, —N$R^7R^8$, —N($R^7$)C(O)$R^8$, —N($R^7$)S(O)$_2R^8$, —NO$_2$, —CN, —N$_3$ and a group of formula (ii):

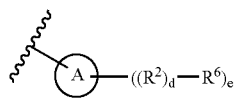

ii wherein:
Ring A is selected from the group consisting of $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S each d is 0 or 1;

e is 0, 1, 2, 3 or 4;

each $R^6$ is the same or different and is independently selected from the group consisting of H, halo, alkyl, alkenyl, alkynyl, cycloalkyl, cycloalkenyl, Ph, Het, —CH(OH)—$R^2$—OH, —C(O)$R^7$, —CO$_2R^7$, —CO$_2$—$R_2$-Ph, —CO$_2$—$R^2$-Het, —C(O)N$R^7R^8$, —C(O)N($R^7$)C(O)$R^7$, —C(O)N($R^7$)CO$_2R^7$, —C(O)N($R^7$)C(O)N$R^7R^8$, —C(O)N($R^7$)S(O)$_2R^7$, —C(S)$R^7$, —C(S)N$R^7R^8$, —C(=N$R^7$)$R^8$, —C(=N$R^7$)N$R^7R^8$, —C$R^7$=N—O$R^8$, =O, —O$R^7$, —OC(O)$R^7$, —OC(O)Ph, —OC(O)Het, —OC(O)N$R^7R^8$, —O—$R^2$—S(O)$_2R^7$, —S(O)$_fR^7$, —S(O)$_2$N$R^7R^8$, —S(O)$_2$Ph, —S(O)$_2$Het, —N$R^7R^8$, —N($R^7$)C(O)$R^8$, —N($R^7$)CO$_2R^8$, —N($R^7$)—$R^2$—CO$_2R^8$, —N($R^7$)C(O)N$R^7R^8$, —N($R^7$)—$R^2$—C(O)N$R^7R^8$, —N($R^7$)C(O)Ph, —N($R^7$)C(O)Het, —N($R^7$)Ph, —N($R^7$)Het, —N($R^7$)C(O)$R^7$—$R^2$—N$R^7R^8$, —N($R^7$)C(O)N($R^7$)Ph, —N($R^7$)C(O)N($R^7$)Het, —N($R^7$)C(O)N($R^7$)—$R^2$-Het, —N($R^7$)S(O)$_2R^8$, —N($R^7$)—$R^2$—S(O)$_2R^8$, —NO$_2$, —CN and —N$_3$;

wherein when $Q^1$ is defined where b is 1 and c is 0, $R^3$ is not halo, —C(O)$R^7$, —C(O)N$R^7R^8$, —CO$_2R^7$, —C(S)$R^7$, —C(S)N$R^7R^8$, —C(=N$R^7$)$R^8$, —C(=N$R^7$)N$R^7R^8$, —C$R^7$=N—O$R^7$, —O$R^7$, —S(O)$_fR^7$, —S(O)$_2$N$R^7R^8$, —N$R^7R^8$, —N($R^7$)C(O)$R^8$, —N($R^7$)S(O)$_2R^8$, —NO$_2$, —CN or —N$_3$;

wherein when $Q^2$ is defined where bb is 1 and cc is 0, $R^4$ is not halo, —C(O)$R^7$, —C(O)N$R^7R^8$, —CO$_2R^7$, —C(S)$R^7$, —C(S)N$R^7R^8$, —C(=N$R^7$)$R^8$, —C(=N$R^7$)N$R^7R^8$, —C$R^7$=N—O$R^7$, —O$R^7$, —S(O)$_fR^7$, —S(O)$_2$N$R^7R^8$, —N$R^7R^8$, —N($R^7$)C(O)$R^8$, —N($R^7$)S(O)$_2R^8$, —NO$_2$, —CN or —N$_3$;

$R^5$ is selected from the group consisting of H, halo, alkyl, cycloalkyl, O$R^7$, —S(O)$_fR^7$, —N$R^7R^8$, —NHC(O)$R^7$, —NHC(O)N$R^7R^8$ and —NHS(O)$_2R^7$;

f is 0, 1 or 2; and each $R^7$ and each $R^8$ are the same or different and are each independently selected from the group consisting of H, alkyl, alkenyl, alkynyl, cycloalkyl and cycloalkenyl;

wherein when $R^1$ is —CO$_2$CH$_3$ and n is 0, $Q^1$ is not —OH;

or a pharmaceutically acceptable salt, solvate or physiologically functional derivative thereof.

Also disclosed are pharmaceutical compositions containing these compounds, processes for their preparation and methods for treatment of conditions mediated by PLK using these compounds.

BRIEF SUMMARY OF THE INVENTION

According to a first aspect of the invention there is provided compounds of formula (I):

wherein:
$R^1$ is selected from H, halo, alkyl, haloalkyl, —O$R^7$, —CN, —C(O)N$R^7R^8$, —S(O)$_2R^7$, —$R^5$—S(O)$_2R^7$, —N$R^7R^8$, —N$R^7$C(O)$R^8$, Ph, and Het$^1$;

Ph is phenyl optionally substituted 1 or 2 times with halo, alkyl, haloalkyl, —O$R^7$, —CN, —S(O)$_2R^7$ and —N$R^7R^8$;

Het$^1$ is a 5-6 membered heteroaryl having 1, 2 or 3 heteroatoms selected from M, O and S, optionally substituted 1 or 2 times with a substituent selected from halo, alkyl, haloalkyl, —O$R^7$, —CN, —S(O)$_2R^7$, —N$R^7R^8$, Het$^2$, —$R^5$-Het$^2$, N$R^7$-Het$^2$, and oxo;

Het$^2$ is a 5-6 membered heterocycle having 1 or 2 heteroatoms selected from H, O and S, optionally substituted 1 or 2 times with a substituent selected from alkyl, —O$R^7$, —N$R^7R^8$, —C(O)N$R^7R^8$, —S(O)$_2R^7$, and oxo;

$R^2$ is selected from H, halo, alkyl, haloalkyl, —O$R^7$, —CN, —C(O)N$R^7R^8$, —S(O)$_2R^7$, —$R^5$—S(O)$_2R^7$, —S(O)$_2$N$R^7R^8$, —$R^5$—S(O)$_2$N$R^7R^8$, —N$R^7R^8$, and —N$R^7$C(O)$R^8$;

$R^3$ is H, alkyl or haloalkyl;

$Z^1$, $Z^2$ and $Z^3$ are each the same or different and are independently C, CH or N, wherein at least one of $Z^1$, $Z^2$ and $Z^3$ is C or CH;

d is 0, 1 or 2;

each $R^4$ is the same or different and is independently halo, alkyl or haloalkyl;

$Y^1$ is —O— or —N($R^7$)—;

a is 0 or 1;

each $R^5$ is the same or different and is independently $C_{1-3}$alkylene;

Ring A is a 5-6 membered heterocycle having 1 or 2 heteroatoms selected from N, O and S;

b is 0, 1 or 2;

each $R^6$ is the same or different and is independently selected from halo, alkyl, haloalkyl, alkenyl, —CN, —$R^5$—CN, —CO$_2R^7$, —$R^5$—CO$_2R^7$, —C(O)N$R^7R^8$, —$R^5$—C(O)N$R^7R^8$, —O$R^7$, —$R^5$—O$R^7$, —S(O)$_2R^7$, —$R^5$—S(O)$_2R^7$, —S(O)$_2$N$R^7R^8$, —$R^5$—S(O)$_2$N$R^7R^8$, —N$R^7R^8$, —$R^5$—N$R^7R^8$, —N$R^7$C(O)$R^8$, —N$R^7$S(O)$_2R^8$, —N$R^7$C(O)N$R^7R^8$, —N$R^7$C(O)$_2R^8$ and oxo;

each $R^7$ and each $R^8$ are the same or different and are each independently selected from H, alkyl, haloalkyl, alkenyl, haloalkenyl, alkynyl, cycloalkyl and cycloalkenyl;

and pharmaceutically acceptable salts thereof.

In second aspect, there is provided an enantiomerically enriched compound of formula (I) having the stereochemistry depicted in formula (I-1).

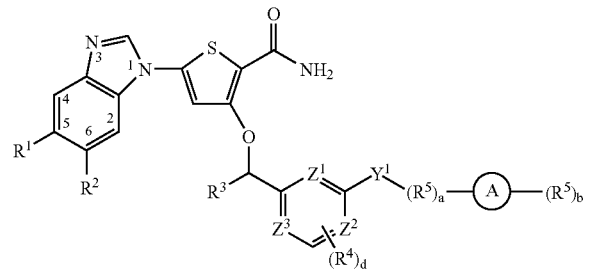

I

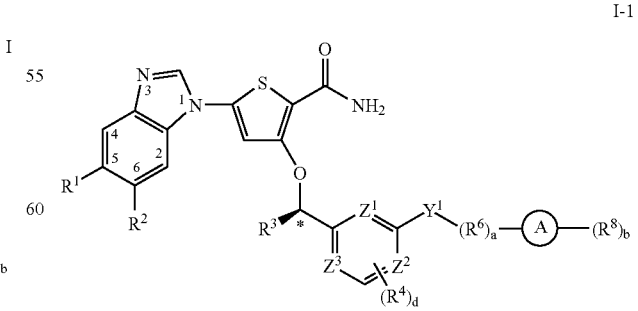

I-1 wherein * indicates a chiral carbon and all variables are as defined above.

In third aspect, there is provided compounds of formula (XL)

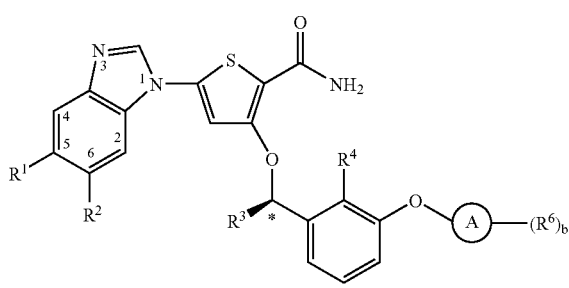

wherein:
R¹ is selected from H, halo, alkyl, haloalkyl, —OR⁷, —CN, —C(O)NR⁷R⁸, —S(O)₂R⁷, —R⁵—S(O)₂R⁷ and Het¹;
Het¹ is a 5-6 membered heteroaryl having 1, 2 or 3 heteroatoms selected from H, O and S, optionally substituted 1 or 2 times with a substituent selected from alkyl, haloalkyl, —OR⁷, —CN, —S(O)₂R⁷, —NR⁷R⁸ and oxo;
R² is selected from H, halo, alkyl, haloalkyl, —OR⁷, —CN, —C(O)NR⁷R⁸, —S(O)₂R⁷, —R⁵—S(O)₂R⁷, —S(O)₂NR⁷R⁸, —R⁵—S(O)₂NR⁷R⁸, —NR⁷R⁸, and —NR⁷C(O)R⁸;
R³ is alkyl;
* indicates a chiral carbon;
R⁴ is H or halo;
each R⁵ is the same or different and is independently C₁₋₃alkylene;
Ring A is a 5-6 membered heterocycle having 1 or 2 heteroatoms selected from N, O and S;
b is 0 or 1;
each R⁶ is the same or different and is independently selected from halo, alkyl, haloalkyl, —CO₂R⁷, —R⁵—CO₂R⁷, —OR⁷, —R⁵—OR⁷, —S(O)₂R⁷, —R⁵—S(O)₂R⁷, —NR⁷R⁸, —R⁵—NR⁷R⁸ and oxo;
each R⁷ and each R⁸ are the same or different and are each independently selected from H, alkyl and haloalkyl;
and pharmaceutically acceptable salts thereof.

In a fourth aspect of the Invention there is provided a pharmaceutical composition comprising a compound of formula (I), (I-1) or (XL) or a pharmaceutically acceptable salt thereof. In one embodiment, the pharmaceutical composition further comprises a pharmaceutically acceptable carrier, diluent or excipient.

In a fifth aspect of the invention, there is provided a method for treating a condition mediated by PLK in a mammal in need thereof. The method comprises administering to the mammal a therapeutically effective amount of a compound of formula (I), (I-1) or (XL) or a pharmaceutically acceptable salt thereof.

In a sixth aspect of the invention, there is provided a method for treating a susceptible neoplasm in a mammal in need thereof. The method comprises administering to the mammal a therapeutically effective amount of a compound of formula (I), (I-1) or (XL) or a pharmaceutically acceptable salt thereof. The susceptible neoplasm may be selected from the group consisting of breast cancer, colon cancer, lung cancer (including small cell lung cancer and non-small cell lung cancer), prostate cancer, endometrial cancer, gastric cancer, melanoma, ovarian cancer, pancreatic cancer, squamous cell carcinoma, carcinoma of the head and neck, esophageal carcinoma, hepatocellular carcinoma, renal cell cancer, sarcoma (including cancers of connective tissue), bladder cancer, glioma and hematologic malignancies such as lymphoma including aggressive lymphomas and non-Hodgkins lymphoma, and leukemia including acute leukemias. In one particular aspect, there is provided a method of treating breast cancer in a mammal in need thereof, which comprises administering to the mammal a therapeutically effective amount of a compound of formula (I), (I-1) or (XL) or a pharmaceutically acceptable salt thereof. In one particular aspect, there is provided a method of treating ovarian cancer in a mammal in need thereof, which comprises administering to the mammal a therapeutically effective amount of a compound of formula (I), (I-1) or (XL) or a pharmaceutically acceptable salt thereof. In one particular aspect, there is provided a method of treating non-small cell lung cancer in a mammal in need thereof, which comprises administering to the mammal a therapeutically effective amount of a compound of formula (I), (I-1) or (XL) or a pharmaceutically acceptable salt thereof, in one particular aspect, there is provided a method of treating prostate cancer in a mammal in need thereof, which comprises administering to the mammal a therapeutically effective amount of a compound of formula (I), (I-1) or (XL) or a pharmaceutically acceptable salt thereof, in one particular aspect, there is provided a method of treating a hematologic malignancy in a mammal in need thereof, which comprises administering to the mammal a therapeutically effective amount of a compound of formula (I), (I-1) or (XL) or a pharmaceutically acceptable salt thereof.

In a seventh aspect of the invention, there is provided a method for treating a condition characterized by Inappropriate cellular proliferation. The method comprises contacting the cell with a therapeutically effective amount of a compound of formula (I), (I-1) or (XL) or a pharmaceutically acceptable salt thereof.

In an eighth aspect, the present invention provides a method for inhibiting proliferation of a cell. The method comprises contacting the cell with an amount of a compound of formula (I), (I-1) or (XL) or a pharmaceutically acceptable salt thereof.

In another aspect, the present invention provides a method for inhibiting mitosis in a cell. The method comprises administering to the cell an amount of a compound of formula (I), (I-1) or (XL) or a pharmaceutically acceptable salt thereof.

In another aspect, the present invention provides a process for preparing a compound of formula (I) wherein Y¹ is O, or a pharmaceutically acceptable salt thereof. The process comprises the steps of:
a) reacting the compound of formula (VII):

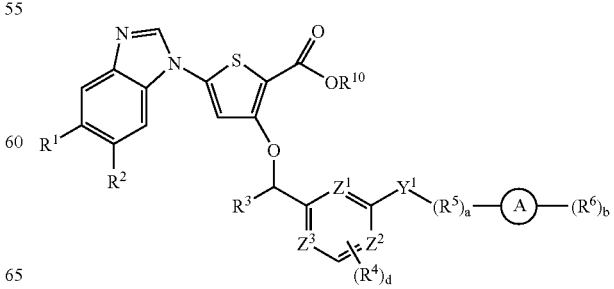

wherein $R^{10}$ is selected from alkyl and suitable carboxylic acid protecting groups; and all other variables are as defined in claim 1,
with ammonia to prepare a compound of formula (I);
b) optionally separating the compound of formula (I) info enantiomers of formula (I);
c) optionally converting the compound of formula (I) to a pharmaceutically acceptable salt thereof; and
d) optionally converting the compound of formula (I) or a pharmaceutically acceptable salt thereof to a different compound of formula (I) or a pharmaceutically acceptable salt thereof.

In another aspect, the present invention provides a process for preparing a compound of formula (I) wherein $Y^1$ is NH, or a pharmaceutically acceptable salt thereof. The process comprises the steps of:
a) reacting the compound of formula (XXXIII):

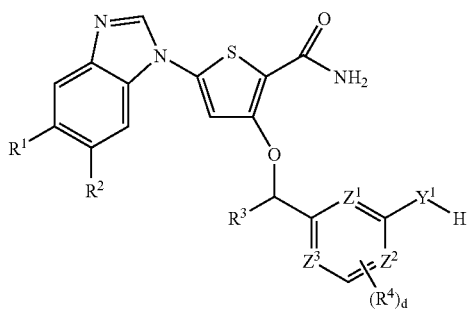

XXXIII wherein all variables are as defined above,
with a compound of formula (XXXIV):

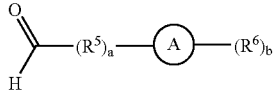

XXXIV to prepare a compound of formula (I);
b) optionally separating the compound of formula (I) into enantiomers;
c) optionally converting the compound of formula (I) to a pharmaceutically acceptable salt thereof; and
d) optionally converting the compound of formula (I) or a pharmaceutically acceptable salt thereof to a different compound of formula (I) or a pharmaceutically acceptable salt thereof.

In another aspect, the present invention provides a compound of formula (I), (I-1) or (XL) or a pharmaceutically acceptable salt thereof for use in therapy.

In yet another aspect, the present invention provides a compound of formula (I), (I-1) or (XL) or a pharmaceutically acceptable salt thereof for use in the treatment of a condition mediated by PLK in a mammal in need thereof.

In yet another aspect, the present invention provides a compound of formula (I), (I-1) or (XL) or a pharmaceutically acceptable salt thereof for use in the treatment of a susceptible neoplasm, such as breast cancer, colon cancer, small cell lung cancer, non-small cell lung cancer, prostate cancer, endometrial cancer, gastric cancer, melanoma, ovarian cancer, pancreatic cancer, squamous cell carcinoma, carcinoma of the head and neck, esophageal carcinoma, hepatocellular carcinoma, renal cell cancer, sarcoma, bladder cancer, glioma and hematologic malignancies, in a mammal. In one particular aspect, there is provided a compound of formula (I), (I-1) or (XL) or a pharmaceutically acceptable salt thereof, for use in the treatment of breast cancer, ovarian cancer, non-small cell long cancer, prostate cancer, or a hematologic malignancy in a mammal.

in another aspect, the present invention provides a compound of formula (I), (I-1) or (XL) or a pharmaceutically acceptable salt thereof, for use in the treatment of a condition characterized by inappropriate cellular proliferation.

In yet another aspect, the present invention provides a compound of formula (I), (I-1) or (XL) or a pharmaceutically acceptable salt thereof, for use in inhibiting proliferation of a cell.

In yet another aspect, the present invention provides a compound of formula (I), (I-1) or (XL) or a pharmaceutically acceptable salt thereof, for use in inhibiting mitosis in a cell, In yet another aspect, the present invention provides the use of a compound of formula (I), (I-1) or (XL) or a pharmaceutically acceptable salt thereof, for the preparation of a medicament for the treatment of condition mediated by PLK in a mammal.

In yet another aspect, the present invention provides the use of a compound of formula (I), (I-1) or (XL) or a pharmaceutically acceptable salt thereof, for the preparation of a medicament for the treatment of a susceptible neoplasm, such as breast cancer, colon cancer, small cell lung cancer, non-small cell lung cancer, prostate cancer, endometrial cancer, gastric cancer, melanoma, ovarian cancer, pancreatic cancer, squamous cell carcinoma, carcinoma of the head and neck, esophageal carcinoma, hepatocellular carcinoma, renal cell cancer, sarcoma, bladder cancer, glioma and hematologic malignancies, in a mammal.

In yet another aspect, the present invention provides the use of a compound of formula (I), (I-1) or (XL) or a pharmaceutically acceptable salt thereof, for the preparation of a medicament for the treatment of breast cancer, ovarian cancer, non small cell lung cancer, prostate cancer or a hematologic malignancy in a mammal.

In yet another aspect, the present invention provides the use of a compound of formula (I), (I-1) or (XL) or a pharmaceutically acceptable salt thereof, for the treatment of a condition characterized by inappropriate cellular proliferation in a mammal.

In yet another aspect, the present invention provides the use a compound of formula (I), (I-1) or (XL) or a pharmaceutically acceptable salt thereof, for the preparation of a medicament for Inhibiting proliferation of a cell In yet another aspect, the present invention provides the use of a compound of formula (I), (I-1) or (XL) or a pharmaceutically acceptable salt thereof, for the preparation of a medicament for inhibiting mitosis in a cell.

In yet another aspect, the present invention provides a pharmaceutical composition comprising a compound of formula (I), (I-1) or (XL) or a pharmaceutically acceptable salt thereof, for use in the treatment of a susceptible neoplasm, such as breast cancer, colon cancer, small cell lung cancer, non-small cell lung cancer, prostate cancer, endometrial cancer, gastric cancer, melanoma, ovarian cancer, pancreatic cancer, squamous cell carcinoma, carcinoma of the head and neck, esophageal carcinoma, hepatocellular carcinoma, renal cell cancer, sarcoma, bladder cancer, glioma and hematologic malignancies, in a mammal.

DETAILED DESCRIPTION OF THE INVENTION

As used herein, "compound(s) of formula (I)" means any compound having the structural formula (I) as defined by the variable definitions provided, solvates, including hydrates thereof, and amorphous and crystal forms, including polymorphic forms thereof, in the case of compounds of formula (I) which possess one or more chiral centres, the compounds may be in the form of a racemic mixture, or one or more isomerically enriched or pure stereoisomers, including enantiomers and disastereomers thereof. Stereoisomerism of the compounds is discussed in further detail below. "Compound(s) of formula (I)" includes the racemic form as well as the enriched or pure enantiomers and diastereomers (e.g., compounds of formula (I-1). Where a compound of the Invention contains an alkenyl or alkenylene group, cis. (E) and trans (Z) isomerism may also occur. In such embodiments, "compound(s) of formula (I)" includes the individual cis/trans isomers of the compound, which will be indicated using conventional, cis/trans nomenclature. It should also be understood that compounds of formula (I) may exist in tautomeric forms other than that shown in the formula and alternative tautomeric forms are also included within "compound(s) of formula (I)."

Similarly, "compound(s) of formula (XL)" means any compound having the structural formula (XL) as defined by the variable definitions provided, solvates, including hydrates thereof, and amorphous and crystal forms, Including polymorphic forms, thereof. "Compound(s) of formula (XL)" includes the racemic form as well as the enriched or pure enantiomers and diasteriomers. "Compound(s) of formula (XL)" also includes the individual cis/trans isomers of the compound of the invention. It should also be understood that compounds of formula (XL) may exist in tautomeric forms other than that shown in the formula and alternative tautomeric forms are also included within "compound(s) of formula (XL)."

As used herein, "compound(s) of the invention" refers to compounds of formula (I), compounds of formula (I-1) and compounds of formula (XL) (each as defined above) or a pharmaceutically acceptable sail thereof.

Also, with respect to isolatable intermediates such as for example, compounds of formula (V) and (VII) (among others described below) the phrase "a compound of formula (number)" means a compound having that formula and pharmaceutically acceptable salts thereof.

As used herein, the terms "alkyl" (and "alkylene") refer to straight or branched hydrocarbon chains containing from 1 to 8 carbon atoms. Examples of "alky" as used herein include, but are not limited to, methyl, ethyl, n-propyl, isopropyl, n-butyl, isobutyl, tert-butyl and n-pentyl. Examples of "alkylene" as used herein include, but are not limited to, methylene, ethylene, propylene, isopropylene, butylene, and isobutylene.

The term "haloalkyl" refers to alkyl (as defined above) substituted one or more times with a halogen. Thus, the term "haloalkyl" includes perhaloalkyls such as trifluoromethyl, as well as trifluoroethyl, among other halogenated alkyls.

As used herein, the term "alkenyl" (and "alkenylene") refers to straight or branched hydrocarbon chains containing from 2 to 8 carbon atoms (unless a different number of atoms is specified) and at least one and up to three carbon-carbon double bonds. Examples of "alkenyl" as used herein include, but are not limited to ethenyl and propenyl. Examples of "alkenylene" as used herein include, but are not limited to ethenylene and propenylene.

The term "haloalkenyl" refers to alkenyl (as defined above) substituted one or more times with a halogen.

As used herein, the term "alkynyl" refers to straight or branched hydrocarbon chains containing from 2 to 8 carbon atoms (unless a different number of atoms is specified) and at least one and up to three carbon-carbon triple bonds. Examples of "alkynyl" as used herein include, but are not limited lo ethynyl and propynyl.

As used herein, the term "cydoalkyl" refers to a non-aromatic monocyclic carbocyclic ring having from 3 to 8 carbon atoms (unless a different number of atoms is specified) and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on any available carbon with one or more (e.g., 1, 2 or 3) substituents which may be the same or different and are independently selected from the group consisting of halo, $C_{1-3}$alkyl and $C_{1-3}$haloalkyl. Preferred cycloalkyl groups include $C_{3-6}$cycloalkyl and substituted $C_{3-8}$cycloalkyl.

As used herein, the term "cycloalkenyl" refers to a non-aromatic monocyclic carbocyclic ring having from 3 to 8 carbon atoms (unless a different number of atoms is specified) and up to 3 carbon-carbon double bonds. "Cycloalkenyl" includes by way of example cyclobutenyl, cyclopentenyl and cyclohexenyl. "Cycloaikenyl" also includes substituted cycloalkenyl. The cycloalkenyl may optionally be substituted on any available carbon with one or more (e.g., 1, 2 or 3) substituents which may be the same or different and are independently selected from the group consisting of halo, $C_{1-3}$alkyl and $C_{1-3}$haloalkyl.

The term "halo" or "halogen" refers to fluorine, chlorine, bromine and iodine.

The term "oxo" as used herein refers to the group =O attached directly to a carbon atom of a hydrocarbon ring (i.e., cycloalkenyl, aryl, heterocycle or heteroaryl ring) or attached directly to a N or S to yield-N-oxides, sulfones and sulfoxides wherein the N or S are atoms of a heterocyclic or heteroaryl ring.

The terms "heterocycle" and "heterocyclic" are synonomous and refer to monocyclic saturated or unsaturated non-aromatic groups and fused bicyclic saturated or unsaturated non-aromatic groups, having the specified number of members and including 1, 2 or 3 heteroatoms selected from N, O and S (unless a different number of heteroatoms is specified), in all embodiments wherein the heterocycle includes 2 or more heteroatoms, the heteroatoms may be the same or different and are independently selected from N, O and S. In all embodiments wherein the compound of formula (I) includes two or more heterocyclic groups, the heterocyclic groups may be the same or different and are independently selected. Examples of particular heterocyclic groups include but are not limited to tetrahydrofuran, dihydropyran, tetrahydropyran, pyran, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like.

The term "heteroaryl" refers to aromatic monocyclic groups and aromatic fused bicyclic groups and fused bicyclic groups which have both aromatic and non-aromatic rings, each having the specified number of members and including 1, 2, 3, or 4 heteroatoms selected from N, O and S (unless a different number of heteroatoms is specified). In all embodiments wherein the heteroaryl includes 2 or more heteroatoms, the heteroatoms may be the same or different and are independently selected from N, O and S. In all embodiments wherein the compound of formula (I) includes two or more heteroaryl groups, the heteroaryl groups may be the same or different and are Independently selected. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention provides compounds of formula (I):

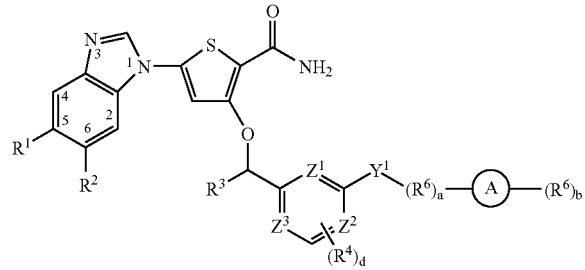

I wherein:
$R^1$ is selected from H, halo, alkyl, haloalkyl, —$OR^7$, —CN, —C(O)$NR^7R^8$, —S(O)$_2R^7$, —$R^5$—S(O)$_2R^7$, —$NR^7R^8$, —$NR^7$C(O)$R^8$, Ph, and $Het^1$;
  Ph is phenyl optionally substituted 1 or 2 times with halo, alkyl, haloalkyl, —$OR^7$, —CN, —S(O)$_2R^7$ and —$NR^7R^8$;
  $Het^1$ is a 5-6 membered heteroaryl having 1, 2 or 3 heteroatoms selected from N, O and S, optionally substituted 1 or 2 times with a substituent selected from halo, alkyl, haloalkyl, —$OR^7$, —CN, —S(O)$_2R^7$, —$NR^7R^8$, $Het^2$, —$R^5$-$Het^2$, $NR^7$-$Het^2$, and oxo;
  $Het^2$ is a 5-6 membered heterocycle having 1 or 2 heteroatoms selected from N, O and S, optionally substituted 1 or 2 times with a substituent selected from alkyl, —$OR^7$, —$NR^7R^8$, —C(O)$NR^7R^8$, —S(O)$_2R^7$, and oxo;
$R^2$ is selected from H, halo, alkyl, haloalkyl, —$OR^7$, —CN, —C(O)$NR^7R^8$, —S(O)$_2R^7$, —$R^5$—S(O)$_2R^7$, —S(O)$_2$$NR^7R^8$, —$R^5$—S(O)$_2NR^7R^8$, $NR^7R^8$, and —$NR^7$C(O)$R^8$;
$R^3$ is H, alkyl or haloalkyl;
$Z^1$, $Z^2$ and $Z^3$ are each the same or different and are Independently C, CH or N, wherein at least one of $Z^1$, $Z^2$ and $Z^3$ is C or CH;
d is 0, 1 or 2;
each $R^4$ is the same or different and is independently halo, alkyl or haloalkyl;
$Y^1$ is —O— or —N($R^7$)—;
a is 0 or 1;
each $R^5$ is the same or different and is independently $C_{1-3}$alkylene;
Ring A is a 5-8 membered heterocycle having 1 or 2 heteroatoms selected from N, O and S;
b is 0, 1 or 2;
each $R^6$ is the same or different and is independently selected from halo, alkyl, haloalkyl, alkenyl, —CN, —$R^5$—CN, —CO$_2R^7$, —$R^5$—CO$_2R^7$, —C(O)$NR^7R^8$, —$R^5$—C(O)$NR^7R^8$, —$OR^7$, —$R^5$—$OR^7$, —S(O)$_2R^7$, —$R^5$—S(O)$_2R^7$, —S(O)$_2NR^7R^8$, —$R^5$—S(O)$_2NR^7R^8$, —$NR^7R^8$, —$R^5$—$NR^7R^8$, —$NR^7$C(O)$R^8$, —$NR^7$S(O)$_2R^8$, —$NR^7$C(O)$NR^7R^8$, —$NR^7$C(O)$_2R^8$ and oxo;
each $R^7$ and each $R^8$ are the same or different and are each independently selected from H, alkyl, haloalkyl, alkenyl, haloalkenyl, alkynyl, cycloalkyl and cycloalkenyl;

and pharmaceutically acceptable salts thereof.

In one embodiment, the compounds of the invention are defined wherein $R^1$ is selected from H, halo, alkyl, haloalkyl, —$OR^7$, —S(O)$_2R^7$ and $Het^1$, or any subset thereof. In another embodiment, $R^1$ is selected from H, halo, alkyl, —$OR^7$ and $Het^1$, or any subset thereof, in a further embodiment, $R^1$ is selected from H, halo, —O-alkyl, —O-haloalkyl and $Het^1$, or any subset thereof. In another embodiment, $R^1$ is selected from H, halo, —O—$C_{1-3}$alkyl and $Het^1$, or any subset thereof, in on particular embodiment, $R^1$ is halo. In one particular embodiment, $R^1$ is —O—$C_{1-3}$alkyl. In one particular embodiment, $R^1$ is $Het^1$.

In one embodiment, the compounds of the invention are defined wherein $R^2$ is selected from H, halo, alkyl, haloalkyl, —$OR^7$, —CN, —S(O)$_2R^7$ and —$R^5$—S(O)$_2R^7$, or any subset thereof, in another embodiment, $R^2$ is selected from H, halo, alkyl, —$OR^7$, —CN and —$R^5$—S(O)$_2R^7$, or any subset thereof. In another embodiment, $R^2$ is selected from H, halo, $C_{1-3}$alkyl, —O—$C_{1-3}$alkyl, —O—$C_{1-3}$haloalkyl, and —$R^5$—S(O)$_2$-alkyl, or any subset thereof. In one particular embodiment, $R^2$ is H. In one particular embodiment, $R^2$ is halo. In one particular embodiment, $R^2$ is —O—$C_{1-3}$alkyl or —O—$C_{1-3}$haloalkyl.

In one embodiment of the present invention, the compounds of the invention are defined wherein both $R^1$ and $R^2$ are the same or different and are halo, in another embodiment, both $R^1$ and $R^2$ are the same or different and are selected from —O—$C_{1-3}$alkyl and —O—$C_{1-3}$haloalkyl. In another embodiment, $R^1$ is $Het^1$ and $R^2$ is H.

In one embodiment, the compounds of the invention are defined wherein $Het^1$ is a 5-6 membered heteroaryl having 1, 2 or 3 heteroatoms selected from N, O and S, optionally substituted 1 or 2 times with a substituent selected from alkyl, haloalkyl, $NR^7$-$Het^2$, and oxo. in another embodiment, $Het^1$ is a 5-6 membered heteroaryl having 1, 2 or 3 heteroatoms selected from N, O and S, optionally substituted 1 or 2 times with a substituent selected from $C_{1-3}$alkyl, NH-$Het^2$ and oxo. In another embodiment, $Het^1$ is a 5-6 membered heteroaryl having 1, 2 or 3 heteroatoms selected from N, O and S, optionally substituted 1 or 2 times with a substituent selected from $C_{1-3}$alkyl and oxo. In a further embodiment, $Het^1$ is selected from pyridinyl, pyrazolyl and oxadiazolyl, each optionally substituted 1 or 2 times with a substituent selected from $C_{1-3}$alkyl and oxo.

In one embodiment, the compounds of the invention are defined wherein $Het^2$ is a 6 membered heterocycle having 1 or 2 heteroatoms selected from N, O and S, optionally substituted 1 or 2 times with a substituent selected from alkyl and oxo. In one embodiment, $Het^2$ is piperidyl, optionally substituted 1 or 2 times with a substituent selected from alkyl and oxo. In one embodiment, $Het^2$ is N-methyl piperidyl.

Specific examples of groups defining $R^1$ include but are not limited to H; F; Cl; —O-alkyl, such as —O—$CH_3$; —O-haloalkyl, such as —O—$CF_3$; pyridyl or substituted pyridyl such as methyl pyridyl and N-oxo pyridyl; pyrazolyl or substituted pyrazolyl such as N-methyl pyrazolyl and H-oxo pyrazolyl; and oxadiazolyl or substituted oxadiazolyl such as methyl oxadiazolyl.

Specific examples of groups defining $R^2$ include but are not limited to H; F; Cl; Br; CN, —O-alkyl, such as —O—$CH_3$; —O-haloalkyl, such as —O—$CF_3$; —$SO_2$-alkyl such as —$SO_2CH_3$; —$CH_2$—$SO_2$-alkyl such as —$CH_2$—$SO_2CH_3$.

In one embodiment, the compounds of the invention are defined wherein $R^3$ is alkyl or haloalkyl, or any subset thereof. In one embodiment, $R^3$ is $C_{1-3}$alkyl or $C_{1-3}$haloalkyl; or any subset thereof. In one particular embodiment, $R^3$ Is $C_{1-3}$alkyl. In one preferred embodiment, $R^3$ is methyl.

If $Z^1$, $Z^2$ or $Z^3$ is C, it is understood that $R^4$ is bound at that position. In one embodiment, the compounds of the invention are defined wherein $Z^1$, $Z^2$ and $Z^3$ are each C or CH. In one embodiment, one of $Z^1$, $Z^2$ and $Z^3$ is N and the other two are C or CH. In one embodiment, both $Z^1$ and $Z^2$ are N and $Z^3$ is CH.

In one embodiment, the compounds of the invention are defined wherein d is 0 or 1. In one particular embodiment, d is 1.

The substituent $R^4$ may be bound to any suitable C. In one embodiment, the compounds of the invention are defined wherein each $R^4$ is the same or different and is independently halo, $C_{1-3}$alkyl or $C_{1-3}$haloalkyl, or any subset thereof. In one embodiment, each $R^4$ is halo. In one particular embodiment, each $R^4$ is Cl or F. In one particular embodiment, each $R^4$ is Cl.

In one embodiment, the compounds of the invention are defined wherein $Y^1$ is —O— or —N(H)—. In one particular embodiment, $Y^1$ is —O—.

In one embodiment, the compounds of the invention are defined wherein a is 0. In one particular embodiment, the compounds of the invention are defined wherein a is 1 and $(R^5)_a$ is $C_{1-3}$alkylene.

In one embodiment, the compounds of the invention are defined wherein Ring A is a 6 membered heterocycle having 1 or 2 heteroatoms selected from N, O and S. in one embodiment, Ring A is a 6 membered heterocycle having 1 N atom and optionally 1 additional heteroatom selected from N, O and S. Specific examples of groups defining Ring A include but are not limited to pyrrolidinyl, piperidinyl, morpholinyl, thiomorpholinyl, and piperazinyl. In one embodiment, Ring A is piperidinyl.

In one embodiment, the compounds of the invention are defined wherein b is 0 or 1. In one embodiment, b is 0. In one embodiment, b is 1.

In one embodiment, the compounds of the invention are defined wherein each $R^6$ is the same or different and is independently selected from halo, alkyl, haloalkyl, —$R^5$-haloalkyl, —CN, —$CO_2R^7$, —$R^5$—$CO_2R^7$, —$C(O)NR^7R^8$, —$OR^7$, —$R^5$—$OR^7$, —$S(O)_2R^7$, —$R^5$—$S(O)_2R^7$, —$NR^7R^8$, —$R^5$—$NR^7R^8$, and oxo, or any subset thereof. In one embodiment, each $R^6$ is the same or different and is independently selected from halo, alkyl, haloalkyl, —$CO_2R^7$, —$OR^7$, —$S(O)_2R^7$, —$R^5$—$S(O)_2R^7$, —$NR^7R^8$, and oxo, or any subset thereof. In one embodiment, each $R^6$ is the same or different and is independently selected from alkyl, haloalkyl, $R^5$—$S(O)_2R^7$, or any subset thereof. In one particular embodiment, b is 1 and $R^6$ is $R^5$—$S(O)_2R^7$. In one particular embodiment, each $R^6$ is the same or different and is independently selected from $C_{1-3}$alkyl and trifluoromethyl. In one particular embodiment, b is 1 and $R^6$ is $C_{1-3}$alkyl.

In one embodiment, the moiety

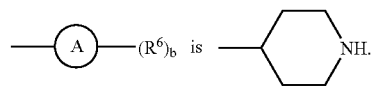

In one embodiment, the moiety

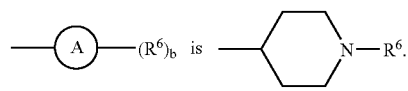

In one embodiment, the moiety

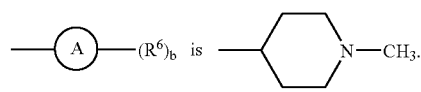

In one embodiment, the compounds of the invention are defined wherein each $R^7$ and each $R^8$ are the same or different and are each independently selected from H, alkyl, haloalkyl and alkenyl, or any subset thereof. In one embodiment, each $R^7$ and each $R^8$ are the same or different and are each independently selected from H and alkyl. In one embodiment, each $R^7$ and each $R^8$ are the same or different and are each independently selected from H and $C_{1-3}$alkyl.

Compounds of the invention exist in stereoisomers forms (e.g. they contain one or more chiral or asymmetric carbon atoms). The term "chiral" refers to a molecule that is not superimposable on its mirror image. The term "chira;" refers to a molecule that is superimposable on Its mirror image.

The term "stereoisomers" refers to compounds which are have a common chemical constitution but differ in the arrangement of the atoms or groups in space. Stereoisomers may be optical isomers or geometric isomers. Optical isomers include both enantiomers and diastereomers. An "enantiomer" is one of a pair of optical isomers containing a chiral carbon atom whose molecular configuration have left- and right-hand (chiral) forms. That is, "enantiomer" refers to each of a pair of optical isomers of a compound which are non-superimposable mirror images of one another. A "diastereomer" is one of a pair of optical isomers of a compound with two or more centers of dissymmetry and whose molecules are not mirror images of one another. The nomenclature of a chiral center is governed by the (R)—(S) system. Whether a particular compound is designated as the "R" or "S" enantiomer according to the system depends upon the nature of the atoms or groups which are bound to the chiral carbon.

Enantiomers differ in their behavior toward plane-polarized light, that is, their optical activity. An enantiomer that rotates plane-polarized light in a clockwise direction is said to be dextrorotatory and is designated by the symbol "d" or "(+)" for positive rotation. An enantiomer that rotates plane-polarized light in the counterclockwise direction is said to be levorotatory and is designated by the symbol "I" or "(-)" for negative rotation. There is no correlation between the configuration of enantiomers and the direction in which they rotate plane-polarized light. There is also no necessary correlation between the (R) and (S) designation and the direction of rotation of the plane-polarized light. The optical activity, or direction of rotation of plane-polarized light, of an enantiomer of a compound of the invention may be determined using conventional techniques.

The compounds of the present invention may be in racemix mixture, enantiomerically enriched or enantiomerically pure form. The terms "racemate" and "racemic mixture" as used herein refer to a mixture of the (R)- and the (S)-optical isomers (e.g., enantiomers) of a compound in equal, i.e. 50:50 proportion.

The term "enantiomerically enriched" as used herein refers to preparations comprising a mixture of optical isomers in which the quantity of one enantiomer is higher than the quantity of the other. Thus, "enantiomerically enriched" refers to mixtures of optical isomers wherein the ratio of enantiomer is greater than 50:50, An enantiomerically enriched compound comprises greater than 50% by weight of one enantiomer relative to the other. For example enantiomerically enriched 3-[((1R)-1-{2-Chloro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide refers to a composition comprising greater than 50% by weight of the (R)-enantiomer relative to the (S)-enantiomer of the compound. In one embodiment, an enantiomerically enriched compound comprises at least 75% by weight of one enantiomer relative to the other, in another embodiment, an enantiomerically enriched compound comprises at least 80% by weight of one enantiomer relative to the other, in one particular embodiment, an enantiomerically enriched compound comprises at least 85% by weight of one enantiomer relative to the other.

The term "enantiomerically pure" as used herein refers to enantiomerically enriched compounds comprising at least 90% by weight of one enantiomer relative to the other. In one embodiment, an enantiomerically pure compound comprises at least 95% by weight of one enantiomer relative to the other. In one particular embodiment, an enantiomerically pure compound comprises at least 99% by weight of one enantiomer relative to the other.

In one embodiment, the present invention provides an enantiomerically enriched compound of formula (I), having the stereochemistry depicted in formula (I-1):

I-1

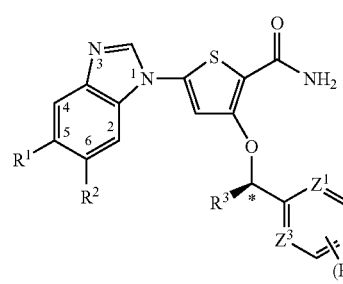

wherein * Indicates a chiral carbon and all variables are as defined above, and pharmaceutically acceptable salts thereof. The foregoing specific embodiments of the invention described above for the variables defining compounds of the invention are equally applicable to compounds of formula (I-1). in one embodiment, the present invention provides and enantiomerically pure compound of formula (I-1).

In one particular embodiment, the present invention provides a compound of formula (XI):

XL

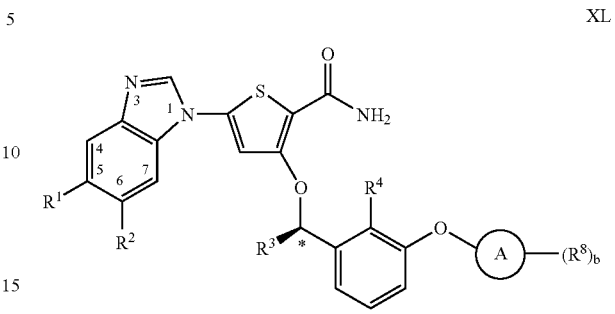

wherein:
$R^1$ is selected from H, halo, alkyl, haloalkyl, —$OR^7$, —CN, —$C(O)NR^7R^8$, —$S(O)_2R^7$, —$R^5$—$S(O)_2R^7$ and $Het^1$;
$Het^1$ is a 5-6 membered heteroaryl having 1, 2 or 3 heteroatoms selected from H, O and S, optionally substituted 1 or 2 times with a substituent selected from alkyl, haloalkyl, —$OR^7$, —CN, —$S(O)_2R^7$. —$NR^7R^8$ and oxo;
$R^2$ is selected from H, halo, alkyl, haloalkyl, —$OR^7$, —CN, —$C(O)NR^7R^8$, —$S(O)_2R^7$, —$R^5$—$S(O)_2R^7$, —$S(O)_2NR^7R^8$, —$R^5$—$S(O)_2NR^7R^8$, —$NR^7R^8$, and —$NR^7C(O)R^8$;
$R^3$ is alkyl;
* indicates a chiral carbon;
$R^4$ is H or halo;
each $R^5$ is the same or different and is independently $C_{1-3}$alkylene;
Ring A is a 5-6 membered heterocycle having 1 or 2 heteroatoms selected from N, O and S;
b is 0 or 1;
each $R^6$ is the same or different and is independently selected from halo, alkyl, haloalkyl, —$CO_2R^7$, —$R^5$—$CO_2R^7$, —$OR^7$, —$R^5$—$OR^7$, —$S(O)_2R^7$, —$R^5$—$S(O)_2R^7$, —$NR^7R^8$, —$R^5$—$NR^7R^8$ and oxo;
each $R^7$ and each $R^8$ are the same or different and are each independently selected from H, alkyl and haloalkyl;

or a pharmaceutically acceptable salt thereof.

The foregoing specific embodiments of the invention described above for the variables defining compounds of the invention are equally applicable to compounds of formula (XL).

In one embodiment, the present invention provides an enantiomerically enriched compound of formula (XL). In one embodiment, the present invention provides an enantiomerically pure compound of formula (XL).

It is to be understood that the present invention includes all combinations and subsets of the particular groups defined hereinabove.

Specific examples of compounds within the scope of the present invention include those recited in the Examples which follow, racemic mixtures, all enantiomers, and pharmaceutically acceptable salts thereof.

One example of a preferred compound of the present invention is 3-({(1R)-1-[2-chloro-3-(4-piperidinyloxy)phenyl]ethyl}oxy)-5-[5-(2-methyl-4-pyridinyl)-1H-benzimidazol-1-yl]-2-thiophenecarboxamide and pharmaceutically acceptable salts thereof.

One example of a preferred compound of the present invention is 3-({(1R)-1-[2-chloro-3-(4-piperidinyloxy)phenyl]

ethyl}oxy)-5-[5-(1-methyl-1H-pyrazol-4-yl)-1H-benzimidazol-1-yl]-2-thiophenecarboxamide and pharmaceutically acceptable salts thereof.

One example of a preferred compound of the present invention is 3-[((1R)-1-{2-chloro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide and pharmaceutically acceptable salts thereof. In one preferred embodiment, 3-[((1R)-1-{2-chloro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide is in the form of the free base.

It will be appreciated by those skilled in the art that the compounds of the invention may be utilized in the form of a pharmaceutically acceptable salt thereof. The pharmaceutically acceptable salts of the compounds of the invention (or the enantiomerically enriched or pure forms thereof) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, trifluoroacetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like. In one embodiment, the compounds of the invention are in the hydrochloride or citrate salt form.

Other acids such as oxalic, while not in themselves pharmaceutically acceptable, may be useful in the preparation of salts useful as intermediates in obtaining the compounds of the invention and their pharmaceutical acceptable salts. More specific examples of suitable basic salts include sodium, lithium, potassium, magnesium, aluminum, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I) or an enaniomerically enriched or pure form thereof) and a solvent. Solvents, by way of example, include water, methanol, ethanol, or acetic acid. The compounds of formula (I) may be in the form of a hydrate, including for example, a monohydrate or a dihydrate.

Processes for preparing pharmaceutically acceptable salts and solvates of the compounds of the invention are conventional in the art. See, e.g., Burger's Medicinal Chemistry And Drug Discovery 5th Edition, Vol 1: Principles And Practice.

As will be apparent to those skilled in the art, in the processes described below for the preparation of the compounds of the invention, certain Intermediates, may alternatively be in the form of pharmaceutically acceptable salts of the compound. Those terms as applied to any intermediate employed in the process of preparing the compounds of the invention have the same meanings as noted above with respect to the compounds of the invention. Processes for preparing pharmaceutically acceptable salts of such intermediates are known in the art and are analogous to the process for preparing pharmaceutically acceptable salts of the compounds of the invention.

The compounds of the invention are typically inhibitors of PLK, in particular, PLK1. By PLK inhibitor is meant a compound which exhibits $pIC_{50}$ greater than 6 in the PLK Inhibition assay described below in the examples or an $IC_{50}$ less than 10 μM in the Cell-Titer Glo or Methylene Blue Cell Growth Inhibition assays described below in the examples; more particularly a PLK inhibitor is a compound which exhibits a $pIC_{50}$ greater than 7 in the PLK inhibition assay or an $IC_{50}$ less than 1 μM in the Cell-Titer Glo or Methylene Blue Cell Growth Inhibition assay using the methods described in the examples below.

The present invention further provides compounds of the invention for use in medical therapy in an animal, e.g. a mammal such as a human. In particular, the present invention provides compounds for use in the treatment of a condition mediated by PLK, particularly PLK1. In one embodiment, the present invention provides compounds for use in the treatment of a condition attenuated by inhibition of PLK, particularly PLK1. The present invention also provides compounds for use in the treatment of a susceptible neoplasm. In particular, the present invention provides compounds for use in the treatment of a variety of solid tumors including but not limited to breast cancer, ovarian cancer, non-small cell lung cancer and prostate cancer as well as hematologic malignancies including but not limited to acute leukemias and aggressive lymphomas and non-Hodgkins lymphomas. "Acute leukemias" includes both acute myeloid leukemias and acute lymphoid leukemias. See, M. Harris, et al., J Clin. Onc. (1999) 17(12):3835-3849. "Aggressive lymphomas" is a term of art. See, J. Chan, Hematological Onc. (2001) 19:129-150.

The present invention provides compounds for use in treating a condition characterized by inappropriate cellular proliferation. The present invention also provides compounds for use in inhibiting proliferation of a cell. The present invention also provides compounds for use in inhibiting mitosis in a cell.

The present invention provides methods for the treatment of several conditions or diseases, all of which comprise the step of administering a therapeutically effective amount of a compound of the invention. As used herein, the term "treatment" refers to alleviating the specified condition, eliminating or reducing the symptoms of the condition, slowing or eliminating the progression of the condition and preventing or delaying the reoccurrence of the condition in a previously afflicted subject.

As used herein, the term "therapeutically effective amount" means an amount of a compound of the invention which is sufficient, in the subject to which it is administered, to elicit the biological or medical response of a cell culture, tissue, system, animal (including human) that is being sought, for instance, by a researcher or clinician. For example, a therapeutically effective amount of a compound of the invention for the treatment of a condition mediated by PLK, particularly PLK1, is an amount sufficient to treat the PLK mediated condition in the subject. Similarly, a therapeutically effective amount of a compound of the invention for the treatment of a susceptible neoplasm is an amount sufficient to treat the susceptible neoplasm in the subject, in one embodiment of the present invention, the therapeutically effective amount of a compound of the invention is an amount sufficient to treat breast cancer in a human in need thereof, in one embodiment of the present invention, a therapeutically effective amount of a compound of the invention is an amount sufficient to regulate, modulate, bind or inhibit PLK, particularly PLK1.

The precise therapeutically effective amount of the compounds of the invention will depend on a number of factors including, but not limited to, the age and weight of the subject being treated, the precise condition or disease requiring treatment and its severity, the nature of the formulation, and the route of administration, and will ultimately be at the discretion of the attendant physician or veterinarian. Typically, the compound of the invention will be given for treatment in the range of 0.1 to 200 mg/kg body weight of recipient (animal) per day, per dose or per cycle of treatment and more usually in the range of 1 to 100 mg/kg body weight per day, per dose or per cycle of treatment. Acceptable daily dosages, may be from about 0.1 to about 2000 mg per day, per dose or per cycle of treatment, and preferably from about 0.1 to about 1000 mg per day. per dose or per cycle of treatment.

As one aspect, the present invention provides methods of regulating, modulating, binding, or inhibiting PLK for the treatment of conditions mediated by PLK, particularly PLK1. "Regulating, modulating, binding or inhibiting PLK" refers to regulating, modulating, binding or inhibiting PLK, particularly PLK1 activity, as well as regulating, modulating, binding or inhibiting overexpression of PLK, particularly PLK1. Such conditions include certain neoplasms (including cancers and tumors) which have been associated with PLK, particularly PLK1, and conditions characterized by inappropriate cellular proliferation.

The present invention provides a method for treating a condition mediated by PLK, particularly PLK1 which comprises administering to the animal a therapeutically effective amount of the compound of the invention. This method and other methods of the present invention are useful for the treatment of animals such as mammals and in particular humans. Conditions which are mediated by PLK are known in the art and include but are not limited to neoplasms and conditions characterized by inappropriate cellular proliferation.

The present invention also provides a method for treating a susceptible neoplasm (cancer or tumor) in an animal such as a mammal (e.g., a human) in need thereof, which method comprises administering to the animal a therapeutically effective amount of the compound of the invention. "Susceptible neoplasm" as used herein refers to neoplasms which are susceptible to treatment with a PLK, particularly PLK1, Inhibitor. Neoplasms which have been associated with PLK and are therefore susceptible to treatment with a PLK inhibitor are known in the art, and include both primary and metastatic tumors and cancers. See e.g., M. Whitfield et al. (2006) *Nature Reviews/Cancer* 6:99. For example, susceptible neoplasms within the scope of the present invention include but are not limited to breast cancer, colon cancer, lung cancer (including small cell lung cancer and non-small cell lung cancer), prostate cancer, endometrial cancer, gastric cancer, melanoma, ovarian cancer, pancreatic cancer, squamous cell carcinoma, carcinoma of the head and neck, esophageal carcinoma, hepatocellular carcinoma, renal cell cancer, sarcoma (including cancers of connective tissue), bladder cancer, glioma and hematologic malignancies such as lymphoma including aggressive lymphomas and non-Hodgkins lymphoma, and leukemia including acute leukemias. in one particular embodiment, the present invention provides a method of treating breast cancer in an animal, such as a mammal (e.g., a human) in need thereof by administering a therapeutically effective amount of a compound of the present invention. In another particular embodiment, the present invention provides a method of treating ovarian cancer in an animal, such as a mammal (e.g., a human) in need thereof by administering a therapeutically effective amount of a compound of the present invention. In another particular embodiment, the present invention provides a method of treating non-small cell lung cancer in an animal, such as a mammal (e.g., a human) in need thereof by administering a therapeutically effective amount of a compound of the present invention. In another particular embodiment, the present invention provides a method of treating prostate cancer in an animal, such as a mammal (e.g., a human) in need thereof by administering a therapeutically effective amount of a compound of the present invention. In another particular embodiment, the present invention provides a method of treating hematologic malignancies including lymphoma, such as aggressive lymphoma and non—Hodgkins lymphoma, and leukemia such as acute leukemia in an animal, such as a mammal (e.g., a human) in need thereof by administering a therapeutically effective amount of a compound of the present invention.

The compounds of the invention can be used alone in the treatment of such susceptible neoplasms or some compounds may be used to provide additive or possibly synergistic effects with one or more other compounds of the invention, or in combination with certain existing chemotherapies and/or other anti-neoplastic therapies. In addition, the compounds of the invention may in some instances be used to restore effectiveness of certain existing chemotherapies and/or other anti—neoplastic therapies. As used herein, "anti-neoplastic therapies" includes but is not limited to cytotoxic chemotherapy, cytostatic chemotherapy, hormonal therapy, targeted kinase inhibitors, therapeutic monoclonal antibodies, surgery and radiation therapy.

The present invention also provides a method for treating a condition characterized by inappropriate cellular proliferation in an animal, such as a mammal (e.g., a human) in need thereof. The method comprises administering a therapeutically effective amount of a compound of the present invention. By "inappropriate cellular proliferation" is meant cellular proliferation resulting from inappropriate cell growth, cellular proliferation resulting from excessive cell division, cellular proliferation resulting from cell division at an accelerated rate, cellular proliferation resulting from inappropriate cell survival, and/or cellular proliferation in a normal cell occurring at a normal rate, which is nevertheless undesired. Conditions characterized by inappropriate cellular proliferation include but are not limited to neoplasms, blood vessel proliferative disorders, fibrotic disorders, mesangial cell proliferative disorders and inflammatory/immune-mediated diseases. Stood vessel proliferative disorders include arthritis and restenosis. Fibrotic disorders include hepatic cirrhosis and atherosclerosis. Mesangial cell proliferative disorders include glomerulonephritis, malignant nephrosclerosis and glomerulopathies. Inflammatory/immune-mediated disorders include psoriasis, chronic wound healing, organ transplant rejection, thrombotic microangiopathy syndromes, and neurodegenerative diseases. Osteoarthritis and other osteoclast proliferation dependent diseases of excess bone resorbtion are examples of conditions characterized by inappropriate cellular proliferation in which the cellular proliferation occurs in normal cells at a normal rate, but is nevertheless undesired.

The present invention also provides a method for inhibiting proliferation of a cell, which method comprises contacting the cell with an amount of a compound of the invention sufficient to inhibit proliferation of the cell. In one particular embodiment, the cell is a neoplastic cell. In one particular embodiment, the cell is an inappropriately proliferative cell. The term "inappropriately proliferative cell" as used herein refers to cells that grow inappropriately (abnormally), cells that divide excessively or at an accelerated rate, cells that inappropriately (abnormally) survive and/or normal cells that proliferate at a normal rate but for which proliferation is undesired. Neoplastic cells (including cancer cells) are an example of inappropriately proliferative cells but are not the only inappropriately proliferative cells.

PLK is essential for cellular mitosis and accordingly, the compounds of the invention are believed to be effective for inhibiting mitosis, "inhibiting mitosis" refers to inhibiting the entry into the M phase of the cell cycle, inhibiting the normal progression of the M phase of the cell cycle once M phase has been entered and inhibiting the normal exit from the M phase of the cell cycle. Thus, the compounds of the present invention may inhibit mitosis by inhibiting the cell's entry into mitosis, by inhibiting the cell's progression through mitosis or by inhibiting the cell's exit from mitosis. As one aspect, the present invention provides a method for inhibiting mitosis in a cell, which method comprises administering to the cell an amount of a compound of the invention sufficient to inhibit mitosis, in one particular embodiment, the cell is a neoplastic cell. In one particular embodiment, the cell is an inappropriately proliferative cell.

The present invention also provides the use of a compound of the invention for the preparation of a medicament for the treatment of condition mediated by PLK, particularly PLK1, in an animal, such as a mammal (e.g., a human), The present invention further provides the use of a compound for the preparation of a medicament for the treatment of a susceptible neoplasm in an animal, particularly a mammal (e.g., a human), in particular, the present invention provides the use of a compound for the preparation of a medicament for the treatment of breast cancer. The present invention also provides the use of a compound for the preparation of a medicament for the treatment of ovarian cancer. The present invention provides the use of a compound for the preparation of a medicament for the treatment of non-small cell lung cancer. The present invention provides the use of a compound for the preparation of a medicament for the treatment of prostate cancer. The present invention provides the use of a compound for the preparation of a medicament for the treatment of hematologic malignancies such as acute leukemias, aggressive lymphomas and non-Hodgkins lymphomas. The present invention further provides the use of a compound for the preparation of a medicament for the treatment of a condition characterized by inappropriate cellular proliferation. The present invention further provides the use of a compound for the preparation of a medicament for inhibiting proliferation of a cell. The present invention further provides the use of a compound for the preparation of a medicament for inhibiting mitosis in a cell.

While it is possible that, for use in therapy, a therapeutically effective amount of a compound of the invention may be administered as the raw chemical, it is typically presented as the active ingredient of a pharmaceutical composition or formulation. Accordingly, the invention further provides a pharmaceutical composition comprising a compound of the invention. The pharmaceutical composition may further comprise one or more pharmaceutically acceptable carriers, diluents, and/or excipients. The carriers), diluent(s) and/or excipient(s) must be acceptable in the sense of being compatible with the other ingredients of the formulation and not deleterious to the recipient thereof, in accordance with another aspect of the invention there is also provided a process for the preparation of a pharmaceutical formulation including admixing a compound of the invention with one or more pharmaceutically acceptable carriers, diluents and/or excipients.

Pharmaceutical formulations may be presented in unit dose form containing a predetermined amount of active ingredient per unit dose. Such a unit may contain a therapeutically effective dose of the compound of the invention (in any form) or a fraction of a therapeutically effective dose such that multiple unit dosage forms might be administered at a given time to achieve the desired therapeutically effective dose. Preferred unit dosage formulations are those containing a dally dose or sub-dose, as herein above recited, or an appropriate fraction thereof, of an active ingredient (compound of the invention). Furthermore, such pharmaceutical formulations may be prepared by any of the methods well known in the pharmacy art.

Pharmaceutical formulations may be adapted for administration by any appropriate route, for example by the oral (including tablets, capsules, liquid-filed capsules, disintegrating tablets, controlled release tablets, buccal, sublingual, etc.), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can he run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the invention may also be delivered by the use of monoclonal antibodies as individual carriers to which the compound molecules are coupled. The compounds may also be coupled with soluble polymers as targetable drug carriers. Such polymers can include peptides, polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time, For example, the active ingredient may be delivered from the patch by iontophoresis as generally described in *Pharmaceutical Research,* 3(6):318 (1986), Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active Ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators. Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous Injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

In the above-described methods of treatment and uses, a compound of the invention may be employed alone, in combination with one or more other compounds of the invention or in combination with other therapeutic agents and/or in combination with other anti-neoplastic therapies, in particular. In methods of treating conditions mediated by PLK and methods of treating susceptible neoplasms, combination with oilier chemotherapeutic agents is envisaged as well as combination with surgical therapy and radiation therapy. The term "chemotherapeutic" as used herein refers to any chemical agent having a therapeutic effect on the subject to which it is administered. "Chemotherapeutic" agents include but are not limited to anti-neoplastic agents, analgesics and anti-emetics. As used herein, "anti-neoplastic agents" include both cytostatic and cytotoxic agents such as but not limited to cytotoxic chemotherapy, hormonal therapy, targeted kinase inhibitors and therapeutic monoclonal antibodies. Combination therapies according to the present invention thus comprise the administration of at least one compound of the invention and the use of at least one other cancer treatment method. In one embodiment, combination therapies according to the present invention comprise the administration of at least one compound of the invention and at least one other chemotherapeutic agent. In one particular embodiment, the present invention comprises the administration of at least one compound of the invention and at least one anti-neoplastic agent. As an additional aspect, the present invention provides the methods of treatment and uses as described above, which comprise administering a compound of the invention together with at least one chemotherapeutic agent, in one particular embodiment, the chemotherapeutic agent is an anti-neoplastic agent. In another embodiment, the present invention provides a pharmaceutical composition as described above further comprising at least one other chemotherapeutic agent, more particularly, the chemotherapeutic agent is an anti-neoplastic agent.

Typically, any chemotherapeutic agent that has activity versus a susceptible neoplasm being treated may be utilized in combination with the compounds of the invention, provided that the particular agent is clinically compatible with therapy employing a compound of the invention. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphor-ines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase anglogenesis inhibitors; immunotherapeutic agents; proapoptotic agents; and cell cycle signaling inhibitors.

Anti-microtubule or antimitotic agents are phase specific agents active against the microtubules of tumor cells during M or the mitosis phase of the cell cycle. Examples of anti-microtubule agents include, but are not limited to, diterpenoids and vinca alkaloids. Examples of diterpenoids include, but are not limited to, paclitaxel and its analog docetaxel. Examples of vinca alkaloids include, but are not limited to, vinblastine, vincristine, and vinorelbine. Platinum coordination complexes are non-phase specific anti-neoplastic agents, which are interactive with DNA. The platinum complexes enter tumor cells, undergo, aquation and form infra- and interstrand crosslinks with DNA causing adverse biological effects to the tumor. Examples of platinum coordination complexes include, but are not limited to, oxaliplatin, cisplatin and carboplatin.

Alkylating agents are non-phase specific anti-neoplastic agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Antibiotic chemotherapeutic agents are non-phase specific agents, which bind or Intercalate with DNA, Typically, such action results in stable DNA complexes or strand breakage, which disrupts ordinary function of the nucleic acids leading to cell death. Examples of antibiotic anti-neoplastic agents include, but are not limited to, actinomycins such as dactino-mycin, anthracyclins such as daunorubicin and doxorubicin; and bleomycins. Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DMA causing DMA strand breaks. The strand breaks accumulate and cell death follows. Examples of epipodophyllotoxins include, but are not limited to, etoposide and teniposide.

Antimetabolite neoplastic agents are phase specific antineoplastic agents that act at S phase (DNA synthesis) of the cell cycle by inhibiting DMA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine and thioguanine.

Camptothecins, including, camptothecin and camptothecin derivatives are available or under development as Topoisomerase I inhibitors. Camptotheeins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin. Hormones and hormonal analogues are useful compounds for treating cancers in which there is a relationship between the hormone(s) and growth and/or lack of growth of the cancer. Examples of hormones and hormonal analogues believed to be useful in the treatment of neoplasms include, but are not limited to, adrenocorti-costeroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene and iodoxyfene useful in the treatment of hormone dependent breast carcinoma; and gonadotropin-releasing hormone (GnRH) and analogues thereof, such as goserelin acetate and leuprolide, which stimulate the release of leutinizing hormone (LH) and/or follicle stimulating hormone (FSH) with short-term or intermittent use but lead to suppression of LH and FSH with long-term use indicated for the treatment prostatic carcinoma, and hormone dependent breast carcinoma.

Signal transduction pathway inhibitors are those inhibitors which block or inhibit a chemical process which evokes an intracellular change. As used herein this change is cell proliferation, survival, anglogenesis or differentiation. Signal tranduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are sometimes termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr, ErbB2 and ErbB4,), platelet derived growth factor receptor (PDGFr), vascular endothelial growth factor receptor (VEGFR), tyrosine kinase with immunoglobulin-like and epidermal growth factor homology domains (TIE-2), insulin growth factor-I receptor (IGF-I), macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth factor receptors are under development and include ligand antagonists, antibodies, tyrosine kinase inhibitors, anti-sense oligonucleotides and aptamers. Growth factor receptors and agents that inhibit growth factor receptor function are described, for instance, in Kath, John C, Exp. Opin. Ther. Patents (2000) 10(6):803-318; Shawver et al DDT Vol 2, No. 2 February 1897: and Lofts, F. J. et al, "Growth Factor Receptors as Targets", New Molecular Targets for Cancer Chemotherapy, Ed. Workman, Paul and Kerr, David, CRC Press 1894, London, Tyrosine kinases, which are not growth factor receptor kinases are termed non-receptor tyrosine kinases. Non-receptor tyrosine kinases useful in the present invention, which are targets or potential targets of anti-neoplastic drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Ceil Research 8 (5): 485-80; and Bolen, J. B., Brugge, J. S., (1997) Annual Review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (She, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (Rafk), Mitogen or Extracellular Regulated Kinase (MEKs), and Extracellular Regulated Kinases (ERKs); and Protein kinase C family member blockers including blockers of subtypes of PKCs (alpha, beta, gamma, epsilon, mu, lambda, iota, zeta), lkB kinase family (IKKa, IKKb), PKB family kinases, Akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 739-803; Brodt, P, Samani, A., and Navab, R. (2000), Biochemical Pharmacology, 60. 1101-1107; Massague, J., Weis-Garcia, F. (1996) Cancer Surveys. 27:41-84; Philip, P. A., and Harris, A. L. (1995), Cancer Treatment and Research. 78: 3-27, Lackey, K. et al Bioorganic and Medicinal Chemistry Letters, (10), 2000, 223-228; and Martinez-Iacaci. L, et al, Int. J. Cancer (2000), 88(1), 44-52.

Inhibitors of Phosphotidyl Inositol-3 Kinase family members including blockers of PI3-kinase, ATM, DNA-PK, and Ku are also useful in combination with the present invention. Such kinases are discussed in Abraham, R. T. (1998), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer Res, (2000) 60(6), 1541-1545.

Also useful in combination with the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC Press 1994, London.

Another group of signal transduction pathway inhibitors useful in combination with the present invention are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block Ras activation in cells containing wild type mutant Ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Upidology. 9(2)99-102; and BioChim, Biophys. Acta, (1989) 1423(3): 19-30.

As mentioned above, antibodies to receptor kinase ligand binding may also serve as signal transduction inhibitors. This group of signal transduction pathway inhibitors includes the use of humanized antibodies to the extracellular ligand binding domain of receptor tyrosine kinases. For example, Imclone C225 EGFR specific antibody (see Green, M. C. et al, Monoclonal Antibody Therapy for Solid Tumors, Cancer Treat. Rev., (2000), 26(4), 269-286); Herceptin® ErbB2 antibody (see Tyrosine Kinase Signaling in Breast Cancer:ErbB Family Receptor Tyrosine Kinases, Breast Cancer Res., 2000, 2(3), 176-183); and 2CB VEGFR2 specific antibody (see Brekken, R. A. et al, Selective Inhibition of VEGFR2 Activity by a Monoclonal Anti-VEGF Antibody Blocks Tumor Growth in Mice, Cancer Res. (2000) 60, 5117-5124).

Receptor kinase angiogenesis inhibitors may also find use in the present invention, inhibitors of angiogenesis related VEGFR and TIE2 are discussed above in regard to signal transduction inhibitors (both receptors are receptor tyrosine kinases). Other inhibitors may be used in combination with the compounds of the present invention. For example, anti-VEGF antibodies, which do not recognize VEGFR (the receptor tyrosine kinase), but bind to the ligand; small molecule inhibitors of integrin (alpha, beta$_3$) that will inhibit angiogenesis; endostatin and angiostatin (non-RTK) may also prove useful in combination with PLK inhibitors.

Agents used in immunotherapeutic regimens may also be useful in combination with the compounds of the invention.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al., *J. Clin. Oncol.* 18:1812-1823 (2000); and Kitada S et al., *Antisense Res. Dev.* 4:71-79 (1994).

Cell cycle signaling inhibitors inhibit molecules involved in the control of the cell cycle. Cyclin dependent kinases (CDKs) and their interaction with cyclins control progression through the eukaryotic cell cycle. The coordinated activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania, et al., *Exp. Opin. Ther. Patents* 10(2):215-230 (2000).

In one embodiment, the methods of the present invention comprise administering to the animal a compound of the invention in combination with a signal transduction pathway inhibitor, particularly gefitinib (IRESSA®).

The methods and uses employing these combinations may comprise the administration of the compound of the invention and the other chemotherapeutic/anti-neoplastic agent either sequentially in any order or simultaneously in separate or combined pharmaceutical compositions. When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of the invention is used in combination with a chemotherapeutic agent, the dose of each compound may differ from that when the compound is used alone. Appropriate doses will be readily appreciated by those skilled in the art. The appropriate dose of the compound(s) of the invention and the other therapeutically active agent(s) and the relative timings of administration will be selected in order to achieve the desired combined therapeutic effect, and are within the expertise and discretion of the attendant clinician.

The compounds of the invention may be conveniently prepared by the process outlined in Scheme 1 below.

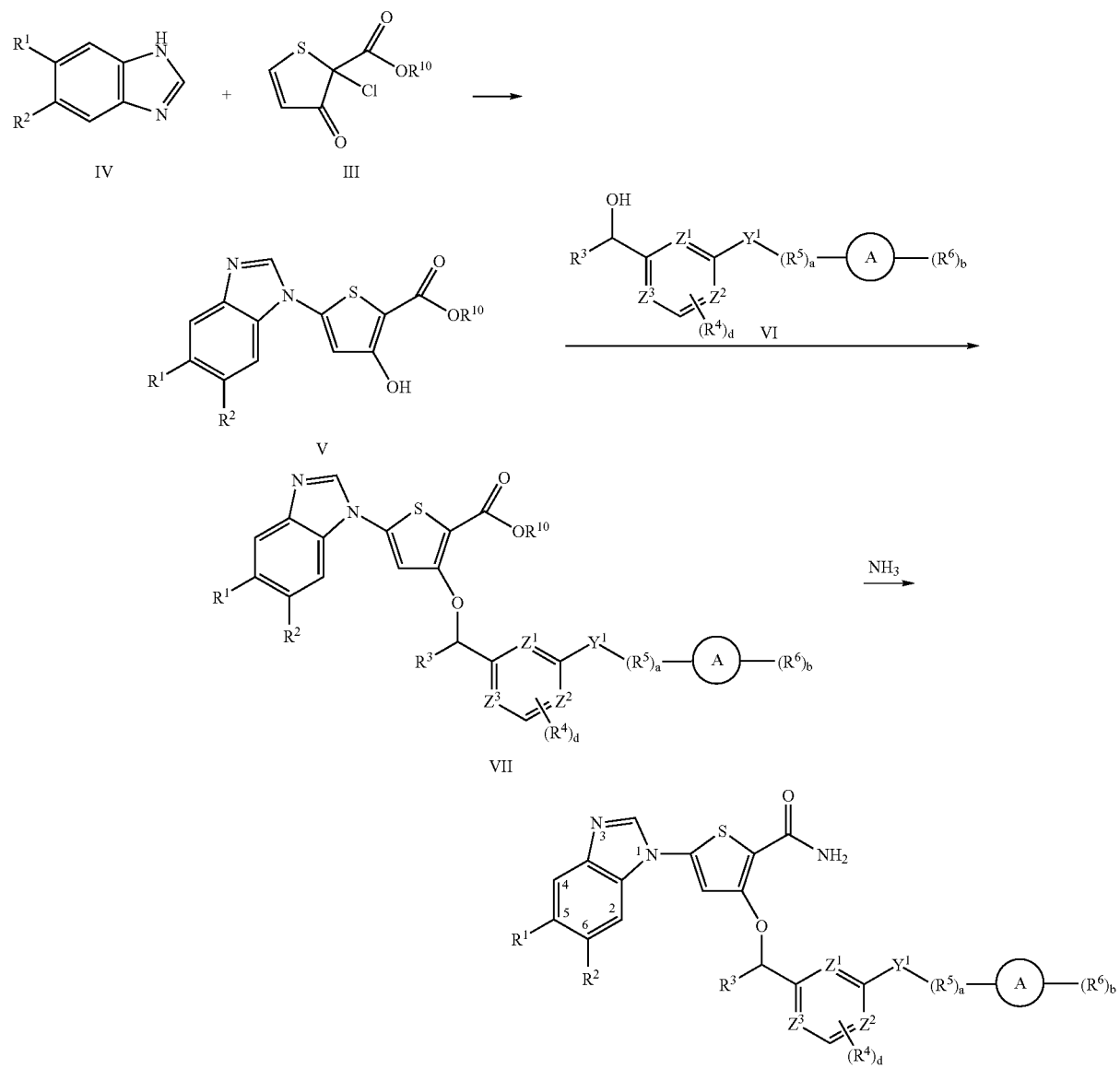

wherein:
Y$^1$ is O;
R$^{10}$ is selected alkyl and suitable carboxylic acid protecting groups; and
all other variables are as defined above.

Generally, the process for preparing the compounds of the invention (all formulas and all variables having been defined above) comprises the steps of:
a) reacting the compound of formula (IV) with a compound of formula (III) to prepare a compound of formula (V);
b) reacting the compound of formula (V) with a compound of formula (VI) to prepare a compound of formula (VII);
c) reacting the compound of formula (VII) with ammonia to prepare a compound of formula (I);
d) optionally separating the compound of formula (I) into enantiomers of formula (I);
e) optionally converting the compound of formula (I) to a pharmaceutically acceptable salt thereof; and
f) optionally converting the compound of formula (I) or a pharmaceutically acceptable salt thereof to a different compound of formula (I) or a pharmaceutically acceptable salt thereof.

As will be apparent to those skilled in the art, the order of the steps in the foregoing reaction is not critical to the practice of the process of the present invention. The foregoing reaction steps may be carried out in any suitable order based upon the knowledge of those skilled in the art. Further, if will be apparent to those skilled in the art that certain reaction steps may be most efficiently performed by installing protecting groups prior to the reaction, which are removed subsequently. The choice of protecting groups as well as general techniques for their installation and removal are within the skill of those in the art.

More specifically, compounds of the invention can be prepared by reacting a compound of formula (VII) with ammonia to prepare a compound of formula (I).

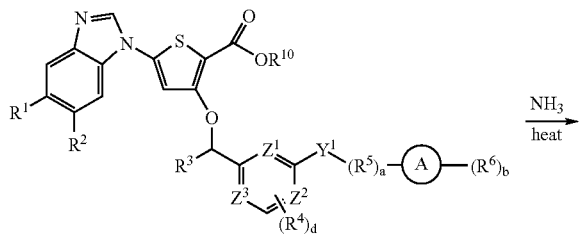

VII wherein all variables are as defined above.

This reaction is typically performed in a sealed vessel with an excess of ammonia. The reaction is typically heated to a temperature of from about 50 to about 120° C., more particularly, about 70° C. Suitable solvents for this reaction include but are not limited to methanol, ethanol, isopropanol, tetrahydrofuran, and dioxane.

A compound of formula (I) wherein R$^3$ is not H, may be separated, using conventional separation techniques (e.g., supercritical fluid chromatography (SFC)) into its enantiomers, the enantiomerically enriched compounds of formula (I-1) and (I-2).

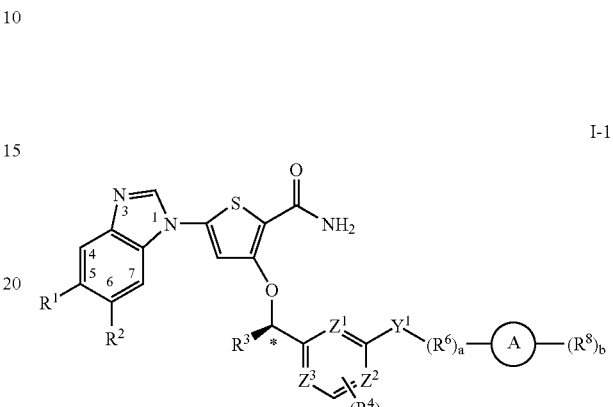

I-1

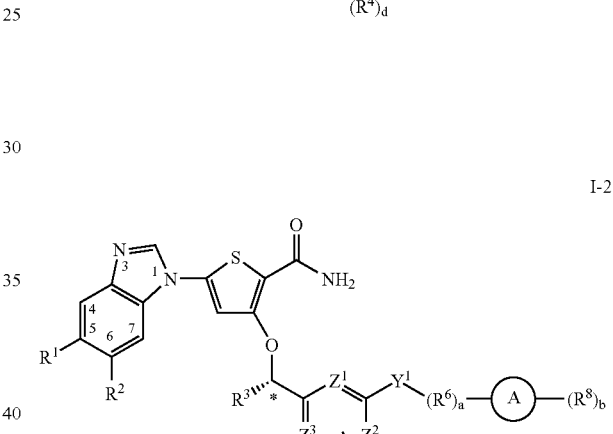

I-2

A compound of formula (VII) may be prepared by reacting a compound of formula (V) with a compound of formula (VI) under Mitsunobu reaction conditions.

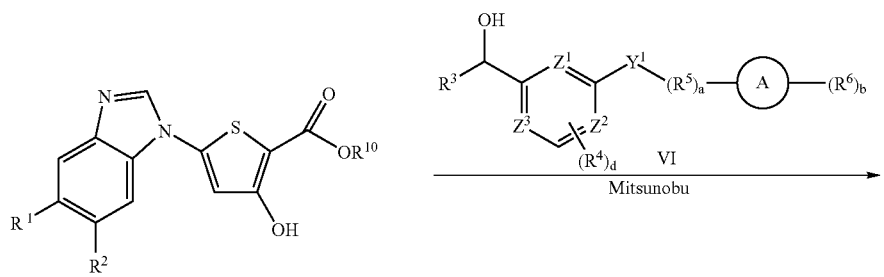

V

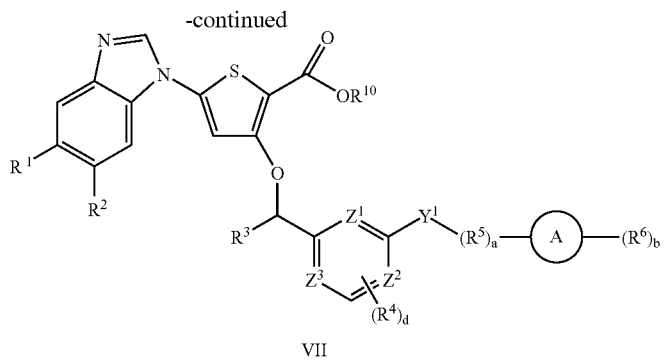

VII wherein all variables are as defined above.

The reaction is carried out in an inert solvent under standard Mitsunobu conditions. See, Hughes, D. L, *Org. React.* 42:335-656 (1892); and Mitsunobu, O., *Synthesis* 1-28 (1981). Typically the compound of formula (V), the compound of formula (VI), a tharylphosphine, and a dialkyl azodicarboxylate are reacted together at room temperature. Examples of suitable triarylphosphines include but are not limited to, triphenylphosphine, tri-p-tolylphosphine, and trimesityiphosphine. Examples of suitable dialkyl azodicarboxylates include but are not limited to, diethyl azodicarboxylate, diisopropyl azodicarboxylate, and di-tert-butyl azodicarboxylate. Examples of suitable inert solvents for this reaction include but are not limited to, tetrahydrofuran, dioxane, 1,2-dimethoxyethane, dichloromethane, and toluene.

If desired, the compound of formula (VII) may be separated using conventional separation techniques (e.g., SFC) into its enantiomers, enantiomerically enriched compounds of formula (VII-1) and (VII-2).

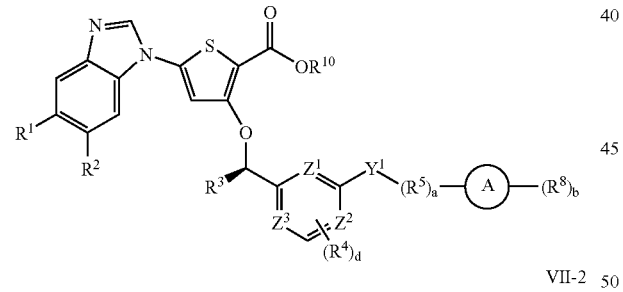

VII-1

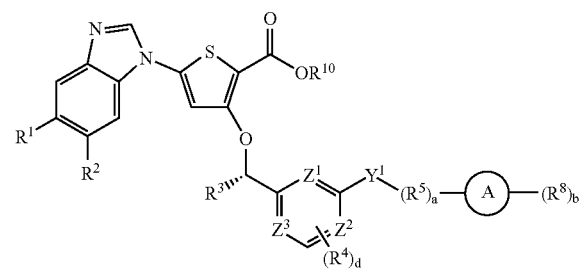

VII-2

As will be apparent to those skilled in the art, reaction of an enantiomerically enriched compound of formula (VII-1) or (VII-2) with ammonia will result in the corresponding enantiomerically enriched compound of formula (I-1) or (I-2), respectively.

The compounds of formula (VI) may be prepared by reducing a compound of formula (XI). The compounds of formula (XI) may be prepared by reacting a compound of formula (IX) with a compound of formula (X) under Mitsunobu reaction conditions.

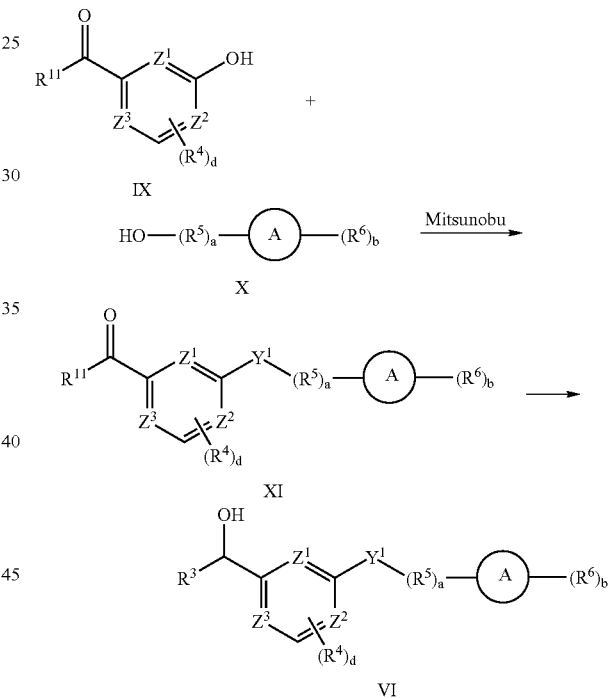

wherein:
$Y^1$ is O;
$R^{11}$ is H or $R^3$; and
all variables are as defined above.

Suitable Mitsunobu reaction conditions and solvents are described above. The Mitsunobu reaction yields a compound of formula (XI).

Compounds of formula (XI), where $R^{11}$ is H, may be reacted with $R^3$—Li (alkyl lithium) or $R^3$—MgCl (alkyl magnesium chloride) to prepare a compound of formula (VI). In one embodiment, the compounds of formula (XI), where $R^{11}$ is H, may be reacted with methyl lithium in the presence of titanium (VI) chloride, or methyl magnesium chloride to prepare a compound of formula (VI) where $R^3$ is methyl. The reaction typically can be carried out in an inert atmosphere.

The suitable solvents may include ether and tetrahydrofuran. The reaction temperature may be in the range of −78° C. to room temperature.

Compounds of formula (XI) may also be reacted with reducing agents such as borane, lithium hydride or sodium borohydrate to prepare a compound of formula (VI). Suitable techniques for conversion of an aldehyde or ketone to an alcohol are well known to those skilled in the art. See, Larock, R. *Comprehensive Organic Transformation (2nd Edition)*, John Wiley & Sons, Inc. (1999) 1075-1077.

In one embodiment, the compound of formula (XI) is reacted with borane/dimethylsulfide complex in tetrahydrofuran and (R)-1-methyl-3,3-diphenyltetrahydro-3H-pyrrolo[1,2-c][1,3,2]oxazaborole in a solvent such as toluene to prepare an enantiomerically enriched compound of formula (VI) having the stereochemistry depicted in formula (VI-1):

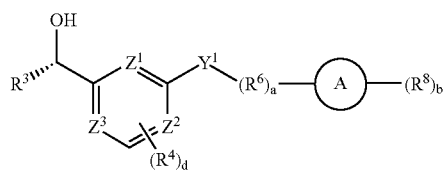

wherein all variables are as defined above.

As will be apparent to those skilled in the art, use of the enantiomerically enriched compound of formula (VI-1) in the reaction with the compound of formula (V) will yield an enantiomerically enriched compound of formula (VII-1) which may be reacted with ammonia to yield the enantiomerically enriched compound of formula (I-1).

The compounds of formula (V) may be prepared by reacting a compound of formula (IV) with a compound of formula (III).

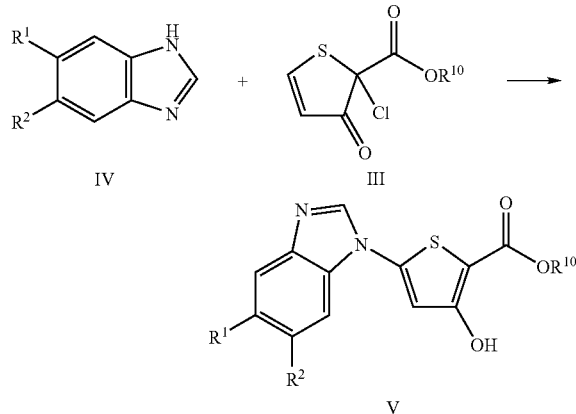

wherein all variables are as defined above.

Processes for the reaction of a compound of formula (IV) with a compound of formula (III) are known to those skilled in the art. See, PCT Int. Appl. WO 2004073612, Such reactions are typically carried out in an inert solvent at room temperature. Examples of suitable inert solvents for this reaction include but are not limited to, chloroform, dichloromethane, tetrahydrofuran, dioxane, and toluene and mixtures of any of the foregoing with acetic acid (e.g., a mixture of chloroform and acetic acid). In one embodiment, the inert solvent is selected from dichloromethane, chloroform, tetrahydrofuran, diethyl ether, and toluene and a mixture of any of the foregoing and acetic acid (e.g. a mixture of chloroform and acetic acid).

The reaction may be carried out in the presence of one to five equivalents of the base additive. The base additive is believed to act as a scavenger for the hydrochloric acid generated during the reaction. Examples of suitable base additives for this reaction include but are not limited to sodium bicarbonate, triethylamine, sodium acetate, N-methylimidazole, pyridine, N-methylbenzimidazole and potassium carbonate. In one embodiment, the base additive is selected from sodium bicarbonate, triethylamine, sodium acetate, N-methylimidazole, pyridine and N-methylbenzimidazole. In one particular embodiment, the base additive is sodium bicarbonate. In one particular embodiment, the base additive is N-methylimidazole. Compounds of formula (IV) may be prepared by a process depicted below:

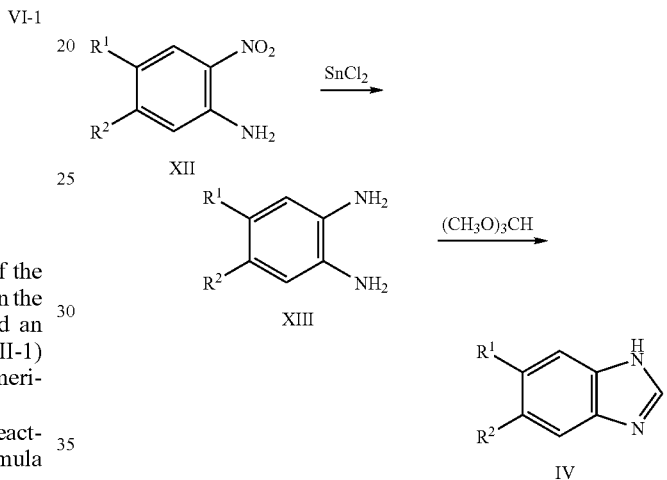

wherein all variables are as defined above.

This process comprises the steps of:
a) reducing a 2-nitroaniline of formula (XII) to prepare a substituted 1,2-diamine of formula (XIII); and
b) cyclizing the 1,2-diamine of formula (XIII) with a ring forming reagent, such as trimethylorthoformate, to prepare compounds of formula (IV).

The ring forming reaction may be carried out using conventional techniques. See, White, A., et al., *J. Med. Chem.* 43:4084-4097 (2000); Jiang, J.-L., et al., *Synthetic Comm.* 28:4137-4142 (1998); Tanaka, A., et al., *Chem. Pharm. Bull* 42:560-569 (1994); Tian, W., et al., *Synthesis* 12:1283-1286 (1992); Buckle, D. R., et al., *J. Med. Chem.*, 30:2216-2221 (1987); and Raban, M., et al., *J. Org. Chem.* 50:2205-2210 (1985). This reaction may be carried out neat or in a suitable solvent. The reaction may optionally be heated to a temperature of from about 50 to about 230° C. The reaction is typically carried out with an excess of trimethylorthoformate. An additional acid may be used. Examples of suitable acids include but are not limited to, formic acid, hydrochloric acid, hydrobromic acid, perchloric acid, sulfuric acid, p-toluenesulfonic acid, methanesulfonic acid, and trifluoromethanesulfonic acid. Examples of suitable solvents for this reaction include but are not limited to water, methanol, ethanol, isopropanol, tetrahydrofuran, dichloromethane, toluene, N,N-dimethylformamide, dimethylsulfoxide, and acetonitrile. The reduction of the 2-nitroaniline of formula (XII) may be carried out using conventional techniques and reducing agents such as tin(II) chloride. See, Rangarajan, M., et al., Bioorg. Med. Chem. 8:2591-2600 (2000); White, A. W., et al., J. Med. Chem. 43: 4084-4097 (2000); Silvestri, R., et al., Bioorg. Med. Chem. 8:2305-2309 (2000); Nagaraja, D., et al., Tetrahedron Lett. 40:7855-7856 (1999); Jung, F., et al., J. Med. Chem. 34:1110-1116 (1991); Srivastava, R. P., et al., Pharmazie 45:34-37 (1990); Hankovszky, H. O., et al., Can. J. Chem. 67:1392-1400 (1989); Ladd, D. L., et al., J. Org. Chem., 53:417-420 (1988); Mertens, A., et al., J. Med. Chem. 30:1279-1287 (1987); and Sharma, K. S., et al., Synthesis 4:318-318 (1981). Examples of other suitable reducing agents for this reaction include but are not limited to, palladium with hydrogen, palladium with ammonium formate, platinum oxide with hydrogen, nickel with hydrogen, iron with acetic acid, aluminum with ammonium chloride, borane, sodium dithionite, and hydrazine. The reaction may optionally be heated to between about 50 and about 120° C. Suitable solvents for this reaction vary and include but are not limited to, water, methanol, ethanol, ethyl acetate, tetrahydrofuran, dioxane, and mixtures thereof.

Compounds of formula (III) may be prepared by reacting a compound of formula (II) with sulfuryl chloride.

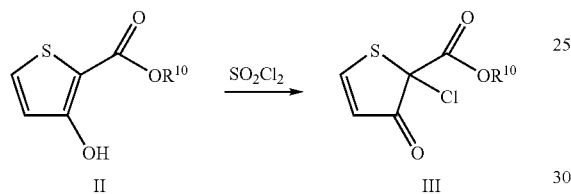

wherein all variables are as defined above.

Compounds of formula (II) are commercially available or can be prepared using conventional techniques. Typically the reaction is carried out at room temperature. Excess sulfuryl chloride may be used if desired. Examples of suitable solvents include but are not limited to chloroform, dichloromethane, and toluene. See, Corral, C.; Lissavetzky, J. Synthesis 847-850 (1984).

In another embodiment, a regioselective compound of formula (V) may be prepared according to the process of Scheme 2:

Scheme 2

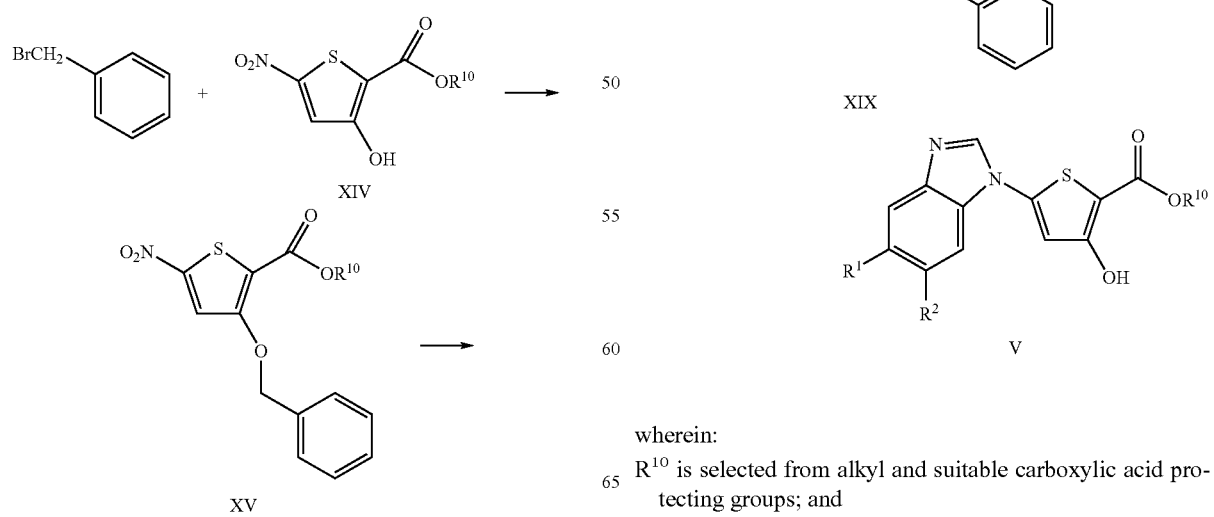

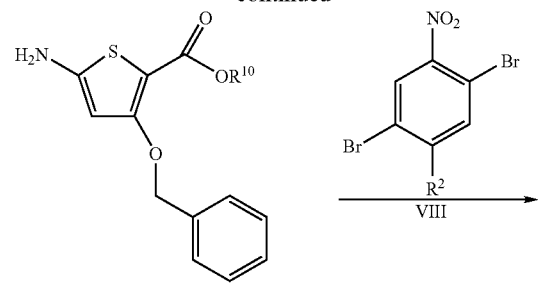

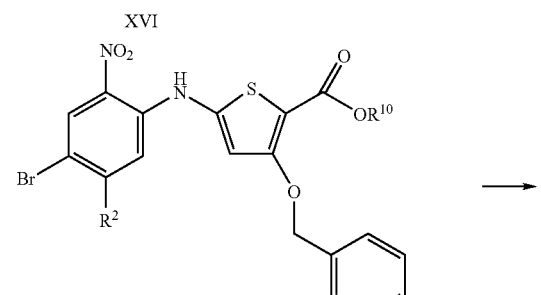

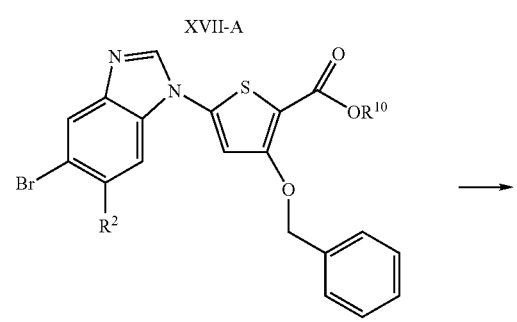

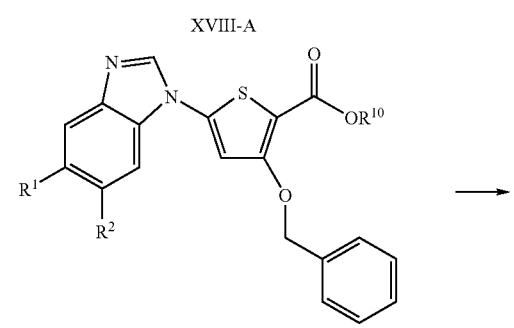

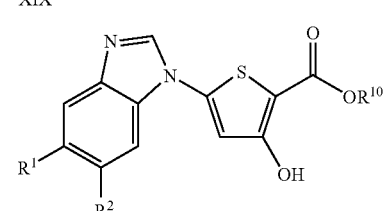

wherein:

$R^{10}$ is selected from alkyl and suitable carboxylic acid protecting groups; and all other variables are as defined above.

Generally, the process for preparing the compounds of formula (V) (all formulas and all variables having been defined above) comprises the steps of:

a) reacting a compound of formula (XIV) with a protecting group, such as benzyl bromide, to prepare a compound of formula (XV);
b) reducing the compound of formula (XV) to prepare a compound of formula (XVI);
c) reacting the compound of formula (XVI) with a 1,4-dibromo-2-nitrobenzene of formula (VIII) to prepare a compound of formula (XVII-A);
d) reducing and cyclizing the compound of formula (XVII-A) to prepare a compound of formula (XVIII-A);
e) reacting the compound of formula (XVIII-A) under conventional cross-coupling reaction conditions to prepare a compound of formula (XIX);
f) reacting the compound of formula (XIX) with acid to prepare a compound of formula (V).

According to this process a compound of formula (V) is prepared by reacting a compound of formula (XIX) with a suitable acid, such as trifluoroacetic acid or hydrochloric acid.

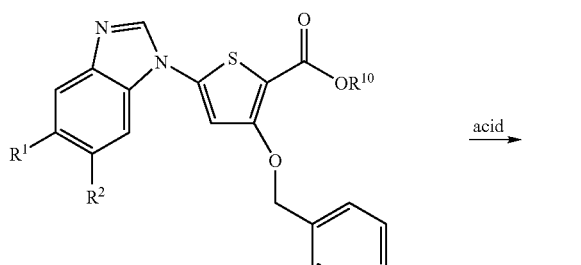

This reaction may be carried out in neat trifluoroacetic acid or in an inert solvent such as dichloromethane at ambient temperature.

The compound of formula (XIX) may be prepared by reacting a compound of formula (XVIII-A) under conventional cross-coupling reaction conditions.

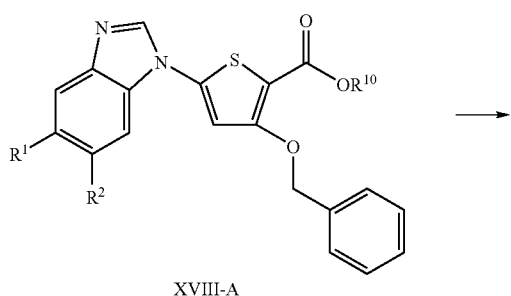

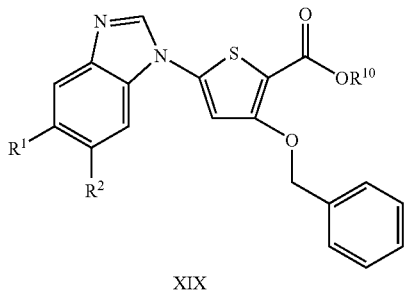

wherein all variables are as defined above.

In particular, a compound of formula (XIX) may be prepared from a compound of formula (XVIII-A) using palladium-catalyzed Suzuki, Stille, or Negishi cross-coupling techniques conventional in the art of organic synthesis. For a review of the Suzuki cross-coupling reaction, see: Miyaura, N.; Suzuki, A. *Chemical Reviews* 1895, 95, 2457-2483. The Suzuki coupling may be carried out using a suitable catalyst such as dichloro[1,1'-bis(diphenylphosphino)ferrocene]palladium(II) dichloromethane adduct, a base such as aqueous sodium carbonate or triethylamine, and a suitable inert solvent such as N,N-dimethylacetamide or tripropanol, optionally in the presence of microwave irradiation, at temperatures from about 50° C. to about 150° C. For a review of the Stille cross-coupling reaction, see: Mitchell, T. N. *Synthesis* 1992, 803-815. The Stille coupling may be carried out using tetrakis (triphenylphoshine)-palladium (0) as the catalyst, in the presence of promoters such as cesium fluoride and copper (I) iodide, in a suitable inert solvent such as N,N-dimethylformamide at a temperature of about 45° C. For a review of the Negishi cross-coupling reaction, see: Negishi, E.; Zingzhong, T. Z.; Qian, M.; Hu, Q.; Huang, Z. *Metal Catalyzed Cross-Coupling Reactions* ($2^{nd}$ Edition), 2004, 2, 815-889. The Negishi coupling may be carried out using dichloro[1,1'-bis(diphenylphoshino)-ferrocene]palladium(II) dichloromethane adduct as the catalyst, in the presence of a promoter such as copper (I) iodide, in a suitable inert solvent such as N,N-dimethylacetamide at a temperature of about 80° C.

A compound of formula (XVIII-A) may be prepared by reducing and cyclizing the compound of formula (XVII-A).

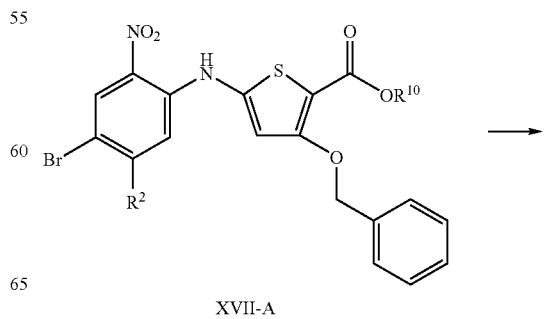

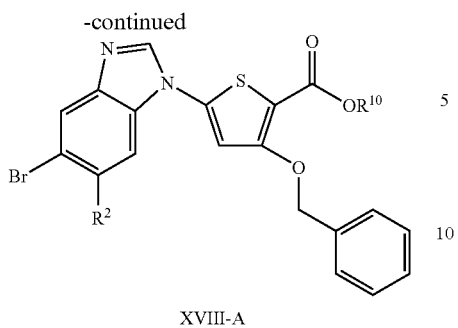

XVIII-A wherein all variables are as described above.

The step of reducing a compound of formula (XVII-A) may be carried out using conventional reduction techniques suitable for such compounds. Suitable reduction conditions will be apparent to those skilled in the art of organic synthesis and may include, for example, palladium on carbon under a hydrogen atmosphere, sulfided platinum on carbon under a hydrogen atmosphere, or iron powder in acetic acid. In one embodiment, the reduction may be effected using conditions such as sulfided platinum on carbon under a hydrogen atmosphere. The reaction may be carried out in an inert solvent at either atmospheric or elevated pressure. Suitable Inert solvents include but are not limited to ethanol, methanol, and ethyl acetate.

Suitable cyclizing agents will be apparent to those skilled in the art of organic synthesis and include, for example triethylorthoformate or trimethylorthoformate, optionally in the presence of an acid catalyst, for example p-toluenesulfonic acid or pyridinium p-toluenesulfonate. In one embodiment, the cyclizing agent is triethylorthoformate and the catalyst is pyridinium p-toluenesulfonate. Conveniently, the reaction of a compound of formula (XVII-A) with the cyclization agent may be carried out neat, at a temperature of from about 25° C. to about 100° C. In one embodiment the reaction is carried out at about 25° C.

In another embodiment, the process of preparing a compound of formula (XVIII-A) may be conveniently carried out by performing a one-pot reduction-cyclization procedure on a compound of formula (XVII-A) using conditions such as sulfided platinum on carbon under a hydrogen atmosphere in the presence of triethylorthoformate and pyridinium p-toluenesulfonate. In this embodiment, triethylorthoformate may be used as a solvent or a co-solvent with another suitable inert solvent, such as ethyl acetate.

A compound of formula (XVII-A) may be prepared by reacting (e.g., coupling) a compound of formula (XVI) with 1,4-dibromo-2-nitrobenzene of formula (VIII).

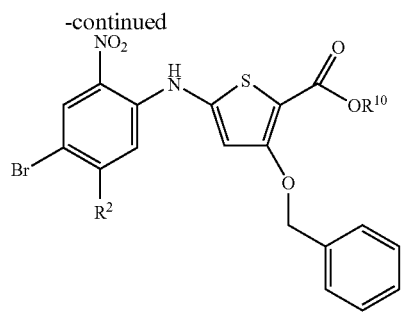

XVII-A wherein all variables are as defined above.

The step of coupling a compound of formula (XVI) with 1,4-dibromo-2-nitrobenzene of formula (VIII) to prepare a compound of formula (XVII-A) may be carried out using coupling techniques conventional in the art of organic synthesis. Examples of suitable coupling reactions include but are not limited to palladium-catalyzed cross-coupling conditions. Palladium catalyzed cross-coupling conditions include but are not limited to reacting the compound of formula (XVI) with 1,4-dibromo-2-nitrobenzene in the presence of a palladium source, optionally a phosphine ligand, and a base in a suitable inert solvent. Examples of suitable palladium sources include but are not limited to tris(dibenzylideneacetone)-dipalladium (0) or acetato(2'-di-t-butylphosphino-1,1'-biphenyl-2-yl)palladium (II), Examples of suitable phosphine ligands include but are not limited to 9,9-dimethyl-4,5-bis (diphenylphosphino)-xanthene. Examples of suitable bases include but are not limited to cesium carbonate, sodium methoxide, and triethylamine. Examples of suitable inert solvents include but are not limited to toluene or 1,4-dioxane. The reaction may be carried out at a temperature of between about room temperature and about 100° C. In one embodiment, the temperature is about 60° C. For a review of palladium-catalyzed cross-couplings of haloarenes and amines, see; Yang, B. H.; Buchwald, S. L. *Journal of Organometallic Chemistry* 1999, 576, 125-148. See also: Yin, J.; Zhao, M. M.; Huffman, M. A.; McNamara, J. M. *Journal of Organic Chemistry* 2002, 4, 3481-3484.

A compound of formula (XVI) may be prepared by reducing a compound of formula (XV) using conventional reduction techniques.

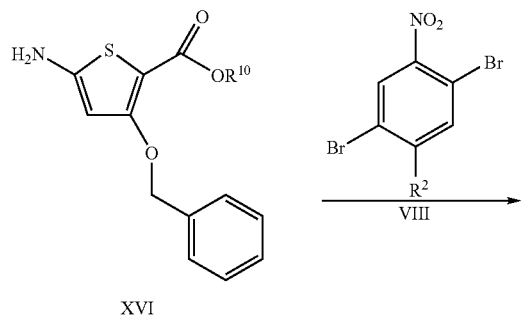

XVI

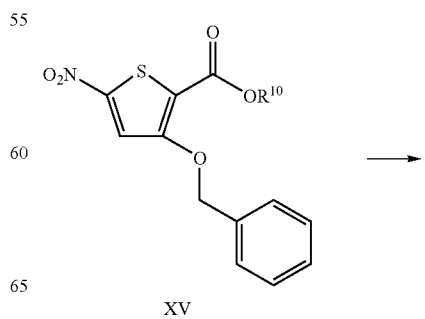

XV

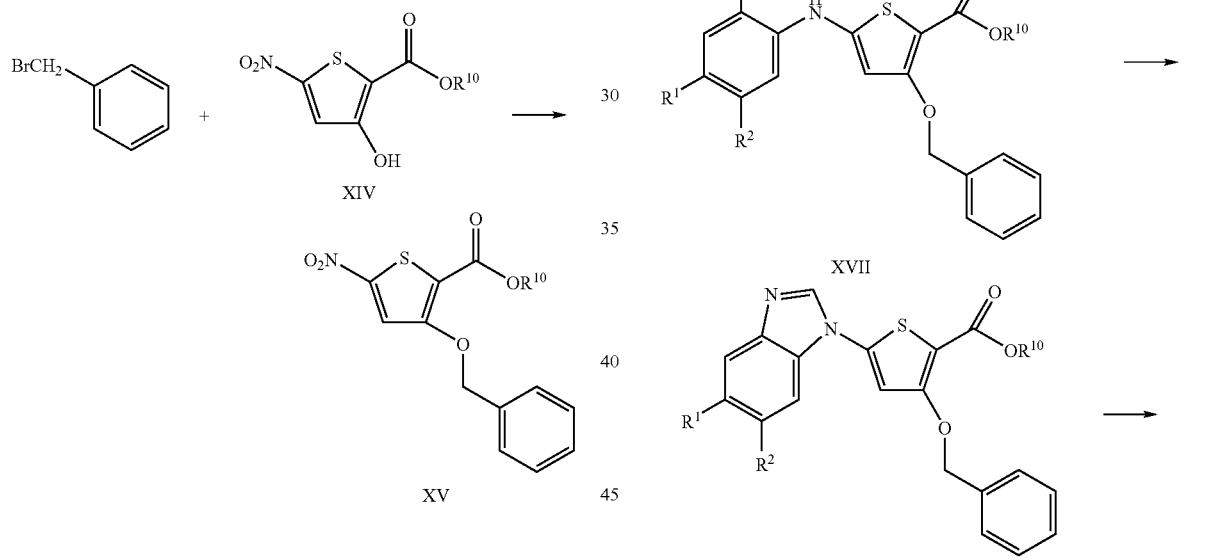

Scheme 3

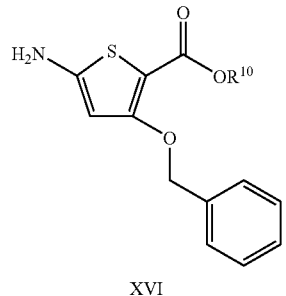
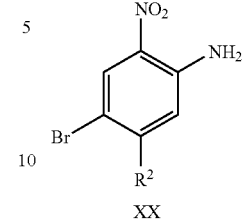
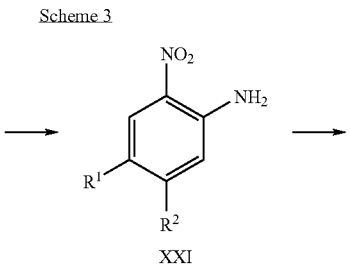

wherein all variables are as defined above.

Appropriate conditions for the reduction reaction will be apparent to those skilled in the art and include, for example, reducing agents, such as iron, in a suitable solvent, such as acetic acid. The reaction may be carried out with elevated temperatures, such as about 50° C.

A compounds of formula (XV) may be prepared by reacting a compound of formula (XIV) with benzyl bromide.

wherein all variables are as defined above.

This reaction may be carried out in an inert solvent, conveniently at room temperature, in the presence of a suitable base. The compound of formula (XIV) and benzyl bromide may be present in equimolar amounts; however, a slight excess of benzyl bromide may be employed if desired. Examples of suitable bases for this reaction include but are not limited to, potassium carbonate, sodium carbonate, cesium carbonate, sodium hydride, and potassium hydride. Examples of suitable inert solvents for this reaction include but are not limited to, N,N-dimethylformamide, tetrahydrofuran, dioxane, and 1,2-dimethoxyethane.

As shown below, the order of the steps in the foregoing reaction is not critical to the process and the steps may be carried out in any suitable order as determined by those skilled in the art. For example, in another embodiment of the present invention, the compounds of formula (V) may be prepared by the process out-lined in Scheme 3.

wherein:
$R^{10}$ is selected from alkyl and suitable carboxylic acid protecting groups; and
all other variables are as defined above.

In particular, this process for preparing the compounds of formula (V) (all formulas and all variables having been defined above) comprises the steps of:

a) reacting a 4-bromo-2-nitroaniline of formula (XX) using a conventional cross-coupling reaction to prepare a compound of formula (XXI);
b) reacting the compound of formula (XXI) with iodine and t-butyl nitrite to prepare a compound of formula (XXII);
c) reacting the compound of formula (XXII) with a compound of formula (XVI) to prepare a compound of formula (XVII);
d) reducing and cyclizing the compound of formula (XVII) to prepare a compound of formula (XIX); and
e) reacting the compound of formula (XIX) with acid to prepare a compound of formula (V).

The reaction of the compound of formula (XIX) with acid to prepare a compound of formula (V) is described above.

According to this process, a compound of formula (XIX) may be prepared by reducing and cyclizing the compound of formula (XVII) using conditions analogous to those described above for the preparation of a compound of formula (XIX) from a compound of formula (XVIII).

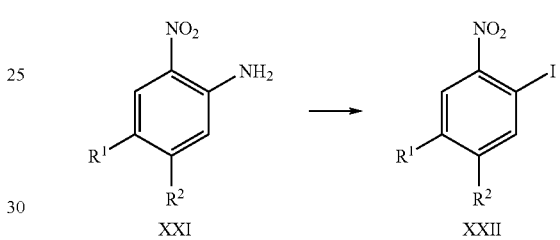

XVII wherein all variables are as defined above.

A compound of formula (XXII) may be prepared by reacting a compound of formula (XXI) with iodine and t-butyl nitrite.

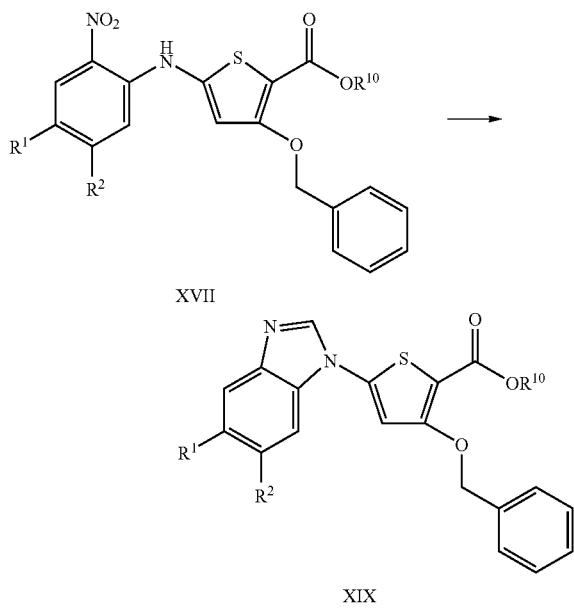

XVII

XIX wherein all variables are as defined above.

A compound of formula (XVII) may be prepared by reacting a compound of formula (XXII) with a compound of formula (XVI) using conditions described above for the reaction of a compound of formula (XVI) with 1,4-dibromo-2-nitrobenzene of formula (VIII).

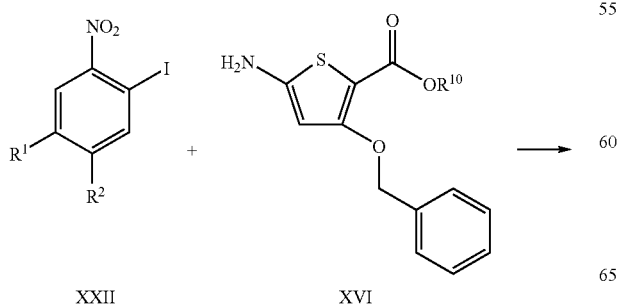

XXII        XVI

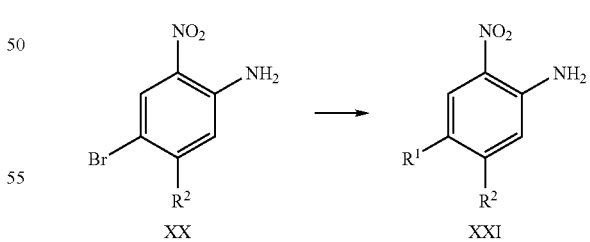

XX          XXI wherein all variables are as defined above.

This reaction may be carried out using a Sandmeyer-like reaction known to those skilled in the art. For transformation of aryl amines to aryl halides, see: Larock, R. *Comprehensive Organic Transformation* (2nd Edition), John Wiley & Sons, Inc. (1999) 678-679, The compound of formula (XXII) may be prepared by reacting a compound of formula (XXI) in an inert atmosphere, at a temperature of 60° C., with iodine and tert-butyl nitrite, in a suitable solvent, such as acetonitrile.

Compounds of formula (XXI) may be prepared by reacting 4-bromo-2-nitroaniline of formula (XX) using conventional cross-coupling reactions such as those described above.

wherein all variables are as defined above.

Compounds of formula (XX) are commercially available or may be prepared using conventional techniques.

In one particular embodiment, the compounds of the invention may be conveniently prepared by the methods outlined in Scheme 4 below.

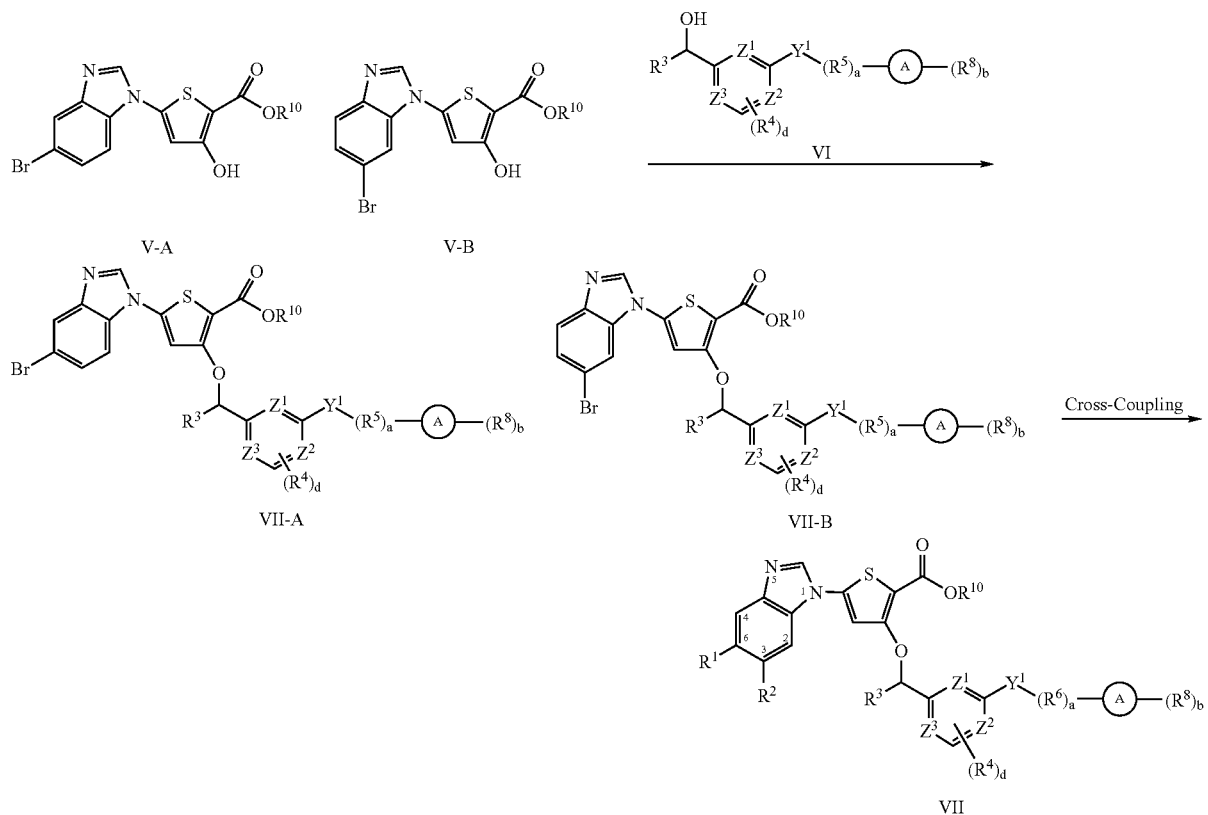

Scheme 4 wherein:
Y¹ is O;
R¹⁰ is selected alkyl and suitable carboxylic add protecting groups;
and all other variables are as defined above.

Generally, the process for preparing compounds of the invention (all formulas and all variables having been defined above) comprises the steps of:
a) reacting regioisomer compounds of formula (V-A) and (V-B) with a compound of formula (VI) to prepare regioisomer compounds of formula (VII-A) and (VII-B); and
b) reacting the regioisomer compounds of formula (VII-A) and (VII-B) under conventional cross-coupling reaction conditions to prepare a compound of formula (VII).

A compound of formula (VII) prepared according to this process may be reacted with ammonia to prepare a compound of formula (I) as described above. A compound of formula (VII) may also be separated into its enantiomers as described above.

It will be apparent to those skilled in the art that certain reaction steps may be most-efficiently performed by installing protecting groups prior to the reaction, which are removed subsequently. The choice of protecting groups as well as general techniques for their installation and removal are within the skill of those in the art.

Compounds of formula (VII-A) and (VII-B) may be prepared by reacting the compound of formula (V-A) or the compound of formula (V-B), respectively, with a compound of formula (VI) under Mitsunobu reaction conditions, as described above. Br in the compounds of formula (VII-A) and (VII-B) may be further converted to other functional groups using chemistry transformation known to those skilled in the art, for example, conventional cross-coupling reactions to prepare a different compound of formula (VII).

More particularly, the compounds of formula (VII) may be prepared from compounds of formula (VII-A and VII-B) using palladium-catalyzed Suzuki, Stille, or Negishi cross-coupling techniques (described above) which are conventional in the art of organic synthesis.

As will be apparent to those skilled in the art. the order of the steps in the foregoing reaction is not critical to the practice of the process of the present invention. For example, the compounds of formula (VII) may also be prepared by altering the order of the steps such that the cross-coupling reaction is carried out on the regioisomer compounds of formula (V-A) and (V-B) to prepare a compound of formula (V) (as defined in Scheme 1 above) followed by the reaction of a compound of formula (V) with a compound of formula (VI) to prepare a compound of formula (VII). Each of these reaction steps may be carried out using the techniques described above.

As a further embodiment, the compounds of formula (VII-A) and (VII-B) may first be reacted with ammonia to produce the corresponding Br-substituted compounds of formula (I), followed by the cross-coupling reaction to prepare a different compound of formula (I) wherein the Br substituent is displaced by another functional group defined by R¹ and R² above.

The compounds of formula (V-A) and (V-B) may be prepared by reacting 5-bromobenzimidazole with a compound of formula (III).

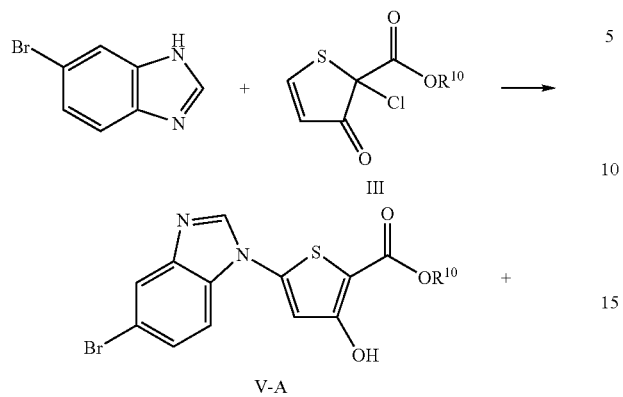

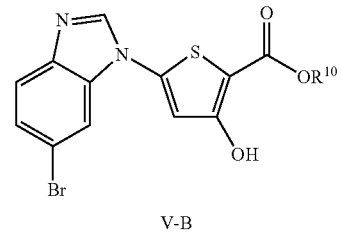

wherein all variables are as defined above.

This reaction may be carried out using the same reaction conditions described above for the preparation of a compound of formula (V).

In another embodiment, the present invention provides another process for preparing compounds of the invention, which is out-lined in Scheme 5 below.

Scheme 5

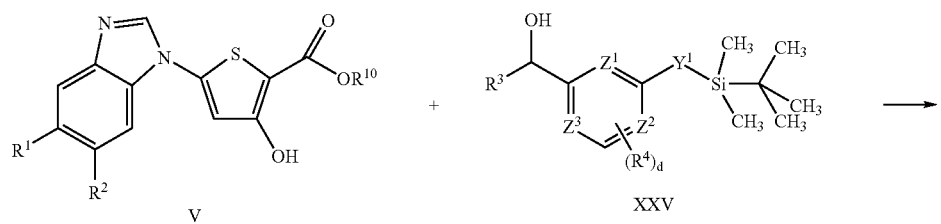

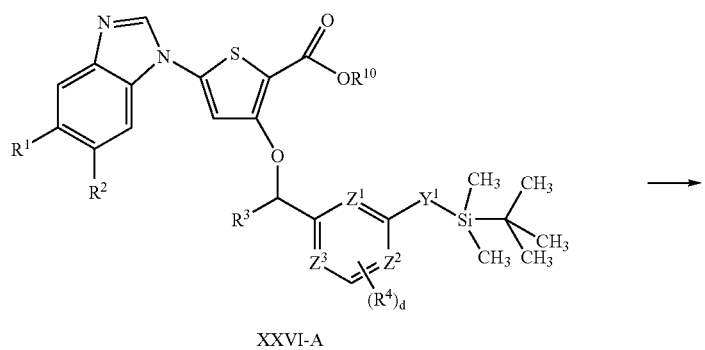

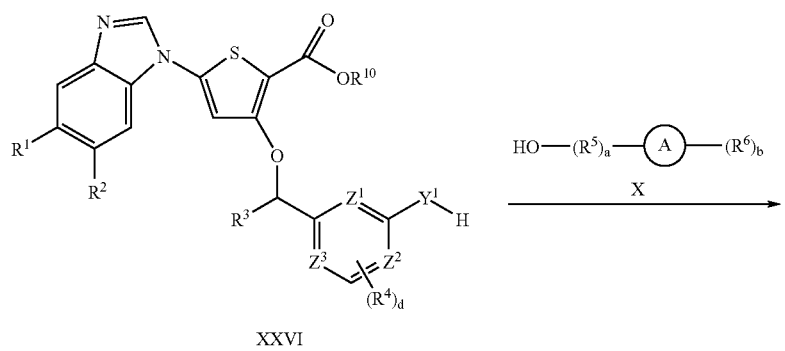

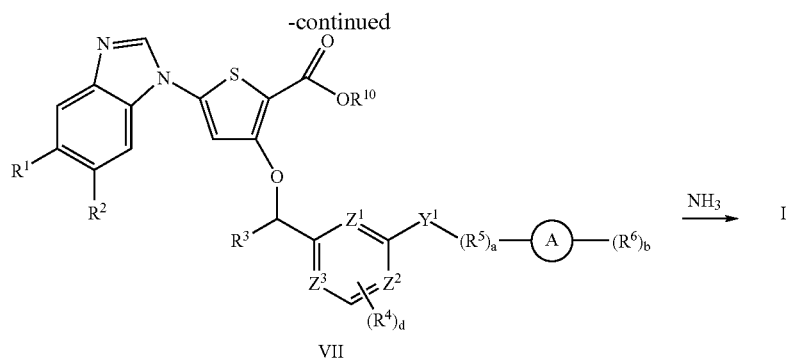

VII wherein;

R[10] is selected from alkyl and suitable carboxylic acid protecting groups;

Y[1] is O; and all other variables are as defined above.

Generally, the process for preparing the compounds of the invention (all formulas and all variables having been defined above) comprises the steps of:

a) reacting the compound of formula (V) with a compound of formula (XXV) to prepare a compound of formula (XXVI-A) and removing the protecting group to prepare a compound of formula (XXVI);
b) reacting the compound of formula (XXVI) with a compound of formula (X) to prepare a compound of formula (VII);
c) reacting the compound of formula (VII) with ammonia to prepare a compound of formula (I);
d) optionally separating the compound of formula (I) into enantiomers;
e) optionally converting the compound of formula (I) to a pharmaceutically acceptable salt thereof; and
f) optionally converting the compound of formula (I) or a pharmaceutically acceptable salt thereof to a different compound of formula (I) or a pharmaceutically acceptable salt thereof.

As will be apparent to those skilled in the art, the order of the steps in the foregoing reaction is not critical to the practice of the process of the present invention. The foregoing reaction steps may be carried out in any suitable order based upon the knowledge of those skilled in the art. Further, it will be apparent to those skilled in the art that certain reaction steps may be most efficiently performed by installing protecting groups prior to the reaction, which are removed subsequently. The choice of protecting groups as well as general techniques for their installation and removal are within the skill of those in the art.

The reaction of the compound of formula (VII) with ammonia to prepare a compound of formula (I) is described above.

According to this method, a compound of formula (VII) is prepared by reacting the compound of formula (XXVI) with a compound of formula (X) using conventional Mitsunobu reaction conditions such as those described above for preparation of the compound of formula (VII) by reaction of the compound of formula (V) with a compound of formula (VI).

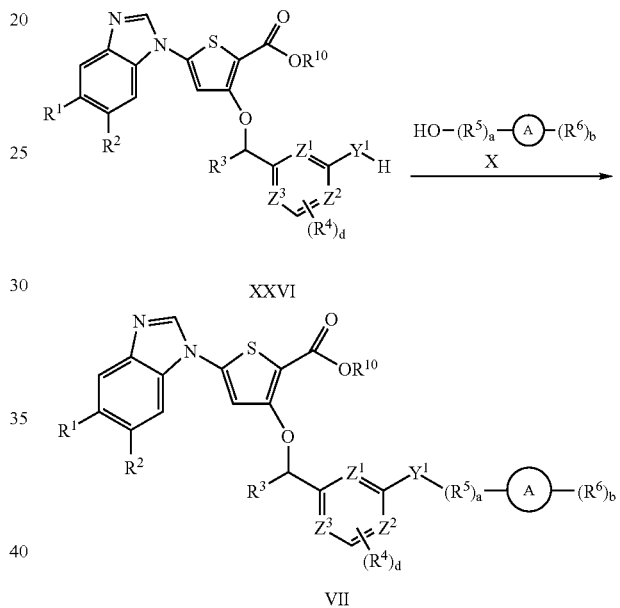

wherein all variables are as defined above.

If desired, the enantiomers of the compound of formula (VII) may be separated as described above to yield the enantiomerically enriched compounds of formula (VII-1) and (VII-2), which may then be used in the foregoing process to ultimately yield an enantiomerically enriched compound of formula (I-1) or (I-2), respectively.

Compounds of formula (X) are commercially available or may be prepared using conventional techniques. A compound of formula (XXVI) may be prepared by removing the silyl protecting group from the compound of formula (XXVI-A) using conventional techniques, such as reaction with tetrabutylammonium fluoride. See, Kocienski, P. J. *Protecting Groups*, Georg Thieme Verlag, Stuttgart, 1994; and Greene, T. W., Wuts, P. G. M. *Protecting Groups in Organic Synthesis* (2nd Edition), J. Wiley and Sons, 1991.

A compound of formula (XXVI-A) may be prepared by reacting a compound of formula (V) with a compound of formula (XXV) using conventional Mitsunobu reaction conditions such as those described.

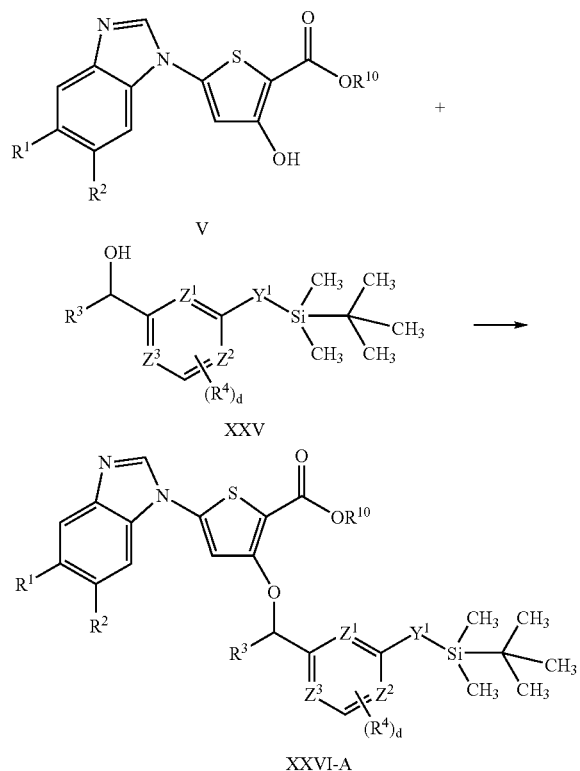

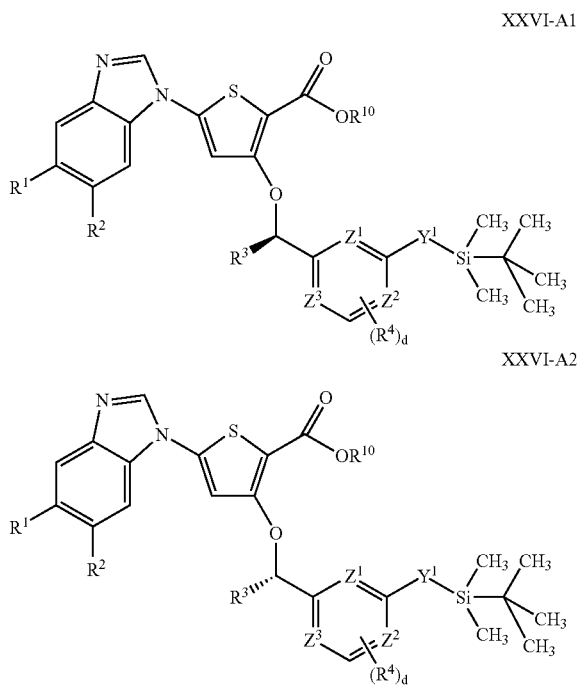

wherein all variables are as defined above.

If desired, the enantiomers of the compound of formula (XXVI-A) may be separated as described above to yield the enantiomerically enriched compounds of formula (XXVI-A1) and (XXVI-A2), which may then be used in the foregoing process to ultimately yield an enantiomerically enriched compound of formula (I-1) or (I-2), respectively.

Processes for the preparation of compounds of formula (V) are described above.

Compounds of formula (XXV) may be prepared according to the following reaction scheme.

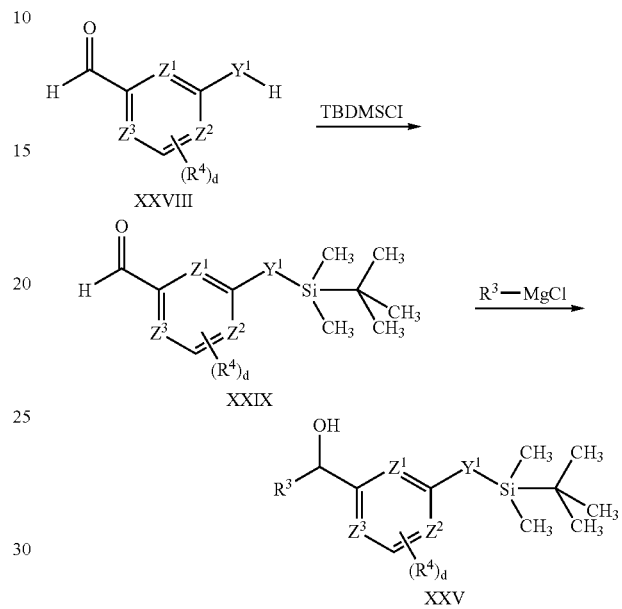

wherein all variables are as defined above.

The compounds of formula (XXVIII) are commercially available or may be prepared using conventional techniques known to those skilled in the art. The t-butyl-dimethylsilyl protecting group is installed using conventional techniques to prepare the compound of formula (XXIX). See, Kocienski, P. J. *Protecting Groups*, Georg Thieme Verlag, Stuttgart, 1994; and Greene, T. W., Wuts, P. G. M. *Protecting Groups in Organic Synthesis* ($2^{nd}$ *Edition*), J. Wiley and Sons, 1991. The compound of formula (XXIX) is reacted with a magnesium chloride of the formula $R^3$—MgCl to prepare the compound of formula (XXV). if desired, the enantiomers of the compound of formula (XXV) may be separated using conventional separation techniques (e.g., supercritical fluid chromatography (SFC)) to yield the enantiomerically enriched compound of formula (XXV-1)

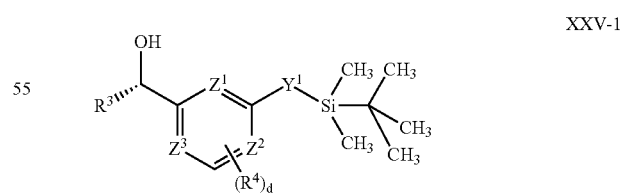

which may then be used in the foregoing process to ultimately yield an enantiomerically enriched compound of formula (I-1).

In another embodiment, the present invention provides another process for preparing compounds of the invention, which is out-lined in Scheme 6 below.

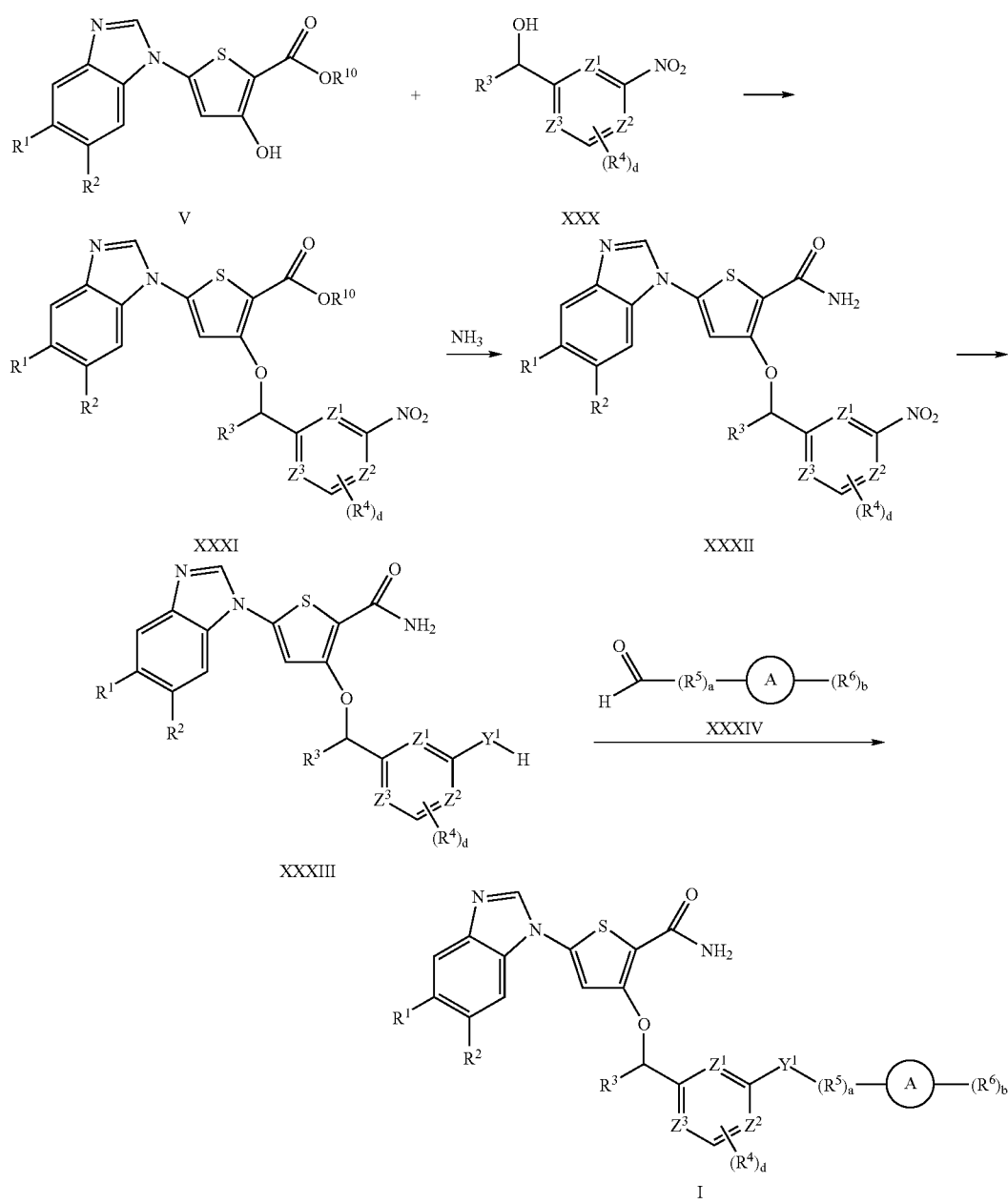

Scheme 6 wherein:

R[10] is selected from alkyl and suitable carboxylic acid protecting groups;

Y[1] is NH; and all other variables are as defined above.

Generally, the process for preparing the compounds of the invention (all formulas and all variables having been defined above) comprises the steps of:

a) reacting the compound of formula (V) with a compound of formula (XXX) to prepare a compound of formula (XXXI);

b) reacting the compound of formula (XXXI) with ammonia to prepare a compound of formula (XXXII);

c) reducing the compound of formula (XXXII) to prepare a compound of formula (XXXIII);

d) reacting the compound of formula (XXXIII) with a compound of formula (XXXIV) to prepare a compound of formula (I);

e) optionally separating the compound of formula (I) into enantiomers;

f) optionally converting the compound of formula (I) to a pharmaceutically acceptable salt thereof; and g) optionally converting the compound of formula (I) or a pharmaceutically acceptable salt thereof to a different compound of formula (I) or a pharmaceutically acceptable salt thereof.

As will be apparent to those skilled in the art, the order of the steps in the foregoing reaction is not critical to the practice of the process of the present invention. The foregoing reaction steps may be carried out in any suitable order based upon the knowledge of those skilled in the art. Further, if will be apparent to those skilled in the art that certain reaction steps may be most efficiently performed by installing protecting groups prior to the reaction, which are removed subsequently. The choice of protecting groups as well as general techniques for their installation and removal are within the skill of those in the art.

More specifically, according to this method, a compound of formula (I) wherein $Y^1$ is NH may be prepared by reacting the compound of formula (XXXIII) with a compound of formula (XXXIV) using conventional reductive amination reaction conditions. See, Larock, R. C. *Comprehensive Organic Transformation* ($2^{nd}$ Edition), Wiley-VCH, 1999.

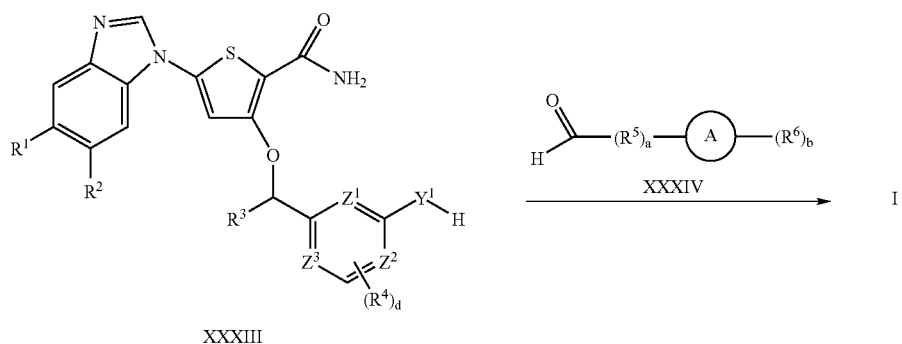

XXXIII wherein all variables are as defined above.

Compounds of formula (XXXIII) maybe prepared by reduction of a compound of formula (XXXIII) using conventional nitro reaction conditions such as those described above.

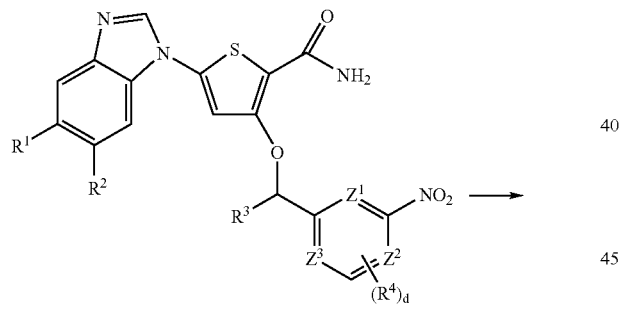

XXXII

XXXIII wherein all variables are as defined above.

If desired, the enantiomers of the compound of formula (XXXIII) may be separated using conventional separation techniques (e.g., SFC) to yield the enantiomerically enriched compounds of formula (XXXIII-1) and (XXXIII-2)

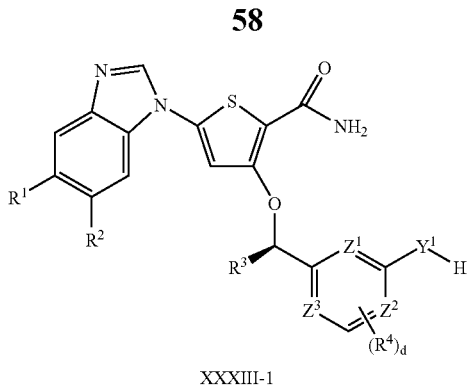

XXXIII-1

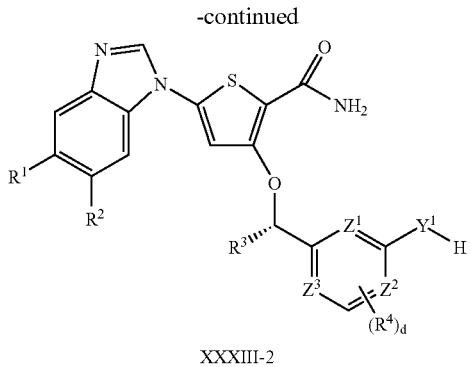

-continued

XXXIII-2 which may then be used in the foregoing process to ultimately yield an enantiomerically enriched compound of formula (I-1) or (I-2), respectively.

Compounds of formula (XXXII) may be prepared by reaction of the compound of formula (XXXI) with ammonia using reaction conditions such as those described above.

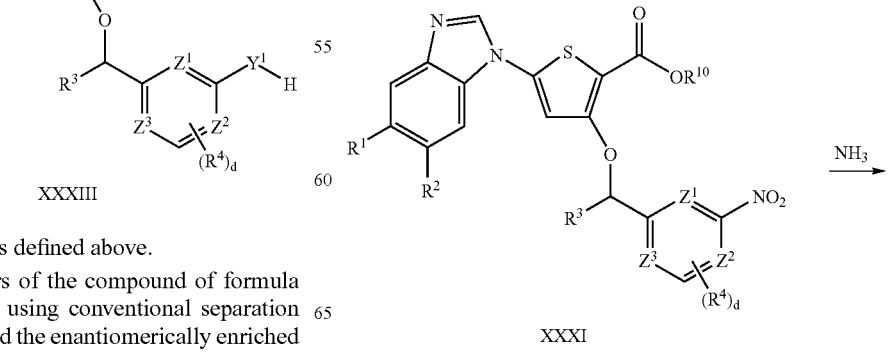

XXXI

-continued

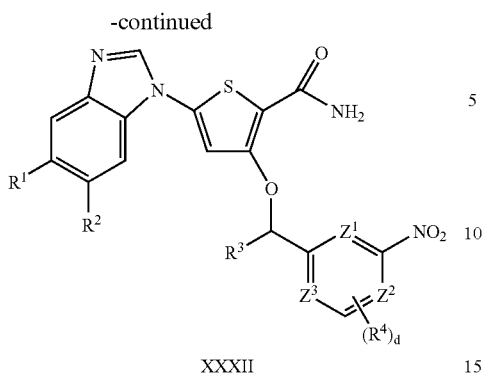

XXXII wherein all variables are as defined above.

If desired, the enantiomers of the compound of formula (XXXII) may be separated using conventional separation techniques (e.g., SFC) to yield the enantiomerically enriched compounds of formula (XXXII-1) and (XXXII-2)

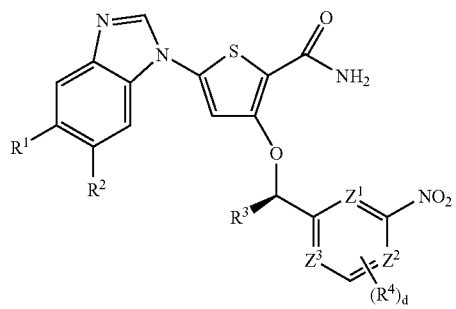

XXXII-1

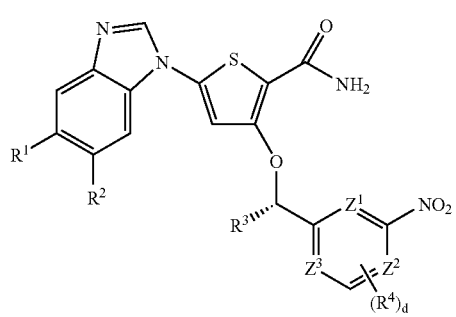

XXXII-2 which may then be used in the foregoing process to ultimately yield an enantiomerically enriched compound of formula (I-1) or (I-2), respectively, Compounds of formula (XXXI) may be prepared by reacting a compound of formula (V) with a compound of formula (XXX) using conventional Mitsunobu reaction conditions such as those described above.

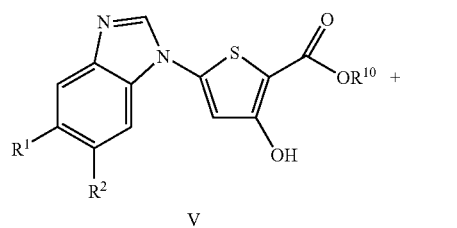

V

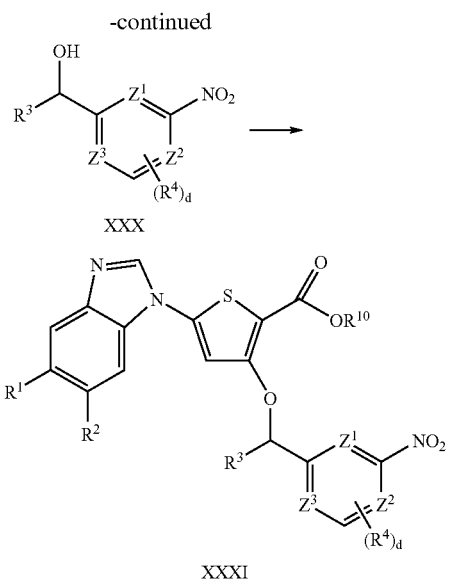

wherein all variables are as defined above.

If desired, the enantiomers of the compound of formula (XXXI) may be separated using conventional separation techniques (e.g., SFC) to yield the enantiomerically enriched compounds of formula (XXXI-1) and (XXXI-2)

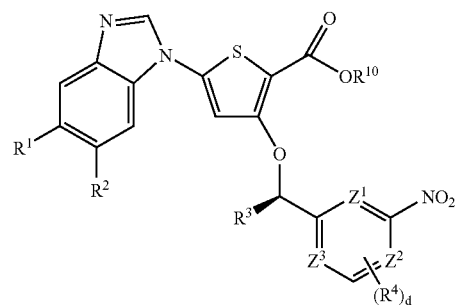

XXXI-1

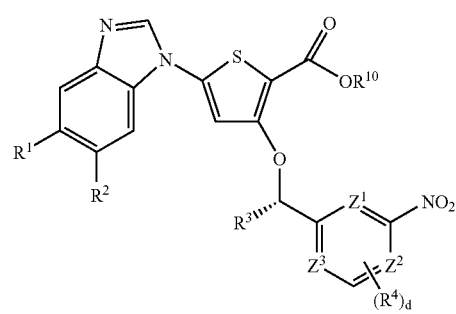

XXXI-2 which may then be used in the foregoing process to ultimately yield an enantiomerically enriched compound of formula (I-1) or (I-2), respectively. Compounds of formula (XXX) may be prepared as follows.

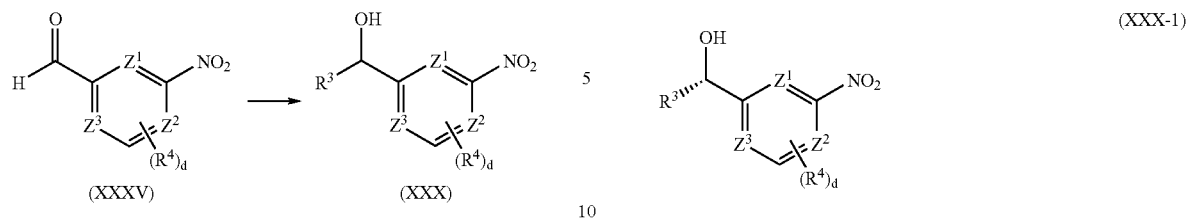

wherein all variables are as defined above.

The compounds of formula (XXXV) are commercially available or may be prepared using conventional techniques known to those skilled in the art. The compound of formula (XXXV) is reacted with an alkyl lithium of the formula $R^3$—Li in the presence of titanium tetrachloride to prepare the compound of formula (XXX). If desired, the enantiomers of the compound of formula (XXX) may be separated using conventional separation techniques (e.g., supercritical fluid chromatography (SFC)) to yield the enantiomerically enriched compound of formula (XXX-1)

which may then be used in the foregoing process to ultimately yield an enantiomerically enriched compound of formula (I-1).

A compound of formula (I) maybe converted into a different compound of formula (I) using techniques known to those skilled in the art.

In one embodiment, a compound of formula (I-1A) may be converted to a compound of formula (I-1B) using standard deprotection reaction conditions. A compound of formula (I-1B) may be converted to a compound of formula (I-1C) using Michael addition reactions known to those skilled in the art.

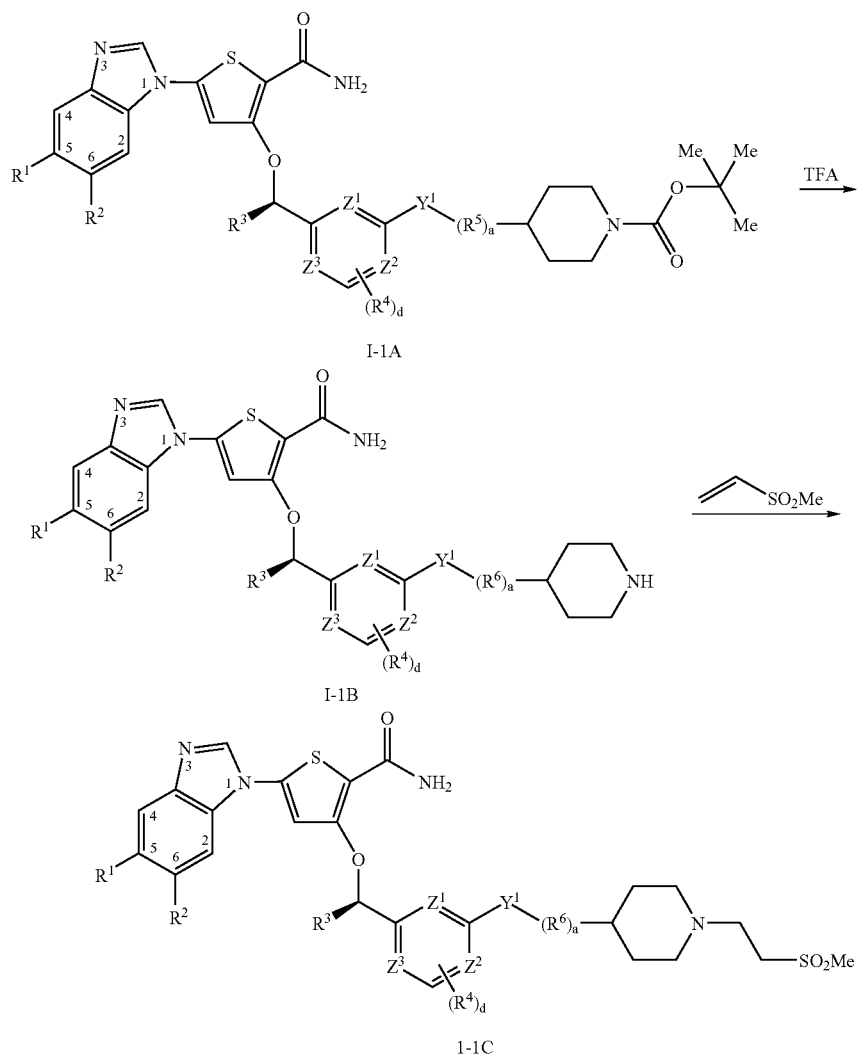

wherein all variables are as defined above.

The compound of formula (I-1A) may be converted to a compound of formula (I-1B) using neat trifluoroacetic acid (TFA) or trifluoroacetic acid in a suitable solvent such as dichloromethane. The compound of formula (I-1B) may then be converted to a compound of formula (I-1C) using methyl vinyl sulfone in a suitable solvent such as tetrahydrofuran.

In another embodiment, a compound of formula (I-1B) may be converted to a compound of formula (I-1D) using reductive alkylation condition.

etoxyborohydride, in the presence of a suitable acid such as acetic acid, and in a suitable solvent such as dichloromethane and methanol.

In another embodiment, a compound of formula (I-1E) may be converted to a compound of formula I-1F) using oxidation conditions. A compound of formula (I-1F) may be converted to a compound of formula (I-1G) using standard deprotection conditions.

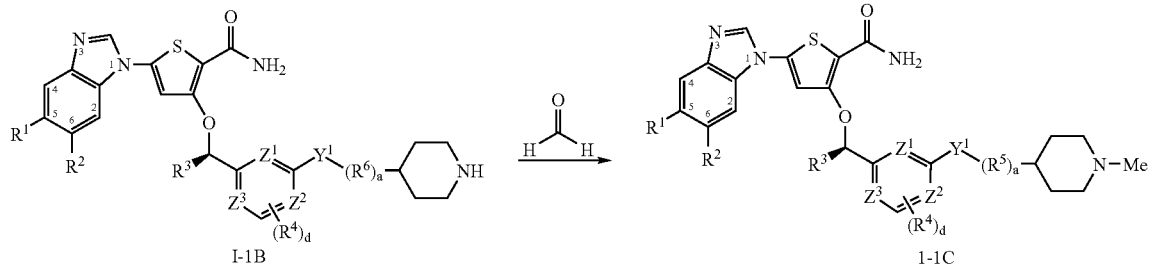

wherein all variables are as defined above.

The compound of formula (I-1B) may be converted to a compound of formula (I-1D) by reacting the compound of formula (I-1B) with appropriate ketones or aldehydes such as formaldehyde, and reducing agents such as sodium triac-

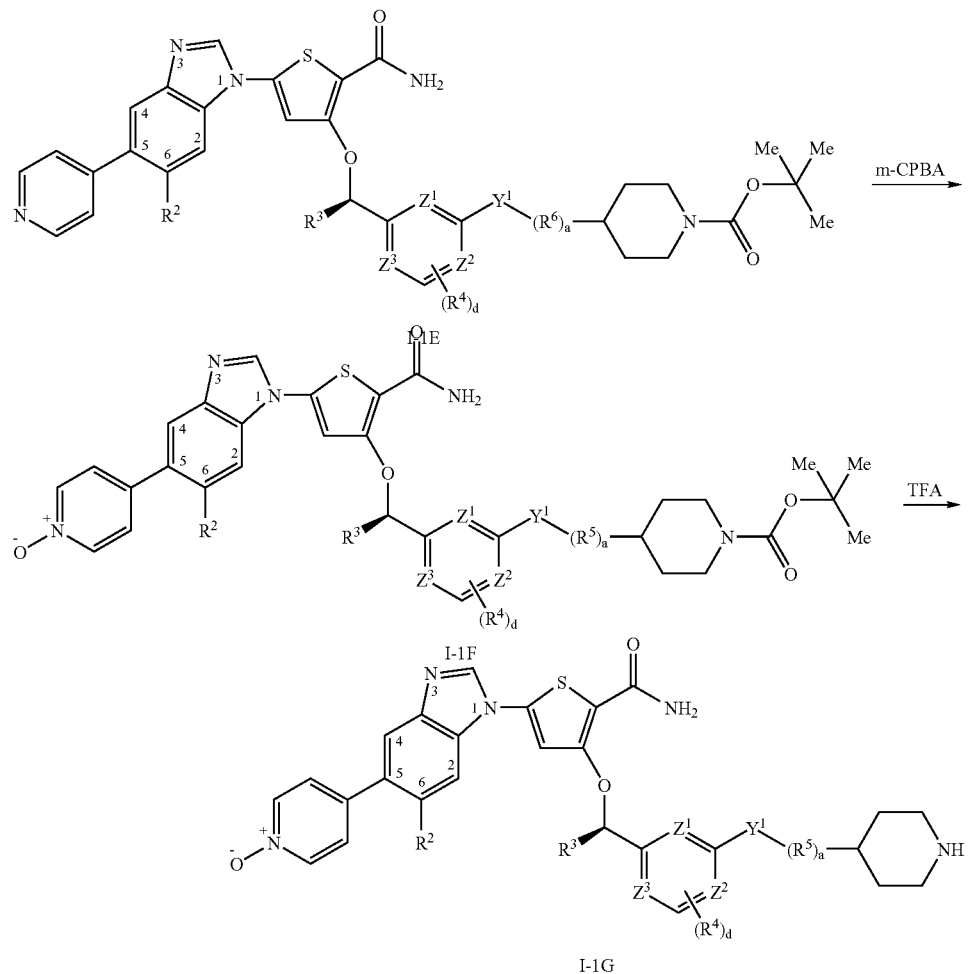

wherein all variables are as defined above.

A compound of formula (I-1E) may be converted to a compound of formula (I-1F) using oxidizing agents such as m-chloroperoxybenzoic acid (m-CPBA) in appropriate solvents such as dichloromethane or chloroform at room temperature. A compound of formula (I-1F) may be converted to a compound of formula (I-1G) using neat trifluoroacetic acid (TFA) or trifluoroacetic acid in a suitable solvent such as dichloromethane.

Based upon this disclosure and the examples contained herein one skilled in the art can readily convert a compound of formula (I) or (I-1) or a pharmaceutically acceptable salt thereof into another compound of formula (I) or (I-1) or a pharmaceutically acceptable salt thereof.

The following abbreviations as employed in the examples, have the recited meanings.

| | |
|---|---|
| g | gram(s) |
| mg | milligram(s) |
| mol | mole(s) |
| mmol | millimole(s) |
| N | normal |
| L | liter(s) |
| mL | milliliter(s) |
| μL | microliter(s) |
| h | hour(s) |
| min | minute(s) |
| ° C. | degrees Centigrade |
| HCl | hydrochloric acid |
| DCM | dichloromethane |
| CHCl$_3$ | chloroform |
| Me | methyl; —CH$_3$ |
| MeOH | methanol |
| EtOH | ethanol |
| i-PrOH | isopropanol |
| EtOAc | ethyl acetate |
| THF | tetrahydrofuran |
| TFA | trifluoroacetic acid |
| DMA | N,N-dimethylacetamide |
| DMF | N,N-dimethylformamide |
| NH$_4$Cl | ammonium chloride |
| MgSO$_4$ | magnesium sulfate |
| NaOH | sodium hydroxide |
| NaHCO$_3$ | sodium bicarbonate |
| Na$_2$CO$_3$ | sodium carbonate |
| K$_2$CO$_3$ | potassium carbonate |
| Cs$_2$CO$_3$ | cesium carbonate |
| Na$_2$SO$_4$ | sodium sulfate |
| N$_2$ | nitrogen |
| H$_2$ | hydrogen |
| rt | room temperature |
| Cl$_2$Pd(dppf) | dichloro[1,1'-bis(diphenylphosphino)ferrocene] palladium(II) |
| XANTPHOS | (4,5-Bis(diphenylphosphino)-9,9-dimethylxanthene) is a commercially available catalyst, from Aldrich |
| SFC | supercritical fluid chromatography |
| TLC | thin layer chromatography. |
| ee | enantiomeric excess |

Reagents are commercially available or are prepared according to procedures in the literature, in the following structures, "Me" refers to the group —CH$_3$.

All references to "ether" are to diethyl ether; brine refers to a saturated aqueous solution of NaCl. Unless otherwise indicated, all temperatures are expressed in ° C. (degrees Centigrade). All reactions are conducted under an Inert atmosphere at rt unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SGIEX-APIIII spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution or mass spectrometry (electrospray or AP). Flash column chromatography was performed on silica gel (230-400 mesh, Merck) or using automated silica gel chromatography (Isco, Inc. Sq 16× or 100 sg Combiflash).

Reported HPLC retention times (RT) were obtained on a Waters 2795 instrument attached to a Waters 996 diode array defector reading 210-500nm. The column used was a Synergi IVIax-RP (50×2 mm) model #00B-4337-B0. Solvent gradient was 15% MeOH:water to 100% MeOH (0.1% formic acid) over 6 min. Flow rate was 0.8 mL/min. Injection volume was 3 μL.

INTERMEDIATE 1

(1S)-1-(2-Chloro-3-nitrophenyl)ethanol

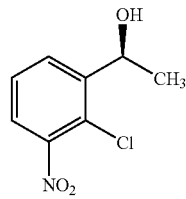

To ether cooled to −78° C. was added titanium (IV) chloride (0.85 mL, 7.8 mmol) and a 1.6M solution of methyl lithium in ether (4.9 ml, 7.8 mmol). After warming the mixture to −40° C., it was transferred via double-tipped needle to a −78° C. ether solution of 2-chloro-3-nitrobenzaldehyde (1.0 g, 5.6 mmol), which can be synthesized according to the procedure in J. Med. Chem. 1088, 31, 936-944. The reaction was allowed to slowly warm to rt and was quenched with the addition of MeOH and water. The layers were separated, and the aqueous phase was extracted with EtOAc. The combined organic phases were washed with brine, dried over MgSO$_4$ and concentrated to an oil. The crude material was purified by flash column chromatography (10% EtOAc:hexanes) to give 0.98 g of the racemic compound (84%). The enantiomers were separated using packed column supercritical fluid chromatography (SFC) on a 3×25 cm Dalcel® AD-H column with a 90 g/min total flow (81 q/min CO$_2$-90%) (9 g/min MeOH-10%) to give the title compound as a yellow oil. $^1$H NMR (400 MHz, d$_6$-DMSO) δ 7.86 (m, 1H), 7.58 (m, 1H), 5.62 (d, J=4.4 Hz, 1H), 5.06 (m, 1H), 1.30 (d, J=6.4 Hz, 3H).

INTERMEDIATE 2

Methyl 5-(5-chloro-1H-benzimidaz-1-yl)-3-{[(1R)-1-(2-chloro-3-hydroxyphenyl)ethyl]oxy}-2-thiophenecarboxylate

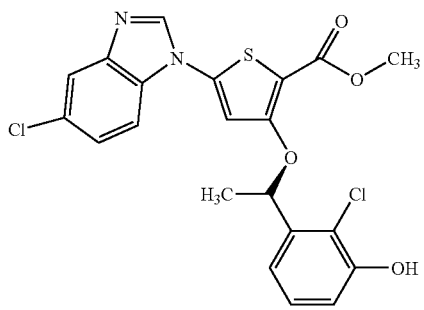

Step A—Methyl 5-(5-chloro-1H-benzimidazol-1-yl)-3-{[(1,1-dimethylethyl)-(dimethyl)silyl]oxy}-2-thiophenecarboxylate

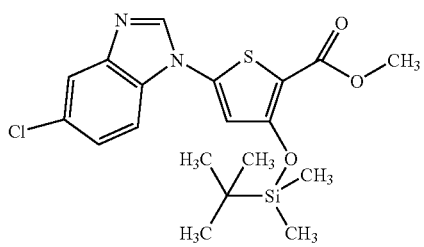

To a mixture of chlorobenzimidazole (7.0 g, 48 mmol) and methyl 2-chloro-3-oxo-2,3-dihydro-2-thiophenecarboxylate (*Synthesis*, 1984, 10, 847-850) (9.8 g, 51 mmol) in 400 mL of chloroform was added N-methylimidazole (5.5 mL, 69 mmol). After 16 h, tert-butylchlorodimethylsilane (6.9 g, 46 mmol) and N-methylimidazole (3.7 mL, 48 mmol) was added. The reaction mixture was diluted with water and the layers were separated. The aqueous phase was extracted with DCM. The combined organic layers were washed with water, dried over $MgSO_4$ and concentrated onto silica gel. The crude material was purified by flash column chromatography (0-100% 25% EtOAc/hexanes) to give 5.8 g of the desired product (30%). $^1$H NMR (400 MHz, $d_6$-DMSO) δ 8.79 (s, 1H), 7.88 (d, J=2.0 Hz, 1H), 7.81 (d, J=8.8 Hz, 1H), 7.44 (dd, J=8.8 and 2.0 Hz, 1H), 7.25 (s, 1H), 3.78 (s, 3H), 0.99 (s, 9H), 0.27 (s, 6H).

Step B—Methyl 5-(5-chloro-1H-benzimidazol-1-yl)-3-hydroxy-2-thiophene-carboxylate

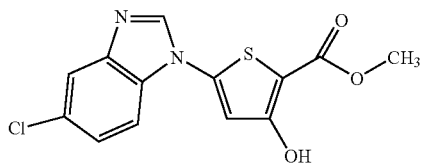

To a solution of methyl 5-(5-chloro-1H-benzimidazol-1-yl)-3-{[1,1-dimethylethyl)-(dimethyl)silyl}oxy)-2-thiophenecarboxylate (2.0 g, 4.7 mmol) in 40 mL of THF cooled to 0° C. was added a 1M solution of tetrabutylammonium fluoride in THF. The reaction was diluted with MeOH and concentrated onto silica gel. The crude material was purified by flash column chromatography to give 1.4 g of the desired product (97%). $^1$H NMR (400 MHz, $d_6$-DMSO) δ 10.87 (s, 1H), 8.73 (s, 1H), 7.88 (d, J=1.8 Hz, 1H), 7.79 (d, J=8.8 Hz, 1H), 7.42 (dd, J=8.8 and 1.6 Hz, 1H), 7.12 (s, 1H), 3.76 (s, 3H).

Step C—Methyl 5-(5-chloro-1H-benzimidazol-1-yl)-3-{[(1R)-1-(2-chloro-3-hydroxyphenyl)ethyl]oxy}-2-thiophenecarboxylate (Title Compound)

To a solution of methyl 5-(5-chloro-1H-benzimidazol-1-yl)-3-{[(1R)-1-(2-chloro-3-hydroxyphenyl)ethyl]oxy}-2-thiophenecarboxylate (330 mg, 1.1 mmol) and (1S)-1-(2-chloro-3-{[(1,1-dimethylethyl)(dimethyl)silyl]oxy}-phenyl)ethanol (Intermediate 17, 370 mg, 1.3 mmol) in DCM was added polymer-supported triphenylphosphine (920 mg, 2.2 mmol) and di-tert-butylazodicarboxylate (510 mg, 2.2 mmol). After 2 h, the reaction was filtered and the resin was washed with alternating DCM and MeOH. The filtrate was concentrated onto silica gel and purified by flash column chromatography (0-100% 5% MeOH/DCM and DCM). Fractions containing desired product were concentrated and dissolved in 5 mL of THF. The solution was cooled to 0° C. and a 1M solution of tetrabutylammonium fluoride in THF (1.1 mL, 1.1 mmol) was added. After 30 min, the reaction was diluted with MeOH and concentrated onto silica gel. The crude material was purified by flash column chromatography (0-100% 10% MeOH/DCM+1% $NH_4OH$ and DCM) to give 395 mg of the desired product (77%). $^1$H NMR (400 MHz, $d_6$-DMSO) δ 10.27 (s, 1H), 8.70 (s, 1H), 7.86 (s, 1H), 7.59 (d, J=8.8 Hz, 1H), 7.39 (d, J=8.8 Hz, 1H), 7.32 (s, 1H), 7.17-7.09 (m, 2H), 8.89 (d, J=8.0 Hz, 1H), 5.91 (m, 1H), 3.79 (s, 3H), 1.58 (d, J=8.0 Hz, 3H).

INTERMEDIATE 3

Methyl 3-[(1R)-1-(2-chloro-3-hydroxyphenyl)ethoxy]-5-(6-cyano-1H-benzimidazol-1-yl)thiophene-2-carboxylate

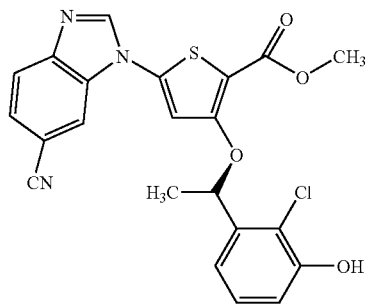

Step A-1H-benzimidazole-5-carbonitrile

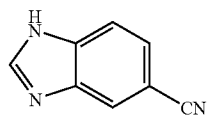

A stirred mixture of 3,4-diaminobenzonitrile (1.0 g, 7.5 mmol), catalytic formic acid (2 drops) and triethylorthoformate (15 mL, 90 mmol) was heated at 80° C. for 1 h, then cooled to rt, concentrated under vacuum and chromatographed on silica gel, eluting with a gradient of 0.5-to-10% MeOH/DCM, with 1% ammonium hydroxide, to give 803 mg (75%) of the title compound as a brown solid. MS (ESI): 143 $[M+H]^+$.

Step B—Methyl 5-(5-cyano-1H-benzimidazol-1-yl)-3-hydroxy-2-thiophene-carboxylate and methyl 5-(6-cyano-1H-benzimidazol-1-yl)-3-hydroxy-2-thiophenecarboxylate

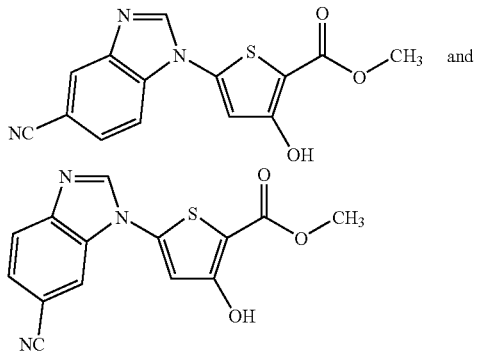

To a stirred mixture of 1H-benzimidazole-5-carbonitrile (1.9 g, 12 mmol) in DMF (28 ml) and CHCl$_3$ (88 ml) was added N-methylimidazole (3.0 mL, 38 mmol) followed by methyl 2-chloro-3-oxo-2,3-dihydro-2-thiophenecarboxylate (Synthesis, 1984, 10, 847-850), (2.7 g, 14 mmol). The reaction was then warmed to 35° C. and stirred for 72 h. The reaction was cooled to rt and diluted with EtOAc (800 mL) and aqueous 0.5N HCl (200 mL). The aqueous layer was extracted with EtOAc (2×). The aqueous layer was then treated with aqueous (saturated) NaHCO$_3$ until the pH was 7.0, then extracted again with EtOAc. The combined organic layers were then washed with water (2×), brine, dried over MgSO$_4$, concentrated under vacuum and chromatographed on silica gel (120 g), eluting with a gradient of 30-to-90% EtOAc/hexane to give 1.9 g (52%) of an approximate 1:1 regioisomer mixture of the title compounds as a yellow solid. MS (ESI): 299 [M+H]$^+$.

Step C—Methyl 5-(6-cyano-1H-benzimidazol-1-yl)-3-({(1R)-1-[2-(trifluoromethyl)phenyl]ethyl}oxy)-2-thiophenecarboxylate

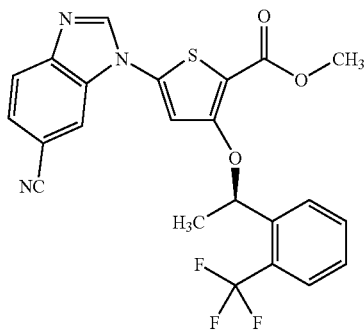

A slurry of methyl 5-(5-cyano-1H-benzimidazol-1-yl)-3-hydroxy-2-thiophene-carboxylate and methyl 5-(6-cyano-1H-benzimidazol-1-yl)-3-hydroxy-2-thiophenecarboxylate (1.9 g, 6.4 mmol), (1S)-1-[2-(trifluoromethyl)phenyl]ethanol (1.9 g, 9.6 mmol) and polystyrene-triphenylphosphine (6.2 g, 13 mmol, loading 2.12 mmol/g) in DCM (130 ml) was stirred at 30° C. for 10 min, then di-tert-butylazadicarboxylate (3.0 g, 13 mmol) was added. The reaction was stirred at 30° C. for 12 h, then poured through filter paper, washing the resin solid with DCM and MeOH. The filtrate was concentrated under vacuum and chromatographed on silica gel (330 g), eluting with a gradient of 10-to-50% EtOAc/hexane to give 782 mg (25%) of the title compound as a light yellow solid. $^1$H NMR (400 MHz, DMSO-d$_6$): δ 8.86 (s, 1H), 8.08 (s, 1H), 8.01-7.94 (m, 2H), 7.80-7.71 (m, 4H), 7.54 (t, J=7.89 Hz, 1H), 7.44 (s, 1H), 8.01 (q, J=8.10 Hz, 1H), 3.84 (s, 3H), 1.88 (d, J=8.23 Hz, 3H); MS (ESI): 471 [M+H]$^+$.

Step D—Methyl 5-(6-cyano-1H-benzimidazol-1-yl)-3-hydroxythiophene-2-carboxylate

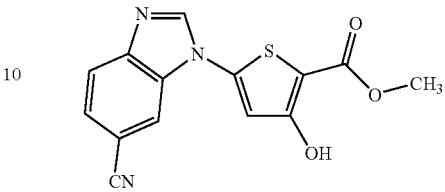

A solution of methyl 5-(6-cyano-1H-benzimidazol-1-yl)-3-{(1R)-1-[2-(trifluoromethyl)phenyl]ethoxy}thiophene-2-carboxylate (724 mg, 1.54 mmol) in 10 ml of TFA was heated at 70° C. for 16 h, The reaction was concentrated and the residue was taken up in MeOH. The solution was neutralized with 7N ammonia in MeOH. The reaction was concentrated and the solid was triturated with ether. The solid was rinsed with water and ether and dried to give 388 mg of the desired product (84%), Step E—Methyl 3-[(1R)-1-(3-{[tert-butyl(dimethyl)sliyl]oxy}-2-chlorophenyl)ethoxy]-5-(6-cyano-1H-benzimidazol-1-yl)thiophene-2-carboxylate

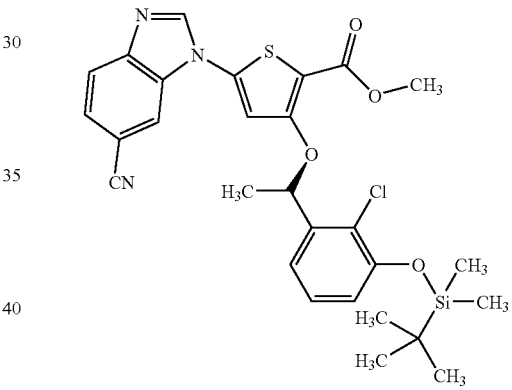

To a slurry of methyl 5-(6-cyano-1H-benzimidazol-1-yl)-3-hydroxythiophene-2-carboxylate (390 mg, 1.3 mmol) in 13 ml of DCM was added (1S)-1-(2-chloro-3-{[(1,1-dimethylethyl)(dimethyl)silyl]oxy}phenyl)ethanol (460 mg, 1.6 mmol), triphenylphosphine (880 mg, 2.8 mmol) and di-tert-butylazadicarboxylate (600 mg, 2.6 mmol). The reaction was concentrated onto silica gel and purified by flash column chromatography to give 440 mg of the desired product (60%). $^1$H NMR (400 MHz, d$_6$-DMSO) δ 8.84 (s, 1H), 8.22 (s, 1H), 7.94 (d, J=7.6 Hz, 1H), 7.74 (d, J=8.4 Hz, 1H), 7.41 (s, 1H), 7.32-7.25 (m, 2H), 6.93 (d, J=7.6 Hz, 1H), 5.97 (m, 1H), 3.80 (s, 3H), 1.60 (d, J=6.4 Hz, 3H), 0.90 (s, 9H), 0.14 (s, 3H), 0.08 (s, 3H).

Step F—Methyl 3-[(1R)-1-(2-chloro-3-hydroxyphenyl)ethoxy]-5-(6-cyano-1H-benzimidazol-1-yl)thiophene-2-carboxylate (Title Compound)

To a solution of methyl 3-[(1R)-1-(3-{[tert-butyl(dimethyl)silyl]oxy}-2-chlorophenyl)ethoxy]-5-(6-cyano-1H-benzimidazol-1-yl)thiophene-2-carboxylate (420 mg, 0.74 mmol) in THF cooled to 0° C. was added a 1M solution of tetrabutylammonium fluoride in THF (0.8 ml, 0.81 mmol). MeOH was added and the reaction was concentrated onto silica gel. The crude material was purified by flash column chromatography to give 291 mg of the title compound (87%). ¹H NMR (400 MHz, d₆-DMSO) δ 8.90 (s, 1H), 8.31 (s, 1H), 7.96 (d, J=8.4 Hz, 1H), 7.76 (dd, J=8.2 and 1.4 Hz, 1H), 7.20 (s, 1H), 3.78 (s, 3H).

INTERMEDIATE 4

Methyl 5-(5-bromo-1H-benzimidazol-1-yl)-3-{[tert-butyl(dimethyl)silyl]oxy}thiophene-2-carboxylate; and

INTERMEDIATE 5

Methyl 5-(6-bromo-1H-benzimidazol-1-yl)-3-{[tert-butyl(dimethyl)silyl]oxy}thiophene-2-carboxylate

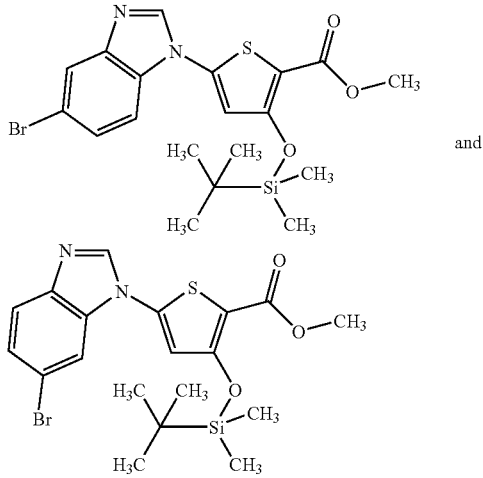

and

Step A—4-Bromobenzene-1,2-diamine

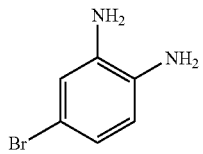

A mixture of 4-bromo-2-nitroaniline (50 g, 230 mmol) and Tin (II) chloride (174 g, 920 mmol) in 1.2 L of EtOH was heated at 80° C. for 16 h. The reaction was cooled to rt and brought to a basic pH with the addition of 5N and 1N NaOH, Once basic, 2 L of EtOAc was added and the mixture stirred. The organic layer was decanted off. This process was repeated until the EtOAc decant provided very little material. The organic solution was washed with brine, dried over MgSO₄ and concentrated to give 48.9 g of crude product. ¹H NMR (400 MHz, d₆-DMSO) δ 6.60 (d, J=2.4 Hz, 1H), 6.45 (dd, J=8.0 and 2.4 Hz, 1H), 6.39 (d, J=8.0 Hz, 1H), 4.83 (br s, 4H).

Step B—5-Bromo-1H-benzimidazole

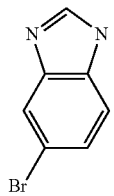

A solution of crude, impure 4-bromobenzene-1,2-diamine (48.9 g, 230 mmol), trimethylorthoformate (75 mL, 690 mmol), and 6 mL of formic acid was heated at 80° C. After 18 h, the reaction was concentrated to give 46.2 g of a crude, impure orange residue. ¹H NMR (400 MHz, d₆-DMSO) δ 8.24 (s, 1H), 7.77 (d, J=1.6 Hz, 1H), 7.53 (d, J=8.8 Hz, 1H), 7.30 (dd, J=8.8 and 1.8 Hz, 1H).

Step C—Methyl 5-(5-bromo-1H-benzimidazol-1-yl)-3-{[tert-butyl(dimethyl)silyl]oxy}thiophene-2-carboxylate and methyl 5-(6-bromo-1H-benzimidazol-1-yl)-3-{[tert-butyl(dimethyl)silyl]oxy}thiophene-2-carboxylate (Title Compounds)

To a solution of crude, impure 5-bromobenzimidazole (48.2 g) and methyl 2-chloro-3-oxo-2,3-dihydrothiophene-2-carboxylate (42 g, 220 mmol) in 800 mL of CHCl₃ was added N-methylimidazole (28 ml, 350 mmol). After 16 h, N-methylimidazole (17 mL, 220 mmol) and tert-butylchlorodimethylsilane (36 g, 240 mmol) was added. When TLC showed the reaction to be complete, the solution was diluted with water. The layers were separated. The organic phase was washed with water, dried over MgSO₄ and concentrated onto celite. The crude mixture was purified by flash column chromatography (0-25% EtOAc:hexanes) in batches to separate the 2 regioisomers, giving 33.5 g of Intermediate 4 eluting first and 29.2 g of Intermediate 5 eluting second (58%). (Intermediate 4, 5-Br) ¹H NMR (400 MHz, d₆-DMSO) δ 8.77 (s, 1H), 8.01 (d, J=1.6 Hz, 1H), 7.78 (d, J=8.8 Hz, 1H), 7.58(dd, J=8.8 and 1.6 Hz, 1H), 7.25 (s, 1H), 3.78 (s, 3H), 0.99 (s, 9H), 0.27 (s, 6H). (Intermediate 5, 6-Br) ¹H NMR (400 MHz, d₆-DMSG) δ 8.71 (s, 1H), 7.88 (d, J=1.6 Hz, 1H), 7.73 (d, J=8.8 Hz, 1H), 7.50 (dd, J=8.8 and 2.0 Hz, 1H), 7.26 (s, 1H), 3.77 (s, 3H), 0.99 (s, 9H), 0.28 (s, 6H).

INTERMEDIATE 6

Methyl 5-(6-bromo-1H-benzimidazol-1-yl)-3-{[(1R)-1-(2-chloro-3-hydroxyphenyl)ethyl]oxy}-2-thiophenecarboxylate

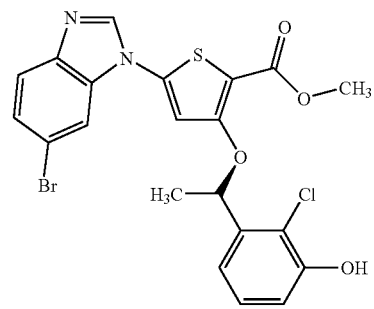

Step A—Methyl 5-(6-bromo-1H-benzimidazol-1-yl)-3-hydroxy-2-thiophenecarboxylate

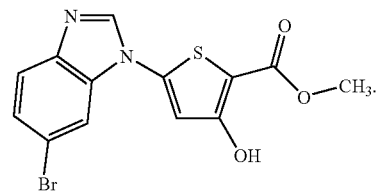

To a solution of methyl 5-(6-bromo-1H-benzimidazol-1-yl)-3-{[tert-butyl(dimethyl)-silyl]oxy}thiophene-2-carboxylate (Intermediate 5, 25 g, 54 mmol) in 540 mL THF was added a 1M solution of tetrabutyl ammonium fluoride in THF (60 mL, 60 mmol). After 1.5 h, the reaction was diluted with saturated aqueous NH₄Cl (200 mL). After 15 min, the slurry was further diluted with water (750 mL) and EtOAc (1 L). The aqueous layer was separated and brought to pH 3 by the addition of 1M HCl. The aqueous solution was extracted several times with EtOAc. The combined organic layers were washed with 0.1M HCl, dried over MgSO₄, and concentrated to give 19.4 g of the desired product which was used without further purification (100%). ¹H NMR (400 MHz, d₆-DMSO)

δ 8.62 (s, 1H), 7.90 (d, J=1.6 Hz, 1H), 7.72 (d, J=8.4 Hz, 1H), 7.47 (d, J=8.6 and 1.8 Hz, 1H), 6.83 (s, 1H), 3.66 (s, 3H).

Step B—Methyl 5-(6-bromo-1H-benzimidazol-1-yl)-3-{[(1R)-1-(2-chloro-3-{[(1,1-dimethylethyl)(dimethyl)silyl]oxy}phenyl)ethyl]oxy}-2-thiophenecarboxylate

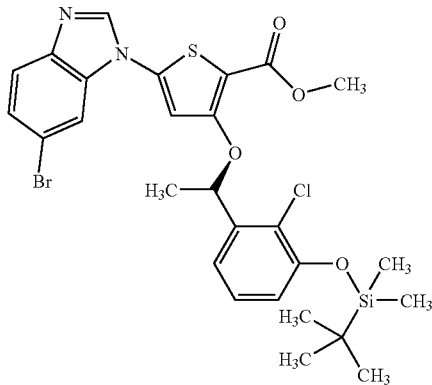

Methyl 5-(6-bromo-1H-benzimidazol-1-yl)-3-hydroxy-2-thiophenecarboxylate (250 mg, 0.70 mmol) and (1S)-1-(2-chloro-3-{[(1,1-dimethylethyl)(dimethyl)silyl]oxy}-phenyl) ethanol (240 mg, 0.84 mmol) were coupled using a procedure analogous to Intermediate 3, Step E to give 420 mg of the desired product with impurity. $^1$H NMR (400 MHz, d$_6$-DMSO) δ 8.63 (s, 1H), 7.81 (s, J=1.6 Hz, 1H), 7.72 (s, J=8.4 Hz, 1H), 7.49 (dd, J=8.8 and 2.0 Hz, 1H), 7.36 (s, 1H), 7.32-7.26 (m, 2H), 6.94 (dd, J=7.0 and 2.6 Hz, 1H), 5.97 (m, 1H), 3.81 (s, 3H), 1.61 (d, J=6.4 Hz, 3H), 0.92 (s, 9H), 0.15 (s, 3H), 0.10 (s, 3H).

Step C—Methyl 5-(6-bromo-1H-benzimidazol-1-yl)-3-{[(1R)-1-(2-chloro-3-hydroxyphenyl)ethyl]oxy}-2-thiophenecarboxylate (Title Compound)

Methyl 5-(6-bromo-1H-benzimidazol-1-yl)-3-{[(1R)-1-(2-chloro-3-{[(1,1-dimethylethyl)(dimethyl)silyl]oxy}phenyl)ethyl]oxy}-2-thiophenecarboxylate (420 mg, 0.67 mmol) was deprotected using a procedure analogous to Intermediate 3, Step F to give 343 mg of the desired product with impurity.

$^1$H NMR (400 MHz, d$_6$-DMSO) δ 10.22 (s, 1H), 8.63 (s, 1H), 7.76 (s, 1H), 7.71 (d, J=8.8 Hz, 1H), 7.48 (d, J=8.8 Hz, 1H), 7.34 (s, 1H), 7.19-7.15 (m, 1H), 7.10 (d, J=7.6 Hz, 1H), 6.89 (d, J=7.6 Hz, 1H), 5.93 (m, 1H), 3.79 (s, 3H), 1.58 (d, J=6.4 Hz, 3H).

INTERMEDIATE 7

Methyl 5-(5-bromo-1H-benzimidazol-1-yl)-3-hydroxy-2-thiophenecarboxylate

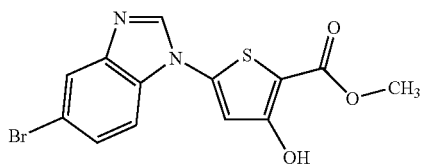

A solution of methyl 5-(5-bromo-1H-benzimidazol-1-yl)-3-[(phenylmethyl)oxy]-2-thiophenecarboxylate (15 g, 3.4 mmol) in 10 ml of TFA was heated to 50° C. After 6 h, the reaction was concentrated. The residue was dissolved in MeOH and neutralized with 7N ammonia in MeOH. The slurry was diluted with ether and filtered. The solid was washed with water and air-dried to give 1.0 g of the title compound (85%).

In an alternative procedure, to a solution of methyl 5-(5-bromo-1H-benzimidazol-1-yl)-3-{[tert-butyl(dimethyl)-silyl]oxy}thiophene-2-carboxylate (12 g, 25 mmol) in 250 mL of THF cooled to 0° C. was added a 1M solution of tetrabutylammonium fluoride in THF (28 ml, 28 mmol). The reaction was quenched with water and extracted with EtOAc. The combined organic layers were washed with water, dried over MgSO$_4$ and concentrated onto silica gel. The crude material was purified by flash column chromatography (0-5% MeOH/DCM) to give the title compound.

$^1$H NMR (400 MHz, d$_6$-DMSO) δ 10.85 (s, 1H), 8.71 (s, 1H), 8.00 (s, 1H), 7.75 (d, J=8.8 Hz, 1H), 7.54 (d, J=8.4 Hz, 1H), 7.12 (s, 1H), 3.78 (s, 3H).

INTERMEDIATE 8

Methyl 5-(5-bromo-1H-benzimidazol-1-yl)-3-{[(1R)-1-(2-chloro-3-{[(1,1-dimethylethyl)(dimethyl)sllyl]oxy}phenyl)ethyl]oxy}-2-thiophenecarboxylate

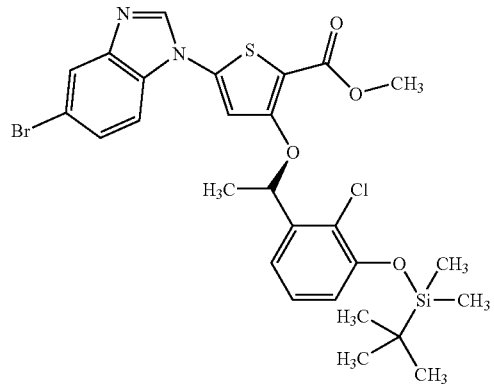

Methyl 5-(5-bromo-1H-benzimidazol-1-yl)-3-hydroxy-2-thiophenecarboxylate (1.0 g, 2.9 mmol) and (1S)-1-(2-chloro-3-{[(1,1-dimethylethyl)(dimethyl)silyl]-oxy}phenyl) ethanol (1.0 g, 3.5 mmol) were coupled using a procedure analogous to Intermediate 3, Step E to give 1.6 g of the title compound (89%). $^1$H NMR (400 MHz, d$_6$-DMSO) δ 8.69 (s, 1H), 8.00 (s, J=1.6 Hz, 1H), 7.59 (d, J=8.8 Hz, 1H), 7.50 (dd, J=8.8 and 1.6 Hz, 1H), 7.34-7.28 (m, 3H), 6.96 (dd, J=6.8 and 2.8 Hz, 1H), 5.93 (m, 1H), 3.81 (s, 3H), 1.60 (d, J=6.0 Hz, 3H), 0.94 (s, 9H), 0.17 (s, 3H), 0.13 (s, 3H).

INTERMEDIATE 9

Methyl 3-{[(1R)-1-(2-chloro-3-hydroxyphenyl)ethyl]oxy}-5-[5-(6-methyl-3-pyridinyl)-1H-benzimidazol-1-yl]-2-thiophenecarboxylate

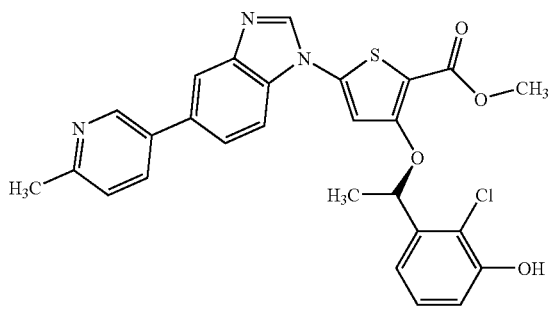

To a solution of methyl 5-(5-bromo-1H-benzimidazol-1-yl)-3-{[(1R)-1-(2-chloro-3-{[(1,1-dimethylethyl)(dimethyl)silyl]oxy}phenyl)ethyl]oxy}-2-thiophenecarboxylate (300 mg, 0.48 mmol) in 4.5 mL of DMA was added 2-picoline-5-boronic acid hydrate (79 mg, 0.58 mmol), 1M Na$_2$CO$_3$ (1.44 ml, 1.44 mmol) and Cl$_2$Pd(dppf) (41 mg, 0.05 mmol), and the reaction was heated to 80° C. The dark reaction was concentrated onto silica gel and purified by flash column chromatography to give the title compound, which was triturated into ether (147 mg, 59%). $^1$H NMR (400 MHz, d$_6$-DMSO) δ 10.26 (s, 1H), 8.80 (s, 1H), 8.70 (s, 1H), 8.08 (s, 1H), 8.01 (dd, J=8.0 and 2.4 Hz, 1H), 7.68 (m, 2H), 7.34-7.32 (m, 2H), 7.20-7.11 (m, 2H), 6.91 (d, J=8.0 Hz, 1H), 5.93 (m, 1H), 3.70 (s, 3H), 2.49 (s, 3H), 1.60 (d, J=6.0 Hz, 3H).

INTERMEDIATE 10

Methyl 3-{[(1R)-1-(2-chloro-3-hydroxyphenyl)ethyl]oxy}-5-[5-(3-pyridinyl)-1H-benzimidazol-1-yl]-2-thiophenecarboxylate

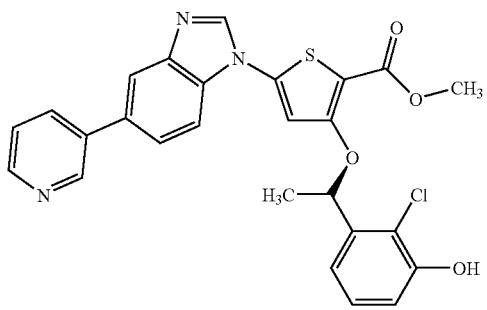

Methyl 5-(5-bromo-1H-benzimidazol-1-yl)-3-{[(1R)-1-(2-chloro-3-{[(1,1-dimethylethyl)(dimethyl)silyl]oxy}phenyl)ethyl]oxy}-2-thiophenecarboxylate (Intermediate 8, 500 mg, 0.80 mmol) and pyridine-3-boronic acid (120 mg, 0.96 mmol) were coupled using a procedure analogous to Intermediate 9 to give 213 mg of the title compound (53%). MS m/z=506 [M+H]$^+$.

INTERMEDIATE 11A

Methyl 5-(1H-benzimidazol-1-yl)-3-{[(1R)-1-(2-chloro-3-hydroxyphenyl)ethyl]oxy}-2-thiophenecarboxylate

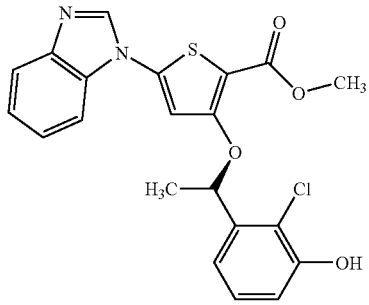

Title compound (2.2 g) was prepared from methyl 5-(1H-benzimidazol-1-yl)-3-hydroxy-2-thiophenecarboxylate (*J. Heterocyclic Chem.*, 1987, 24, 1301-1303) (1.9 g, 7.0 mmol) and (1S)-1-(2-chloro-3-{[(1,1-dimethylethyl)(dimethyl)silyl]oxy}phenyl)ethanol (Intermediate 17, 2.0 g, 7.0 mmol) using a procedure analogous to Intermediate 2, Step C.

INTERMEDIATE 11B

Methyl 5-(1H-benzimidazol-1-yl)-3-[((1R)-1-{3-[(2-bromoethyl)oxy]-2-chlorphenyl}ethyl)oxy]-2-thiophenecarboxylate

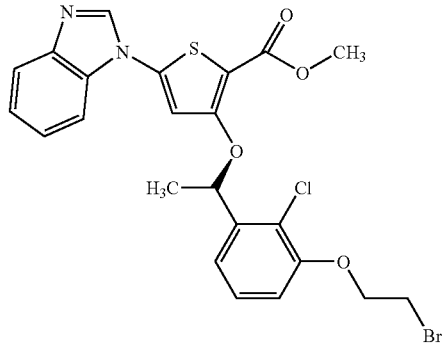

Methyl 5-(1H-benzimidazol-1-yl)-3-{[(1R)-1-(2-chloro-3-hydroxyphenyl)ethyl]oxy}-2-thiophenecarboxylate (Intermediate 11A, 600 mg, 1.4 mmol) and 2-bromoethanol (120 μL, 1.7 mmol) were coupled using a procedure analogous to Example 4, Step A to give 529 mg of the title compound (71%), $^1$H NMR (400 MHz, d$_6$-DMSO) δ 8.85 (s, 1H), 7.77 (d, J=7.2 Hz, 1H), 7.64 (d, J=8.0 Hz, 1H), 7.39-7.31 (m, 5H), 7.10 (dd, J=8.0 and 1.6 Hz, 1H), 5.98 (m, 1H), 4.40-4.37 (m, 2H), 3.81-3.79 (m, 5H), 1.81 (d, J=6.0 Hz, 3H).

INTERMEDIATE 12

Methyl 5-(5-chloro-1H-benzimidazol-1-yl)-3-({(1R)-1-[2-chloro-3-(4-piperidinyloxy)phenyl]ethyl}oxy)-2-thiophenecarboxylate

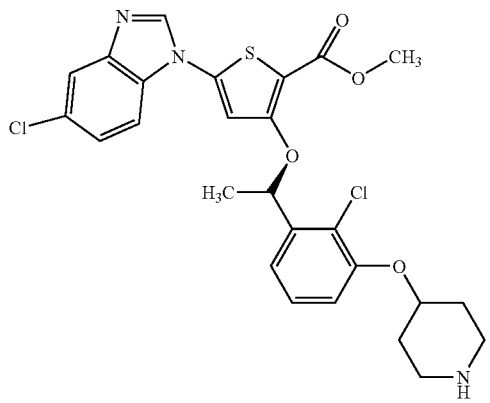

1,1-Dimethylethyl 4-({2-chloro-3-[(1R)-1-({5-(5-chloro-1H-benzimidazol-1-yl)-2-[(methyloxy)carbonyl]-3-thienyl}oxy)ethyl]phenyl}oxy)-1-piperidinecarboxylate (Example 8, Step B, 690 mg, 1.07 mmol) was deprotected according to the procedure analogous to Example 5, Step C to give the title compound (576 mg, 99% yield). $^1$H HMR (400 MHz, d$_6$-DMSO) δ 8.71 (s, 1H), 7.97 (br s, 1H), 7.86 (s, 1H), 7.67 (d, J=8.8 Hz, 1H), 7.41-7.32 (m, 4H), 7.18 (d, J=7.6 Hz, 1H), 5.95 (m, 1H), 4.89 (m, 1H), 3.80 (s, 3H), 3.17-3.12 (m, 2H), 3.01 (m, 2H), 2.00 (m, 2H), 1.78 (m, 2H), 1.59 (d, J=6.0 Hz, 3H).

INTERMEDIATE 13

Methyl 3-({(1R)-1-[2-chloro-3-(4-piperidinyloxy)phenyl]ethyl}oxy)-5-[5-(1-methyl-1H-pyrazol-4-yl)-1H-benzimidazol-1-yl]-2-thiophenecarboxylate

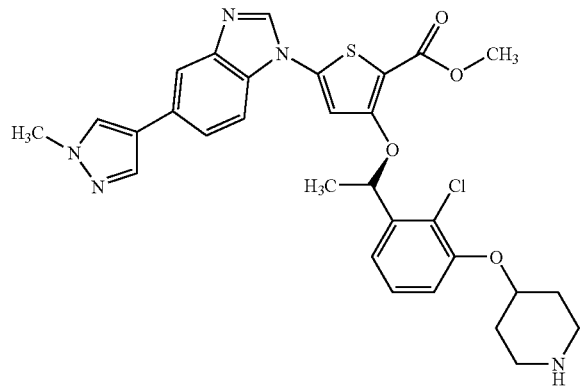

1,1-Dimethylethyl 4-({2-chloro-3-[(1R)-1-({2-[(methyloxy)carbonyl]-5-[5-(1-methyl-1H-pyrazol-4-yl)-1H-benzimidazol-1-yl]-3-thienyl}oxy)ethyl]phenyl}oxy)-1-piperidinecarboxylate (Example 46, Step A, 1.0 g, 1.4 mmol) was deprotected according to the procedure analogous to Example 5, Step C to give 850 mg of the title compound in quantitative yield.

$^1$H NMR (400 MHz, d$_6$-DMSO) δ 8.62 (s, 1H), 8.17 (s, 1H), 7.95 (s, 1H), 7.90 (s, 1H), 7.61-7.55 (m, 2H), 7.38-7.30 (m, 3H), 7.17 (d, J=8.0 Hz, 1H), 5.97 (m, 1H), 4.65 (m, 1H), 3.85 (s, 3H), 3.80 (s, 3H), 3.09 (m, 2H), 2.90 (m, 2H), 1.96 (m, 2H), 1.72 (m, 2H), 1.60 (d, J=6.4 Hz, 3H).

INTERMEDIATE 14

(1S)-1-(2-chloro-3-{[(1,1-dimethylethyl)(diphenyl)sylil]oxy}-4-fluorophenyl)ethanol

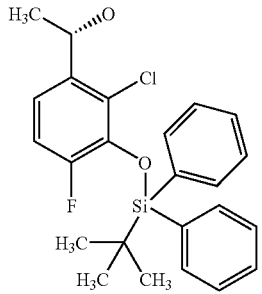

Step A—2-Chloro-3-{[(1,1-dimethylethyl)(diphenyl)silyl]oxy}-4-fluorobenzaldehyde

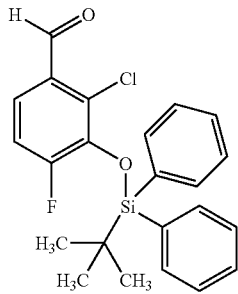

To a solution of 2-chloro-4-fluoro-3-(methyloxy)benzaldehyde (which can be synthesized following the procedure found in PCT Int. Appl. WO 2004073612) (2.0 g, 11 mmol) in 80 mL of DCM was added a 1M solution of boron tribromide in DCM (42 mL, 4.0 mmol). After 16 h, the reaction was carefully quenched with the addition of ice water and 1N HCl, and the mixture was stirred for 1 h. The layers were separated and the aqueous phase was extracted with EtOAc. The combined organic layers were extracted with 1N NaOH. These extracts were acidified with conc. HCl. The aqueous phase was extracted with DCM until TLC showed no more product. The organic extractions were dried over MgSO$_4$ and concentrated to an orange residue. The orange residue was dissolved in 100 mL of DCM. Imidazole (1.4 g, 21 mmol) and tert-butylchlorodiphenylsilane (2.6 mL, 10 mmol) were added, and the solution was stirred until the reaction was complete. The solution was diluted with water and the two layers were separated. The organic phase was washed with water and the aqeous phase was back-extracted with DCM. The combined organic solutions were dried over MgSO$_4$ and concentrated onto silica gel. The crude material was purified by flash column chromatography (0-20% EtOAc:Hexanes) to give 2.2 g of the desired product (50%). $^1$H NMR (400 MHz, d$_6$-DMSO) δ 10.24 (s, 1H), 7.65-7.63 (m, 4H), 7.48-7.39 (m, 7H), 7.22-7.18 (m, 1H), 1.07 (s, 9H).

Step B—1-(2-Chloro-3-{[(1,1-dimethylethyl)(diphenyl)silyl]oxy}-4-fluorophenyl)ethanol

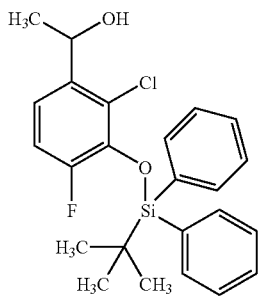

To a solution of 2-chloro-3-{[(1,1-dimethylethyl)(diphenyl)silyl]oxy}-4-fluorobenzaldehyde (2.2 g, 5.3 mmol) in THF cooled to 0° C. was added a 3M solution of methyl magnesium chloride in THF (2.2 mL, 6.4 mmol). When TLC showed the reaction to be complete, the reaction was quenched with the addition of water. The aqueous solution was extracted with DCM. The combined organic phases were washed with water, dried over MgSO$_4$ and concentrated onto silica gel. The crude material was purified by flash column chromatography to give 1.8 g of the desired product (77%). $^1$H NMR (400 MHz, d$_6$-DMSO) δ 7.65-7.59 (m, 4H), 7.45-7.36 (m, 8H), 7.14-7.11 (m, 1H), 7.02-6.97 (m, 1H), 5.35 (m, 1H), 4.96-4.93 (m, 1H), 1.24 (d, J=6.0 Hz, 3H), 1.05 (s, 9H).

Step C—1-(2-Chloro-3-{[(1,1-dimethylethyl)(diphenyl)silyl]oxy}-4-fluorophenyl)ethanone

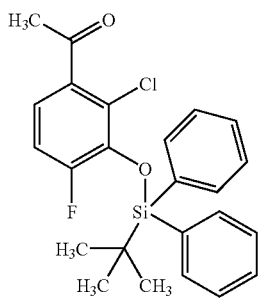

To a solution of 1-(2-Chloro-3-{[(1,1-dimethylethyl)(diphenyl)silyl]oxy}-4-fluorophenyl)ethanol (1.8 g, 4.1 mmol) in DCM was added NaHCO₃ (1.7 g, 20 mmol), water (0.07 ml, 4.1 mmol) and [1,1,1-tris(acetyloxy)-1,1-dihydro-1,2-benziodoxol-3-(1H)-one (2.1 g, 4.9 mmol). When TLC showed the reaction to be complete, the solution was quenched with the slow addition of 50 ml of saturated aq. NaHCO₃ solution and 50 ml of saturated aq. Na₂S₂O₃ solution, and the mixture was stirred vigorously for 1.5 h. The layers were separated and the aqueous phase was extracted with DCM. The combined organic phases were washed with water, dried over MgSO₄ and concentrated onto silica gel. The crude material was purified by flash column chromatography to give 1.70 g of the desired product (97%). ¹H NMR (400 MHz, d₆-DMSO) δ 7.63-7.61 (m, 4H), 7.47-7.37 (m, 6H), 7.26-7.23 (m, 1H), 7.13-7.08 (m, 1H), 2.52 (s, 3H), 1.04 (s, 9H).

Step D—(1S)-1-(2-chloro-3-{[(1,1-dimethylethyl)(diphenyl)silyl]oxy}-4-fluorophenyl)ethanol (Title Compound)

1-(2-Chloro-3-{[(1,1-dimethylethyl)(diphenyl)silyl]oxy}-4-fluorophenyl)ethanone (1.7 g, 4.0 mmol) was subjected to chiral reduction using a procedure analogous to Intermediate 17, Step B to give the title compound with an ee of 64%. The enantiomers were separated using packed column SFC on a Diacel Chiralcel OJ-H column using a mobile phase with 20% MeOH in carbon dioxide. The (S)-enantiomer eluted first with a retention time of 3.6 min at a flow rate of 2 mL/min on the analytical instrument; the (R)-enantiomer eluted at 5.7 min. ¹H NMR (400 MHz, d₆-DMSO) δ 7.65-7.59 (m, 4H), 7.45-7.36 (m, 6H), 7.14-7.11 (m, 1H), 7.02-6.97 (m, 1H), 5.35 (m, 1H), 4.96-4.93 (m, 1H), 1.24 (d, J=6.0 Hz, 3H), 1.05 (s, 9H).

INTERMEDIATE 15

1-(2-Chloro-3-{[(1,1-dimethylethyl)(diphenyl)silyl]oxy}-6-fluorophenyl)ethanol

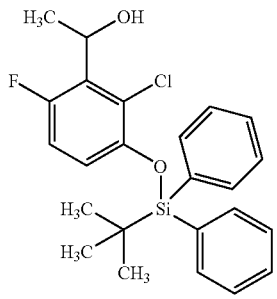

Step A—2-Chloro-3-{[(1,1-dimethylethyl)(diphenyl)silyl]oxy}-6-fluorobenzaldehyde

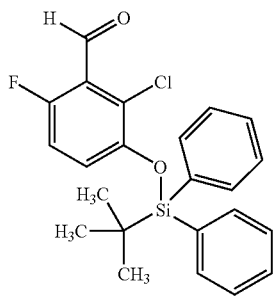

2-Chloro-3-{[(1,1-dimethylethyl)(diphenyl)silyl]oxy}-6-fluorobenzaldehyde was prepared from 2-chloro-6-fluoro-3-methoxybenzaldehyde using a procedure analogous to Intermediate 14, Step A. ¹H NMR (400 MHz, d₆-DMSO) δ 10.29 (s, 1H), 7.88-7.85 (m, 4H), 7.52-7.43 (m, 5H), 7.07-7.02 (m, 1H), 7.88-7.65 (m, 1H), 1.06 (s, 9H).

Step B—1-(2-Chloro-3-{[(1,1-dimethylethyl)(diphenyl)silyl]oxy}-6-fluorophenyl)ethanol (Title Compound)

2-Chloro-3-{[(1,1-dimethylethyl)(diphenyl)silyl]oxy}-6-fluorobenzaldehyde was methylated using a procedure analogous to Intermediate 14, Step B to give 11.8 g of the title compound (75% over 3 steps). ¹H NMR (400 MHz, d₆-DMSO) δ 7.85-7.63 (m, 4H), 7.50-7.42 (m, 6H), 6.82-6.77 (m, 1H), 6.32-8.28 (m, 1H), 5.33 (d, J=4.4 Hz, 1H), 5.28-5.22 (m, 1H), 1.41 (d, J=6.4 Hz, 3H), 1.04 (s, 9H),

INTERMEDIATE 16

Methyl 3-hydroxy-5-[5-(1-methyl-1H-pyrazol-4-yl)-1-H-benzimidazol-1-yl]-2-thiophenecarboxylate

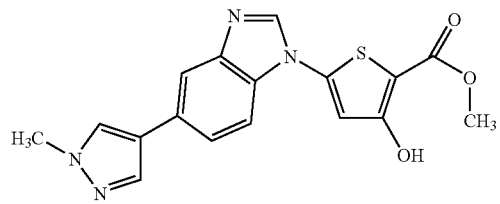

Step A—Methyl 5-[5-(1-methyl-1H-pyrazol-4-yl)-1H-benzimidazol-1-yl]-3-[(phenylmethyl)oxy]-2-thiophenecarboxylate

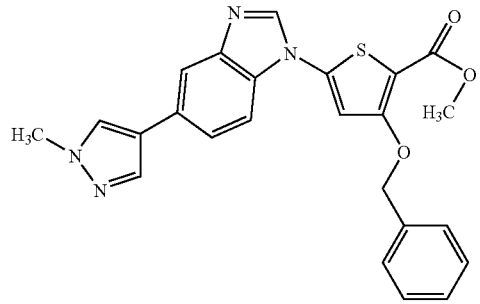

To a solution of methyl 5-(5-bromo-1H-benzimidazol-1-yl)-3-[(phenylmethyl)oxy]-2-thiophenecarboxylate (Intermediate 28, 2.8 g, 6.3 mmol) in DMA (60 mL) and 1N aqueous Na₂CO₃ (20 ml) was added 1-methyl-4-(4,4,5,5-tetramethyl-1,3,2-dioxaborolan-2-yl)-1H-pyrazole (1.6 g, 7.5 mmol), followed by Cl₂Pd(dppf) (0.60 g, 0.75 mmol), and the reaction mixture was heated to 80° C. for 1 h. The solution was filtered cooled to rt, diluted with EtOAc (250 mL) and washed with water (3×200 mL). The organic layer was dried over MgSO₄, filtered, and silica gel (10 g) was added. The volatiles were evaporated under reduced pressure, and the pre-adsorbed solids were loaded info a solid loading cartridge and subjected to a gradient elution using DCM (100%) to DCM:MeOH:ammonium hydroxide (90:10:1) using a RediSep silica gel cartridge (40 g; ISCO). The appropriate fractions were combined and concentrated under reduced pressure to give 1.6 g (3.6 mmol) of the title compound. ¹H NMR (400 MHz, CDCl₃): δ 8.03 (s, 1H), 7.90 (s, 1H), 7.79 (s, 1H), 7.64 (s, 1H), 7.54-7.32 (m, 7H), 6.88 (s, 1H), 5.32 (s, 2H), 3.96 (s, 3H), 3.90 (s, 3H).

Step B—Methyl 3-hydroxy-5-[5-(1-methyl-1H-pyrazol-4-yl)-1H-benzimidazol-1-yl]-2-thiophenecarboxylate (Title Compound)

To methyl 5-[5-(1-methyl-1H-pyrazol-4-yl)-1H-benzimidazol-1-yl]-3-[(phenylmethyl)oxy]-2-thiophenecarboxylate (1.6 g, 3.6 mmol) was added TFA (20 mL) and the mixture was stirred at rt for 18 h. The solution was concentrated to give an oil and DCM (20 mL) was added resulting in the precipitation of a solid. The acid was neutralized by addition of 7N ammonia in MeOH and the solution diluted with DCM and MeOH so that all the solid dissolved. Silica gel (10 g) was added and the volatiles were evaporated under reduced pressure, and the pre-adsorbed solids were loaded into a solid loading cartridge and subjected to a gradient elution using DCM (100%) to DCM:MeOH:ammonium hydroxide (90:10:1) using a RediSep silica gel cartridge (40 g; ISCO). The appropriate fractions were combined and concentrated under reduced pressure to give 1.3 g (3.6 mmol) of the title compound as a white solid. $^1$H NMR (400 MHz, DMSO-$d_6$): δ 8.64 (s, 1H), 8.17 (s, 1H), 7.96 (d, J=1.1 Hz, 1H), 7.91 (d, J=0.7 Hz, 1H), 7.74 (d, J=8.4 Hz, 1H), 7.60 (dd, J=8.4, 1.7 Hz, 1H), 7.11 (s, 1H), 3.84 (s, 3H), 3.76 (s, 3H).

ALTERNATIVE ROUTE TO INTERMEDIATE 16

Step A: Methyl 5-[5-(1-methyl-1H-pyrazol-4-yl)-1H-benzimidazol-1-yl]-3-[(phenylmethyl)oxy]-2-thiophenecarboxylate

Step A1—4-(1-Methyl-1H-pyrazol-4-yl)-2-nitroaniline

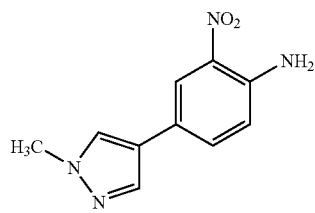

4-Bromo-2-nitroaniline (1.0 g, 4.6 mmol) and 1-methyl-4-(4,4,5,5-tetramethyl-1,3,2-dioxaborolan-2-yl)-1H-pyrazole (1.1 g, 5.1 mmol) were dissolved in 13 ml of DMA, placed under nitrogen, and heated to 80° C. A 2N aqueous solution of $Na_2CO_3$ was added, followed by $PdCl_2(dppf)$ dichloromethane adduct (0.076 g, 0.90 mmol). Reaction was stirred at 80° C. for 1 h and then cooled to rt, poured into 150 ml of water and extracted with EtOAc (3×), Combined organics were dried over anhydrous $MgSO_4$, filtered, concentrated onto silica gel, and purified by flash chromatography using 0-50% EtOAc/hexanes. 4-(1-Methyl-1H-pyrazol-4-yl)-2-nitroaniline was isolated as a bright orange solid (1.0 g, 99%). MS (ESI): 219 [M+H]$^+$.

Step A2—4-(4-Iodo-3-nitrophenyl)-1-methyl-1H-pyrazole

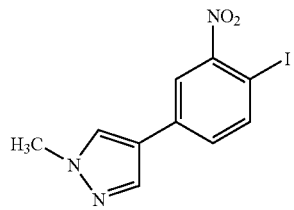

Iodine (3.5 g, 14 mmol), acetonitrile (40 ml), and test-butyl nitrite (0.82 mL, 6.9 mmol) were combined under $N_2$ in a 3-neck round bottom flask fitted with reflux condenser and an addition funnel. The mixture was stirred at rt. To the addition funnel was added a solution of 4-(1-methyl-1H-pyrazol-4-yl)-2-nitroaniline (1.0 g, 4.6 mmol) dissolved in DCM (20 mL) and DMSO (2 mL). This solution was added dropwise to flask at rt. The reaction was placed in a 60° C. oil bath and after 5-10 minutes bubbles began appearing. The reaction was stirred for an additional 2 h at 60° C. and then the heat was turned off and the reaction stirred at rt overnight. Aqueous sodium sulfite solution was added and the mixture was extracted with EtOAc (3×). Combined organic layers were dried over anhydrous $MgSO_4$, filtered, concentrated onto silica gel and purified by flash chromatography using 20-60% EtOAc/hexanes. 1.43 g (95%) of 4-(4-iodo-3-nitrophenyl)-1-methyl-1H-pyrazole was isolated as a yellow solid. MS (ESI): 330, 331 [M+H]$^+$.

Step A3—Methyl 5-{[4-(1-methyl-1H-pyrazol-4-yl)-2-nitrophenyl]amino}-3-[(phenylmethyl)oxy]-2-thiophenecarboxylate

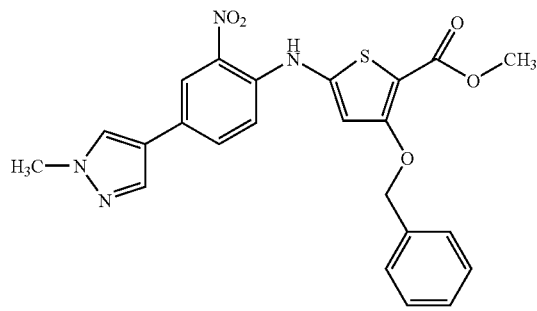

Methyl 5-amino-3-[(phenylmethyl)oxy]-2-thiophenecarboxylate (1.0 g, 3.8 mmol) and 4-(4-iodo-3-nitrophenyl)-1-methyl-1H-pyrazole (1.3 g, 3.8 mmol) were dissolved In anhydrous toluene (30 mL) and degassed with $N_2$ gas for 30 min. Cesium carbonate (6.2 g, 19 mmol) was added followed by XANTPHOS and trisdibenzylideneacetone palladium (II). The mixture was heated to 80° C. for 2 h and was then absorbed directly onto silica gel and flash chromatographed using 0-50% EtOAc/$CH_2Cl_2$. 1.62 g (98%) of methyl 5-{[4-(1-methyl-1H-pyrazol-4-yl)-2-nitrophenyl]amlno}-3-[(phenylmethyl)oxy]-2-thiophenecarboxylate was isolated as a dark red/purple solid. MS (ESI): 485 [M+H]$^+$.

Step A4—Methyl 5-[5-(1-methyl-1H-pyrazol-4-yl)-1H-benzoimidazol-1-yl]-3-[(phenylmethyl)oxy]-2-thiophenecarboxylate (Title Compound)

Methyl 5-{[4-(1-methyl-1H-pyrazol-4-yl)-2-nitrophenyl]amino}-3-[(phenylmethyl)oxy]-2-thiophenecarboxylate (1.0 g, 2.2 mmol) from a different batch than that made in Step A3, was dissolved In MeOH (30 mL). Trimethylorthoformate (6.0 mL, 54 mmol) was added followed by formic acid (0.81 ml, 21.5 mmol). Zinc dust (0.70 g, 11 mmol) was added and the reaction mixture was heated to 70° C. for 2 h and then cooled to rt. The reaction mixture was filtered through a pad of celite which was then washed with 20% MeOH/DCM. The crude reaction mixture was concentrated to remove the MeOH and the remaining mixture was poured into half-saturated aqueous $NaHCO_3$ solution and then extracted with a mixture of 4:1 DCM:i-PrOH. The combined organics were dried over anhydrous $MgSO_4$ and purified by flash chromatography to give 850 mg (89%) of the title compound, methyl 5-[5-(1-methyl-1H-pyrazol-4-yl)-1H-benzimidazol-1-yl]-3-[(phenylmethyl)oxy]-2-thiophenecarboxylate. MS (ESI): 445 [M+H]+

ALTERNATIVE ROUTE TO INTERMEDIATE 16

Methyl 3-hydroxy-5-[5-(1-methyl-1H-pyrizol-4-yl)-1H-benzimidazol-1-yl]-2-thiophenecarboxylate

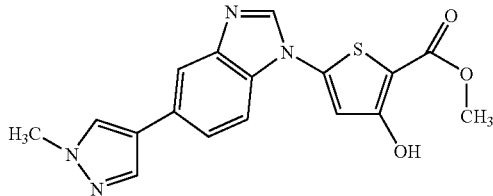

Methyl 5-(5-bromo-1H-benzimidazol-1-yl)-3-{[(1,1-dimethylethyl)(dimethyl)silyl]oxy}-2-thiophenecarboxylate (20 g, 43 mmol) and 1-methyl-4-(4,4,5,5-tetramethyl-1,3,2-dioxaborolan-2-yl)-1H-pyrazole (11 g, 53 mmol) were dissolved in DMF (285 mL) with stirring in a flask equipped with an overhead stirrer, reflux condenser, and thermometer. The solution was degassed for 15 min by bubbling N₂ through the stirring solution. PdCl₂ (dppf) (0.53 g, 0.73 mmol) was added followed by 1.6 M K₂CO₃ (142 mL), The reaction was heated to 80° C. and stirred for 2 h. The reaction was cooled to rt and transferred to 2 L flask. The mixture was acidified with acetic acid and then diluted with 1 L of water. The product was collected by filtration to give 14.3 g (94%) of the title compound as a solid. MS (ESI): 355 [M+H]+.

INTERMEDIATE 17

(1S)-1-(2-chloro-3-{[(1,1-dimethylethyl)(dimethyl)silyl]oxy}-phenyl)ethanol

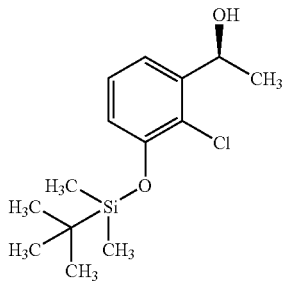

Step A—1-(2-Chlcro-3-{[(1,1-dimethylethyl)(dimethyl)silyl]oxy}phenyl)ethanone

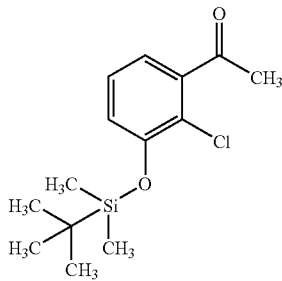

To a solution of 1-(2-chloro-3-hydroxyphenyl)ethanone (8.4 g, 50 mmol) which can be synthesized according to the procedure in *Proceedings of the Indiana Academy of Science* 1883, 92, 145-151 and imidazole (3.8 g, 55 mmol) in DCM (100 ml) was added chloro(tert-butyl)dimethylsilane (8.3 g, 55 mmol). The solution was stirred for 1 h and silica (20 g) was added. The volatiles were evaporated under reduced pressure, and the pre-adsorbed solids were loaded into a solid loading cartridge and subjected to a gradient elution using hexanes (100%) to hexanes:EtOAc (90:10) using a RediSep silica gel cartridge (120 g; ISCO). The appropriate fractions were combined and concentrated under reduced pressure to give 7.1 g (25 mmol) of the title compound. ¹H NMR (400 MHz, CDCl₃): δ 7.16 (dd, J=8.0, 7.7 Hz, 1H), 7.04 (dd, J=7.7, 1.5 Hz, 1H), 6.96 (dd, 8.0, 1.5 Hz, 1H), 2.60 (s, 3H), 1.02 (s, 9H), 0.23 (s, 6H).

Step B—(1S)-1-(2-chloro-3-{[(1,1-dimethylethyl)(dimethyl)silyl]oxy}phenyl)ethanol (Title Compound)

To a solution of borane, dimethylsulfide complex (1.8 ml, 30 mmol) in THF (10 mL) was added a 1H-solution of (R)-1-methyl-3,3-diphenyltetrahydro-3H-pyrrolo[1,2-c][1,3,2]oxaborole in toluene (0.25 ml, 0.25 mmol). To this mixture was slowly added over 2 h a solution of 1-(2-chloro-3-{[(1,1-dimethylethyl)(dimethyl)sliyl]oxy}phenyl)ethanone in THF (50 mL). The solution was stirred an additional 18 h then MeOH was added dropwise to quench any excess borane. The volatiles were evaporated under reduced pressure, and DCM was added (50 mL). The resulting white solid was removed by filtration and the silica was added to the filtrate. The volatiles were evaporated under reduced pressure and the pre-adsorbed solids were loaded Into a solid loading cartridge and subjected to a gradient elution using hexanes (100%) to hexanes:EtOAc (80:20) using a RediSep silica gel cartridge (120 g; ISGO). The appropriate fractions were combined and concentrated under reduced pressure to give 8.8 g (24 mmol) of the title compound as a white solid. ¹H NMR (400 MHz, CDCl₃): δ 7.19-7.12 (m, 2H), 6.81-6.79 (m, 1H), 5.30-5.25 (m, 1H), 1.93 (d, J=3.6 Hz, 1H) 1.47 (d, J=6.4 Hz, 3H), 1.02 (s, 9H), 0.21 (s, 3H), 0.21 (s, 3H).

Alternatively, Intermediate 17 can be prepare by the following method.

Step A—2-chloro-3-{[(1,1-dimethylethyl)(dimethyl)silyl]oxy}benzaldehyde

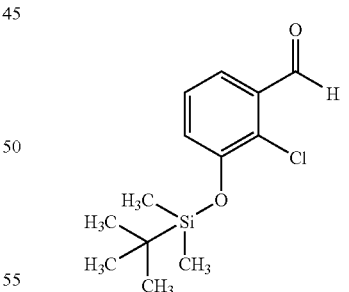

To a solution of 2-chloro-3-hydroxybenzaldehyde (30.0 g, 192 mmol) which was purchased from Sigma-Aldrich and imidazole (15.6 g, 230 mmol) in THF (200 ml) was added chloro(tert-butyl)dimethylsiiane (30.0 g, 200 mmol). The solution was stirred for overnight. The solution was poured into water and extracted with ether (2×300 ml). The ether layers were dried (MgSO₄), filtered and the volatiles removed under reduced pressure to give 51.0 g (188 mmol) of the title compound. ¹H NMR (400 MHz, CDCl₃): δ 10.49 (s, 1H), 7.54 (dd, J=7.7, 1.6 Hz, 1H), 7.24 (dd, J=8.0, 7.7 Hz, 1H), 7.13 (dd, J=8.0, 1.6 Hz, 1H), 1.05 (s, 9H), 0.25 (s, 6H).

Step B—(1S)-1-(2-chloro-3-{[(1,1-dimethylethyl)(dimethyl)silyl]oxy}phenyl)ethanol (Title Compound)

To a solution of 2-chloro-3-{[(1,1-dimethylethyl)(dimethyl)silyl]oxy}-benzaldehyde (50.0 g, 184 mmol) in THF (500 mL) cooled to −78° C. was added a 3M solution of methylmagnesiumchloride in THF (67.0 mL 202 mmol). The solution was allowed to warm to rt and then water was added to quenched the reaction. The solution was extracted with ether, dried (MgSO$_4$), filtered and the volatiles were evaporated under reduced pressure to give 50.0 g of the racemic title compound as a colorless oil. The enantiomers were separated using SFC on a 3×25 cm OJ-H column with a 90 g/min total flow, 92/8 CO2/MeOH, 103bar, 27° C. The desired (S) enantiomer eluted first under these separation conditions. Upon standing, the enantiopure title compound solidified.

INTERMEDIATE 18

Methyl 3-{[(1R)-1-(2-chloro-3-hydroxyphenyl)ethyl]oxy}-5-[5-(1-methyl-1H-pyrazol-4-yl)-1H-benzimidazol-1-yl]-2-thiophenecarboxylate

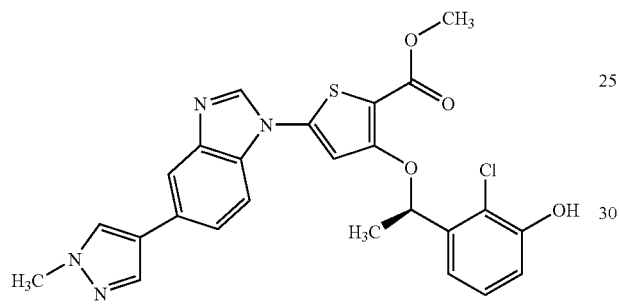

Step A—Methyl 3-{[(1R)-1-(2-chloro-3-{[(1,1dimethylethyl)(dimethyl)silyl]oxy}phenyl)ethyl]oxy}-5-[5-(1-methyl-1H-pyrazol-4-yl)-1H-benzimidazol-1-yl]-2-thiophenecarboxylate

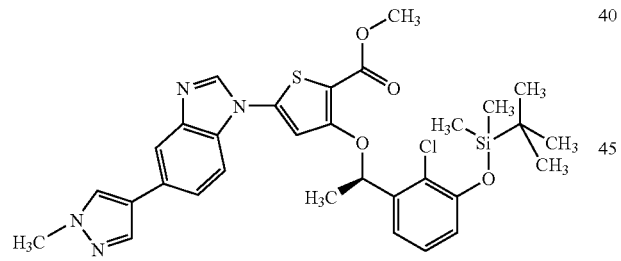

To a slurry of methyl 3-hydroxy-5-[5-(1-methyl-1H-pyrazol-3-yl)-1H-benzimidazol-1-yl]-2-thiophenecarboxylate (Intermediate 16, 0.71 g, 2.0 mmol) and (1S)-1-(2-chloro-3-{[(1,1-dimethylethyl)(dimethyl)silyl]oxy}phenyl)-ethanol (Intermediate 17, 0.63 g, 2.2 mmol) in DCM (20 ml) was added triphenylphosphine (1.1 g, 4.0 mmol) and di-tert-butyl azodicarboxylate (0.92 g, 4.0 mmol). The clear, yellow solution was stirred 1 h then silica (5 g) was
> added. The volatiles were evaporated under reduced pressure and the pre-adsorbed solids were loaded into a solid loading cartridge and subjected to a gradient elution using DCM (100%) to DCM:MeOH:ammonium hydroxide (90:10:1) using a RedlSep silica gel cartridge (40 g; ISCO). The appropriate fractions were combined and concentrated under reduced pressure to give 1.1 g (1.8 mmol) of the title compound as a white solid. 1H NMR (400 MHz, CDCl$_3$); δ 7.98 (s, 1H), 7.87 (s, 1H), 7.78 (s, 1H), 7.64 (s, 1H), 7.46-7.44 (m, 2H), 7.26-7.23 (m, 1H), 7.16 (dd, J=7.9, 7.8 Hz 1H), 6.85-6.83 (m, 1H), 5.82 (q, J=6.3 Hz, 1H), 3.96 (s, 3H), 3.91 (s, 3H), 1.72 (d, J=6.3 Hz, 3H), 1.01 (s, 9H), 0.21 (s, 3H), 0.19 (s, 3H).

Step B—Methyl 3-{[(1R)-1-(2-chloro-3-hydroxyphenyl)ethyl]oxy}-5-[5-(1-methyl-1H-pyrazol-4-yl)-1H-benzimidazol-1-yl]-2-thiophenecarboxylate (Title Compound)

To a solution of methyl 3-{[(1R)-1-(2-chloro-3-{[(1,1-dimethylethyl)(dimethyl)silyl]oxy}phenyl)ethyl]oxy}-5-[5-(1-methyl-1H-pyrazol-4-yl)-1H-benzimidazol-1-yl]-2-thiophenecarboxylate (0.72 g, 1.2 mmol) in THF (5 mL) was added a solution of 1N tetrabutylammonium fluoride in THF (1.4 mL, 1.4 mmol). After 10 min, silica (5 g) was added, the volatiles were evaporated under reduced pressure and the pre-adsorbed solids were loaded into a solid loading cartridge and subjected to a gradient elution using DCM (100%) to DCM:MeOH:ammonium hydroxide (80:20:1) using a RediSep silica gel cartridge (12 g; ISCO). The appropriate fractions were combined and concentrated under reduced pressure to give 0.53 g (1.0 mmol) of the title compound as a light yellow foam. 1H NMR (400 MHz, CDCl$_3$): δ 7.97 (s, 1H), 7.87 (s, 1H), 7.78 (s, 1H), 7.63 (s, 1H), 7.46-7.44 (m, 1H), 7.38 (d, J=7.8 Hz, 1H), 7.24-7.20 (m, 2H), 7.01-6.97 (m, 1H), 6.64 (s, 1H) 5.73 (q, J=6.4 Hz, 1H), 3.95 (s, 3H), 3.91 (s, 3H), 1.73 (d, J=6.4 Hz, 3H).

INTERMEDIATE 19

Methyl 5-[5,6-bis(methyloxy)-1H-benzimidazol-1-yl]-3-{[(1R)-1-(2-chloro-3-hydroxyphenyl)ethyl]oxy}-2-thiophenecarboxylate

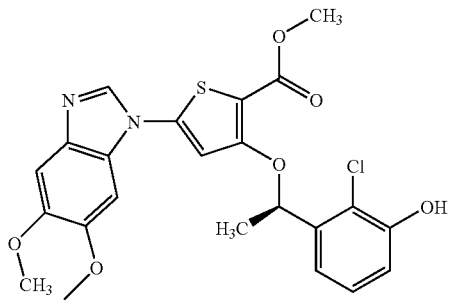

Step A—Methyl 5-[5,6-bis(methyloxy)-1H-benzimidazol-1-yl]-3-{[(1R)-1-(2-chloro-3-{[(1,1-dimethylethyl)(dimethyl)silyl]oxy}phenyl)ethyl]oxy}-2-thiophenecarboxylate

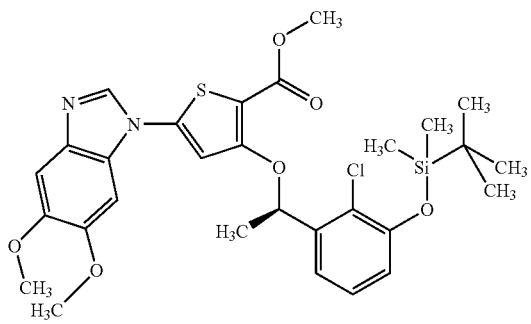

Methyl 5-[5,6-bis(methyloxy)-1H-benzimidazol-1-yl]-3-hydrcxy-2-thiophenecarboxylate (which can be synthesized following the procedure found in PCT Int. Appl. WO 2004073612) (3.3 g, 10 mmol) and (1S)-1-(2-chloro-3-{[(1,1-dimethylethyl)(dimethyl)silyl]oxy}phenyl)ethanol (Intermediate 17, 2.9 g, 10 mmol) were coupled using a procedure analogous to Intermediate 18, Step A to give 4.8 g of the desired product (80%) 1H NMR (400 MHz, CDCl$_3$): δ 7.85 (s, 1H), 7.27-7.14 (m, 3H), 6.92 (s, 1H), 6.82 (d, J=8.0 Hz, 1.6, 1H), 6.64 (s, 1H), 5.80 (q, J=6.4 Hz, 1H), 3.94 (s, 3H), 3.92 (s, 3H), 3.88 (s, 3H), 1.72 (d, J=6.4 Hz, 3H).

Step B—Methyl 5-[5,6-bis(methyloxy)-1H-benzimidazol-1-yl]-3-{[(1R)-1-(2-chloro-3-hydroxyphenyl)ethyl]oxy}-2-thiophenecarboxylate (Title Compound)

Methyl 5-[5,6-bis(methyloxy)-1H-benzimidazol-1-yl]-3-{[(1R)-1-(2-chloro-3-{[(1,1-dimethylethyl)(dimethyl)siiyl]oxy}phenyl)ethyl]oxy}-2-thiophenecarboxylate (4.8 g, 8.0 mmol) was deprotected using a procedure analogous to Intermediate 18, Step B to give 2.0 g (51%) of the title compound. 1H HMR (400 MHz, DMSO): δ 10.29 (s, 1H), 8.42 (s, 1H), 7.33 (s, 1H), 7.24 (s, 1H), 7.19 (dd, J=8.0, 7.8 Hz, 1H) 7.10 (dd, J=7.8, 1.4 Hz, 1H), 7.06 (s, 1H), 6.90 (dd, J=8.0, 1.4, 1H), 5.97 (q, J=6.4 Hz, 1H), 3.82 (s, 3H), 3.81 (s, 3H), 3.80 (s, 3H), 1.61 (d, J=6.4 Hz, 3H).

INTERMEDIATE 20

Methyl 3-{[(1R)-1-(2-chloro-3-hydroxyphenyl)ethyl]oxy}-5-[5-(2-methyl-4-pyridinyl)-1H-benzimidazol-1-yl]-2-thiophenecarboxylate

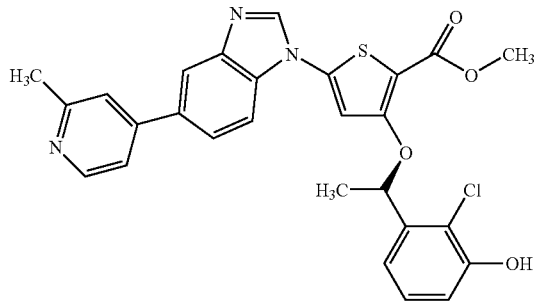

Methyl 5-(5-bromo-1H-benzimidazol-1-yl)-3-{[(1R)-1-(2-chloro-3-{[(1,1-dimethylethyl)(dimethyl)silyl]oxy}phenyl)ethyl]oxy}-2-thiophenecarboxylate (Intermediate 8, 400 mg, 0.64 mmol) and (2-methyl-4-pyridinyl)boronic acid (105 mg, 0.77 mmol) were coupled using a procedure analogous to Intermediate 9 to give the title compound (126 mg, 38%). $^1$H NMR (400 MHz, d$_6$-DMSO) δ 8.54 (s, 1H), 8.09 (s, 1H), 7.62-7.22 (m, 8H), 7.03 (dd, J=6.9, 2.5 Hz, 1H), 6.69 (s, 1H) 5.77 (q, J=6.4 Hz, 1H), 3.93 (s, 3H), 2.64 (s, 3H), 1.77 (d, J=6.4 Hz, 3H).

INTERMEDIATE 21

Methyl 5-(6-chloro-1H-benzimidazol-1-yl)-3-{[(1R)-1-(2-chloro-3-hydroxyphenyl)ethyl]oxy}-2-thiophenecarboxylate

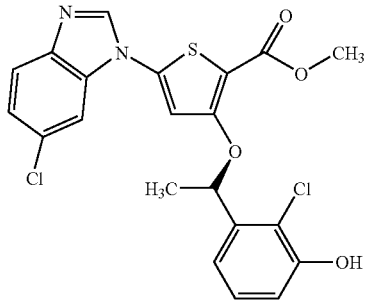

Step A—Methyl 5-(6-chloro-1H-benzimidazol-1-yl)-3-{[(1,1-dimethylethyl)-(dimethyl)silyl]oxy}-2-thiophenecarboxylate

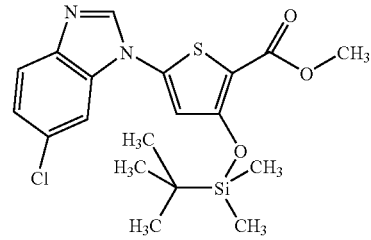

To a mixture of chlorobenzimidazole (7.0 g, 46 mmol) and methyl 2-chloro-3-oxo-2,3-dihydro-2-thiophenecarboxylate (9.8 g, 51 mmol) in 400 mL of CHCl$_3$ was added N-methylimidazole (5.5 mL, 69 mmol). After 18 h, tert-butylchlorodimethylsilane (6.9 g, 46 mmol) and N-methylimidazole (3.7 mL, 46 mmol) was added. The reaction mixture was diluted with water and the layers were separated. The aqueous phase was extracted with DCM, The combined organic layers were washed with water, dried over MgSO$_4$ and concentrated onto silica gel. The crude material was purified by flash column chromatography (0-100% 25% EtOAc/hexanes) to give the desired product.

$^1$H NMR (400 MHz, d$_6$-DMSO) δ 8.74 (s, 1H), 7.80 (d, J=8.6 Hz, 1H), 7.78 (d, J=2.1 Hz, 1H), 7.40 (dd, J=8.6 and 2.1 Hz, 1H), 7.28 (s, 1H), 3.77 (s, 3H), 1.00 (s, 9H), 0.27 (s, 6H).

Step B—Methyl 5-(6-chloro-1H-benzimidazol-1-yl)-3-hydroxy-2-thiophene-carboxylate

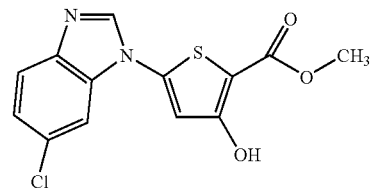

Methyl 5-(6-chloro-1H-benzimidazol-1-yl)-3-{[(1,1-dimethylethyl)-(dimethyl)silyl]oxy}-2-thiophenecarboxylate (2.0 g, 4.7 mmol) was deprotected using a procedure analogous to Intermediate 2, Step B to give 1.4 g of the desired product (97%). $^1$H NMR (400 MHz, d$_6$-DMSO) δ 8.65 (s, 1H), 7.77 (d, J=1.9 Hz, 1H), 7.77 (d, J=8.7 Hz, 1H), 7.36 (dd, J=8.7 and 1.9 Hz, 1H), 6.96 (s, 1H), 3.70 (s, 3H).

Step C—Methyl 5-(6-chloro-1H-benzimidazol-1-yl)-3-{[1R)-1-(2-chloro-3-hydroxyphenyl)ethyl]oxy}-2-thiophenecarboxylate (Title Compound)

Methyl 5-(6-chloro-1H-benzimidazol-1-yl)-3-{[(1R)-1-(2-chloro-3-hydroxyphenyl)ethyl]oxy}-2-thiophenecarboxylate (500 mg, 1.7 mmol) and (1S)-1-(2-chloro-3-{[(1,1-dimethylethyl)(dimethyl)silyl]oxy}phenyl)ethanol (600 mg, 2.0 mmol) were coupled using a procedure analogous to Intermediate 2, Step C to give 450 mg of the desired product (77%). $^1$H NMR (400 MHz, d$_6$-DMSO) δ 10.24 (s, 1H), 8.65 (s, 1H), 7.77 (d, J=8.4 Hz, 1H), 7.63 (d, J=1.6 Hz, 1H), 7.36 (dd, J=8.6, 2.0 Hz, 1H), 7.34 (s, 1H), 7.17 (dd, J=8.0, 7.7 Hz 1H), 7.10 (dd, J=8.0, 1.6 Hz, 1H), 6.89 (dd, J=8.0, 1.6 Hz, 1H), 5.94 (q, J=6.4 Hz, 1H), 3.79 (s, 3H), 1.58 (d, J=6.4 Hz, 3H).

INTERMEDIATE 22

1,1-Dimethylethyl 4-({2-chloro-3-[(1S)-1-hydroxyethyl]phenyl}oxy)-1-piperidinecarboxylate

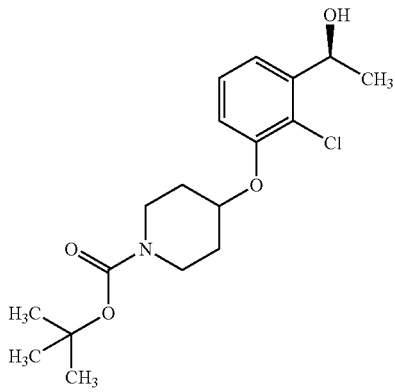

Step A—1,1-Dimethylethyl 4-[(3-acetyl-2-chlorophenyl)oxy]-1-piperidinecarboxylate

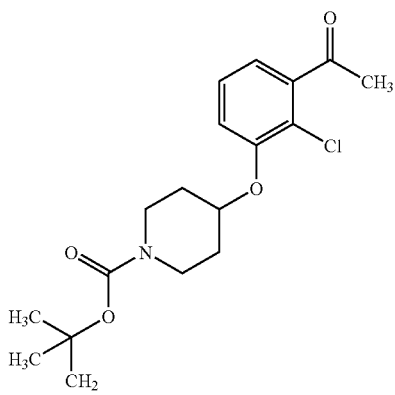

To a solution of 2-chloro-3-hydroxyacetophenone (35 g, 205 mmol) in ether (500 mL) was added 4-hydroxy-N-Boc-piperdine (45 g, 225 mmol), triphenylphosphine (65 g, 246 mmol) and finally di-tert-butylazodicarboxylate (57 g, 246 mmol) at such a rate that the solvent barely refluxes (over ~15 min). The reaction was stirred for 2 h, filtered to remove the triphenylphosphine oxide which precipitated during the reaction, then washed with 1N NaOH (200 mL), water (200 mL) and brine (200 mL). The organics were dried over MgSO$_4$, filtered and concentrated onto silica (100 g) on a rotovap. The preabsorbed solids were split into two batches and each purified on a 330 g ISCO column using a gradient of 100% DCM for 60 min to 80:20 DCM:EtOAc over 30 min, hold at 80:20 for 30 min. The appropriate fractions were combined, and the solvent removed to obtain 55 g of the title compound as a white solid (76%), 1H NMR (400 MHz, DMSO): δ 7.37-7.33 (m, 2H), 7.17-7.13 (m, 1H), 4.74-4.67 (m, 1H), 3.97-3.90 (m, 2H), 3.32-3.23 (m, 2H), 2.53 (s, 3H), 1.91-1.82 (m, 2H), 1.63-1.53 (m, 2H), 1.39 (s, 9H).

Step B—1,1-Dimethylethyl 4-({2-chloro-3-[(1S)-1-hydroxyethyl]phenyl}oxy)-1-piperidinecarboxylate (Title Compound)

To a solution of borane-dimethylsulfide complex (7.2 ml, 72 mmol) in THF (100 ml) was added a 1M solution of (R)-1-methyl-3,3-diphenyltetrahydro-3H-pyrrolo[1,2-c][1,3,2]oxazaborole in toluene (1.0 mL, 1.0 mmol). To this mixture was slowly added over 2 h a solution of 1,1-dimethylethyl 4-[(3-acetyl-2-chlorophenyl)oxy]-1-piperidinecarboxylate (36 g, 102 mmol) in THF (300 mL). The solution was stirred an additional 18 h then MeOH was added dropwise to quench any excess borane. To the solution was added silica (100 g) and the volatiles were evaporated under reduced pressure. The preabsorbed solids were purified In four batches on 120 g ISCO columns using a gradient of 100% hexanes to 55:45 hexanes:EtOAc over 40 min. After combining the fractions and removing the solvent, 26 g of the title compound was obtained as a white solid (70%). Chiral analysis showed 92% ee (AD-H column). The title compound could be further purified to >99% ee using SFC on a 3×25 cm AD-H column with a 90 g/min total flow, 90/10 CO2/MeOH, 103 bar, 27° C. The desired (S) enantiomer eluted first under these separation conditions. 1H NMR (400 MHz, DMSO): δ 7.34-7.22 (m, 2H), 7.13-7.09 (m, 1H), 5.33 (d, J=4.3 Hz, 1H), 5.10-5.01 (m, 1H), 4.71-4.62 (m, 1H), 3.66-3.54 (m, 2H), 3.37-3.26 (m, 2H), 1.96-1.82 (m, 2H), 1.70-1.53 (m, 2H), 1.44 (s, 9H), 1.32 (d, J=6.3 Hz, 3H).

INTERMEDIATE 23

Methyl 3-{[(1R)-1-(2-chloro-3-hydroxyphenyl)ethyl]oxy}-5-{6-[(methylsulfonyl)methyl]-1H-benzimidazol-1-yl}-2-thiophenecarboxylate

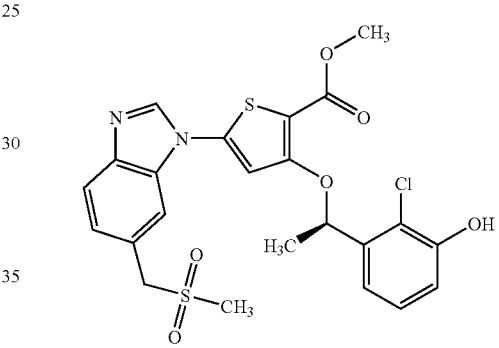

Step A—Methyl 5-[6-(chloromethyl)-1H-benzimidazol-1-yl]-3-{[(1R)-1-(2-chlorophenyl)ethyl]oxy}-2-thiophenecarboxylate

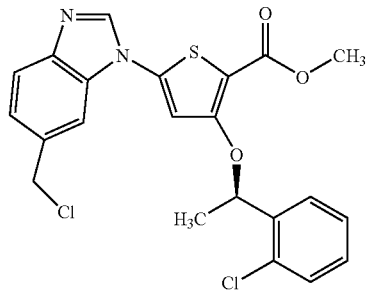

To a stirred solution of methyl methyl 3-{[(1R)-1-(2-chlorophenyl)ethyl]oxy}-5-[6-(hydroxymethyl)-1H-benzimidazol-1-yl]-2-thiophenecarboxylate (Intermediate 32, 3.0 g, 6.8 mmol), and triphenylphosphine (2.4 g, 9.1 mmol) in DCM (85 ml) was added N-chlorosuccinimide (1.2 g, 9.1 mmol). The reaction was then heated to reflux and stirred for 20 min, then cooled to rt. The reaction was diluted with DCM (400 mL) and half saturated aqueous brine solution (150 ml). The aqueous layer was then extracted with CH$_2$Cl$_2$. The combined organic layers were dried over Na$_2$SO$_4$, concentrated under vacuum and purified by silica gel chromatography (0 to 50% EtOAc:DCM) to give 2.86 g (90%) of the title compound as a white solid. MS (ESI): 461 [M+H]$^+$.

Step B—Methyl 3-{[(1R)-1-(2-chlorophenyl)ethyl]oxy}-5-{6-[(methylsulfonyl)methyl]-1H-benzimidazol-1-yl}-2-thiophenecarboxylate

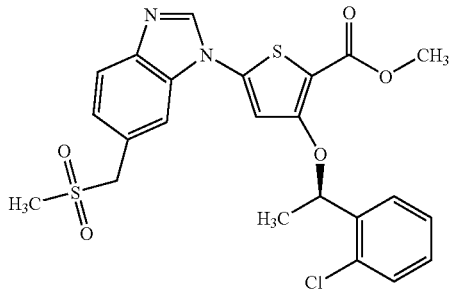

A mixture of methyl 5-[6-(chloromethyl)-1H-benzimidazol-1-yl]-3-{[(1R)-1-(2-chlorophenyl)ethyl]oxy}-2-thiophenecarboxylate (0.68 g, 1.5 mmol), methanesulfonic acid sodium salt (0.19 g, 1.3 mmol) and EtOH (15.0 ml) was added to a high-pressure glass reaction flask. The flask was sealed, then heated to 85° C. for approx. 16 h. The flask was cooled to rt, opened, and the reaction mixture concentrated under vacuum, then purified by silica gel chromatography (0 to 50% EtOAc:DCM) to give 0.61 g (92%) of the title compound as a light yellow solid. MS (ESI): 505 [M+H]+.

Step C—Methyl 3-hydroxy-5-{6-[(methylsulfonyl)methyl]-1H-benzimidazol-1-yl}-2-thiophenecarboxylate

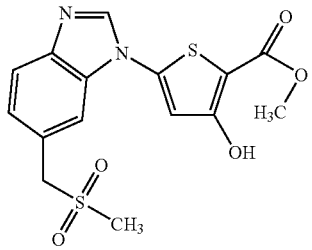

To methyl 3-{[(1R)-1-(2-chlorophenyl)ethyl]oxy}-5-{6-[(methylsulfonyl)methyl]-1H-benzimidazol-1-yl}-2-thiophenecarboxylate (0.61 g, 1.2 mmol) in DCM (5 mL) was added TFA (7 mL) and the mixture was stirred at 40° C. for 2 h. The volatiles were evaporated under reduced pressure and the residue was purified by flash column chromatography (0 to 80% EtOAc:DCM) to give 0.35 g (80%) of the title compound as a solid. MS (ESI): 367 [M+H]+.

Step D—Methyl 3-{[(1R)-1-(2-chloro-3-{[(1,1-dimethylethyl)(dimethyl)silyl]oxy}phenyl)ethyl]oxy}-5-{6-[(methylsulfonyl)methyl]-1H-benzimidazol-1-yl}-2-thiophenecarboxylate

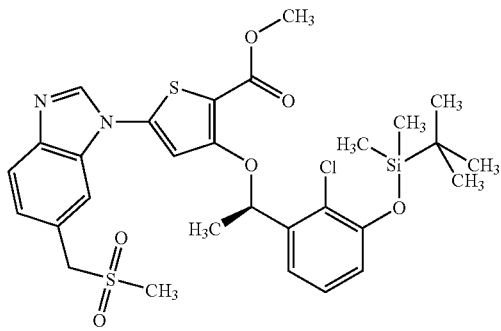

To a slurry of methyl 3-hydroxy-5-{6-[(methylsulfonyl)methyl]-1H-benzimidazol-1-yl}-2-thiophenecarboxylate (0.29 g, 0.80 mmol) and (1S)-1-(2-chloro-3-{[(1,1-dimethylethyl)(dimethyl)silyl]oxy}phenyl)ethanol (Intermediate 17, 0.51 g, 1.9 mmol) in THF (10 mL) was added 4-(diphenylphosphanyl)-N,N-dimethylaniline (0.72 g, 2.4 mmol) and di-tert-butylazodicarboxylate (0.55 g, 2.4 mmol). The clear, yellow solution was stirred for 24 h, and then silica gel (3 g) was added. The volatiles were evaporated under reduced pressure 5 and the residue was purified by flash column chromatography (0 to 50% EtOAc:DCM) to give 0.24 g (47%) of the title compound as a white solid. MS (ESI): 635 [M+H]+.

Step E—Methyl 3-{[(1R)-1-(2-chloro-3-hydroxyphenyl)ethyl]oxy}-5-{6-[(methylsulfonyl)methyl]-1H-benzimidazol-1-yl}-2-thiophenecarboxylate
(Title Compound)

To a solution of methyl 3-{[(1R)-1-(2-chloro-3-{[(1,1-dimethylethyl)(dimethyl)silyl]oxy}phenyl)ethyl]oxy}-5-{6-[(methylsulfonyl)methyl]-1H-benzimidazol-1-yl}-2-thiophenecarboxylate (0.24 g, 0.38 mmol) In MeOH (10 mL) was added a cesium fluoride (0.5 g, 3.3 mmol). The mixture was heated to 60° C. for 4 h and then cooled to room temperature, The reaction was partitioned between EtOAc (200 mL) and water (100 mL). The layers were separated, and the organics were washed with water (1×50 mL), dried over MgSO4, filtered and evaporated under reduced pressure to afford 0.16 g (78%) of the title compound as a white solid. MS (ESI): 521 [M+H]+.

INTERMEDIATE 24

4-Bromo-3-nitrophenyl trifluoromethyl ether

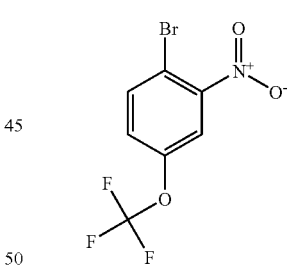

To a solution of 2-nitro-4-[(trifluoromethyl)oxy]aniline (2.0 g, 9.0 mmol) in acetonitrile (50 mL) was added tert-butylnitrile (7.4 g, 72 mmol). The solution was stirred 2 min and then Copper(II) bromide (40 g, 180 mmol) was added. The solution stirred for 1 h at rt. The reaction was partitioned between EtOAc (500 mL) and 1N HCl (aq) (100 mL). The layers were separated, and the organics were washed with 1N HCl (aq) (3×50 mL), dried over MgSO4, filtered, and the volatiles were evaporated under reduced pressure, and the residue was purified by flash column chromatography (0 to 20% EtOAc:hexanes) to give 2.0 g (78%) of the title compound. 1H NMR (400 MHz, CDCl3): δ 7.78 (d, J=8.79 Hz, 1H), 7.76 (s, 1H), 7.32 (s, 1H, J=8.79 Hz).

INTERMEDIATE 25

Methyl 3-{[(1R)-1-(2-chloro-3-hydroxyphenyl)ethyl]oxy}-5-{5-[(trifluoromethyl)oxy]-1H-benzimidazol-1-yl}-2-thiophenecarboxylate

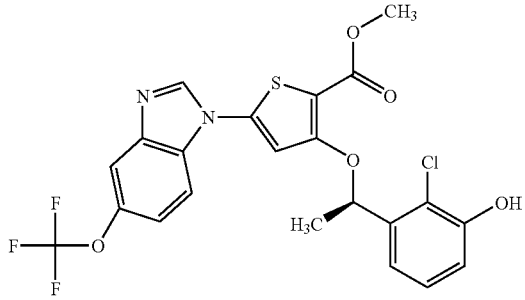

Step A—Methyl 3-{[(1R)-1-(2-chlorophenyl)ethyl]oxy}-5-({2-nitro-4-[(trifluoromethyl)oxy]phenyl}amino)-2-thiophenecarboxylate

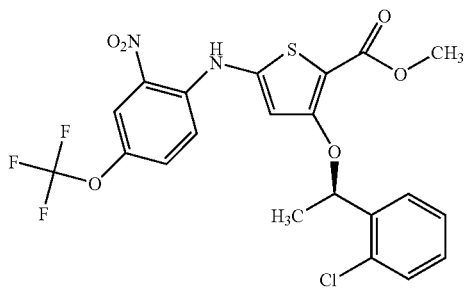

4-Bromo-3-nitrophenyl trifluoromethyl ether (2.0 g, 7.0 mmol) and methyl 5-amino-3-{[(1R)-1-(2-chlorophenyl)ethyl]oxy}-2-thiophenecarboxylate (2.2 g, 7.0 mmol) were dissolved in 1,4-dioxane (80 mL) with stirring in a flask equipped with a stir bar, reflux condenser, and thermometer. The solution was degassed for 15 min by bubbling $N_2$ through the stirring solution. 9,9-Dimethyl-4,5-bis(diphenylphosphino)xanthene (0.18 g, 0.31 mmol), cesium carbonate (11 g, 35 mmol), and tris(dibenzylideneacetone)dipalladium(0) (0.13 g, 0.14 mmol) were added. The reaction was heated to 60° C. and stirred for 16 h. The reaction was cooled to rt and filtered through Celite. The solid was washed with 20% MeOH in DCM. The volatiles were evaporated under reduced pressure and the residue was purified by flash column chromatography (0 to 50% EtOAc:DCM) to give 3.5 g (97%) of the title compound as a solid. MS (ESI): 516 [M+H]+.

Step B—Methyl 3-hydroxy-5-{5-[(trifluoromethyl)oxy]-1H-benzimidazol-1-yl}-2-thiophenecarboxylate

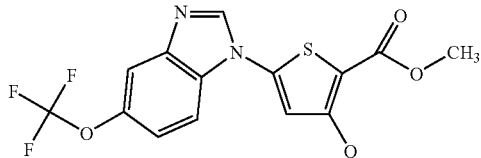

Methyl 3-{[(1R)-1-(2-chlorophenyl)ethyl]oxy}-5-({2-nitro-4-[(trifluoromethyl)oxy]phenyl}amino)-2-thiophenecarboxylate (3.5 g, 6.8 mmol) was dissolved in EtOAc (100 mL) with stirring. Sulfided platinum (5% weight on carbon, 1.32 g) was added, and the reaction was placed under 50 atm of $H_2$. After 36 h the reaction was filtered through a Celite pad washing with EtOAc. The filtrate was concentrated to afford 3.3 g of methyl 5-({2-amino-4-[(trifluoromethyl)oxy]phenyl}amino)-3-{[(1R)-1-(2-chlorophenyl)ethyl]oxy}-2-thiophenecarboxylate which was immediately dissolved in trimethyl orthoformate (50 mL) with stirring. Pyridinium p-toluenesulfonate (0.26 g, 1.0 mmol) was added in a single portion. The reaction was stirred for 24 h. The volatiles were evaporated under reduced pressure and the residue was dissolved in $CHCl_3$ (30 mL) and TFA (30 mL). The mixture was heated to 60° C. for 2 h. The volatiles were evaporated under reduced pressure and the residue was quenched by the addition of 7 N ammonia in MeOH (40 mL). The volatiles were evaporated under reduced pressure and the residue was partitioned between DCM (200 mL) and water (100 mL). The layers were separated, and the organics were washed with water (3×50 mL), dried over $Na_2SO_4$, filtered and evaporated under reduced pressure. The resulting solid was taken up as a suspension in ether/hexanes(1/9), filtered and washed with ether/hexanes(1/9) to afford 1.5 g (62%) of the title compound as a solid. MS (ESI): 359 [M+H]+.

Step C—Methyl 3-{[(1R)-1-(2-chloro-3-hydroxyphenyl)ethyl]oxy}-5-{5-[(trifluoromethyl)oxy]-1H-benzimidazol-1-yl}-2-thiophenecarboxylate (Title Compound)

To a slurry of methyl 3-hydroxy-5-{5-[(trifluoromethyl)oxy]-1H-benzimidazol-1-yl}-2-thiophenecarboxylate (0.71 g, 2.0 mmol) and (1S)-1-(2-chloro-3-{[(1,1-dimethylethyl)(dimethyl)silyl]oxy}phenyl)ethanol (Intermediate 17, 0.63 g, 2.2 mmol) so DCM (20 mL) was added triphenylphosphine (1.1 g, 4.0 mmol) and di-tert-butylazodicarboxylate (0.92 g, 4.0 mmol). The clear, yellow solution was stirred for 1 h, then silica gel (5 g) was added. The volatiles were evaporated under reduced pressure and the residue was purified by flash column chromatography (0 to 50% EtOAc:DCM) to give 1.1 g (1.8 mmol) of the methyl 3-{[(1R)-1-(2-chloro-3-{[(1,1-dimethylethyl)(dimethyl)silyl]oxy}phenyl)ethyl]oxy}-5-[5-(1-methyl-1H-pyrazol-4-yl)-1H-benzimidazol-1-yl]-2-thiophenecarboxylate which was dissolved in THF (15 mL). 1 N tetrabutylammonium fluoride in THF (1.8 mL, 1.8 mmol) was added. After 10 min, silica (3 g) was added, the volatiles were evaporated under reduced pressure and the residue was purified by flash column chromatography (0 to 70% EtOAc:DCM) to afford 0.36 g (47%) of the title compound as a solid.
$^1H$ NMR (400 MHz, $CD_3OD$): δ 8.48 (s, 1H), 7.63 (s, 1H), 7.40 (d, J=8.97 Hz, 1H), 7.30 (d, J=8.79 Hz, 1H), 7.13 (m, 2H), 7.0 (s, 1H), 6.8 (d, J=7.51 Hz, 1H), 5.95 (q, J=6.17 Hz, 1H), 3.88 (s, 3H), 1.68(d, J=6.23 Hz, 3H).

INTERMEDIATE 26

Methyl 3-{[(1R)-1-(2-chloro-3-hydroxyphenyl)ethyl]oxy}-5-{6-[(trifluoromethyl)oxy]-1H-benzimidazol-1-yl}-2-thiophenecarboxylate

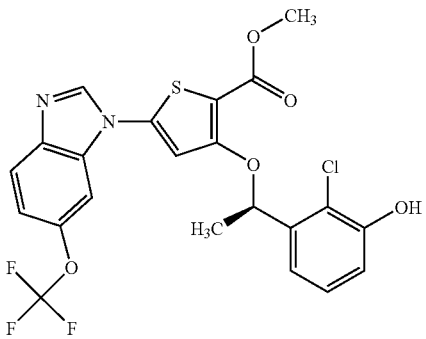

The title compound was prepared using procedures analogous to Intermediate 25. MS (ESI): 513 [M+H]+.

INTERMEDIATE 27

Methyl 3-{[(1R)-1-(2-chloro-3-hydroxyphenyl)ethyl]oxy}-5-(5,6-difluoro-1H-benzimidazol-1-yl)-2-thiophenecarboxylate

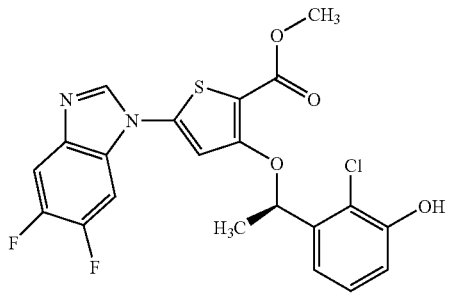

Step A—Methyl 5-(5,6-difluoro-1H-benzimidazol-1-yl)-3-hydroxy-2-thiophenecarboxylate

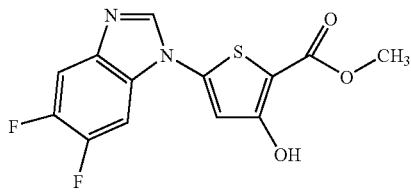

To a mixture of 5,6-difluoro-1H-benzimidazole (0.5 g, 3.2 mmol) and 2-chloro-3-oxo-2,3-dihydro-2-thiophenecarboxylate (0.72 g, 3.7 mmol) in 10 mL of CHCl$_3$ was added N-methylimidazole (0.4 g, 4.9 mmol) and NaHCO$_3$ (0.82 g, 9.7 mmol). The mixture was heated to 55° C. for 24 h. Silica gel (2 g) was added and the volatiles were evaporated under reduced pressure and the residue was purified by flash column chromatography (0 to 50% EtOAc:DCM) to afford 0.71 g of the titled compound. MS (ESI): 311 [M+H]$^+$.

Step B—Methyl 3-{[(1R)-1-(2-chloro-3-hydroxyphenyl)ethyl]oxy}-5-(5,6-difluoro-1H-benzimidazol-1-yl)-2-thiophenecarboxylate (Title Compound)

The title compound was prepared using a procedure analogous to Intermediate 25, Step C. MS (ESI); 465 [M+H]$^+$.

INTERMEDIATE 28

Methyl 5-(5-bromo-1H-benzimidazol-1-yl)-3-[(phenylmethyl)oxy]-2-thiophenecarboxylate

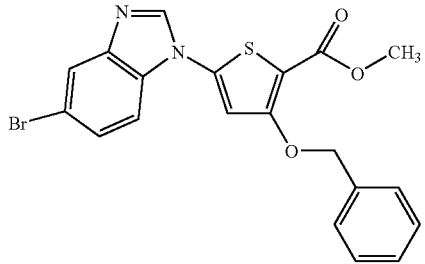

Step A—Methyl 5-nitro-3-[(phenylmethyl)oxy]-2-thiophenecarboxylate

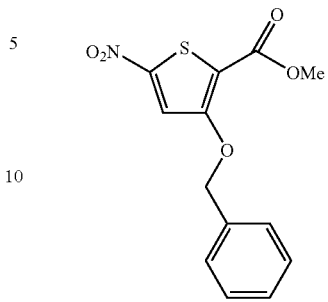

To a solution of methyl 3-hydroxy-5-nitro-2-thiophenecarboxylate, which can be prepared according to the procedure in *J. Chem. Research (M)*, 2001 1001-1004, (26.4 g, 130 mmol) in DMF (300 mL) was added K$_2$CO$_3$ (20.0 g, 145 mmol), followed by benzyl bromide (22.3 g, 130 mmol), and the reaction mixture was stirred at rt for 18 h. The solution was filtered to remove the solids, and the filtrate was poured slowly into 1 N HCl (600 mL). A yellow solid precipitated, and this solid was collected by vacuum filtration and was washed with water (3×300 mL) providing 37.0 g (97%) of the title compound.

$^1$H NMR (400 MHz, DMSO-d$_6$): δ 8.23 (s, 1H), 7.48-7.28 (m, 5H), 5.37 (s, 2H), 3.79 (s, 3H).

Step B—Methyl 5-amino-3-[(phenylmethyl)oxy]-2-thiophenecarboxylate

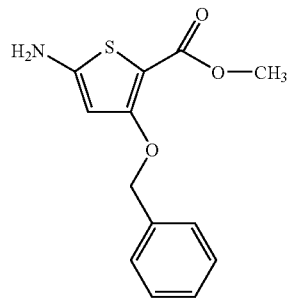

To a flask equipped with a temperature probe, an overhead mechanical stirrer, a reflux condenser, and an addition funnel was added iron powder (38.3 g, 650 mmol) and acetic acid (230 mL). The iron/acetic acid slurry was 5 stirred mechanically and heated to an internal temperature of 50° C. To the addition funnel was added a solution of methyl 5-nitro-3-[(phenylmethyl)oxy]-2-thiophenecarboxylate (37.0 g, 126 mmol) in acetic acid (300 mL). The solution in the addition funnel was then added dropwise to the iron/acetic acid slurry at a rate such that the internal temperature was maintained at <60° C. (2.5 h total addition time). The reaction mixture was cooled to rt, and the entire mixture was then filtered through filter paper to remove insoluble material, rinsing with DCM (500 mL). The solution was concentrated to about 200 mL, rediluted with EtOAc (500 mL) and then quenched by addition of 6 N NaOH (250 mL) and saturated aqueous NaHCO$_3$ (200 mL). The aqueous and organic fractions were separated. The aqueous fraction was extracted with EtOAc (2×400 mL). The organic fractions were combined, dried over MgSO$_4$, filtered, and concentrated to afford 27.0 g (82%) of the title compound as a tan solid. $^1$H NMR (400 MHz, DMSO-d$_6$): δ 7.42-7.26 (m, 5H), 6.78 (s, 2H), 5.76 (s, 1H), 5.10 (s, 2H), 3.56 (s, 3H); MS (ESI): 286 [M+H]$^+$.

Step C—Methyl 5-[(4-bromo-2-nitrophenyl)amIno]-3-[(phenylmethyl)oxy]-2-thiophenecarboxylate

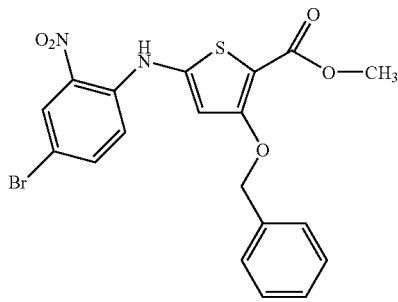

Methyl 5-amino-3-[(phenylmethyl)oxy]-2-thiophenecarboxylate (3.2 g, 12 mmol) and 1,4-dibromo-2-nitrobenzene (3.9 g, 14 mmol) were dissolved in 1,4-dioxane (100 mL). The solution was degassed for 15 min by bubbling $N_2$ through the stirring solution. XANTPHOS (0.32 g, 0.55 mmol), cesium carbonate (20 g, 63 mmol), and tris(dibenzylideneacetone)dipalladium(0) (0.23 g, 0.25 mmol) were added. The reaction was heated to 60° C. and stirred for 16 h. The reaction was cooled to rt and filtered through Celite. The solid was washed with 20% MeOH in DCM. Silica gel was added and the volatiles were evaporated under reduced pressure and the residue was purified by flash column chromatography (DCM to EtOAc) to give 3.9 g (70%) of the title compound as a solid. $^1$H NMR (400 MHz, CDCl$_3$): δ 9.54 (s, 1H), 8.33 (s, 1H), 7.53-7.20 (m, 7H), 6.56 (s, 1H), 5.23 (s, 2H), 3.85 (s, 3H).

Step D—Methyl 5-(5-bromo-1H-benzimidazol-1-yl)-3-[(phenylmethyl)oxy]-2-thiophenecarboxylate (Title Compound)

Methyl 5-[(4-bromo-2-nitrophenyl)amino]-3-[(phenylmethyl)oxy]-2-thiophenecarboxylate (3.9 g, 8.5 mmol) was dissolved in EtOAc (100 mL) with stirring. Sulfided platinum (5% weight on carbon, 1.3 g) was added, and the reaction was placed under 50 psi of $H_2$. After 16 h, additional sulfided platinum (5% weight on carbon, 1.3 g) was added, and the reaction was placed under 50 psi of $H_2$. After an additional 24 h, the reaction was filtered through a Celite pad washing with EtOAc. The filtrate was concentrated to afford 3.8 g of methyl 5-({2-amino-4-[(trifluoromethyl)oxy]phenyl}amino)-3-{[(1R)-1-(2-chlorophenyl)ethyl]oxy}-2-thiophenecarboxylate which was immediately dissolved in trimethyl orthoformate (50 mL) with stirring. Formic acid (1.0 mL, 26 mmol) was added and the reaction was stirred at 60° C. for 24 h. The volatiles were evaporated under reduced pressure and the residue was partitioned between DCM (200 mL) and water (100 mL). The layers were separated, and the organics were washed with water (3×50 mL), dried over MgSO$_4$ and filtered. Silica gel was added and the solvent evaporated under reduced pressure, and the residue was purified by flash column chromatography (Hexanes to EtOAc) to afford 3.3 g (87%) of the title compound as a solid. $^1$H NMR (400 MHz, CDCl$_3$): δ 8.05 (d, 1H), 8.01-7.99 (m, 1H), 7.49-7.35 (m, 6H), 7.26 (s, 1H), 6.88 (s, 1H), 5.33 (s, 2H), 3.91 (s, 3H); MS (ESI): 443 & 445 [M+1 & M+3]$^+$.

INTERMEDIATE 29

Methyl 5-amino-3-({(1R)-1-[2-(trifluoromethyl)phenyl]ethyl}oxy)-2-thiophenecarboxylate

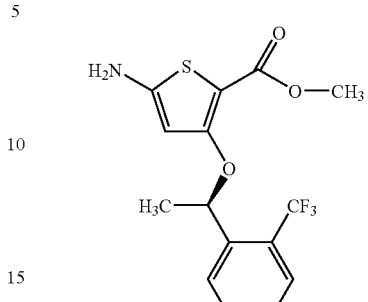

Step A—Methyl 5-nitro-3-({(1R)-1-[2-(trifluoromethyl)phenyl]ethyl}oxy)-2-thiophenecarboxylate

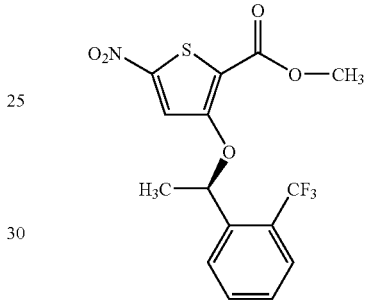

A slurry of polymer-supported triphenylphosphine (62.4 g, 2.21 mmol/g, 138 mmol) in DCM (1.0 L) was stirred at rt for 10 minutes. The mixture was cooled to 0° C. Methyl 3-hydroxy-5-nitro-2-thiophenecarboxylate (20.0 g, 98.4 mmol), which may be prepared in a manner analogous to the literature procedure (Barker, J. M.; Huddleston, P. R.; Wood, M. L.; Burkitt, S. A. *Journal of Chemical Research* (Miniprint) 2001, 1001-1022) was added, followed by (1S)-1-[2-(trifluoromethyl)phenyl]ethanol (26.2 g, 138 mmol) and di-tert-butyl azodicarboxylate (31.7 g, 138 mmol), The reaction mixture was stirred at rt for 21.25 h and then was filtered through a fritted funnel and concentrated. The residue was treated with 4 N HCl in 1,4-dioxane (300 mL) and stirred at rt for 3 h. The mixture was then quenched by addition of 3 N NaOH (300 mL) and saturated aqueous NaHCO$_3$ (200 mL). The mixture was extracted with DCM (3×250 mL). The combined organic fractions were dried over MgSO$_4$, filtered, and concentrated onto silica gel. Purification by column chromatography (0 to 25% EtOAc:hexanes) provided 36.1 g (98%) of the title compound as yellow oil. $^1$H NMR (300 MHz, CDCl$_3$): δ 7.82 (d, 1H, J=7.8 Hz), 7.68 (d, 1H, J=7.8 Hz), 7.59 (t 1H, J=7.4 Hz), 7.46 (s, 1H), 7.42 (t, 1H, J=7.6 Hz), 5.77 (q, 1H, J=6.1 Hz), 3.94 (s, 3H), 1.74 (d, 3H, J=6.1 Hz).

Step B—Methyl 5-amino-3-({(1R)-1-[2-(trifluoromethyl)phenyl]ethyl}oxy)-2-thiophenecarboxylate (Title Compound)

To a flask equipped with a temperature probe, an overhead mechanical stirrer, a reflux condenser, and an addition funnel was added iron powder (26.8 g, 481 mmol) and acetic acid (130 mL). The iron/acetic acid slurry was stirred mechanically and heated to an internal temperature of 50° C. To the addition funnel was added a solution of methyl 5-nitro-3-({(1R)-1-[2-(trifluoromethyl)phenyl]ethyl}oxy)-2-thiophenecarboxylate (36.1 g, 96.1 mmol) in acetic acid (160 mL). The solution in the addition funnel was then added dropwise to the iron/acetic acid slurry at a rate such that the internal temperature was maintained at <60°C. (2.5 h total addition time). The reaction mixture was cooled to room temperature, diluted with DCM (500 mL), and then quenched by addition of 6 N sodium hydroxide (750 mL) and saturated aqueous NaHCO$_3$ (200 mL), The entire mixture was then filtered through a pad of Celite to remove insoluble material, rinsing the Celite with additional DCM (250 mL). The aqueous and organic fractions were separated. The aqueous fraction was extracted with EtOAc (2×400 mL). The organic fractions were combined, dried over MgSO$_4$, filtered, and concentrated to afford 30.7 g (92%) of the title compound as an orange solid.

$^1$H NMR (300 MHz, CDCl$_3$): δ 7.89 (d, 1H, J=7.7 Hz), 7.62 (d, 1H, J=7.7 Hz), 7.56 (t, 1H, J=7.7 Hz), 7.36 (t, 1H, J=7.7 Hz), 5.72 (s, 1H), 5.65 (q, 1H, J=6.3 Hz), 4.26 (br s, 2H), 3.80 (s, 3H), 1.66 (d, 3H, J=6.3 Hz); MS (APCI): 368.00 [M+Na]$^+$.

INTERMEDIATE 30

Methyl 5-amino-3-{[(1R)-1-(2-chlorophenyl)ethyl]-oxy}-2-thiophenecarboxylate

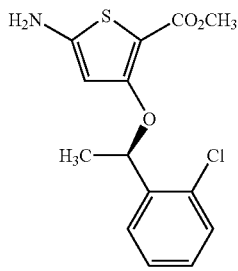

Step A—Methyl 3-{[(1R)-1-(2-chlorophenyl)ethyl]oxy}-5-nitro-2-thiophenecarboxylate

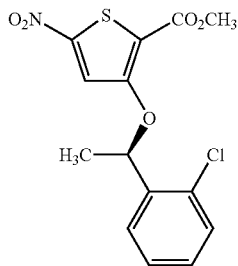

Methyl 3-{[(1R)-1-(2-chlorophenyl)ethyl]oxy}-5-nitro-2-thiophenecarboxylate was prepared from methyl 3-hydroxy-5-nitro-2-thiophenecarboxylate and (1S)-1-(2-chlorophenyl)ethanol by a procedure analogous to Intermediate 29, Step A. $^1$H NMR (400 MHz, DMSO-d$_6$): δ 7.96 (s, 1H), 7.65 (dd, 1H, J=1.7, 7.8 Hz), 7.47 (dd, 1H, J=1.5, 7.7 Hz), 7.40 (dt, 1H, J=1.3, 7.5 Hz), 7.34 (dt, 1H, J=1.9, 7.5 Hz), 5.98 (q, 1H, J=6.0 Hz), 3.85 (s, 3H), 1.59 (d, 3H, J=6.2 Hz).

Step B—Methyl 5-amino-3-{[(1R)-1-(2-chlorophenyl)ethyl]oxy}-2-thiophenecarboxylate (Title Compound)

Methyl 5-amino-3-{[(1R)-1-(2-chlorophenyl)ethyl]oxy}-2-thiophenecarboxylate was prepared from methyl 3-{[(1R)-1-(2-chlorophenyl)ethyl]oxy}-5-nitro-2-thiophenecarboxylate by a procedure analogous to Intermediate 29, Step B. $^1$H NMR (400 MHz, DMSO-d$_6$): δ 7.54 (dd, 1H, J=1.8, 7.9 Hz), 7.45 (dd, 1H, J=1.4, 7.7 Hz), 7.37 (dt, 1H, J=1.4, 7.7 Hz), 7.31 (dt, 1H, J=1.8, 7.6 Hz), 6.76 (br s, 2H), 5.57 (q, 1H, J=6.2 Hz), 5.49 (s, 1H), 3.63 (s, 3H), 1.51 (d, 3H, J=6.4 Hz); MS (ESI): 334.03 [M+Na]$^+$.

INTERMEDIATE 31

Methyl 5-[6-(hydroxymethyl)-1H-benzimidazol-1-yl]-3-({(1R)-1-[2-(trifluoromethyl)phenyl]ethyl}oxy)thiophene-2-carboxylate

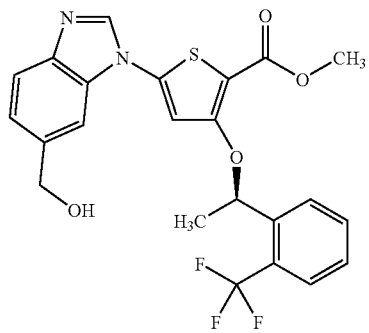

Step A—5-(Hydroxymethyl)-2-nitrophenol

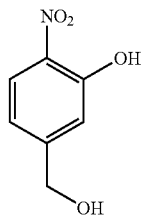

To a mixture of 3-hydroxy-4-nitrobenzoic acid (5.0 g, 27 mmol) in 1,2-dichloroethane (100 mL) was added trimethyl borate (4.9 mL, 44 mmol), followed by boron trifluoride diethyl etherate (5.5 mL, 44 mmol). Borane-pyridine complex (4.1 mL, 41 mmol) was then slowly added drop wise. The reaction was stirred 4 h at rt, then cooled to 0° C. and quenched with MeOH (10 mL). The mixture was concentrated under vacuum and the residue taken up in toluene (200 mL), then extracted with aqueous 1 N NaOH (3×100 mL). The combined aqueous layers were adjusted to pH 1.0 by addition of 12 N HCl, then extracted with EtOAc (3×250 mL). The combined organic layers were washed with water, brine, dried over MgSO$_4$ and concentrated under vacuum to give 4.55 g (98%) of the title compound as a light yellow solid. $^1$H NMR (400 MHz, DMSO-d$_6$): δ 10.87 (s, 1H), 7.85 (d, 1H, J=8.6 Hz), 7.08 (s, 1H), 6.88 (dd, 1H, J=1.19, 8.51 Hz), 5.43 (s, 1H), 3.33 (s, 2H).

Step B—3-Hydroxy-4-nitrobenzyl pivalate

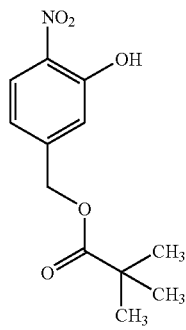

A mixture of 5-(hydroxymethyl)-2-nitrophenol (11.4 g, 67.2 mmol) and 3-(2,2-dimethylpropanoyl)-1,3-thiazolidine-2-thione (15.0 g, 73.9 mmol), which may be prepared in a manner analogous to the literature procedure (Yamada, S. *Tetrahedron Letters* 1992, 33, 2171-2174), was stirred in toluene (670 mL) at 100° C. for 40 h, then cooled to rt. The reaction was concentrated under vacuum to a volume of approximately 200 mL and the resulting slurry was filtered through filter paper, washing the solid with cold toluene. The filtrate was then concentrated under vacuum and purified by silica gel chromatography eluting with a gradient of 0-to-20% EtOAc/hexanes to give 11.1 g (65%) of the title compound as a clear yellow oil. $^1$H NMR (400 MHz, DMSO-d$_6$): δ 11.05 (s, 1H), 7.87 (d, 1H, J=8.42 Hz), 7.06 (s, 1H), 6.90 (dd, 1H, J=1.46, 8.42 Hz), 5.09 (s, 2H), 1.18 (s, 9H).

Step C—4-Nitro-3-{[(trifluoromethyl)sulfonyl]oxy}benzyl pivalate

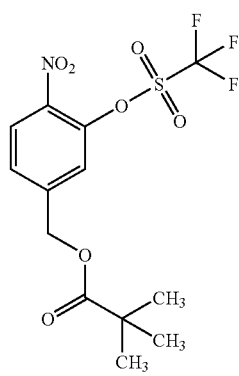

To a stirred, cooled (0° C.) solution of 3-hydroxy-4-nitrobenzyl pivalate (11.1 g, 43.9 mmol) and N-phenyltrifluoromethanesulfonimide (16.5 g, 46.2 mmol) in DCM (220 mL) was slowly added N,N-diisopropylethylamine (15.5 mL, 88.9 mmol). The reaction was stirred for 45 min at 0° C., then 45 min at rt. The reaction was then concentrated under vacuum and purified by silica gel chromatography eluting with a gradient of 5-to-20% EtOAc/hexanes to give 16.9 g (99%) of the title compound as an off white solid. $^1$H NMR (400 MHz, DMSO-d$_6$): δ 8.36 (d, 1H, J=8.42 Hz), 7.75-7.69 (m, 2H), 5.27 (s, 2H), 1.19 (s, 9H).

Step D—Methyl 5-[(5-{[(2,2-dimethylpropanoyl)oxy]methyl}-2-nitrophenyl)amino]-3-({(1R)-1-[2-(trifluoromethyl)phenyl]ethyl}oxy)thiophene-2-carboxylate

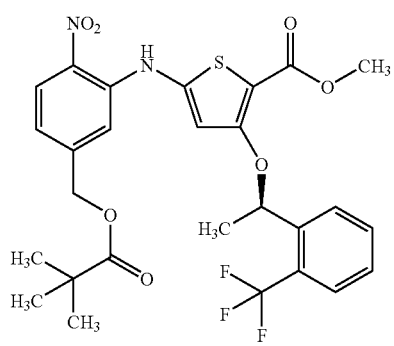

A mixture of 4-nitro-3-([(trifluoromethyl)sulfonyl]oxy)benzyl pivalate (1.0 g, 2.6 mmol), methyl 5-amino-3-({(1R)-1-[2-(trifluoromethyl)phenyl]ethyl}-oxy)thiophene-2-carboxylate (1.3 g, 3.9 mmol), tetrakis(triphenylphosphine)palladium (0) (150 mg, 0.13 mmol), triphenylphosphine (68 mg, 0.26 mmol) and K$_2$CO$_3$ (900 mg, 6.5 mmol) were stirred in toluene (5.2 mL) at 100 ° C. for 2 h, then cooled to rt and filtered through Celite, washing with EtOAc and DCM. The filtrate was concentrated under vacuum and purified by silica gel chromatography eluting with a gradient of 5-to-25% EtOAc/hexane to give 1.26 g (84%) of the title compound as a red oil $^1$H NMR (400 MHz, DMSO-d$_6$): δ 9.75 (s, 1H), 8.09 (d, 1H, J=8.6 Hz), 7.89 (d, 1H, J=7.87 Hz), 7.69-7.78 (m, 2H), 7.52 (t, J=7.59 Hz), 7.34 (s, 1H), 7.01 (dd, 1H, J=1.46, 8.60 Hz), 6.62 (s, 1H), 5.70-5.75 (m, 1H), 5.07 (s, 2H), 3.74 (s, 3H), 1.58 (d, 3H, J=6.22 Hz), 1.13 (s, 9H).

Step E—Methyl 5-[(2-amino-5-{[(2,2-dimethylpropanoyl)oxy]methyl}phenyl)amino]-3-({(1R)-1-[2-(trifluoromethyl)phenyl]ethyl}oxy)thiophene-2-carboxylate

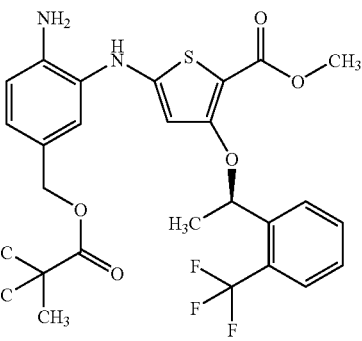

A mixture of methyl 5-[(5-{[(2,2-dimethylpropanoyl)oxy]methyl}-2-nitrophenyl)amino]-3-({(1R)-1-[2-(trifluoromethyl)phenyl]ethyl}oxy)thiophene-2-carboxylate (2.4 g, from a different batch using procedure analogous to Intermediate 31, Step D 4.2 mmol) and platinum (sulfided, 5 wt % on carbon) (811 mg, 0.21 mmol) in EtOAc (30 ml) was added to a high-pressure reaction flask. The reaction was purged with vacuum and N$_2$ gas, then H$_2$ gas was applied at 50 psi for 1 h. The reaction mixture was filtered through Celite, washing with EtOAc. The filtrate was concentrated under vacuum to give 2.3 g (99%) of the title compound as a tan solid. $^1$H NMR (400 MHz, DMSO-d$_6$): δ 8.62 (s, 1H), 7.84 (d, 1H, J=7.87 Hz), 7.72 (dd, 2H, J=7.60, 13.09 Hz), 7.50 (t, 1H, J=7.60 Hz), 7.01 (d, 1H, J=1.46 Hz), 6.88 (dd, 1H, J=1.74, 8.15 Hz), 6.68 (d, 1H, J=8.24 Hz), 5.83 (s, 1H), 5.59-5.65 (m, 1H), 4.97 (s, 2H), 4.85 (s, 2H), 3.64 (s, 3H), 1.55 (d, 3H, J=6.23 Hz), 1.11 (s, 9H); MS (ESI): 551 [M+H]$^+$.

Step F—Methyl 5-(6-{[(2,2-dimethylpropanoyl)oxy]methyl}-1H-benzimidazol-1-yl)-3-({(1R)-1-[2-(trifluoromethyl)phenyl]ethyl}oxy)thiophene-2-carboxylate

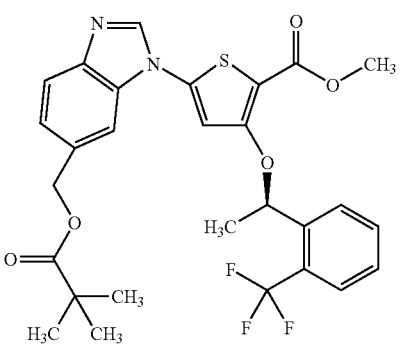

To a mixture of methyl 5-[(2-amino-5-{[(2,2-dimethylpropanoyl)oxy]methyl}phenyl)amino]-3-({(1R)-1-[2-(trifluoromethyl)phenyl]ethyl}-oxy)thiophene-2-carboxylate (2.3 g, 4.1 mmol) in triethylorthoformate (10 mL, 60 mmol) and DCM (3 mL) was added pyridinium p-toluenesulfonate (100 mg, 0.40 mmol). The reaction was stirred at 40° C. for 1 h, then cooled to rt. The entire reaction mixture was loaded onto silica gel and purified by silica gel chromatography eluting with a gradient of 0-to-50% EtOAc/hexanes to give 2.0 g (86%) of the title compound as a light tan solid. $^1$H NMR (400 MHz, DMSO-d$_6$): δ 8.65 (s, 1H), 7.99 (d, 1H, J=7.87 Hz), 7.75-7.80 (m, 2H), 7.72 (d, 1H, J=7.87 Hz), 7.63 (s, 1H), 7.53 (t, 1H, J=7.60 Hz), 7.40 (s, 1H), 7.35 (d, 1H, J=8.42 Hz), 5.96 (q, 1H, J=6.10 Hz), 5.21 (s, 2H), 3.83 (s, 3H), 1.65 (d, 3H, J=6.23 Hz), 1.16 (s, 9H); MS (ESI): 581 [M+H]$^+$.

Step G—Methyl 5-[6-(hydroxymethyl)-1H-benzimidazol-1-yl]-3-({(1R)-1-[2-(trifluoromethyl)phenyl]ethyl}oxy)thiophene-2-carboxylate (Title Compound)

To a stirred solution of methyl 5-(6-{[(2,2-dimethylpropanoyl)oxy]methyl}-1H-benzimidazol-1-yl)-3-({(1R)-1-[2-(trifluoromethyl)phenyl]ethyl}oxy)thiophene-2-carboxylate (5.21 g, from a different batch using procedure analogous to Intermediate 31, Step F, 9.30 mmol) in MeOH (24 mL) was added 0.5M NaOH in MeOH (24.0 ml, 12.0 mmol). The reaction was stirred at rt for 72 h, then quenched with acetic acid (2 mL). The mixture was diluted with DCM (350 mL) and half saturated aqueous brine solution (150 mL), The aqueous layer was extracted with DCM (250 mL). The combined organics were dried over MgSO$_4$ and concentrated under vacuum to give 4.40 g (99%) of the title compound as a light yellow solid. $^1$H NMR (400 MHz, DMSO-d$_6$): δ 8.58 (s, 1H), 7.99 (d, 1H, J=7.87 Hz), 7.69-7.81 (m, 3H), 7.51-7.58 (m, 2H), 7.38 (s, 1H), 7.30 (d, 1H, J=8.42), 5.96 (q, 1H, J=6.10 Hz), 5.30 (t, 1H, J=5.77 Hz) 4.82 (d, 2H, J=5.86 Hz), 3.83 (s, 3H), 1.65 (d, 3R J=6.23 Hz); MS (ESI): 477 [M+H]$^+$.

INTERMEDIATE 32

Methyl 3-{[(1R)-1-(2-chlororphenyl)ethyl]oxy}-5[6-(hydroxymethyl)-1H-benzimidazol-1-yl]-2thiophenecarboxylate

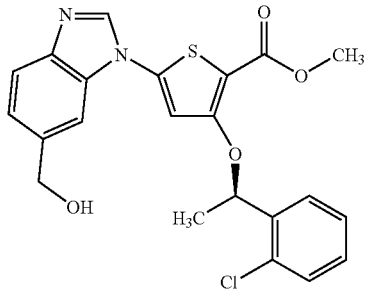

Step A—Methyl 3-{[(1R)-1-(2-chlorophenyl)ethyl]oxy}-5-[(5-{[(2,2-dimethylpropanoyl)oxy]methyl}-2-nitrophenyl)amino]-2-thiophenecarboxylate

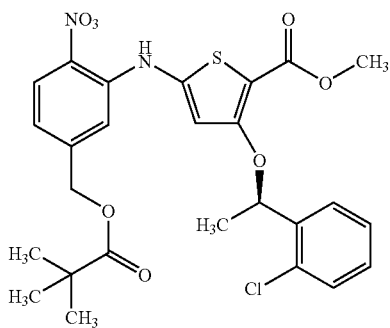

To a mixture of (4-nitro-3-{[(trifluoromethyl)sulfonyl]oxy}phenyl)methyl 2,2-dimethylpropanoate (1.0 g, 2.6 mmol), methyl 5-amino-3-{[(1R)-1-(2-chlorophenyl)ethyl]oxy}-2-thiophenecarboxylate (Intermediate 30) (860 mg, 2.8 mmol), tris(dibenzylideneacetone)dipalladium(0) (70 mg, 0.076 mmol), and XANTPHOS (90 mg, 0.16 mmol) was added toluene (7.0 mL). Stirring was begun, followed by the addition of Cs$_2$CO$_3$ (3.0 g, 9.1 mmol). The reaction was heated to 60° C. and stirred for 30 min, then cooled to rt, diluted with EtOAc and filtered through Celite, washing the solids with EtOAc and DCM. The filtrate was concentrated under vacuum and chromatographed on silica gel (40 g), eluting with a 5-to-15% gradient of acetone/hexane to give 920 mg (65%) of the title compound as a red: solid. $^1$H NMR (400 MHz, DMSO-d$_6$): δ 9.77 (s, 1H), 8.09 (d, 1H, J=8.61 Hz), 7.63 (dd, 1H, J=7.69 and 1.65 Hz), 7.46-7.30 (m, 4H), 7.01 (dd, 1H, J=8.79 and 1.47 Hz), 6.67 (s, 1H), 5.76-5.70 (m, 1H), 5.09 (s, 2H), 3.73 (s, 3H), 1.56 (d, 3H, J=6.23 Hz), 1.14 (s, 9H); MS (ESI): 547 [M+H]$^+$.

Step B—Methyl 5-[(2-amino-5-{[(2,2-dimethylpropanoyl)oxy]methyl}-phenyl)amino]-3-{[(1R)-1-(2-chlorophenyl)ethyl]oxy}-2-thiophenecarboxylate

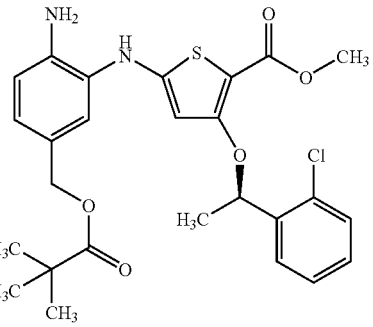

To a high-pressure hydrogenation reaction flask was added methyl 3-{[(1R)-1-(2-chlorophenyl)ethyl]oxy}-5-[(5-{[(2,2-dimethylpropanoyl)oxy]methyl}-2-nitrophenyl)amlno]-2-thiophenecarboxylate (6.5 g, from a different batch using procedure analogous to Intermediate 32, Step A, 12 mmol), 5% by weight platinum on carbon (sulfided) (2.2 g, 0.56 mmol) and EtOAc (95 mL). The flask was purged with N$_2$ (gas) vacuum (3×), then with H$_2$ (gas) vacuum (3×). Hydrogen gas was then applied at 50 psi for 3 h. The reaction mixture was then filtered through Celite, washing the solids with EtOAc and DCM. The filtrate was then concentrated under vacuum to give 5.5 g (89%) of the title compound as a yellow solid. MS (ESI): 517 [M+H]$^+$.

Step C—Methyl 3-{[(1R)-1-(2-chlorophenyl)ethyl]oxy}-5-(6-{[(2,2-dimethylpropanoyl)oxy]methyl}-1H-benzimidazol-1-yl)-2-thiophenecarboxylate

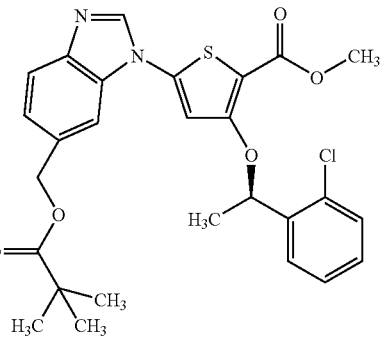

A stirred mixture of methyl 5-[(2-amino-5-{[(2,2-dimethylpropanoyl)oxy]methyl}phenyl)amino]-3-{[(1R)-1-(2- chlorophenyl)ethyl]oxy}-2-thiophenecarboxylate (5.5 g, 11 mmol), pyridinium p-toluene sulfonate (265 mg, 1.0 mmol) and triethylorthoformate (15 mL) was heated to 40° C. for 1 h, then cooled to rt. The entire mixture was poured onto a silica gel cartridge (25 g) and purified by silica gel chromatography (120 g), eluting with 100% hexanes for 10 min, then a 0-to-10% EtOAc/hexane gradient to give 4.71 g (85%) of fee title compound as a yellow solid. MS (ESI): 527 [M+H]⁺.

Step D—Methyl 3-{[(1R)-1-(2-chlorophenyl)ethyl]oxy}-5-[6-(hydroxymethyl)-1H-benzimidazol-1-yl]-2-thiophenecarboxylate (Title Compound)

The title compound was prepared from methyl 3-{[(1R)-1-(2-chlorophenyl)ethyl]oxy}-5-(6-{[(2,2-dimethylpropanoyl)oxy]methyl}-1H-benzimidazol-1-yl)-2-thiophenecarboxylate by a procedure analogous to Intermediate 31, Step G. MS (ESI): 443 [M+H]⁺.

INTERMEDIATE 33

1,1-Dimethylethyl 4-({3-[(1R)-1-({5-(5-bromo-1H-benzimidazol-1-yl)-2-[(methyloxy)carbonyl]-3-thienyl}oxy)ethyl]-2-chlorophenyl}oxy)-1-piperidinecarboxylate

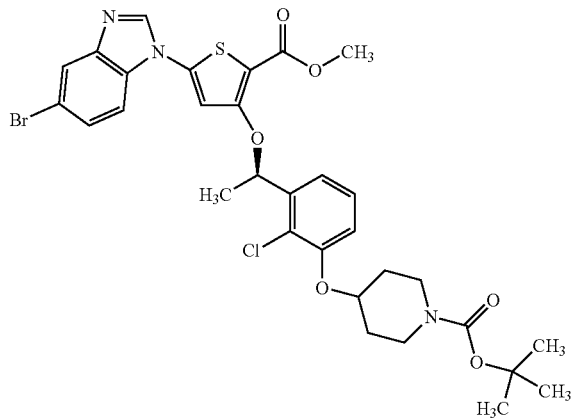

The title compound was prepared from methyl 5-(5-bromo-1H-benzimidazol-1-yl)-3-hydroxy-2-thiophenecarboxylate (0.64 g, 1.8 mmol) and 1,1-dimethylethyl 4-({2-chloro-3-[(1S)-1-hydroxyethyl]phenyl}oxy)-1-piperidinecarboxylate (0.78 g, 2.2 mmol) using a procedure analogous to Intermediate 2, Step C to give 1.22 g of the desired product. MS (ESI): 692.4 [M+H]⁺.

INTERMEDIATE 34

1-{4-{[(1R)-1-(2-Chlorophenyl)ethyl]oxy}-5-[(methyloxy)carbonyl]-2-thienyl}-1H-benzimidazole-5-carboxylic acid

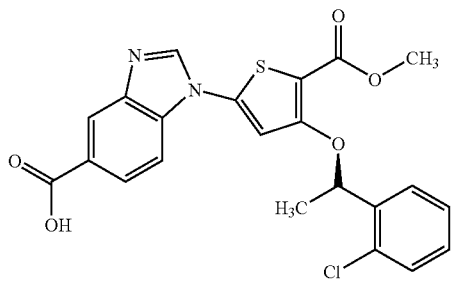

Step A—2-Propen-1-yl 1H-benzimidazole-5-carboxylate

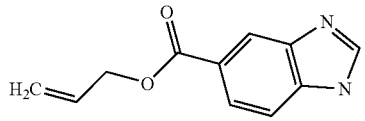

A flask was charged with 20.0 g (123 mmol) of 5-benzimidazole carboxylic add, 7.80 ml (148 mmol) of sulfuric acid and 400 mL of allyl alcohol. The reaction was stirred overnight at 90° C. Most of the allyl alcohol was removed under vacuum, 5% i-PrOH/DCM was added and the mixture neutralized with saturated NaHCO₃ solution. The organics were separated, dried over MgSO₄ and concentrated. The crude product (16.8 g) was used directly in the next step without further purification. MS (APCI); 203 [M+H]⁺.

Step B: 2-Propen-1-yl 1-{4-hydroxy-5-[(methyloxy)carbonyl]-2-thienyl}-1H-benzimidazole-5-carboxylate

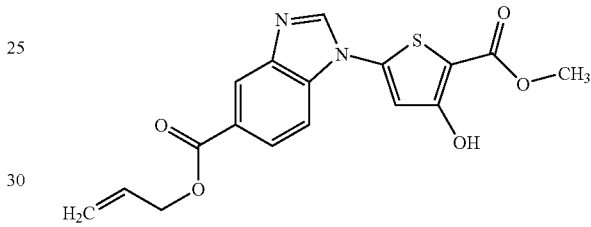

To a flask charged with 11.9 g (58.9 mmol) of 2-propen-1-yl 1H-benzimidazole-5-carboxylate, 11.4 g (58.9 mmol) of methyl 2-chloro-3-oxo-2,3-dihydro-2-thiophenecarboxylate and 14.9 g (177 mmol) of NaHCO₃ was added 200 mL of CHCl₃, followed by 7.1 mL (88.4 mmo) of N-methylimidazole. The reaction was stirred at 45° C. for 8 h, cooled to rt and the slurry adsorbed onto silica gel gel. This was chromatographed to give 8.5 g of the title compound. MS (APCI); 359 [M+H]⁺.

Step C: 2-Propen-1-yl 1-{4-{[(1R)-1-(2-chlorophenyl)ethyl]oxy}-5-[(methyloxy)carbonyl]-2-thsenyl}-1H-benzimidazole-5-carboxylate

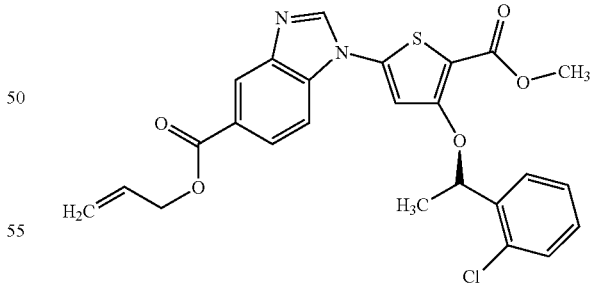

To a solution of 8.41 g (23.5 mmol) of 2-propen-1-yl 1-{4-hydroxy-5-[(methyloxy)carbonyl]-2-thienyl}-1H-benzimidazole-5-carboxylate and 4.40 g (28.2 mmol) of (1S)-1-(2-chlorophenyl)ethanol in 300 mL of DCM was added 24.0 g (47.0 mmol) of polymer-supported triphenylphosphine followed by the portion wise addition of 10.8 g (47.0 mmol) of di-t-butyl azodicarboxylate. The mixture was stirred at rt for 2 h and filtered though a funnel. The filtrate was concentrated, the residue dissolved in 200 mL of HCl (4.0 N in dioxane) and stirred overnight. This solution was neutralized with saturated NaHCO₃ and the organics separated. The organics were concentrated to give 10.4 g of the title compound. MS (APCI): 497 [M+H]³⁰.

Step D—1-{4-{[(1R)-1-(2-Chlorophenyl)ethyl]oxy}-5-[(methyloxy)carbonyl]-2-thienyl}-1H-benzimidazole-5-carboxylic acid (Title Compound)

To a flask charged with 3.00 g (6.05 mmol) of 2-propen-1-yl 1-{4-{[(1R)-1-(2-chlorophenyl)ethyl]oxy}-5-[(methyloxy)carbonyl]-2-thienyl}-1H-benzimidazole-5-carboxylate, was added 50 mL of anhydrous THF, 5.30 mL (60.5 mmol) of morpholine. and 698 mg (0.605 mmol) of tetrakis triphenylphoshine. The reaction was stirred at rt for 1 h, then the solvent removed. The mixture was diluted with EtOAc and neutralized with 100 mL of 0.5 M HCl. The crude product was chromatographed via silica gel chromatography to give 2.20 g of the title compound. MS (APCI): 457 [M+H]⁺.

EXAMPLE 1

5-[5,6-Bis(methyloxy)-1H-benzimidazol-1-yl]-3-[((1R)-1-{2-chloro-3-[(4-piperidinylmethyl)amino]phenyl}ethyl)oxy]-2-thiophenecarboxamide

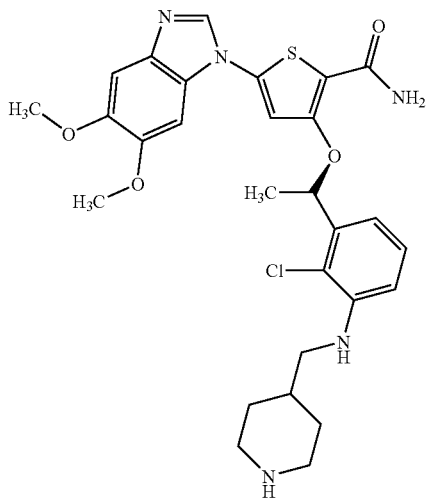

Step A—Methyl 5-[5,6-bis(methyloxy)-1H-benzimidazol-1-yl]-3-{[(1R)-1-(2-chloro-3-nitrophenyl)ethyl]oxy}-2-thiophenecarboxylate

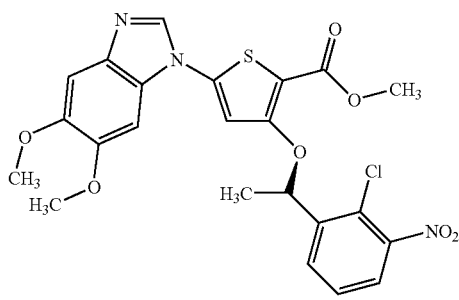

To a solution of methyl 5-[5,6-bis(methyloxy)-1H-benzimidazol-1-yl]-3-hydroxy-2-thiophenecarboxylate (which can be synthesized following the procedure found in PCT Int. Appl. WO 2004073812) (1.1 g, 3.4 mmol) and (1S)-1-(2-chloro-3-nitrophenyl)ethanol (Intermediate 1, 820 mg, 4.1 mmol) in 30 mL of DCM was added polymer supported-triphenylphosphine (3.0 g, 6.8 mmol) and di-tert-butyl azodicarboxylate (1.6 g, 6.8 mmol). After 16 h, the reaction mixture was filtered, and the resin was rinsed with alternating DCM and MeOH. The filtrate was concentrated and purified by flash column chromatography (10-20% EtOAc:hexanes) to give 1.4 g of the desired product (80%). ¹H NMR (400 MHz, d₆-DMSO) δ 8.42 (s, 1H), 8.03 (d, J=8.0 Hz, 1H), 7.98 (d, J=8.0 Hz, 1H), 7.68 (t, J=8.0 Hz, 1H), 7.50 (s, 1H), 7.30 (s, 1H), 7.14 (s, 1H), 6.06 (m, 1H), 3.81 (s, 3H), 3.79 (s, 6H), 1.64 (d, J=6.4 Hz, 3H).

Step B—5-[5,6-Bis(methyloxy)-1H-benzimidazol-1-yl]-3-{[(1R)-1-(2-chloro-3-nitrophenyl)ethyl]oxy}-2-thiophenecarboxamide

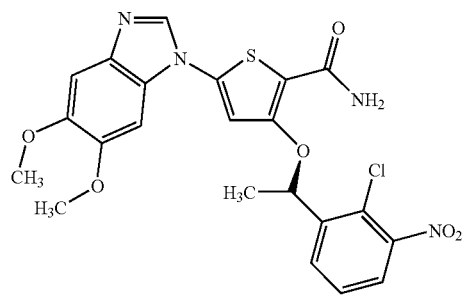

A mixture of methyl 5-[5,6-bis(methyloxy)-1H-benzimidazol-1-yl]-3--{[(1R)-1-(2-chloro-3-nitrophenyl)ethyl]oxy}-2-thiophenecarboxylate (1.4 g, 2.7 mmol) and 7 N ammonia in MeOH in a sealed tube was heated at 80° C. After 16 h, the reaction was cooled to rt. The precipitate was filtered, rinsed with ether and dried to give 1.05 g of the desired product (77%). ¹NMR (400 MHz, d₆-DMSO) δ 8.32 (s, 1H), 7.99-7.96 (m, 2H); 7.80 (br s, 1H), 7.65 (t, J=8.0 Hz, 1H), 7.28 (s, 1H), 7.18 (s, 1H), 7.13 (br s, 1H), 7.06 (s, 1H), 6.06 (m, 1H), 3.78 (s, 3H), 3.76 (s, 3H), 1.72 9d, J=6.4 Hz, 3H).

Step C—3-{[(1R)-1-(3-amino-2-chlorophenyl)ethyl]oxy}-5-[5,6-bis(methyloxy)-1H-benzimidazol-1-yl]-2-thiophenecarboxamide

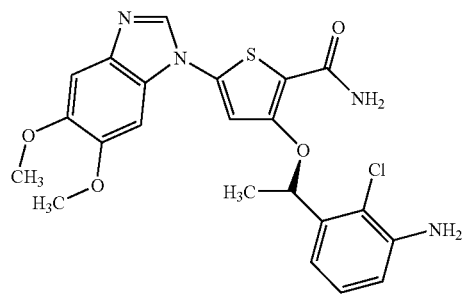

To 5-[5,6-bis(methyloxy)-1H-benzimidazol-1-yl]-3-{[(1R)-1-(2-chloro-3-nitrophenyl)ethyl]oxy}-2-thiophenecarboxamide (1.0 g, 2.0 mmol) and iron powder (0.56 g, 10 mmol) was added acetic acid (6.0 mL, 100 mmol). The dark mixture was heated at 50 ° C. After 30 min, EtOAc was added and 5N NaOH was added to neutralize the mixture. The mixture was filtered through a pad of celite. The organic layer was separated, dried over MgSO₄ and concentrated to give 0.47 g of the desired product (50%). ¹H NMR (400 MHz, d₆-DMSO) δ 8.32 (s, 1H), 7.78 (br s, 1H), 7.28 (s, 1H), 7.06-6.97 (m, 4H), 6.74-6.68 (m, 2H), 5.89 (m, 1H), 5.44 (s, 2H), 3.77 (s, 3H), 3.75 (s, 3H), 1.64 (d, J=6.4 Hz, 3H).

Step D—5-[5,6-Bis(methyloxy)-1H-benzimidazol-1-yl]-3-[((1R)-1-{2-chloro-3-[(4-piperidinylmethyl)amino]phenyl}ethyl)oxy]-2-thiophenecarboxamide (Title Compound)

To a solution of 3-{[(1R)-1-(3-amino-2-chlorophenyl)ethyl]oxy}-5-[5,6-bis(methyloxy)-1H-benzimidazol-1-yl]-2-thiophenecarboxamide (470 mg, 1.0 mmol) in 5 mL of 1,2-dichloroethane was added 1,1-dimethylethyl 4-formyl-1-piperidinecarboxylate (320 mg, 1.5 mmol) and 2 drops of acetic acid. After 40 min, sodium triacetoxyborohydride (420 mg, 2.0 mmol) was added. After 16 h, the reaction was diluted with DCM. The organic solution was washed with sat'd aqueous NaHCO$_3$ and water, dried over MgSO$_4$ and concentrated. The residue was stirred in a 20% TFA and DCM solution. The reaction was concentrated and redissolved in DCM. The organic solution was washed with saturated NaHCO$_3$ and water, dried over MgSO$_4$ and concentrated. The crude material was purified by silica gel chromatography (5-20% 10% NH$_3$OH/MeOH and CH$_2$Cl$_2$) to give 0.126 g of the title compound (22%).

$^1$H NMR (400 MHz, d$_6$-DMSO) δ 8.31 (s, 1H), 7.78 (br s, 1H), 7.28 (s, 1H), 7.13 (m, 1H), 7.07 (br s, 1H), 7.02-7.01 (m, 2H), 6.77 (m, 1H), 6.60 (m, 1H), 5.93 (m, 1H), 5.41 (m, 1H), 3.78 (s, 3H), 3.74 (s, 3H), 2.93 (m, 4H), 2.40 (m, 2H), 1.66-1.57 (m, 6H), 1.07-1.00 (m, 2H). HRMS calculated C$_{28}$H$_{32}$ClN$_5$O$_4$S [M+H]$^+$ 570.1942, found 570.1946.

EXAMPLE 2

5-[5,6-Bis(methyloxy)-1H-benzimidazol-1-yl]-3-{[(1R)-1-(2-chloro-3-{[(1-methyl-4-piperidinyl)methyl]oxy}phenyl)ethyl]oxy}-2-thiophenecarboxamide

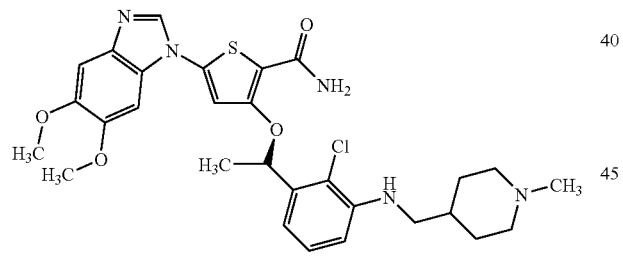

To a solution of 5-[5,6-bis(methyloxy)-1H-benzimidazol-1-yl]-3-[((1R)-1-{2-chloro-3-[(4-piperidinylmethyl)amino]phenyl}ethyl)oxy]-2-thiophenecarboxamide (Example 40, 86 mg, 0.015 mmol) in 2 mL of DCM and 1 mL of MeOH was added formaldehyde (23 μl, 0.30 mmol) and acetic acid (10 μl, 0.18 mmol). After 10 min, sodium triacetoxyborohydride (49 mg, 0.23 mmol) was added and the reaction was stirred for 16 h. The solution was diluted with DCM and washed with saturated NaHCO$_3$ solution and water, dried over MgSO$_4$ and concentrated to give 49 mg of the title compound (56%). $^1$H NMR (400 MHz, d$_6$-DMSO) δ 8.31 (s, 1H), 7.78 (br s, 1H), 7.28 (s, 1H), 7.13 (t, J=7.8 Hz, 1H), 7.07 (br s, 1H), 7.01-7.00 (m, 2H), 6.76 (d, J=7.6 Hz, 1H), 6.60 (d, J=8.0 Hz, 1H), 5.92 (m, 1H), 5.39 (m, 1H), 3.77 (s, 3H), 3.74 (s, 3H), 2.95 (m, 2H), 2.65 (m, 2H), 2.06 (s, 3H), 1.70-1.56 (m, 7H), 1.12-1.09 (m, 2H). HRMS calculated C$_{29}$H$_{34}$ClN$_5$O$_4$S [M+H]$^+$ 584.2098, found 584.2093.

EXAMPLE 3

5-(5-Chloro-1H-benzimidazol-1-yl)-3-((1R)-1-{2-chloro-3-[1-methylpiperidin-4-yl)oxy]phenyl}ethoxy)thiophene-2-carboxamide

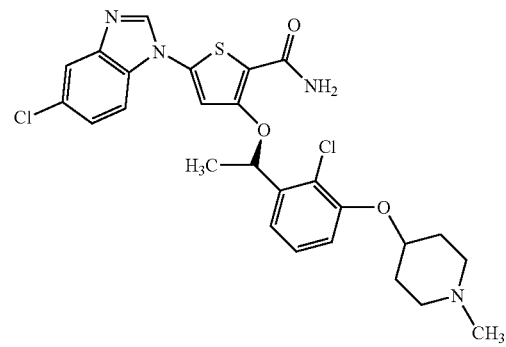

To a slurry of methyl 5-(5-chloro-1H-benzimidazol-1-yl)-3-{[(1R)-1-(2-chloro-3-hydroxyphenyl)ethyl]oxy}-2-thiophenecarboxylate (Intermediate 2, Slap B, 195 mg, 0.42 mmol) in 5 mL of DCM was added 1-methylpiperidin-4-ol (59 μl, 0.50 mmol), triphenylphosphine (220 mg, 0.84 mmol) and di-tert-butylazodicarboxylate (160 mg, 0.84 mmol). After 2 h, the reaction was concentrated onto silica gel and purified by flash column chromatography. Fractions containing desired product were concentrated and stirred in 6 mL of 7 N ammonia in MeOH in a sealed tube heated at 80° C. After 24 h, the reaction was allowed to cool to rt. The precipitate was collected by filtration to give 35 mg of the title compound as a white solid (14% over both steps). $^1$H NMR (400 MHz, d$_6$-DMSO) δ 8.63 (s, 1H), 7.86-7.83 (m, 2H), 7.52 (d, J=8.8 Hz, 1H), 7.37-7.30 (m, 2H), 7.20-7.11 (m, 4H), 5.97 (m, 1H), 4.46 (m, 1H), 2.31-2.12 (m, 5H), 2.60-2.48 (m under DMSO peak, 2H), 1.85 (m, 2H), 1.70 -1.61 (m, 5H).

EXAMPLE 4

3-((1R)-1-{2-chloro-3-[(1-methylpiperidin-4-yl)oxy]phenyl}-ethoxy)-5-(6-cyano-1H-benzimidazol-1-yl)thiophene-2-carboxamide

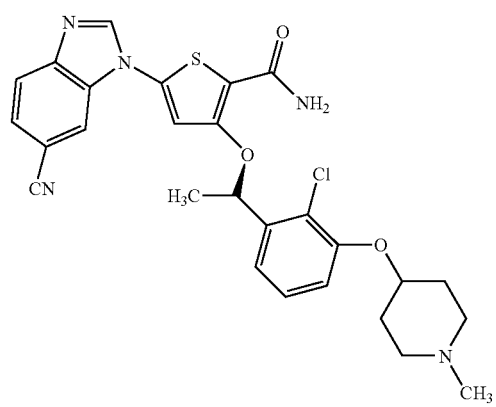

111

Step A—Methyl 3-((1R)-1-{2-chloro-3-[(1-methylpiperidin-4-yl)oxy]phenyl}ethoxy)-5-(6-cyano-1H-benzimidazol-1-yl)thiophene-2-carboxylate

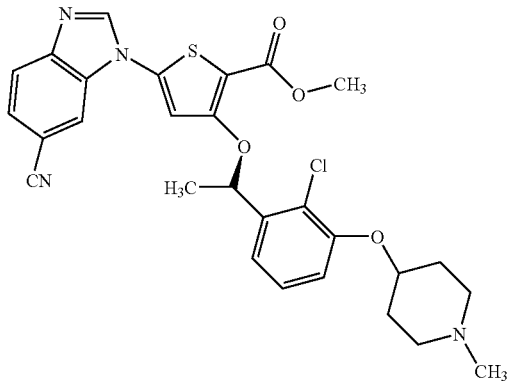

To a solution of methyl 3-[(1R)-1-(2-chloro-3-hydroxyphenyl)ethoxy]-5-(6-cyano-1H-benzimidazol-1-yl)thiophene-2-carboxylate (Intermediate 3, 130 mg, 0.27 mmol) in 5 mL of DCM was added 1-methylpiperidin-4-ol (38 μL, 0.32 mmol), triphenylphosphine (140 mg, 0.54 mmol), and di-tert-butyl azodicarboxylate (120 mg, 0.54 mmol). After the reaction was complete, the solution was concentrated onto silica gel and purified by flash column chromatography (1-100% 10% MeOH/DCM and DCM) to give 125 mg of the desired product (84%). $^1$H NMR (400 MHz, $d_6$-DMSO) δ 8.87 (s, 1H), 8.20 (s, 1H), 7.95 (d, J=8.0 Hz, 1H), 7.75(d, J=8.4 Hz, 1H), 7.46 (s, 1H), 7.35-7.28 (m, 2H), 7.12 (d, J=6.8 Hz, 1H), 5.99 (m, 1H), 4.44 (m, 1H), 3.82 (s, 3H), 2.52 (m, 2H), 2.21-2.13 (m, 5H), 1.86 (m, 2H), 1.66-1.60 (m, 5H).

Step B—3-((1R)-1-{2-Chloro-3-[(1-methylpiperidin-4-yl)oxy]phenyl}ethoxy)-5-(6-cyano-1H-benzimidazol-1-yl)thiophene-2-carboxamide (Title Compound)

A solution of methyl 3-((1R)-1-{2-chloro-3-[(1-methylpiperidin-4-yl)oxy]phenyl}ethoxy)-5-(6-cyano-1H-benzimidazol-1-yl)thiophene-2-carboxylate (120 mg, 0.22 mmol) in 7 ml of a 7N ammonia in MeOH solution was heated in a sealed tube at 80° C. After 1-3 days, the reaction was cooled to rt, concentrated onto silica gel, and purified by flash column chromatography to give 85 mg of the title compound (72%). $^1$H NMR (400 MHz, $d_6$-DMSO) δ 8.80 (s, 1H), 8.09 (s, 1H), 7.94 9d, J=8.4 Hz, 1H), 7.85 (s, 1H), 7.74 (dd, J=8.4 and 1.2 Hz, 1H), 7.32 (d, J=8.0 Hz, 1H), 7.23-7.19 (m, 2H), 7.14-7.12 (m, 2H), 6.01 (m, 1H), 4.44 (m, 1H), 2.52-2.78 (m under DMSO peak, 2H), 2.16-2.11 (m, 5H), 1.84 (m, 2H), 1.70 (d, J=6.4 Hz, 3H), 1.62 (m, 2H). HRMS calculated $C_{27}H_{27}ClN_5O_3S$ [M+H]$^+$ 536.1523, found 536.1519.

112

EXAMPLE 5

3-{(1R)-1-[2-chloro-3(piperidin-4-yloxy)phenyl]ethoxy}-5-(6-cyano-1H-benzimidazol-1-yl)thiophene-2-carboxamide

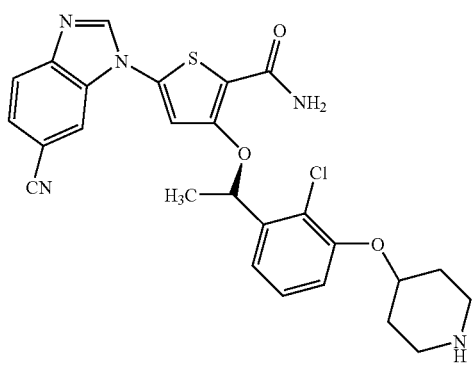

Step A—Tert-butyl 4-[2-chloro-3-((1R)-1-{[5-(6-cyano-1H-benzimidazol-1-yl)-2-(methoxycarbonyl)-3-thienyl]oxy}ethyl)phenoxy]piperidine-1-carboxylate

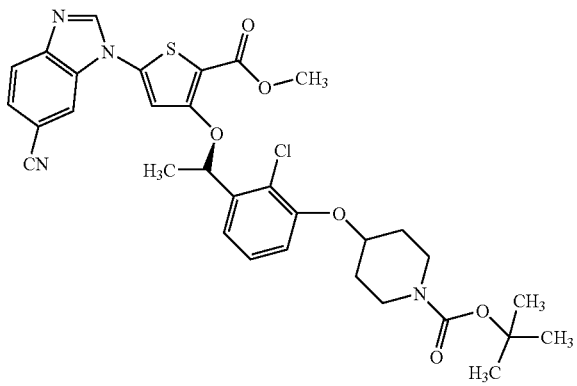

To a solution of methyl 3-[(1R)-1-(2-chloro-3-hydroxyphenyl)ethoxy]-5-(6-cyano-1H-benzimidazol-1-yl)thiophene-2-carboxylate (Intermediate 3, 160 mg, 0.36 mmol) in 5 mL of PCM was added tert-butyl 4-hydroxypiperidine-1-carboxylate (87 mg, 0.43 mmol), triphenylphosphine (190 mg, 0.72 mmol), and di-tert-butyl azodicarboxylate (170 mg, 0.72 mmol). The reaction was concentrated onto silica gel and purified by flash column chromatography to give the desired product plus impurity (264 mg). $^1$H NMR (400 MHz, $d_6$-DMSO) δ 8.87 (s, 1H), 8.20 (s, 1H), 7.95 (d, J=8.4 Hz, 1H), 7.75 (dd, J=8.4 and 1.2 Hz, 1H), 7.48 (s, 1H), 7.37-7.30 (m, 2H), 7.16 (dd, J=7.6 and 1.6 Hz, 1H), 5.99 (m, 1H), 4.64 (m, 1H), 3.82 (s, 3H), 3.53 (m, 2H), 3.24 (m, 2H), 1.83 (m, 2H), 1.61 (d, J=6.0 Hz, 3H), 1.54 (m, 2H), 1.38 (s, 9H).

113
Step B—Tert-butyl 4-[3-((1R)-1-{[2-(aminocarbonyl)-5-(6-cyano-1H-benzimidazol-1-yl)-3-thienyl]oxy}ethyl)-2-chlorophenoxy]piperidine-1-carboxylate

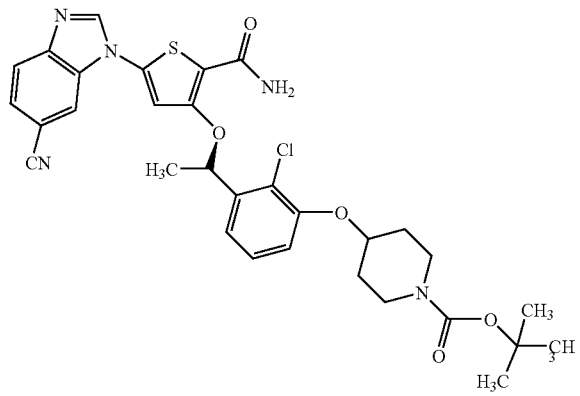

A solution of tert-butyl 4-[2-chloro-3-((1R)-1-{[5-(6-cyano-1H-benzimidazol-1-yl)-2-(methoxycarbonyl)-3-thienyl]oxy}ethyl)phenoxy]piperidine-1-carboxylate (264 mg) in 7 mL of a 7N ammonia in MeOH solution was heated at 80° C. After 1-3 days, the reaction was concentrated onto silica gel and purified by flash column chromatography to give 136 mg of the desired product (61% over steps A and B). $^1$H NMR (400 MHz, d$_6$-DMSO) δ 8.80 (s, 1H), 8.08 (s, 1H), 7.94 (d, J=8.4 Hz, 1H), 7.85 (br s, 1H), 7.73 (dd, J=8.4 and 1.2 Hz, 1H), 7.34 (t, J=8.0 Hz, 1H), 7.25-7.13 (m, 4H), 6.01 (m, 1H), 4.64 (m, 1H), 3.50 (m, 2H), 3.21 (m, 2H), 1.82 (m, 2H), 1.71 9d, J=6.4 Hz, 3H), 1.54 (m, 2H), 1.37 (s, 9H).

Step C—3-{(1R)-1-[2-chloro-3-(piperidin-4-yloxy)phenyl]ethoxy}-5-(6-cyano-1H-benzimidazol-1-yl)thiophene-2-carboxamide (Title Compound)

A solution of tert-butyl 4-[3-((1R)-1-{[2-(aminocarbonyl)-5-(6-cyano-1H-benzimidazol-1-yl)-3-thienyl]oxy}ethyl)-2-chlorophenoxy]piperidin-1-carboxylate (136 mg, 0.22 mmol) was stirred in 5 mL of a 20% TFA/DCM solution. The reaction was concentrated and the residue was taken up in DCM. The solution was neutralized with 7N ammonia in MeOH. The solution was concentrated onto silica gel and purified by flash column chromatography to give 101 mg of the title compound (88%). $^1$H NMR (400 MHz, d$_6$-DMSO) δ 8.79 (s, 1H), 8.45 (br s, 1H), 8.07 (s, 1H), 7.93 (d, J=8,4 Hz, 1H), 7.84 (br s, 1H), 7.73 (d, J=8.4 Hz, 1H), 7.36 (t, J=8.0 Hz, 1H), 7.27-7.25 (m, 2H), 7.19 (d, J=8.0 Hz, 1H), 7.12 (br s, 1H), 6.01 (m, 1H), 4.71 (m, 1H), 3.07 (m, 2H), 2.03 (m, 2H), 1.83 (m, 2H), 1.70 (d, J=6.4 Hz, 3H). HRMS calculated $C_{26}H_{25}ClN_5O_3S$ [M+H]$^+$ 522.1367 found 522.1371.

114
EXAMPLE 6

5-(6-Bromo-1H-benzimidazol-1-yl)-3-[((1R)-1-{2-chloro-3-[(1-methyl-4-piperidinyl)oxy]phenyl}ethyl)oxy]-2-thiophenecarboxamide

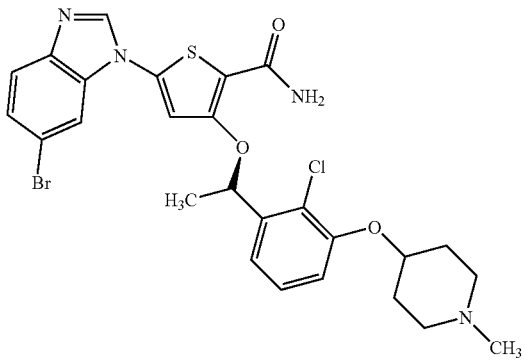

Step A—Methyl 5-(6-bromo-1H-benzimidazol-1-yl)-3-[((1R)-1-{2-chloro-3-[(1-methyl-4-piperidinyl)oxy]phenyl}ethyl)oxy]-2-thiophenecarboxylate Methyl 5-(8-bromo-1H-benzimidazol-1-yl)-3-{[(1R)-1-(2-chloro-3-hydroxyphenyl)ethyl]oxy}-2-thiophenecarboxylate (Intermediate 6, 150 mg, 0.30 mmol) and 1-methylpiperidin-4-ol (35 µL, 0.30 mmol) were coupled using a procedure analogous to Example 4, Step A to give 104 mg of the desired product (57%). $^1$H NMR (400 MHz, d$_6$-DMSO) δ 8.69 (s, 1H), 7.83 (d, J=1.5 Hz, 1H), 7.78 (d, J=8.4 Hz, 1H), 7.54 (dd, J=8.7 and 1.8 Hz, 1H), 7.43 (s, 1H), 7.40-7.31 (m, 3H), 7.17 (m, 1H), 6.03 (m, 1H), 4.49 (m, 1H), 3.86 (s, 3H), 2.57-2.50 (m, under DMSO peak, 2H), 2.17-2.15 (m, 5H), 1.89 (m, 2H), 1.71-1.64 (m, 5H).

Step B—5-(6-Bromo-1H-benzimidazol-1-yl)-3-[((1R)-1-{2-chloro-3-[(1-methyl-4-piperidinyl)oxy]phenyl}ethyl)oxy]-2-thiophenecarboxamide (Title Compound)

Methyl 5-(6-bromo-1H-benzimidazol-1-yl)-3-[((1R)-1-{2-chloro-3-[(1-methyl-4-piperidinyl)oxy]phenyl}ethyl)oxy]-2-thiophenecarboxylate (104 mg, 0.17 mmol) was subjected to an aminolysis reaction analogous to Example 4, Step B to give 61 mg of the title compound (61%). $^1$H NMR (400 MHz, d$_6$-DMSO) δ 8.57 (s, 1H), 7.84 (br s, 1H), 7.71 (d, J=8.8 Hz, 1H), 7.68 (d, J=1.6 Hz, 1H), 7.48 (dd, J=8.6 and 1.8 Hz, 1H), 7.32 (t, J=8.0 Hz, 1H), 7.20 (d, J=7.6 Hz, 1H), 7.16-7.12 (m, 3H), 5.99 (m, 1H), 4.44 (m, 1H), 2.52-2.48 (m under DMSO peak, 2H), 2.11 (m, 5H), 1.85 (m, 2H), 1.69 (d, J=6.4 Hz, 3H), 1.63 (m, 2H). HRMS calculated $C_{26}H_{27}BrClN_4O_3S$ $[M+H]^+$ 589.0676; found 589.0679.

EXAMPLE 7

5-(6-Bromo-1H-benzimidazol-1-yl)-3-({(1R)-1-[2-chloro-3-(4-piperidinyloxy)phenyl]ethyl}oxy)-2-thiophenecarboxamide

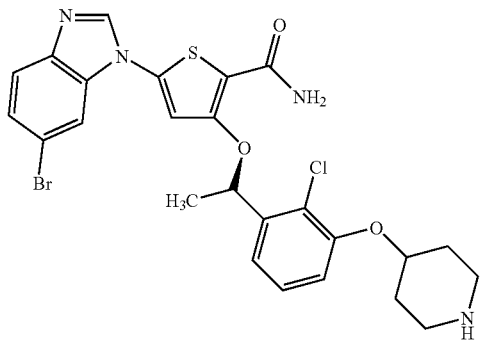

Step A—1,1-Dimethylethyl 4-({3-[(1R)-1-({5-(6-bromo-1H-benzimidazol-1-yl)-2-[(methyloxy)carbonyl]-3-thienyl}oxy)ethyl]-2-chlorophenyl}oxy)-1-piperidinecarboxylate

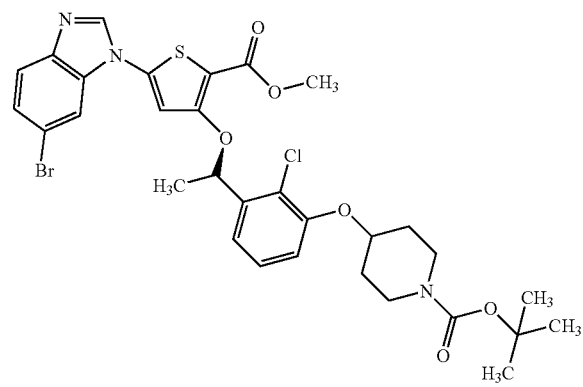

Methyl 5-(6-bromo-1H-benzimidazol-1-yl)-3-{[(1R)-1-(2-chloro-3-hydroxyphenyl)ethyl]oxy}-2-thiophenecarboxylate (Intermediate 6, 193 mg, 0.38 mmol) and tert-butyl 4-hydroxypiperidine-1-carboxylate (76 mg, 0.38 mmol) were coupled using a procedure analogous to Example 5, Step A to give 112 mg of the desired product (43%). $^1$H NMR (400 MHz, $d_6$-DMSO) δ 8.65 (s, 1H), 7.78 (d, 1H, J=1.6 Hz), 7.73 9d, 1H, J=8.8 Hz), 7.49 (dd, 1H, J=8.6 and 1.8 Hz), 7.40 (s, 1H), 7.37-7.29 (m, 2H), 7.17 (dd, 1H, J=8.2 and 1.4 Hz), 5.98 (m, 1H), 4.65 (m, 1H), 3.81 (s, 3H), 3.53 (m, 2H), 3.28 (m, 2H), 1.83 (m, 2H), 1.60 (d, 3H, J=6.0 Hz), 1.55 (m, 2H), 1.38 (s, 9H).

Step B—1,1-Dimethylethyl 4-{[3-((1R)-1-{[2-(aminocarbonyl)-5-(6-bromo-1H-benzimidazol-1-yl)-3-thienyl]oxy}ethyl)-2-chlorophenyl]oxy}-1-piperidinecarboxylate

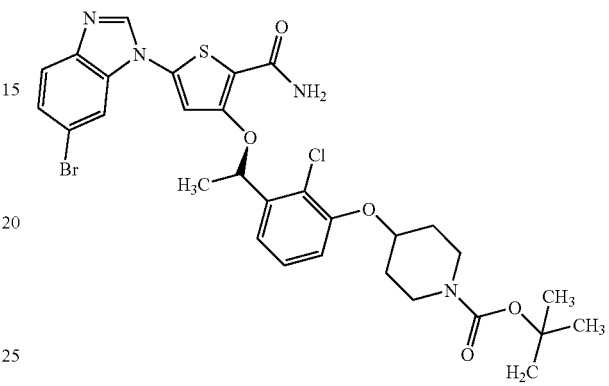

1,1-Dimethylethyl 4-({3-[(1R)-1-({5-(6-bromo-1H-benzimidazol-1-yl)-2-[(methyloxy)carbonyl]-3-thlenyl}oxy)ethyl]-2-chlorophenyl}oxy)-1-piperidinecarboxylate (112 mg, 0.16 mmol) was subjected to an aminolysis procedure analogous to Example 5, Step B to give 81 mg of the desired product (75%). $^1$H NMR (400 MHz, $d_6$-DMSO) δ 8.56 (s, 1H), 7.82 (br s, 1H), 7.70 (d, J=8.8 Hz, 1H), 7.66 (s, 1H), 7.46 (d, J=8.4 Hz, 1H), 7.33 (t, J=8.0 Hz, 1H), 7.22-7.15 (m, 3H), 7.10 (br s, 1H), 5.98 (m, 1H), 4.64 (m, 1H), 3.51 (m, 2H), 3.22 (m, 2H), 1.81 (m, 2H), 1.68 (d, J=6.4 Hz, 3H), 1.56 (m, 2H), 1.36 (s, 9H).

Step C—5-(6-Bromo-1H-benzimidazol-1-yl)-3-({(1R)-1-[2-chloro-3-(4-piperidinyloxy)phenyl]ethyl}oxy)-2-thiophenecarboxamide (Title Compound)

1,1-Dimethylethyl 4-{[3-(1-{[2-(aminocarbonyl)-5-(6-bromo-1H-benzimidazol-1-yl)-3-thienyl]oxy}ethyl)-2-chlorophenyl]oxy}-1-piperidinecarboxylate (81 mg, 0.12 mmol) was deprotected using a procedure analogous to Example 5, Step C to give 58 mg of the title compound (84%). $^1$H NMR (400 MHz, $d_6$-DMSO) δ 8.55 (s, 1H), 7.82 (br s, 1H), 7.70 (d, J=8.8 Hz, 1H), 7.66 (s, 1H), 7.46 (d, J=8.8 Hz, 1H), 7.31 (m, 1H), 7.20-7.11 (m, 4H), 5.97 (m, 1H), 4.48 (m, 1H), 2.90 (m, 2H), 2.54 (m, 2H), 1.83 (m, 2H), 1.68 (d, J=6.4 Hz, 3H), 1.48 (m, 2H). HRMS calculated $C_{25}H_{25}BrClN_4O_3S$ $[M+H]^+$ 575.0519, found 575.0520.

EXAMPLE 8

5-(5-Chloro-1H-benzimidazol-1-yl)-3-({(1R)-1-[2-chloro-3-(4-piperidinyloxy)phenyl]ethyl}oxy)-2-thiophenecarboxamide

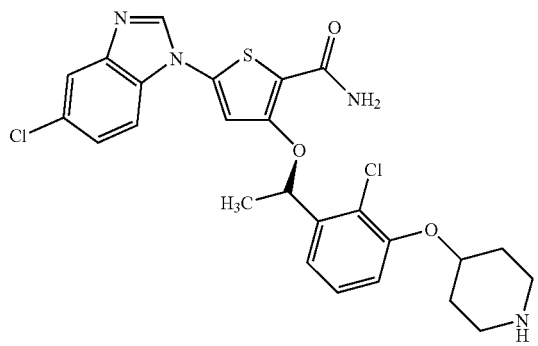

Step A—1,1-Dimethylethyl 4-({2-chloro-3-[(1R)-1-({5-(5-chloro-1H-benzimidazol-1-yl)-2-[(methyloxy)carbonyl]-3-thienyl}oxy)ethyl]phenyl}oxy)-1-piperidinecarboxylate

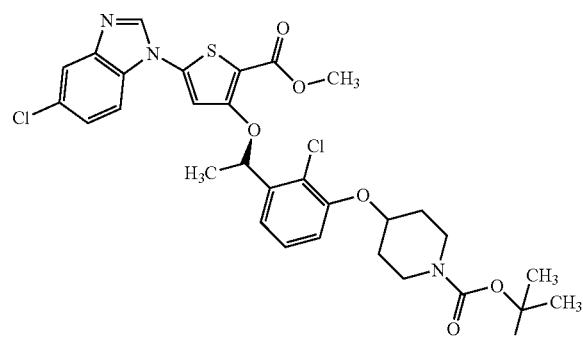

Methyl 5-(5-chloro-1H-benzimidazol-1-yl)-3-{[(1R)-1-(2-chloro-3-hydroxyphenyl)-ethyl]oxy}-2-thiophenecarboxylate (Intermediate 2, 213 mg, 0.46 mmol) and tert-butyl 4-hydroxypiperidine-1-carboxylate (110 mg, 0.55 mmol) were coupled using a procedure analogous to Example 5, Step A to give 210 mg of the desired product (71%). $^1$H NMR (400 MHz, $d_6$-DMSO) δ 8.72 (s, 1H), 7.87 (d, J=1.6 Hz, 1H), 7.65 (d, J=8.8 Hz, 1H), 7.41-7.29 (m, 4H), 7.18 (d, J=6.4 Hz, 1H), 5.95 (m, 1H), 4.66 (m, 1H), 3.81 (s, 3H), 3.56-3.52 (m, 2H), 3.28-3.23 (m, 2H), 1.86-1.83 (m, 2H), 1.61-1.52 (m, 5H), 1.38 (s, 9H).

Step B—1,1-Dimethylethyl 4-{[3-((1R)-1-{[2-(aminocarbonyl)-5-(5-chloro-1H-benzimidazol-1-yl)-3-thienyl]oxy}ethyl)-2-chlorophenyl]oxy}-1-piperidinecarboxylate

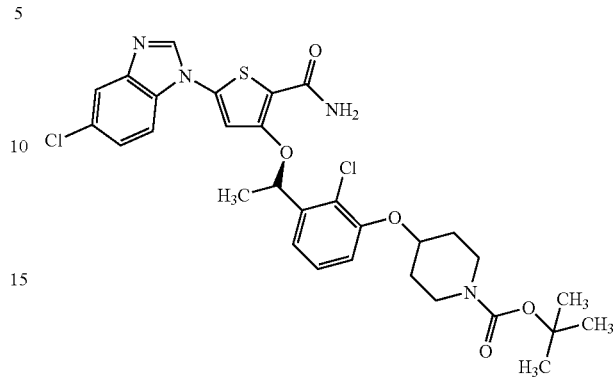

1,1-Dimethylethyl 4-({2-chloro-3-[(1R)-1-({5-(5-chloro-1H-benzimidazol-1-yl)-2-[(methyloxy)carbonyl]-3-thienyl}oxy)ethyl]phenyl}oxy)-1-piperidinecarboxylate (210 mg, 0.32 mmol) was subjected to an aminolysis procedure analogous to Example 5, Step B to give 114 mg of the desired product (56%). $^1$H NMR (400 MHz, $d_6$-DMSO) δ 8.62 (s, 1H), 7.85 (d, J=2.0 Hz, 1H), 7.82 (br s, 1H), 7.52 (d, J=8.4 Hz, 1H), 7.37-7.32 (m, 2H), 7.23-7.16 (m, 3H), 7.10 (br s, 1H), 5.96 (m, 1H), 4.68-4.64 (m, 1H), 3.56-3.52 (m, 2H), 3.28-3.20 (m, 2H), 1.85-1.83 (m, 2H), 1.70 (d, J=6.0 Hz, 3H), 1.58-1.52 (m, 2H), 1.38 (s, 9H).

Step C—5-(5-Chloro-1H-benzimidazol-1-yl)-3-({(1R)-1-[2-chloro-3-(4-piperidinyloxy)phenyl]ethyl}oxy)-2-thiophenecarboxamide (Title Compound)

1,1-Dimethylethyl 4-{[3-((1R)-1-{[2-(aminocarbonyl)-5-(5-chloro-1H-benzimidazol-1-yl)-3-thienyl]oxy}ethyl)-2-chlorophenyl]oxy}-1-piperidinecarboxylate (104 mg, 0.16 mmol) was deprotected using a procedure analogous to Example 5, Step C to give 55 mg of the title compound (65%). $^1$H NMR (400 MHz, $d_6$-DMSO) δ 8.62 (s, 1H), 7.85 (d, J=2.0 Hz, 1H), 7.82 (br s, 1H), 7.51 (d, J=8.8 Hz, 1H), 7.37-7.30 (m, 2H), 7.21-7.15 (m, 3H), 7.10 (br s, 1H), 5.96 (m, 1H), 4.52 (m, 1H), 2.94 (m, 2H), 2.61 (m, 2H), 1.88 (m, 2H), 1.69 (d, J=6.4 Hz, 3H), 1.52 (m, 2H). HRMS calculated $C_{25}H_{25}Cl_2N_4O_3S$ [M+H] 531.1024; found 531.1028.

EXAMPLE 9

3-({(1R)-1-[2-chloro-3-(4-piperidinyloxy)phenyl]ethyl}oxy)-5-[5-(6-methyl-3-pyridinyl)-1H-benzimidazol-1-yl]-2-thiophenecarboxamide

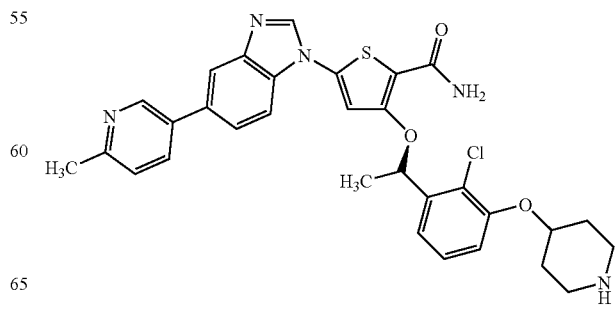

Step A-1,1-Dimethylethyl 4-({2-chloro-3-[(1R)-1-({2-[(methyloxy)carbonyl]-5-[5-(6-methyl-3-pyridinyl)-1H-benzimidazol-1-yl]-3-thianyl}oxy)ethyl]phenyl}oxy)-1-piperidinecarboxylate

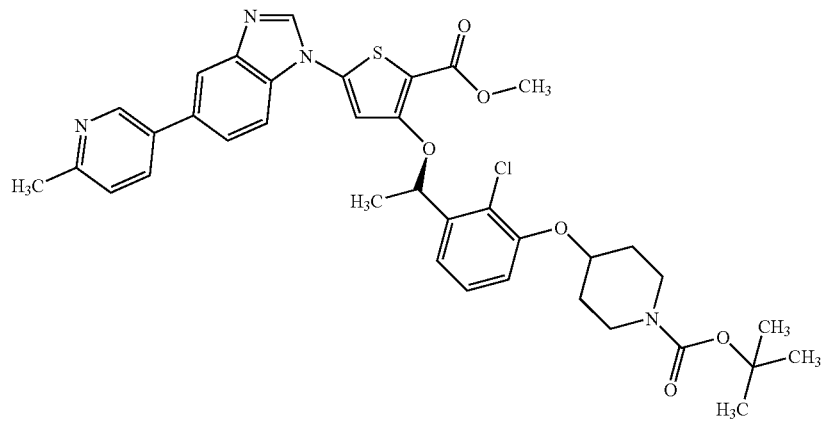

Methyl 3-{[(1R)-1-{2-chloro-3-hydroxyphenyl)ethyl]oxy}-5-[5-(6-methyl-3-pyridinyl}-1H-benzimidazol-1-yl]-2-thiophenecarboxylate (Intermediate 9, 147 mg, 0.28 mmol) and 1,1-dimethylethyl 4-hydroxy-1-piperidinecarboxylate (68 mg, 0.34 mmol) were coupled using a procedure analogous to Example 5, Stop A to give 151 mg of the desired product (76%). $^1$H NMR (400 MHz, d$_6$-DMSO) δ 8.79 (s, 1H), 8.70 (s, 1H), 8.08 (s, 1H), 8.01 (d, J=8.0 Hz, 1H), 7.72-7.66 (m, 2H), 7.40 (s, 1H), 7.36-7.29 (m, 3H), 7.17 (d, J=7.6 Hz, 1H), 5.96 (m, 1H), 4.65 (m, 1H), 3.80 (s, 3H), 3.52 (m, 2H), 3.22 (m, 2H), 2.49 (s, 3H), 1.83 (m, 2H), 1.61-1.54 (m, 5H), 1.35 (s, 9H).

Step B—1,1-Dimethylethyl 4-({3-[(1R)-1-({2-(aminocarbonyl)-5-[5-(6-methyl-3-pyridinyl)-1H-benzimidazol-1-yl]-3-thienyl}oxy)ethyl]-2-chlorophenyl}oxy)-1-piperidinecarboxylate

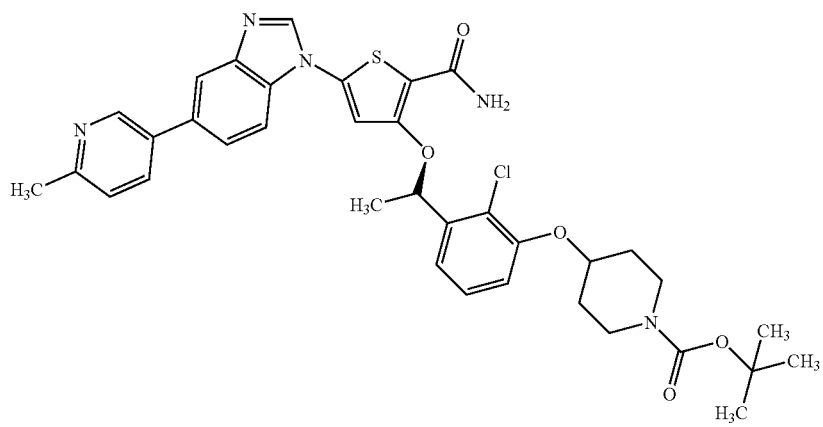

1,1-Dimethylethyl 4-({2-chloro-3-[(1R)-1-({2-[(methyloxy)carbonyl]-5-[5-(8-methyl-3-pyridinyl)-1H-benzimidazol-1yl]-3-thienyl}oxy)ethyl]phenyl}oxy)-1-piperidinecarboxylate (150 mg, 0.21 mmol) was subjected to an aminolysis procedure analogous to Example 5, Step B to give 81 mg of the desired product (56%). $^1$H NMR (400 MHz, d$_6$-DMSO) δ 8.78 (s, 1H), 8.60 (s, 1H), 8.06 (s, 1H), 8.00 (d, J=8.0 Hz, 1H), 7.80 (br s, 1H), 7.64 (d, J=8.4 Hz, 1H), 7.58 (d, J=8.4 Hz, 1H), 7.36-7.23 (m, 2H), 7.21-7.16 (m, 3H), 7.09 (br s, 1H), 5.97 (M, 1H), 4.65 (M, 1H), 3.52 (m, 2H), 3.20 (m, 2H), 2.49 (s, 3H), 1.82 (m, 2H), 1.70 (d, J=6.0 Hz, 3H), 1.54 (m, 2H), 1.34 (s, 9H).

Step C—3-({(1R)-1-[2-chloro-3-(4-piperidinyloxy) phenyl]ethyl}oxy)-5-[5-(6-methyl-3-pyridinyl)-1H-benzimidazol-1-yl]-2-thiophenecarboxamide

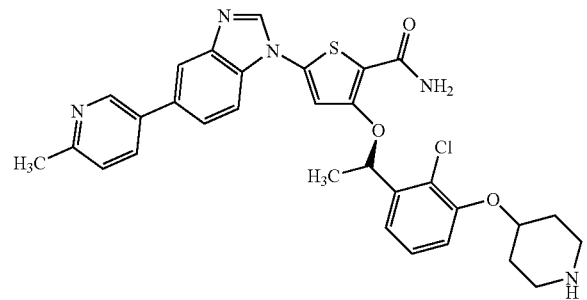

1,1-Dimethylethyl 4-({3-[(1R)-1-({2-(aminocarbonyl)-5-[5-(6-methyl-3-pyridinyl)-1H-benzimidazol-1-yl]-3-thienyl}oxy)ethyl]-2-chlorophenyl}oxy)-1-piperidinecarboxylate (81 mg, 0.12 mmol) was deprotected using a procedure analogous to Example 5, Step C to give 61 mg of the title compound (86%). $^1$H NMR (400 MHz, d$_6$-DMSO) δ 8.80 (d, J=2.0 Hz, 1H), 8.62 (s, 1H), 8.08 (d, J=1.2 Hz, 1H), 8.02 (dd, J=8.0 and 2.8 Hz, 1H), 7.82 (br s, 1H), 7.66 (dd, J=8.4 and 1.6 Hz, 1H), 7.57 (d, J=8.8 Hz, 1H), 7.35-7.31 (m, 2H), 7.21-7.16 (m, 3H), 7.11 (br s, 1H), 5.99 (m, 1H), 4.52-4.47 (m, 1H), 2.92-2.84 (m, 2H), 2.58-2.46 (m under DMSO peak, 5H), 1.87-1.81 (m, 2H)f 1.71 (d, J=6.4 Hz, 3H), 1.50-1.43 (m, 2H). HRMS calculated [M+H]$^+$ C$_{31}$H$_{31}$ClN$_5$O$_3$S 588.1836; found 588.1837.

EXAMPLE 10

3-[((1R)-1-{2-chloro-3-[(1-methyl-4-piperidinyl) oxy]phenyl}ethyl)oxy]-5-[5-(6-methyl-3-pyridinyl)-1H-benzimidazol-1-yl]-2-thiophenecarboxamide

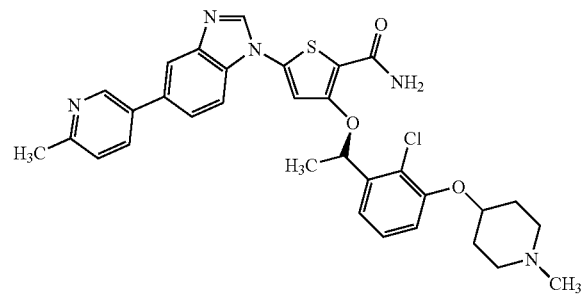

Methyl 3-{[(1R)-1-(2-chloro-3-hydroxyphenyl)ethyl]oxy}-5-[5-(6-methyl-3-pyridinyl)-1H-benzimidazol-1-yl]-2-thiophenecarboxylate (Intermediate 9, 97 mg, 0.19 mmol) was coupled with 1-methyl-4-piperidinol and subjected to aminolysis procedure analogous to Example 3 to give 74 mg of the title compound (65% over both steps). $^1$H NMR (400 MHz, d$_6$-DMSO) δ 8.79 (d, J=2.1 Hz, 1H), 8.61 (s, 1H), 8.08 (s, 1H), 8.01 (dd, J=8.0 and 2.4 Hz, 1H), 7.81 (br s, 1H), 7.66 (m, 1H), 7.57 (d, J=8.4 Hz, 1H), 7.35-7.31 (m, 2H), 7.21-7.14 (m, 3H), 7.10 (br s, 1H), 5.98 (m, 1H), 4.46 (m, 1H), 2.50 (s, 3H), 2.48-2.45 (m under DMSO peak, 2H), 2.18-2.08 (m, 5H), 1.83 (m, 2H), 1.70 (d, J=6.0 Hz, 3H), 1.63 (m, 2H). HRMS calculated [M+H]$^+$ C$_{32}$H$_{33}$ClN$_5$O$_3$S 602.1993; found 602.1993.

EXAMPLE 11

3-[((1R)-1-{2-chloro-3-[(1-methyl-4-piperidinyl) oxy]pheny}ethyl)oxy]-5-[5-(3-pyridinyl)-1H-benzimidazol-1-yl]-2-thiopnenecarboxamide

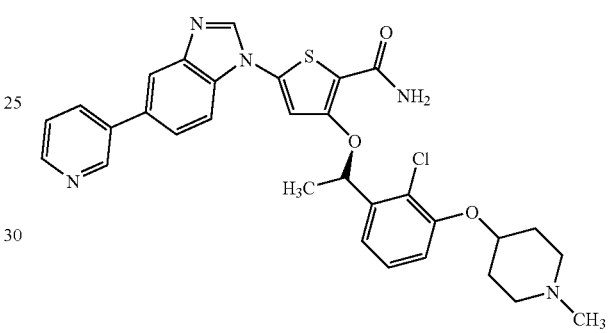

Step A—Methyl 3-[((1R)-1-{2-chloro-3-[(1-methyl-4-piperidinyl)oxy]phenyl}ethyl)oxy]-5-[5-(3-pyridinyl)-1H-benzimidazol-1-yl]-2-thiophenecarboxylate

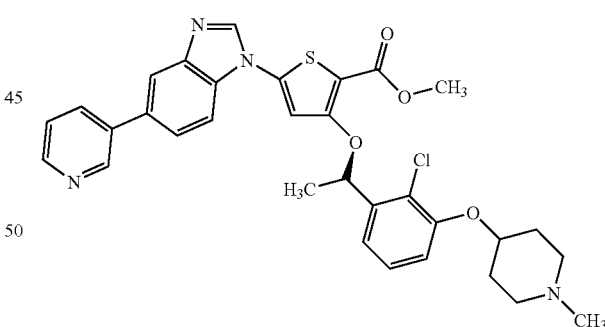

Methyl 3-{[(1R)-1-(2-chloro-3-hydroxyphenyl)ethyl]oxy}-5-[5-(3-pyridinyl)-1H-benzimidazol-1-yl]-2-thiophenecarboxylate (Intermediate 10, 94 mg, 0.19 mmol) and 1-methyl-4-piperidinol (27 µl, 0.23 mmol) were coupled using a procedure analogous to Example 4, Step A to give 97 mg of the desired product (84%). $^1$H NMR (400 MHz, d$_6$-DMSO) δ 8.95 (d, J=2.4 Hz, 1H), 8.73 (s, 1H), 8.57 (dd, J=8.8 and 1.4 Hz, 1H), 8.15-8.13 (m, 2H), 7.73 (m, 2H), 7.49 (dd, J=8.0 and 4.8 Hz, 1H), 7.40 (s, 1H), 7.36-7.28 (m, 2H), 7.15 (d, J=6.8 Hz, 1H), 5.98 (m, 1H), 4.46 (m, 1H), 3.82 (s, 3H), 2.54-2.48 (m under DMSO peak, 2H), 2.17-2.11 (m, 2H), 2.10 (s, 3H), 1.84 (m, 2H), 1.67-1.61 (m, 5H).

Step B—3-[((1R)-1-(2-chloro-3-[(1-methyl-4-piperidinyl)oxy]phenyl)ethyl)oxy]-5-[5-(3-pyridinyl)-1H-benzimidazol-1-yl]-2-thiophenecarboxamide (Title Compound)

Methyl 3-[((1R)-1-{2-chloro-3-[(1-methyl-4-piperidinyl)oxy]phenyl}ethyl)oxy]-5-[5-(3-pyridinyl)-1H-benzimidazol-1-yl]-2-thiophenecarboxylate (90 mg, 0.15 mmol) was subjected to aminolysis procedure analogous to Example 4, Step B to give 37 mg of the title compound (42%). $^1$H NMR (400 MHz, d$_6$-DMSO) δ 8.93 (s, 1H), 8.62 (s, 1H), 8.55 (d, J=4.4 Hz, 1H), 8.13-8.11 (m, 2H), 7.81 (br s, 1H), 7.68 (d, J=8.4 Hz, 1H), 7.58 (d, J=8.4 Hz, 1H), 7.49-7.45 (m, 1H), 7.32 (t, J=8.0 Hz, 1H), 7.20-7.14 (m, 3H), 7.10 (br s, 1H), 5.97 (m, 1H), 4.45 (m, 1H), 2.51-2.47 (m under DMSO peak, 2H), 2.15-2.07 (m, 2H), 2.07 (s, 3H), 1.82 (m, 2H), 1.69 (d, J=6.0 Hz, 3H), 1.62 (m, 2H). HRMS calculated [M+H]$^+$ C$_{31}$H$_{31}$ClN$_5$O$_3$S 588.1836, found 588.1831.

EXAMPLE 12

3-({(1R)-1-[2-chloro-3-(4-piperidinyloxy)phenyl]ethyl}oxy)-5-[5-(pyridinyl)-1H-benzimidazol-1-yl]-2-thiophenecarboxamide

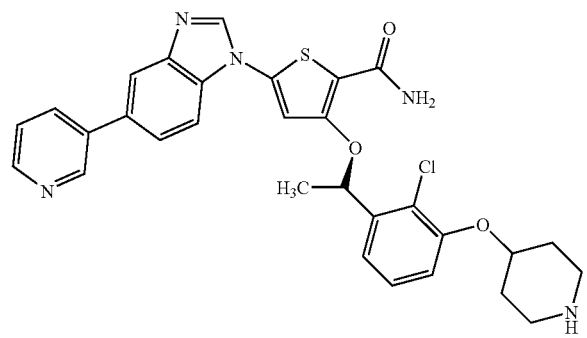

Step A—1,1-Dimethylethyl-4-({2-chloro-3-[(1R)-1-({2-[(methyloxy)carbonyl]-5-[5-(3-pyridinyl)-1H-benzimidazol-1-yl]-3-thienyl}oxy)ethyl]phenyl}oxy)-1-piperidinecarboxylate

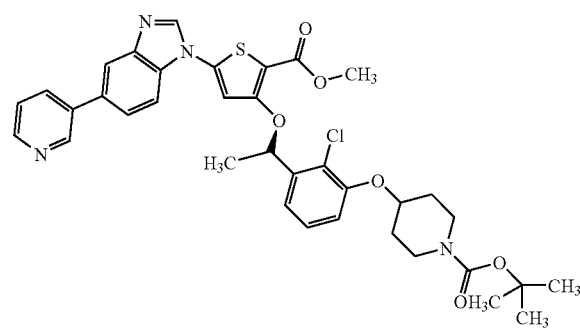

Methyl 3-{[(1R)-1-(2-chloro-3-hydroxyphenyl)ethyl]oxy}-5-[5-(3-pyridinyl)-1H-benzimidazol-1-yl]-2-thiophenecarboxylate (Intermediate 10, 108 mg, 0.21 mmol) and 1,1-dimethylethyl-4-hydroxy-1-piperidinecarboxylate (50 mg, 0.25 mmol) were coupled using a procedure analogous to Example 5, Step A to give 129 mg of the desired product (89%). $^1$H NMR (400 MHz, d$_6$-DMSO) δ 8.95 (d, J=2.0 Hz, 1H), 8.74 (s, 1H), 8.56 (dd, J=4.8 and 1.6 Hz, 1H), 8.15-8.13 (m, 2H), 7.77-7.74 (m, 2H), 7.49 (dd, J=8.0 and 4.8 Hz, 1H), 7.44 (s, 1H), 7.38-7.31 (m, 2H), 7.20-7.18 (m, 1H), 5.98 (m, 1H), 4.66 (m, 1H), 3.82 (s, 3H), 3.53 (m, 2H), 2.25 (m, 2H), 1.85 (m, 2H), 1.62 (d, J=6.4 Hz, 3H), 1.56 (m, 2H), 1.36 (s, 9H).

Step B—1,1-Dimethylethyl 4-({3-[(1R)-1-({2-(aminocarbonyl)-5-[5-(3-pyridinyl)-1H-benzimidazol-1-yl]-3-thienyl}oxy)ethyl]-2-chlorophenyl}oxy)-1-piperidinecarboxylate

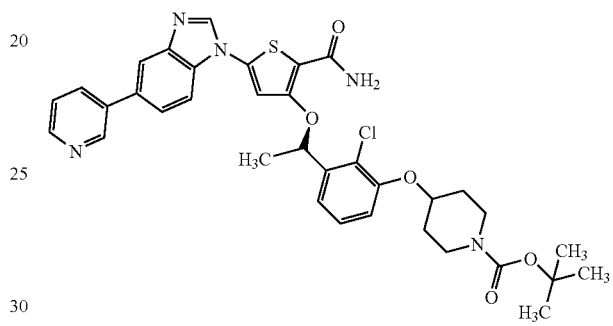

1,1-Dimethylethyl 4-({2-chloro-3-[(1R)-1-({2-[(methyloxy)carbonyl]-5-[5-(3-pyridinyl)-1H-benzimidazol-1-yl]-3-thienyl}oxy)ethyl]pheny}oxy)-1-piperidinecarboxylate (120 mg, 0.17 mmol) was subjected to aminolysis procedure analogous to Example 5, Step B to give 70 mg of the desired product (61%). $^1$H NMR (400 MHz, d$_6$-DMSO) δ 8.93 (s, 1H), 8.62 (s, 1H), 8.55 (d, J=4.4 Hz, 1H), 8.13-8.11 (m, 2H), 7.81 (br s, 1H), 7.69 (d, J=8.4 Hz, 1H), 7.61 (d, J=8.4 Hz, 1H), 7.48-7.45 (m, 1H), 7.34 (t, J=8.0 Hz, 1H), 7.23-7.17 (m, 3H), 7.09 (br s, 1H), 5.98 (m, 1H), 4.65 (m, 1H), 3.51 (m, 2H), 3.20 (m, 2H), 1.82 (m, 2H), 1.70 (d, J=6.0 Hz, 3H), 1.53 (m, 2H), 1.34 (s, 9H).

Step C—3-({(1R)-1-[2-chloro-3-(4-piperidinyloxy)phenyl]ethyl}oxy)-5-[5-(3-pyridinyl)-1H-benzimidazol-1-yl]-2-thiophenecarboxamide (Title Compound)

1,1-Dimethylethyl 4-({3-[(1R)-1-({2-(aminocarbonyl)-5-[5-(3-pyridinyl)-1H-benzimidazol-1-yl]-3-thienyl}oxy)ethyl]-2-chlorophenyl}oxy)-1-piperidinecarboxylate (65 mg, 0.10 mmol) was deprotected using a procedure analogous to Example 5, Step C to give 20 mg of the title compound (36%).

$^1$H NMR (400 MHz, d$_6$-DMSO) δ 8.94 (s, 1H), 8.63 (s, 1H), 8.56 (d, J=4.4 Hz, 1H), 8.14-8.13 (m, 1H), 7.82 (br s, 1H), 7.89 (d, J=8.0 Hz, 1H), 7.59 (d, J=8.4 Hz, 1H), 7.48 (dd, J=7.6 and 4.8 Hz, 1H), 7.33 (t, J=8.0 Hz, 1H), 7.21-7.17 (m, 3H), 7.11 (br s, 1H), 5.99 (m, 1H), 4.50 (m, 1H), 2.90 (m, 2H), 2.48 (m, 2H), 1.85 (m, 2H), 1.71 (d, J=6.0 Hz, 3H), 1.47 (m, 2H). MS (ESI) m/z=574 [M+H]+.

EXAMPLE 13

5-(1H-benzimidazol-1-yl)-3-[((1R)-1-{2-chloro-3-[(1-methyl-4-piperidinyl)gxy]phenyl}ethyl)oxy]-2-thiophenecarboxamide

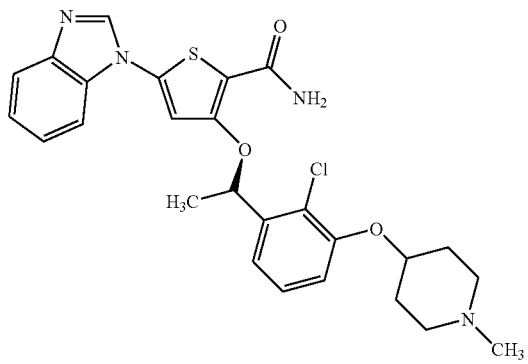

Step A—Methyl 5-(1H-benzimidazol-1-yl)-3-[((1R)-1-{2-chloro-3-[(1-methyl-4-piperidinyl)oxy]phenyl}ethyl)oxy]-2-thiophenecarboxylate

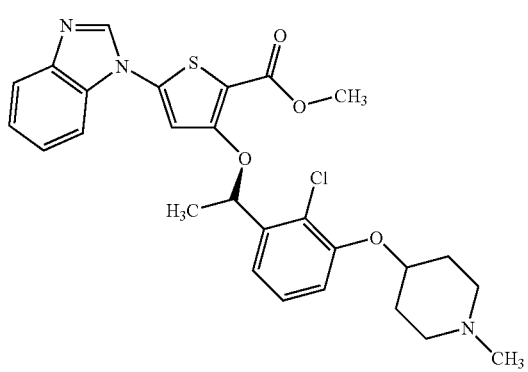

Methyl 5-(1H-benzimidazol-1-yl)-3-{[(1R)-1-(2-chloro-3-hydroxyphenyl)ethyl]oxy}-2-thiophenecarboxylate (Intermediate 11A, 125 mg, 0.29 mmol) and 1-methyl-4-piperidinol (41 µl, 0.35 mmol) were coupled using a procedure analogous to Example 4, Step A to give 84 mg of the desired product (55%). MS m/z=526 [M+H]⁺.

Step B—5-(1H-benzimidazol-1-yl)-3-[((1R)-1-{2-chloro-3-[(1-methyl-4-piperidinyl)oxy]phenyl}ethyl)oxy]-2-thiophenecarboxamide (Title Compound)

Methyl 5-(1H-benzimidazol-1-yl)-3-[((1R)-1-{2-chloro-3-[(1-methyl-4-piperidinyl)oxy]phenyl}ethyl)oxy]-2-thiophenecarboxylate (84 mg, 0.16 mmol) was subjected to aminolysis procedure analogous to Example 4, Step B to give 58 mg of the title compound (71%). ¹H NMR (400 MHz, d₆-DMSO) δ 8.53 (s, 1h), 7.79-7.73 (m, 2H), 7.50-7.48 (m, 1H), 7.34-7.29 (m, 3H), 7.19-7.09 (m, 4H), 5.97 (m, 1H), 4.44 (m, 1H), 2.48-2.47 (m under DMSO peak, 2H), 2.14-2.11 (m, 5H), 1.86 (m, 2H), 1.69 (d, J=6.4 Hz, 3H), 1.70-1.59 (m, 2H). HRMS calculated [M+H]⁺ C₂₆H₂₈ClN₄O₃S 511.1571, found 511.1574.

EXAMPLE 14

5-(1H-Benzimidazol-1-yl)-3-({(1R)-1-[2-chloro-3-(4-piperidinyloxy)phenyl]ethyl}oxy)-2-thiophenecarboxamide

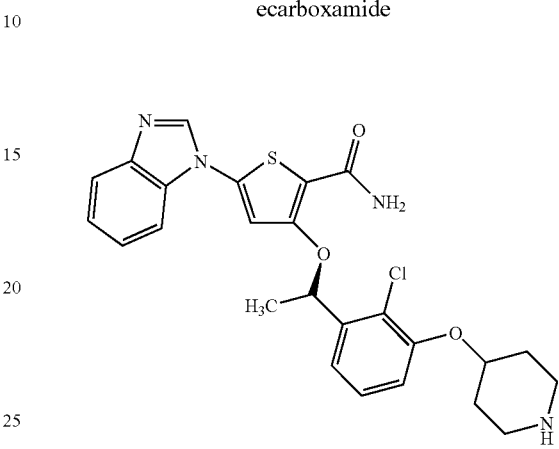

Step A—1,1-Dimethylethyl 4-({3-[(1R)-1-({5-(1H-benzimidazol-1-yl)-2-[(methyloxy)carbonyl]-3-thienyl}oxy)ethyl]-2-chlorophenyl}oxy)-1-piperidinecarboxylate

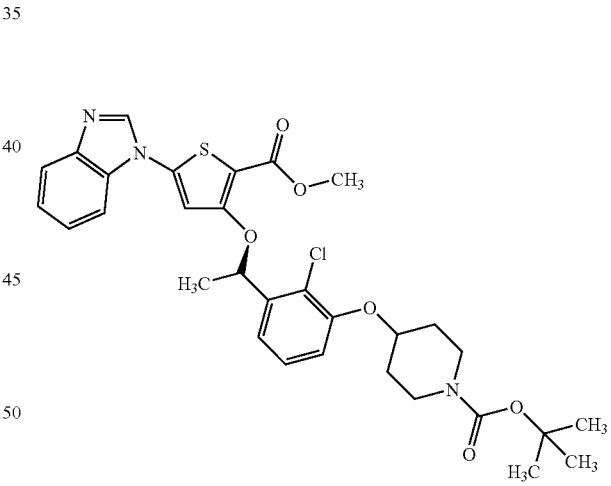

Methyl 5-(1H-benzimidazol-1-yl)-3-{[(1R)-1-(2-chloro-3-hydroxyphenyl)ethyl]oxy}-2-thiophenecarboxylate (Intermediate 11A, 125 mg, 0.29 mmol) and 1,1-dimethylethyl 4-hydroxy-1-piperidinecarboxylate (70 mg, 0.35 mmol) were coupled using a procedure analogous to Exampls 5, Step A to give 103 mg of the desired product (58%). ¹H NMR (400 MHz, d₆-DMSO) δ 8.63 (s, 1H), 7.77-7.75 (m, 1H), 7.63-7.61 (m, 1H), 7.37-7.28 (m, 5H), 7.16 (d, J=8.0 Hz, 1H), 5.95 (m, 1H), 4.64 (m, 1H), 3.80 (s, 3H), 3.53 (M, 2H), 3.28-3.21 (m, 2H), 1.59 (d, J=6.0 Hz, 3H), 1.60-1.52 (m, 2H), 1.37 (s, 9H).

Step B—1,1-Dimethylethyl-4-{[3-((1R)-1-{[2-(aminocarbonyl)-5-(1H-benzimidazol-1-yl)-3-thienyl]oxy}ethyl)-2-chlorophenyl]oxy}-1-piperidinecarboxylate

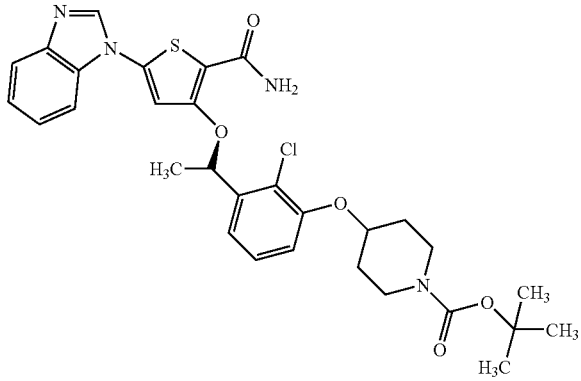

1,1-Dimethylethyl 4-({3-[(1R)-1-({5-(1H-benzimidazol-1-yl)-2-[(methyloxy)carbonyl]-3-thienyl}oxy)ethyl]-2-chlorophenyl}oxy)-1-piperidinecarboxylate (103 mg, 0.17 mmol) was subjected to aminolysis according to the procedure analogous to Example 5, Step B to give 75 mg of the desired product (74%). $^1$H NMR (400 MHz, $d_6$-DMSO) δ 8.55 (s, 1H), 7.80 (br s, 1H), 7.77-7.74 (m, 1H), 7.52-7.49 (m, 1H), 7.36-7.32 (m, 3H), 7.23-7.18 (m, 2H), 7.13 (s, 1H), 7.10 (br s, 1H), 5.98 (m, 1H), 4.67-4.64 (m, 1H), 3.56-3.52 (m, 2H), 3.27-3.21 (m, 2H), 1.85 (m, 2H), 1.70 (d, J=6.4 Hz, 3H), 1.58-1.54 (m, 2H), 1.38 (s, 9H).

Step C—5-(1H-benzimidazol-1-yl)-3-({(1R)-1-[2-chloro-3-(4-piperidinyloxy)phenyl]-ethyl}oxy)-2-thiophenecarboxamide (Title Compound)

1,1-Dimethylethyl 4-{[3-((1R)-1-{[2-(aminocarbonyl)-5-(1H-benzimidazol-1-yl)-3-thienyl]oxy}ethyl)-2-chlorophenyl]oxy}-1-piperidinecarboxylate (75 mg, 0.13 mmol) was deprotected using a procedure analogous to Example 5, Step C to give 65 mg of the title compound (99%). $^1$H NMR (400 MHz, $d_6$-DMSO) δ 8.54 (s, 1H), 7.79 (br s, 1H), 7.75 (m, 1H), 7.50 (m, 1H), 7.36-7.30 (m, 3H), 7.23-7.17 (m, 2H), 7.12 (s, 1H), 7.09 (br s, 1H), 5.97 (m, 1H), 4.62 (m, 1H), 3.05 (m, 2H), 2.83 (m, 2H), 1.96 (m, 2H), 1.70-1.59 (m, 5H). HRMS calculated [M+H]$^+$ $C_{25}H_{26}ClN_4O_3S$ 497.1414, found 497.1421.

EXAMPLE 15

5-(1H-benzimidazol-1-yl)-3-{[(1R)-1-(2-chloro-3-{[2-(4-morpholinyl)ethyl]oxy}phenyl)ethyl]oxy}-2-thiophenecarboxamide

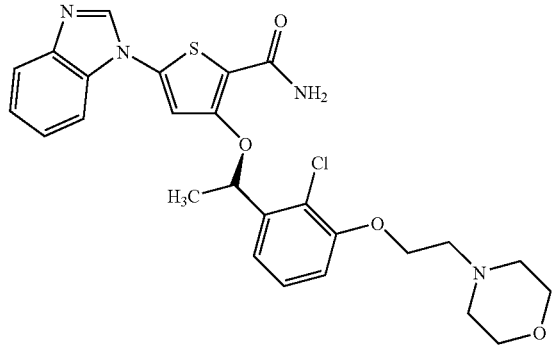

Step A—Methyl 5-(1H-benzimidazol-1-yl)-3-{[(1R)-1-(2-chloro-3-{[2-(4-morpholinyl)-ethyl]oxy}phenyl)ethyl]oxy}-2-thiophenecarboxylate

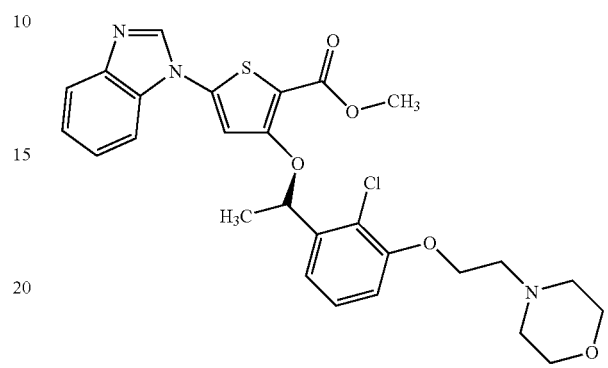

To a solution of methyl 5-(1H-benzimidazol-1-yl)-3-[((1R)-1-{3-[(2-bromoethyl)oxy]-2-chlorophenyl}ethyl)oxy]-2-thiophenecarboxylate (Intermediate 11B, 95 mg, 0.18 mmol) in 2 mL THF was added morpholine (63 μL, 0.72 mmol) and the reaction was heated to 60° C. After 16 h, the reaction was cooled to rt and diluted with DCM. The organic solution was washed with water, dried over $MgSO_4$ and concentrated onto silica gel. The crude material was purified by flash column chromatography to give 73 mg of the desired product (75%). $^1$H NMR (400 MHz, $d_6$-DMSO) δ 8.63 (s, 1H), 7.76 (d, J=7.2 Hz, 1H), 7.59 (d, J=7.6 Hz, 1H), 7.37-7.31 (m, 4H), 7.26 (d, J=7.6H, 1H), 7.09 (d, J=8.0 Hz, 1H), 5.96 (m, 1H), 4.14 (t, J=5.8 Hz, 2H), 3.80 (s, 3H), 3.52 (t, J=4.4 Hz, 4H), 2.69 (t, J=5.6 Hz, 2H), 2.47 (m under DMSO peak, 4H), 1.59 (d, J=6.4 Hz, 3H).

Step B—5-(1H-benzimidazol-1-yl)-3-{[(1R)-1-(2-chloro-3-{[2-(4-morpholinyl)ethyl]-oxy}phenyl)ethyl]oxy}-2-thiophenecarboxamide (Title Compound)

Methyl 5-(1H-benzimidazol-1-yl)-3-{[(1R)-1-(2-chloro-3-{[2-(4-morpholinyl)-ethyl]oxy}phenyl)ethyl]oxy}-2-thiophenecarboxylate (71 mg, 0.13 mmol) was subjected to aminolysis procedure analogous to Example 4, Step B to give 57 mg of the title compound (83%). $^1$H NMR (400 MHz, $d_6$-DMSO) δ 8.53 (s, 1H), 7.79-7.73 (m, 2H), 7.47 (d, J=7.6 Hz, 1H), 7.35-7.31 (m, 3H), 7.19 (d, J=7.6 Hz, 1H), 7.12-7.09 (m, 3H), 5.97 (m, 1H), 4.14 (t, J=5.6 Hz, 2H), 3.51-3.49 (m, 4H), 2.69 (t, J=5.6 Hz, 2H), 2.47 (m under DMSO peak, 4H), 1.68 (d, J=6.4 Hz, 3H). HRMS calculated [M+H]$^+$ $C_{26}H_{28}ClN_4O_4S$ 527.1520, found 527.1527.

EXAMPLE 16

5-(1H-benzimidazol-1-yl)-3-{[(1R)-1-(2-chloro-3-{[2-(1-piperazinyl)ethyl]oxy}phenyl)ethyl]oxy}-2-thiophenecarboxamide

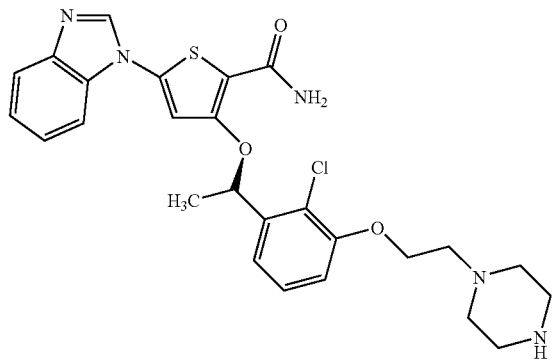

Step A—Methyl 5-(1H-benzimidazol-1-yl)-3-{[(1R)-1-(2-chloro-3-{[2-(1-piperazinyl)ethyl]oxy}phenyl)ethyl]oxy}-2-thiophenecarboxylate

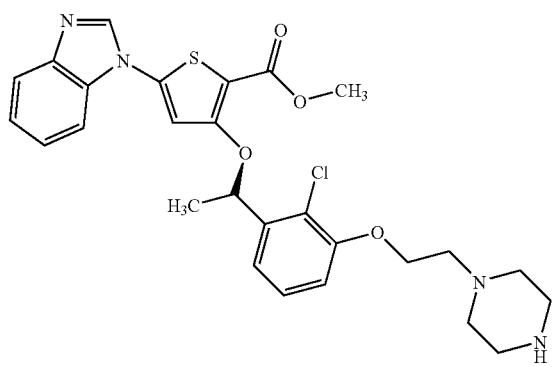

Methyl 5-(1H-benzimidazol-1-yl)-3-[((1R)-1-{3-[(2-bromoethyl)oxy]-2-chlorophenyl}ethyl)oxy]-2-thiophenecarboxylate (Intermediate 11B, 125 mg, 0.23 mmol) and 1,1-dimethylethyl 1-piperazinecarboxylate (171 mg, 0.92 mmol) were coupled using a procedure analogous to Example 15, Step A to give 89 mg of the desired product (61%). $^1$H NMR (400 MHz, d$_6$-DMSO) δ 8.63 (s, 1H), 7.75 (d, J=7.2 Hz, 1H), 7.59 (d, J=7.2 Hz, 1H), 7.38-7.31 (m, 4H), 7.26 (d, J=7.2 Hz, 1H), 7.09 (d, J=8.0 Hz, 1H), 5.96 (m, 1H), 4.13 (t, J=5.6 Hz, 2H), 3.80 (s, 3H), 3.25 (m, 4H), 2.72 (t, J=5.6 Hz, 2H), 2.43 (m, 4H), 1.59 (d, J=6.4 Hz, 3H), 1.35 (s, 9H).

Step B—1,1-Dimethylethyl 4-(2-{[3-((1R)-1-{[2-(aminocarbonyl)-5-(1H-benzimidazol-1-yl)-3-thienyl]oxy}ethyl)-2-chlorophenyl]oxy}ethyl)-1-piperazinecarboxylate

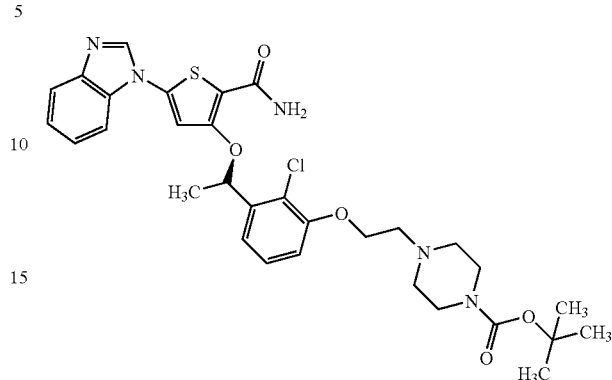

Methyl 5-(1H-benzimidazol-1-yl)-3-{[(1R)-1-(2-chloro-3-{[2-(1-piperazinyl)ethyl]oxy}-phenyl)ethyl]oxy}-2-thiophenecarboxylate (84 mg, 0.13 mmol) was subjected to aminolysis procedure analogous to Example 5, Step B to give 53 mg of the desired product (65%). MS m/z=626 [M+H]$^+$.

Step C—5-(1H-benzimidazol-1-yl)-3-{[(1R)-1-(2-chloro-3-{[2-(1-piperazinyl)ethyl]oxy}phenyl)ethyl]oxy}-2-thiophenecarboxamide (Title Compound)

1,1-Dimethylethyl 4-(2-{[3-((1R)-1-{[2-(aminocarbonyl)-5-(1H-benzimidazol-1-yl)-3-thienyl]oxy}ethyl)-2-chlorophenyl]oxy}ethyl)-1-piperazinecarboxylate (53 mg, 8.5 mmol) was deprotected using procedure analogous to Example 5, Step C to give 44 mg of the title compound (99%). $^1$H NMR (400 MHz, d$_6$-DMSO) δ 8.55 (s, 1H), 7.80 (br s, 1H), 7.77-7.75 (m, 1H), 7.50-7.48 (m, 1H), 7.37-7.33 (m, 3H), 7.21 (d, J=7.6 Hz, 1H), 7.13-7.10 (m, 3H), 5.98 (m, 1H), 4.14 (t, J=5.6 Hz, 2H), 2.80-2.78 (m, 4H), 2.72 (t, J=5.6 Hz, 2H), 2.51 (m, 4H), 1.70 (d, J=6.4 Hz, 3H). HRMS calculated [M+H]$^+$ C$_{26}$H$_{29}$ClN$_5$O$_3$S 526.1680, found 526.1677.

EXAMPLE 17

5-(1H-benzimidazol-1-yl)-3-{[(1R)-1-(2-chloro-3-{[2-(4-methyl-1-piperazinyl)ethyl]oxy}phenyl)ethyl]ocy}-2-thiophenecarboxamide

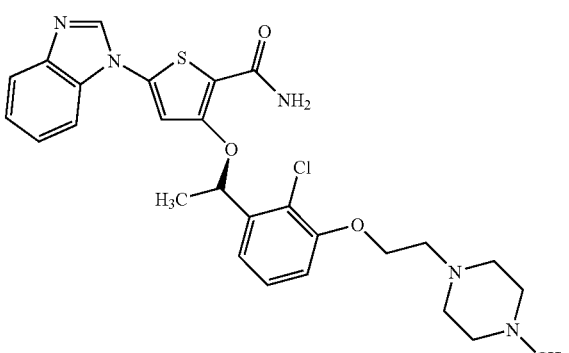

Step A—Methyl 5-(1H-benzimidazol-1-yl)-3-{[(1R)-1-(2-chloro-3-{[2-(4-methyl-1-piperazinyl)ethyl]oxy}phenyl)ethyl]oxy}-2-thiophenecarboxylate

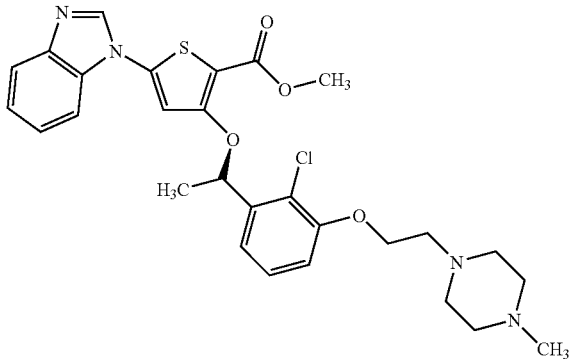

Methyl 5-(1H-benzimidazol-1-yl)-3-[((1R)-1-{3-[(2-bromoethyl)oxy]-2-chlorophenyl}ethyl)oxy]-2-thiophenecarboxylate (Intermediate 11B, 125 mg, 0.23 mmol) and 1-methylpiperazine (102 μL, 0.92 mmol) were coupled using a procedure analogous to Example 15, Step A to give 82 mg of the desired product (64%). $^1$H NMR (400 MHz, d$_6$-DMSO) δ 8.63 (s, 1H), 7.76 (d, J=7.6 Hz, 1H), 7.59 (d, J=7.6 Hz, 1H), 7.39-7.31 (m, 4H), 7.25 (d, J=7.6 Hz, 1H), 7.09 (d, J=8.0 Hz, 1H), 5.95 (m, 1H), 4.11 (t, J=5.8 Hz, 2H), 3.80 (s, 3H), 2.68 (t, J=5.6 Hz, 2H), 2.47 (m under DMSO peak, 4H), 2.24 (m, 4H), 2.08 (s, 3H), 1.59 (d, J=6.4 Hz, 3H).

Step B—5-(1H-benzimidazol-1-yl)-3-{[(1R)-1-(2-chloro-3-{[2-(4-methyl-1-piperazinyl)ethyl]oxy}phenyl)ethyl]oxy}-2-thiophenecarboxamide (Title Compound)

Methyl 5-(1H-benzimidazol-1-yl)-3-{[(1R)-1-(2-chloro-3-{[2-(4-methyl-1-piperazinyl)ethyl]oxy}phenyl)ethyl]oxy}-2-thiophenecarboxylate (80 mg, 0.14 mmol) was subjected to aminolysis procedure analogous to Example 5, Step B to give 69 mg of the title compound (91%). $^1$H NMR (400 MHz, d$_6$-DMSO) δ 8.53 (s, 1H), 7.78-7.73 (m, 2H), 7.47 (d, J=7.6 Hz, 1H), 7.36-7.29 (m, 3H), 7.18 (d, J=8.0 Hz, 1H), 7.11-7.09 (m, 3H), 5.97 (m, 1H), 4.12 (t, J=5.6 Hz, 2H), 2.68 (t, J=5.6 Hz, 2H), 2.47 (m under DMSO peak, 4H), 2.23 9M, 4H), 2.08 (s, 3H), 1.68 (d, J=6.0 Hz, 3H). HRMS calculated [M+H]$^+$ C$_{27}$H$_{31}$ClN$_5$O$_3$S 540.1836, found 540.1837.

EXAMPLE 18

3-[((1R)-1-{2-chloro-3-[(1-methyl-4-piperidinyl)oxy]phenyl}ethyl)oxy]-5-(5-{6-[(1-methyl-4-piperidinyl)amino]-3-pyridinyl}-1H-benzimidazol-1-yl)-2-thiophenecarboxamide

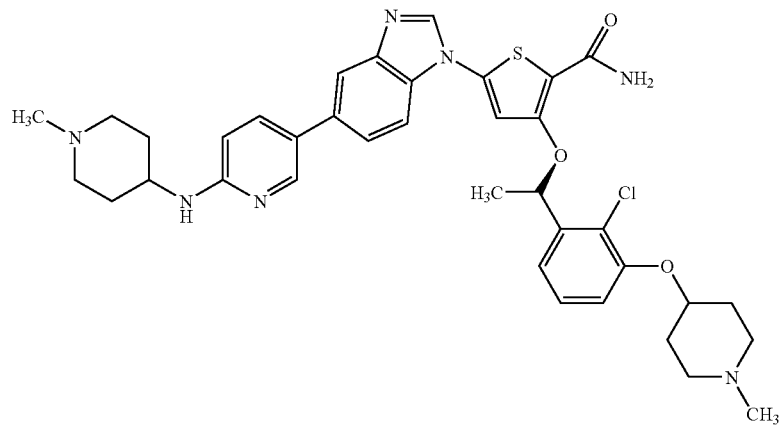

Step A—Methyl 3-{[(1R)-1-(2-chloro-3-hydroxyphenyl)ethyl]oxy}-5-[5-(6-fluoro-3-pyridinyl)-1H-benzimidazol-1-yl]-2-thiophenecarboxylate

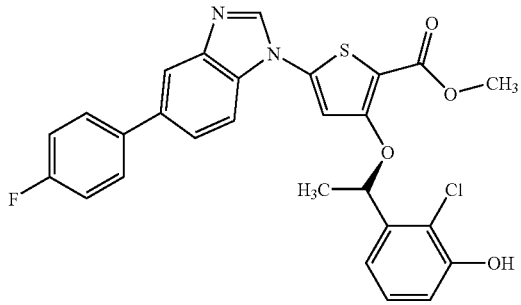

Methyl 5-(5-bromo-1H-benzimidazol-1-yl)-3-{[(1R)-1-(2-chloro-3-{[(1,1-dimethylethyl)(dimethyl)silyl]oxy}phenyl)ethyl]oxy}-2-thiophenecarboxylate (Intermediate 8, 930 mg, 1.5 mmol) and (6-fluoro-3-pyridinyl)boronic acid (250 mg, 1.8 mmol) were coupled using a procedure analogous to Intermediate 9 to give 781 mg of the desired product (99%). $^1$H NMR (400 MHz, $d_6$-DMSO) δ 10.27 (s, 1H), 8.71 (s, 1H), 8.60 (s, 1H), 8.36-8.32 (m, 1H), 8.13 (s, 1H), 7.72-7.67 (m, 2H), 7.35 (s, 1H), 7.27 (dd, J=8.4 and 2.8 Hz, 1H), 7.20-7.11 (m, 2H), 6.90 (d, J=7.6 Hz, 1H), 5.94 (m, 1H), 3.80 (s, 3H), 1.59 (d, J=6.0 Hz, 3H).

Step B—Methyl 3-[((1R)-{2-chloro-3-[(1-methyl-4-piperidinyl)oxy]phenyl}ethyl)oxy]-5-[5-(6-fluoro-3-pyridinyl)-1H-benzimidazol-1-yl]-2-thiophenecarboxylate

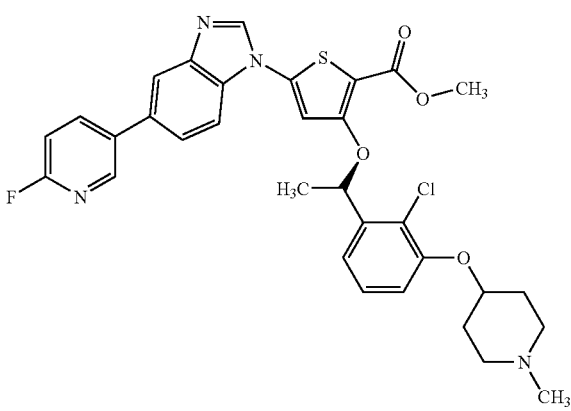

Methyl 3-{[(1R)-1-(2-chloro-3-hydroxyphenyl)ethyl]oxy}-5-[5-(6-fluoro-3-pyridinyl)-1H-benzimidazol-1-yl]-2-thiophenecarboxylate (300 mg, 0.57 mmol) and 1-methyl-4-piperidinol (80 μL, 0.68 mmol) were coupled using a procedure analogous to Example 4, Step A to give 274 mg of the desired product (77%). $^1$H NMR (400 MHz, $d_6$-DMSO) δ 8.70 (s, 1H), 8.59 (s, 1H), 8.35-8.31 (m, 1H), 8.13 (s, 1H), 7.73-7.68 (m, 2H), 7.38 (s, 1H), 7.34-7.25 (m, 3H), 7.13 (d, J=7.6 Hz, 1H), 5.96 (m, 1H), 4.44 (m, 1H), 3.81 (s, 3H), 2.54-2.46 (m, 2H), 2.20-2.11 (m, 5H), 1.83 (m, 2H), 1.66-1.59 (m, 5H).

Step C—3-[((1R)-1-{2-chloro-3-[(1-methyl-4-piperidinyl)oxy]phenyl}ethyl)oxy]-5-[5-(6-fluoro-3-pyridinyl)-1H-benzimidazol-1-yl]-2-thiophenecarboxamide

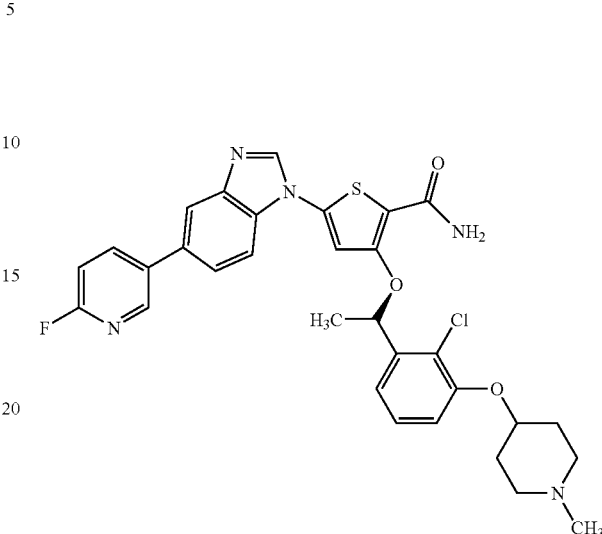

Methyl 3-[((1R)-1-{2-chloro-3-[(1-methyl-4-piperidinyl)oxy]phenyl}ethyl)oxy]-5-[5-(6-fluoro-3-pyridinyl)-1H-benzimidazol-1-yl]-2-thiophenecarboxylate (274 mg, 0.44 mmol) was subjected to aminolysis according to a procedure analogous to Example 4, Step B to give 200 mg of the desired product (75%).

$^1$H NMR (400 MHz, $d_6$-DMSO) δ 8.63 (s, 1H), 8.60 (d, J=2.1 Hz, 1H), 8.37-8.32 (m, 1H), 8.13 (d, J=1.6 Hz, 1H), 7.82 (br s, 1H), 7.69-7.67 (m, 1H), 7.60 (d, J=8.4 Hz, 1H), 7.35-7.27 (m, 2H), 7.21 (d, J=7.6 Hz, 1H), 7.17-7.14 (m, 2H), 7.11 (br s, 1H), 5.99 (m, 1H), 4.45 (m, 1H), 2.52-2.45 (m under DMSO peak, 2H), 2.19-2.06 (m, 5H), 1.85-1.74 (m, 2H), 1.70-1.60 (m, 5H).

Step D—3-[((1R)-1-{2-Chloro-3-[(1-methyl-4-piperidinyl)oxy]phenyl}ethyl)oxy]-5-(5-{6-[(1-methyl-4-piperidinyl)amino]-3-pyridinyl}-1H-benzimidazol-1-yl)-2-thiophenecarboxamide (Title Compound)

3-[((1R)-1-{2-chloro-3-[(1-methyl-4-piperidinyl)oxy]prienyl}ethyl)oxy]-5-[5-(6-fluoro-3-pyridinyl)-1H-benzimidazol-1-yl]-2-thiophenecarboxamide (100 mg, 0.16 mmol) in 1 mL of 1-methyl-4-piperidinamine and 1 mL of i-PrOH was heated in the microwave at 180° C. in cycles of 40 min each until there was more product than starting material. The reaction was diluted with DCM and washed 3× with water. The organic phase was dried over MgSO$_4$ and concentrated. The crude material was purified by reverse phase liquid chromatography to give 16 mg of the title compound (14%). $^1$H NMR (400 MHz, $d_6$-DMSO) δ 8.56 (s, 1H), 8.32 (s, 1H), 7.89 (s, 1H), 7.80 (s, 1H), 7.72-7.70 (m, 1H), 7.53-7.45 (m, 2H), 7.35-7.31 (m, 1H), 7.20-7.10 (m, 4H), 6.54-6.52 (m, 2H), 5.98 (m, 1H), 4.46 (m, 1H), 3.69 (m, 1H), 2.74-2.71 (m, 2H), 2.48 (m under DMSO peak, 2H), 2.16-1.86 (m, 14H), 1.71-1.63 (m, 5H), 1.45-1.42 (m, 2H). MS (ESI) m/z=700.63 [M+H]$^+$.

EXAMPLE 19

5-(5-Chloro-1H-benzimidazol-1-yl)-3-[((1R)-1-{2-chloro-3-[(1-ethyl-4-piperidinyl)oxy]phenyl}ethyl)oxy]-2-thiophenecarboxamide

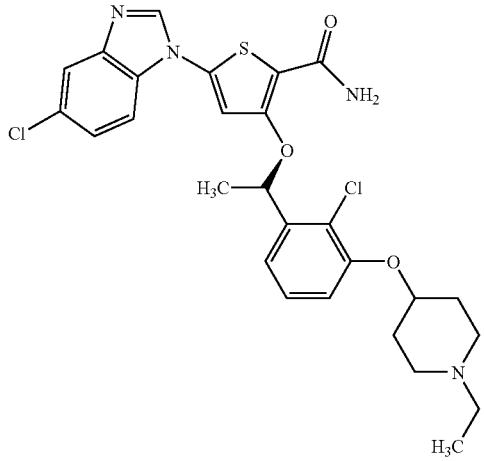

Step A—Methyl 5-(5-chloro-1H-benzimidazol-1-yl)-3-[((1R)-1-{2-chloro-3-[(1-ethyl-4-piperidinyl)oxy]phenyl}ethyl)oxy]-2-thiophenecarboxylate

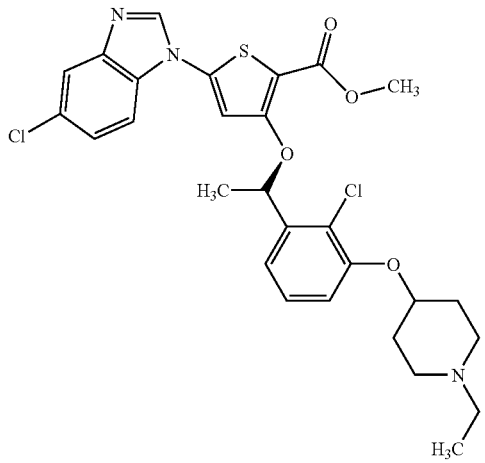

To a solution of methyl 5-(5-chloro-1H-benzimidazol-1-yl)-3-({(1R)-1-[2-chloro-3-(4-piperidinyloxy)phenyl]ethyl}oxy)-2-thiophenecarboxylate (Intermediate 12, 100 mg, 0.18 mmol) in 3 mL of acetonitrile was added $Na_2CO_3$ (23 mg, 0.22 mmol) and bromoethane (67 µL, 0.90 mmol) and the reaction was heated at 75 °C. When the reaction was complete, it was concentrated onto silica gel and purified by flash column chromatography to give 85 mg of the desired product (83%). MS (ESI) m/z=574.23 [M+H]$^+$.

Step B—5-(5-Chloro-1H-benzimidazol-1-yl)-3-[((1R)-1-{2-chloro-3-[(1-ethyl-4-piperidinyl)oxy]phenyl}ethyl)oxy]-2-thiophenecarboxamide (title compound)

Methyl 5-(5-chloro-1H-benzimidazol-1-yl)-3-[((1R)-1-{2-chloro-3-[(1-ethyl-4-piperidinyl)oxy]phenyl}ethyl)oxy]-2-thiophenecarboxylate (85 mg, 0.15 mmol) was subjected to aminolysis procedure analogous to Example 4, Step B to give 68 mg of the title compound (81%). $^1$H NMR (400 MHz, d$_6$-DMSO) δ 8.61 (s, 1H), 7.83 (s, 1H), 7.81 (br s, 1H), 7.59 (d, J=8.8 Hz, 1H), 7.35-7.29 (m, 2H), 7.19-7.09 (m, 4H), 5.95 (m, 1H), 4.45 (m, 1H), 23.58-2.47 (m, 2H), 2.27-2.13 (m, 4H), 1.85 (m, 2H), 1.68 (d, J=6.4 Hz, 3H), 1.61 (m, 2H), 0.94 (t, J=7.0 Hz, 3H). HRMS calculated [M+H]$^+$ $C_{27}H_{29}Cl_2N_4O_3S$ 559.1337, found 559.1337.

EXAMPLE 20

5-(5-Chloro-1H-benzimidazol-1-yl)-3-{[(1R)-1-(2-chloro-3-{[1-(2-hydroxyethyl)-4-piperidinyl]oxy}phenyl)ethyl]oxy}-2-thiophenecarboxamide

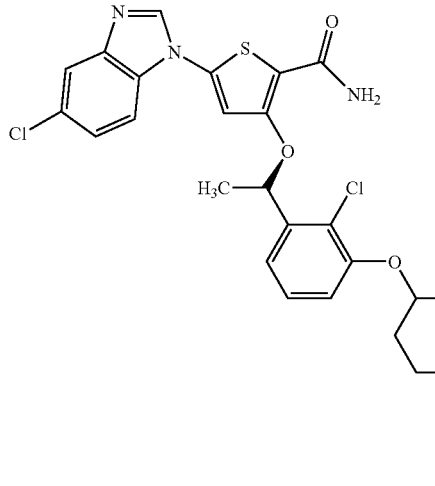

Step A—Methyl 5-(5-chloro-1H-benzimidazol-1-yl)-3-{[(1R)-1-(2-chloro-3-{[1-(2-hydroxyethyl)-4-piperidinyl]oxy}phenyl)ethyl]oxy}-2-thiophenecarboxylate

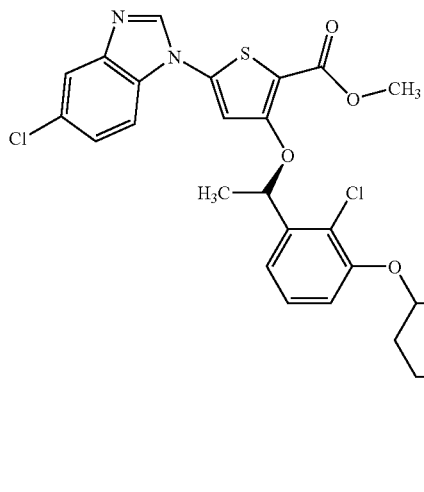

Methyl 5-(5-chloro-1H-benzimidazol-1-yl)-3-({(1R)-1-[2-chloro-3-(4-piperidinyloxy)phenyl]ethyl}oxy)-2-thiophenecarboxylate (Intermediate 12, 100 mg, 0.18 mmol) and 2-bromoethanol (16 µL, 0.22 mmol) were coupled using a procedure analogous to Example 19, Step A to give the (82 mg, 77%) of the desired product. $^1$H NMR (400 MHz, d$_6$-OMSO) δ 8.70 (s, 1H), 7.85 (m, 1H), 7.63 (d, J=8.8 Hz, 1H), 7.39-7.37 (m, 2H), 7.33-7.25 (M, 2H), 7.12 (d, J=7.6 Hz, 1H), 5.93 (m, 1H), 4.44 (m, 1H), 4.31 (M, 1H), 3.80 (s, 3H), 3.46-3.42 (m, 2H), 2.63 (m, 2H), 2.35-2.32 (m, 2H), 2.24 (m, 2H), 1.85 (m, 2H), 1.62-1.58 (m, 5H).

Step B—5-(5-Chloro-1H-benzimidazol-1-yl)-3-{[(1R)-1-(2-chloro-3-{[1-(2-hydroxyethyl)-4-piperidinyl]oxy}phenyl)ethyl]oxy}-2-thiophenecarboxamide (Title Compound)

Methyl 5-(5-chloro-1H-benzimidazol-1-yl)-3-{[(1R)-1-(2-chloro-3-{[1-(2-hydroxyethyl)-4-piperidinyl]oxy}phenyl)ethyl]oxy}-2-thiophenecarboxylate (82 mg, 14 mmol) was subjected to aminolysis procedure analogous to Example 4, Step B to give 68 mg (85%) of the title compound. $^1$H NMR (400 MHz, d$_6$-DMSO) δ 8.61 (s, 1H), 7.84-7.83 (m, 1H), 7.81 (br s, 1H), 7.50 (d, J=8.8 Hz, 1H), 7.36-7.29 (m, 2H), 7.19-7.13 (m, 3H), 7.09 (br s, 1H), 5.95 (m, 1H), 4.44 (m, 2H), 4.32 (m, 1H), 3.44 (q, J=6.0 Hz, 2H), 2.61 (m, 2H), 2.35-2.32 (m, 2H), 2.23 (m, 2H), 1.85 (m, 2H), 1.68 (d, J=6.0 Hz, 3H), 1.61 (m, 2H). HRMS calculated [M+H]$^+$ C$_{26}$H$_{29}$Cl$_2$N$_4$O$_4$S 575.1287, found 575.1297.

EXAMPLE 21

5-(5-Chloro-1H-benzimidazol-1-yl)-3-{[(1R)-1-(2-chloro-3-{[1-(2-fluoroethyl)-4-piperidinyl]oxy}phenyl)ethyl]oxy}-2-thiophenecarboxamide

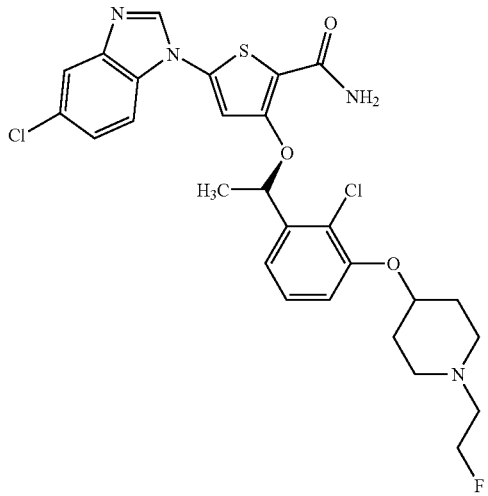

Step A—Methyl 5-(5-chloro-1H-benzimidazol-1-yl)-3-{[(1R)-1-(2-chloro-3-{[1-(2-fluoroethyl)-4-piperidinyl]oxy}phenyl)ethyl]oxy}-2-thiophenecarboxylate

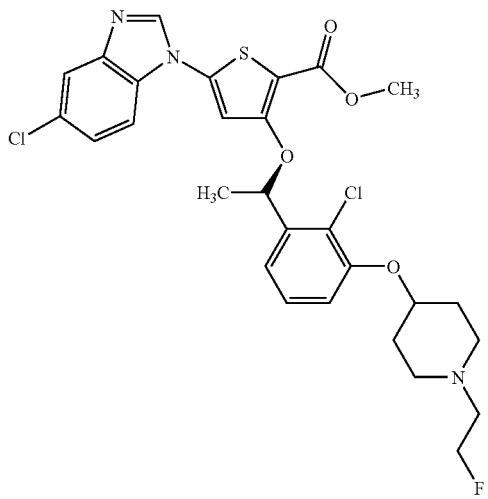

Methyl 5-(5-chloro-1H-benzimidazol-1-yl)-3-({(1R)-1-[2-chloro-3-(4-piperidinyloxy)phenyl]ethyl}oxy)-2-thiophenecarboxylate (Intermediate 12, 100 mg, 0.16 mmol) and 1-bromo-2-fluoroethane were coupled using a procedure analogous to Example 19, Step A to give 79 mg of the desired product (74%). $^1$H NMR (400 MHz, d$_6$-DMSO) δ 8.70 (s, 1H), 7.85 (s, 1H), 7.63 (d, J=8.8 Hz, 1H), 7.39-7.37 (m, 2H), 7.33-7.25 (m, 2H), 7.13 (d, J=7.6 Hz, 1H), 5.94 (m, 1H), 4.55-4.52 (m, 1H), 4.47-4.40 (m, 2H), 3.80 (s, 3H), 3.26-2.59 (m, 3H), 2.55-2.52 (m, 1H), 2.30 (m, 2H), 1.87 (m, 2H), 1.65-1.58 (m, 5H).

Step B—5-(5-Chloro-1H-benzimidazol-1-yl)-3-{[(1R)-1-(2-chloro-3-{[1-(2-fluoroethyl)-4-pipeildinyl]oxy}phenyl)ethyl]oxy}-2-thiophenecarboxamide (Title Compound)

Methyl 5-(5-chloro-1H-benzimidazol-1-yl)-3-{[(1R)-1-(2-chloro-3-{[1-(2-fluoroethyl)-4-piperidinyl]oxy}phenyl)ethyl]oxy}-2-thiophenecarboxylate (79 mg, 0.13 mmol) was subjected to aminolysis procedure analogous to Example 4, Step B to give 24 mg of the title compound (32%). $^1$H NMR (400 MHz, d$_6$-DMSO) δ 8.38 (s, 1H), 7.71 (s, 1H), 7.32-7.28 (m, 3H), 7.15 (d, J=7.6 Hz, 1H), 7.09 (d, J=7.6 Hz, 1H), 6.92 (s, 1H), 6.06-6.02 (m, 1H), 4.62-4.60 (m, 1H), 4.53-4.48 (m, 2H), 2.81-2.26 (M, 4H), 2.50 (m, 1H), 2.43 (m, 1H), 2.40-1.92 (m, 2H), 1.88-1.80 (m, 2H), 1.76 (d, J=6.0 Hz, 3H). HRMS calculated [M+H]$^+$ C$_{27}$H$_{28}$Cl$_2$FN$_4$O$_3$S 577.1243, found 577.1248.

EXAMPLE 22

3-{[(1R)-1-(3-{[1-(2-aminoethyl)-4-piperidinyl]oxy}-2-chlorophenyl)ethyl]oxy}-5-(5-chloro-1H-benzimidazol-1-yl)-2-thiophenecarboxamide

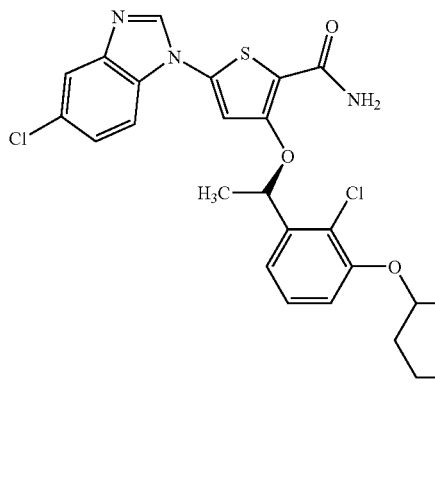

Methyl 5-(5-chloro-1H-benzimidazol-1-yl)-3-{[(1R)-1-(2-chloro-3-{[1-(2-fluoroethyl)-4-piperidinyl]oxy}phenyl)ethyl]oxy}-2-thiophenecarboxylate (Example 21, 79 mg, 0.13 mmol) was subjected to aminolysis procedure analogous to Example 4, Step B to give 43 mg of the title compound (58%). $^1$H NMR (400 MHz, d$_6$-DMSO) δ 8.61 (s, 1H), 7.84-7.80 (m, 2H), 7.50 (d, J=8.8 Hz, 1H), 7.36-7.31 (m, 2H), 7.29-7.09 (m, 4H), 5.95 (m, 1H), 4.46 (m, 1H), 3.29 (s, 2H), 2.56 (m, 4H), 2.25-2.16 (m, 4H), 1.85 (m, 2H), 1.68 (d, J=6.4 Hz, 3H), 1.64-1.59 (m, 2H). HRMS calculated [M+H]$^+$ C$_{27}$H$_{30}$Cl$_2$N$_5$O$_3$S 574.1446, found 574.1437.

EXAMPLE 23

5-(5-Chloro-1H-benzimidazol-1-yl)-3-({[(1R)-1-[2-chloro-3-({1-[2-(methylsulfonyl)ethyl]-4-piperidinyl}oxy)phenyl]ethyl}oxy)-2-thiophenecarboxamide

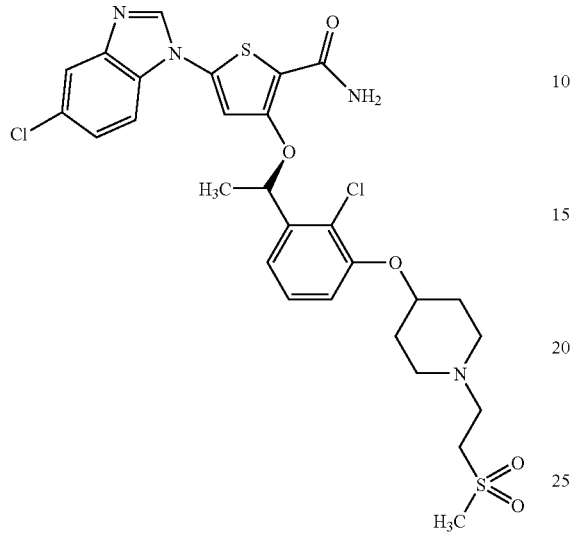

A solution of 5-{5-chloro-1H-benzimidazol-1-yl)-3-({(1R)-1-[2-chloro-3-(4-piperidinyloxy)phenyl]ethyl}oxy)-2-thiophenecarboxamide (Intermediate 12, 112 mg, 0.21 mmol) and methyl vinyl sulfone (22 µL, 0.25 mmol) in 2 mL THF were stirred until the starting material was consumed. The reaction was concentrated onto silica gel and purified by flash column chromatography to give 105 mg of the title compound (78%). $^1$H NMR (400 MHz, d$_6$-DMSO) δ 8.61 (s, 1H), 7.83 (m, 1H), 7.80 (br s, 1H), 7.51 (d, J=8.8 Hz, 1H), 7.36-7.29 (m, 2H), 7.20-7.13 (m, 3H), 7.08 (br s, 1H), 5.95 (m, 1H), 4.48 (m, 1H), 3.25-3.21 (m, 2H), 2.99 (s, 3H), 2.67-2.64 (m, 4H), 2.29 (m, 2H), 1.85 (m, 2H), 1.68 (d, J=6.0 Hz, 3H), 1.62 (m, 2H). HRMS calculated [M+H]$^+$ C$_{28}$H$_{31}$Cl$_2$N$_4$O$_5$S$_2$ 637.1113, found 637.1120.

EXAMPLE 24

5-(5-Chloro-1H-benzimidazol-1-yl)-3-{[(1R)-1-(2-chloro-3-{[1-(1-methylethyl)-4-piperidinyl]oxy}phenyl)ethyl]oxy}-2-thiophenecarboxamide

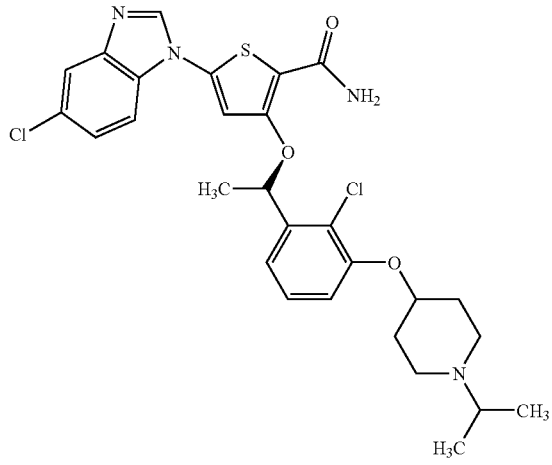

Step A—Methyl 5-(5-chloro-1H-benzimidazol-1-yl)-3-{[(1R)-1-(2-chloro-3-{[1-(1-methylethyl)-4-piperidinyl]oxy}phenyl)ethyl]oxy}-2-thiophenecarboxylate

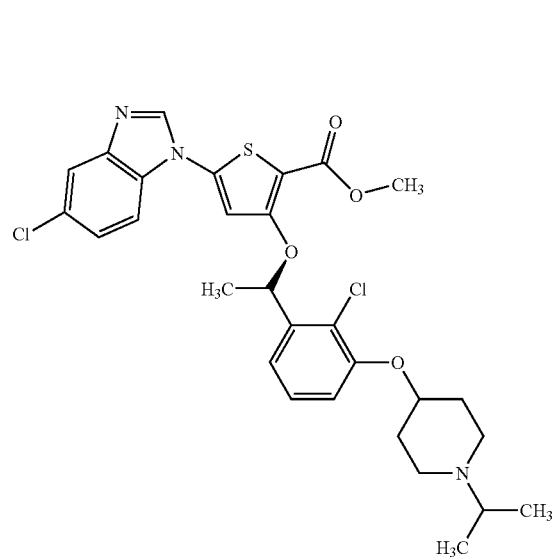

Methyl 5-(5-chloro-1H-benzimidazol-1-yl)-3-({(1R)-1-[2-chloro-3-(4-piperidinyloxy)phenyl]ethyl}oxy)-2-thiophenecarboxylate (Intermediate 12, 100 mg, 0.18 mmol) and 2-bromopropane were coupled using a procedure analogous to Example 19, Step A to give 38 mg of the desired product (36%). MS (ESI) m/z=588.25 [M+H]$^+$.

Step B—5-(5-Chloro-1H-benzimidazol-1-yl)-3-{[(1R)-1-(2-chloro-3-{[1-(1-methylethyl)-4-piperidinyl]oxy}phenyl)ethyl]oxy}-2-thiophenecarboxamide (Title Compound)

Methyl 5-(5-chloro-1H-benzimidazol-1-yl)-3-{[(1R)-1-(2-chloro-3-{[1-(1-methylethyl)-4-piperidinyl]oxy}phenyl)ethyl]oxy}-2-thiophenecarboxylate (38 mg, 0.06 mmol) was subjected to aminolysis procedure analogous to Example 4S Step 3 to give 24 mg of the title compound (71%). $^1$H NMR (400 MHz, d$_6$-DMSO) δ 8.40 (s, 1H), 7.72 (s, 1H), 7.34-7.30 (m, 3H), 7.17 (d, J=7.6 Hz, 1H), 7.11 (d, J=8.4 Hz, 1H), 6.93 (s, 1H), 6.08-6.03 (m, 1H), 4.55 (m, 1H), 2.87-2.83 (m, 1H), 2.78-2.73 (m, 2H), 2.53 (m, 1H), 2.44 (m, 1H), 2.00-1.77 (m, 4H), 1.78 (d, J=6.4 Hz, 3H), 1.07 (d, J=6.4 Hz, 6H). HRMS calculated [M+H]$^+$ C$_{28}$H$_{31}$Cl$_2$N$_4$S 573.1494, found 573.1499.

EXAMPLE 25

3-{[(1R)-1-(2-chloro-3-{[2-(4-morpholinyl)ethyl]oxy}phenyl)ethyl]oxy}-5-[5-(1-methyl-1H-pyrazol-4-yl)-1H-benzimidazol-1-yl]-2-thiophenecarboxamide

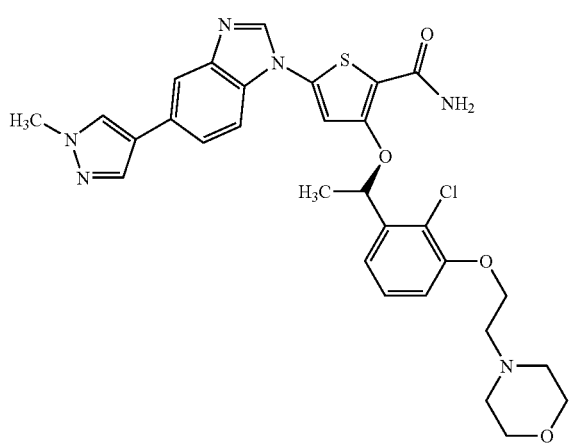

Step A—Methyl 3-[((1R)-1-{3-[(2-bromoethyl)oxy]-2-chlorophenyl}ethyl)oxy]-5-[5-(1-methyl-1H-pyrazol-4-yl)-1H-benzimidazol-1-yl]-2-thiophenecarboxylate

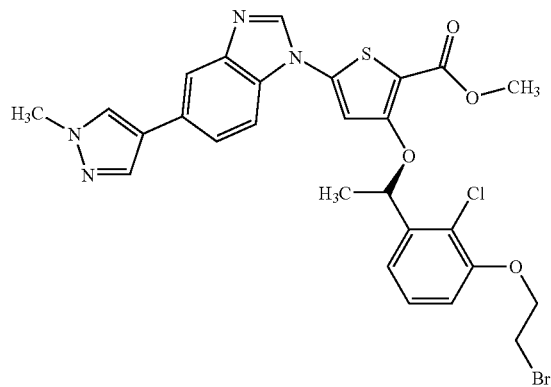

Methyl 3-{[(1R)-1-(2-chloro-3-hydroxyphenyl)ethyl]oxy}-5-[5-(1-methyl-1H-pyrazol-4-yl)-1H-benzimidazol-1-yl]-2-thiophenecarboxylate (Intermediate 18, 200 mg, 0.39 mmol) and 2-bromoethanol (33 μL, 0.47 mmol) were coupled using a procedure analogous to Example 4, Step A to give 191 mg of the desired product (80%). MS (ESI) m/z=615 [M+H]⁺.

Step B—Methyl 3-{[(1R)-1-(2-chloro-3-{[2-(4-morpholinyl)ethyl]oxy}phenyl)ethyl]oxy}-5-[5-(1-methyl-1H-pyrazol-4-yl)-1H-benzimidazol-1-yl]-2-thiophenecarboxylate

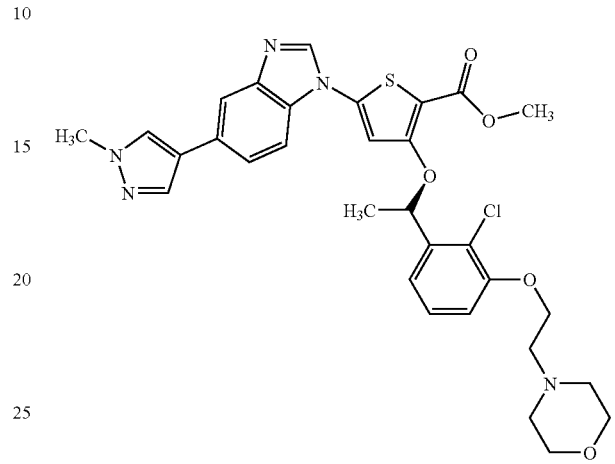

Methyl 3-[((1R)-1-{3-[(2-bromoethyl)oxy]-2-chlorophenyl}ethyl)oxy]-5-[5-(1-methyl-1H-pyrazal-4-yl)-1H-benzimidazol-1-yl]-2-thiophenecarboxylate (191 mg, 0.31 mmol) and morpholine (105 μL, 1.2 mmol) were coupled using a procedure analogous to Example 15, Step A to give 96 mg of the desired product (50%). $^1$H NMR (400 MHz, d$_6$-DMSO) δ 8.63 (s, 1H), 8.19 (s, 1H), 7.96 (s, 1H), 7.92 (s, 1H), 7.57 (s, 2H), 7.37-7.33 (m, 2H), 7.28-7.26 (m, 1H), 7.11 (d, J=8.0 Hz, 1H), 5.98 (m, 1H), 4.16 (t, J=5.8 Hz, 2H), 3.86 (d, 3H), 3.81 (s, 3H), 3.50 (t, J=4.6 Hz, 4H), 2.70 (t, J=5.8 Hz, 2H), 2.48-2.45 (m under DMSO peak, 2H), 1.61 (d, J=6.0 Hz, 3H).

Step C—3-{[(1R)-1-(2-chloro-3-{[2-(4-morpholinyl)ethyl]oxy}phenyl)ethyl]oxy}-5-[5-(1-methyl-1H-pyrazol-4-yl)-1H-benzimidazol-1-yl]-2-thiophenecarboxamide (Title Compound)

Methyl 3-{[(1R)-1-(2-chloro-3-{[2-(4-morpholinyl)ethyl]oxy}phenyl)ethyl]oxy}-5-[5-(1-methyl-1H-pyrazol-4-yl)-1H-benzimidazol-1-yl]-2-thiophenecarboxylate (90 mg, 0.14 mmol) was subjected to aminolysis procedure analogous to Example 4, Step B to give 91 mg of the title compound (99%). $^1$H NMR (400 MHz, d$_6$-DMSO) δ 8.52 (s, 1H), 8.18 (s, 1H), 7.94 (s, 1H), 7.91 (s, 1H), 7.80 (br s, 1H), 7.54 (d, J=8.4 Hz, 1H), 7.45 (d, J=8.4 Hz, 1H), 7.35 (t, J=8.0 Hz, 1H), 7.21 (d, J=7.6 Hz, 1H), 7.14-7.10 (m, 3H), 5.98 (m, 1H), 4.16 (m, 2H), 3.85 (s, 3H), 3.49 (t, J=4.6 Hz, 4H), 2.70 (t, J=5.8 Hz, 2H), 2.48-2.44 (m, 4H), 1.70 (d, J=6.4 Hz, 3H). HRMS calculated [M+H]⁺ C$_{30}$H$_{32}$ClN$_6$O$_4$S 607.1894, found 607.1894.

EXAMPLE 26

5-(5-Chloro-1H-benzimidazol-1-yl)-3-{[(1R)-1-(2-chloro-3-{[2-(4-morpholinyl)ethyl]oxy}phenyl)ethyl]oxy}-2-thiophenecarboxamide

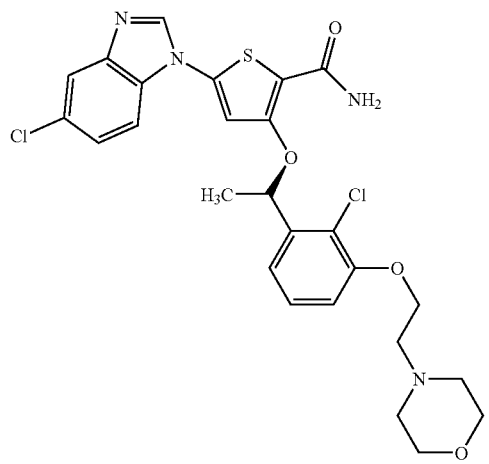

Step A—Methyl 3-[((1R)-1-{3-[(2-bromoethyl)oxy]-2-chlorophenyl}ethyl)oxy]-5-(5-chloro-1H-benzimidazol-1-yl)-2-thiophenecarboxylate

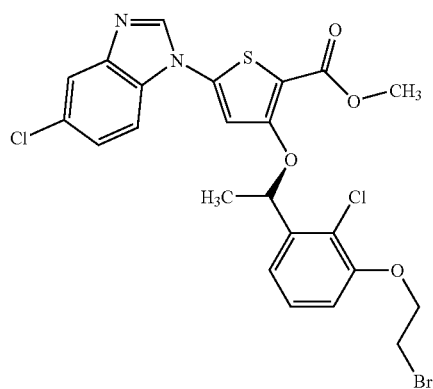

Methyl 5-(5-chloro-1H-benzimidazol-1-yl)-3-{[(1R)-1-(2-chloro-3-hydroxyphenyl)ethyl]oxy}-2-thiophenecarboxylate (Intermediate 2, 200 mg, 0.43 mmol) and 2-bromoethanol (37 μL, 0.52 mmol) were coupled using a 0 procedure analogous to Example 4, Step A to give 132 mg of the desired product (54%). $^1$H NMR (400 MHz, d$_6$-DMSO) δ 8.72 (s, 1H), 7.87 (d, J=2.0 Hz, 1H), 7.66 (d, J=8.8 Hz, 1H), 7.43-7.30 (m, 4H), 7.12-7.10 (m, 1H), 6.00-5.95 (m, 1H), 4.40-4.37 (m, 2H), 3.83-3.79 (m, 5H), 1.60 (d, J=6.4 Hz, 3H).

Step B—Methyl 5-(5-chloro-1H-benzimidazol-1-yl)-3-{[(1R)-1-(2-chloro-3-{[2-(4-morpholinyl)ethyl]oxy}phenyl)ethyl]oxy}-2-thiophenecarboxylate

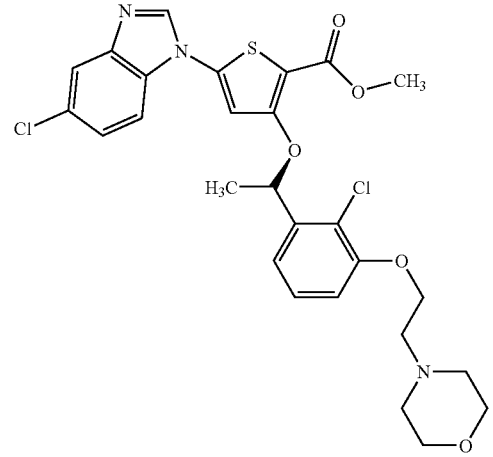

Methyl 3-[((1R)-1-{3-[(2-bromoethyl)oxy]-2-chlorophenyl}ethyl)oxy]-5-(5-chloro-1H-benzimidazol-1-yl)-2-thiophenecarboxylate (130 mg, 0.23 mmol) and morpholine (80 μL, 0.92 mmol) were coupled using a procedure analogous to Example 15, Step A to give 93 mg of the desired product (70%).

$^1$H NMR (400 MHz, d$_6$-DMSO) δ 8.72 (s, 1H), 7.87 (m, 1H), 7.63 (d, J=8.8 Hz, 1H), 7.41-7.32 (m, 3H), 7.27 (d, J=7.2 Hz, 1H), 7.11 (d, J=8.4 Hz, 1H), 5.95 (m, 1H), 4.15 (t, J=5.6 Hz, 2H), 3.81 (s, 3H), 3.52 (t, J=4.4 Hz, 4H), 2.70 (t, J=5.8 Hz, 2H), 2.49-2.48 (m under DMSO, 4H), 1.60 (d, J=6.4 Hz, 3H).

Step C—5-(5-Chloro-1H-benzimidazol-1-yl)-3-{[(1R)-1-(2-chloro-3-{[2-(4-morpholinyl)ethyl]oxy}phenyl)ethyl]oxy}-2-thiophenecarboxamide (Title Compound)

Methyl 5-(5-chloro-1H-benzimidazol-1-yl)-3-{[(1R)-1-(2-chloro-3-{[2-(4-morpholinyl)ethyl]oxy}phenyl)ethyl]oxy}-2-thiophenecarboxylate (90 mg, 0.16 mmol) was subjected to aminolysis according to procedure analogous to Example 4, Step B to give 90 mg of the title compound (99%).

$^1$H NMR (400 MHz, d$_6$-DMSO) δ 8.62 (s, 1H), 7.85 (m, 1H), 7.82 (br s, 1H), 7.50 (d, J=8.4Hz, 1H), 7.38-7.32 (m, 2H), 7.20 (d, J=7.8 Hz, 1H), 7.13-7.11 (m, 3H), 5.97 (m, 1H), 4.15 (t, J=5.6 Hz, 2H), 3.51 (t, J=4.6 Hz, 4H), 2.70 (f, J=5.6 Hz, 2H), 2.49-2.46 (m under DMSO peak, 4H), 1.69 (t, J=6.0 Hz, 3H). HRMS calculated [M+H]$^+$ C$_{26}$H$_{27}$Cl$_2$N$_4$O$_4$S 561.1130, found 561.1134.

EXAMPLE 27

5-(5-Chloro-1H-benzimidazol-1-yl)-3-{[(1R)-1-(2-chloro-3-{[(2R)-2-morpholinylmethyl]oxy}phenyl)ethyl]oxy}-2-thiophenecarboxamide

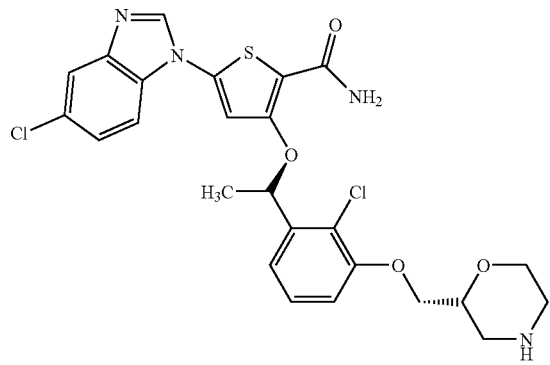

Step A—1,1-Dimethylethyl 2-[({2-chloro-3-[(1R)-1-({5-(5-chloro-1H-benzimidazol-1-yl)-2-[(methyloxy)carbonyl]-3-thienyl}oxy)ethyl]phenyl}oxy)methyl]-4-morpholinecarboxylate

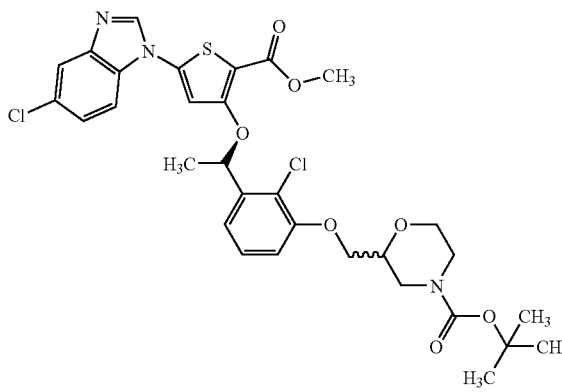

Methyl 5-(5-chloro-1H-benzimidazol-1-yl)-3-{[(1R)-1-(2-chloro-3-hydroxyphenyl)ethyl]oxy}-2-thiophenecarboxylate (Intermediate 2, 153 mg, 0.33 mmol) and 1,1-dimethylethyl 2-(hydroxymethyl)-4-morphoilnecarboxylate (87 mg, 0.40 mmol) were coupled using a procedure analogous to Example 5, Step A to give 145 mg of the desired product (66%). $^1$H NMR (400 MHz, d$_6$-DMSO) δ 8.70 (s, 1H), 7.85 (m, 1H), 7.61 (d, J=8.8 Hz, 1H), 7.42-7.27 (m, 4H), 7.10 (d, J=7.6 Hz, 1H), 5.95 (m, 1H), 4.13-3.94 (m, 3H), 3.84-3.80 (m, 4H), 3.70-3.67 (m, 2H), 3.45-3.39 (m, 1H), 2.85 (m, 2H), 1.59 (d, J=6.4 Hz, 3H), 1.36 (s, 9H).

Step B—1,1-Dimethylethyl (2R)-2-({[3-((1R)-1-{[2-(aminocarbonyl)-5-(5-chloro-1H-benzimidazol-1-yl)-3-thienyl]oxy}ethyl)-2-chlorophenyl]oxy}methyl)-4-morpholinecarboxylate

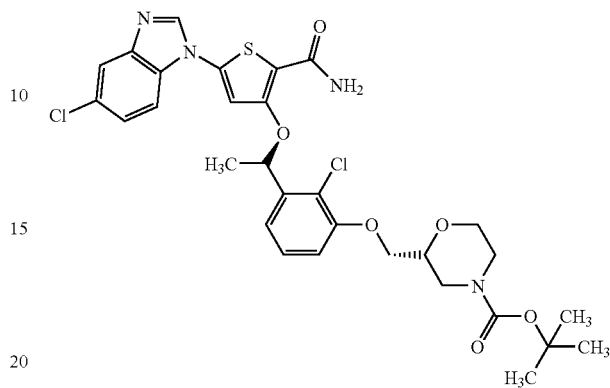

1,1-Dimethylethyl 2-[({2-chloro-3-[(1R)-1-({5-(5-chloro-1H-benzimidazol-1-yl)-2-[(methyloxy)carbonyl]-3-thienyl}oxy)ethyl]phenyl}oxy)methyl]-4-morpholinecarboxylate (145 mg, 0.22 mmol) was subjected to aminolysis according to the procedure analogous to Example 5 Step B to give 108 mg of the racemic product (76%). The diastereomers were separated using packed column supercritical fluid chromatography (SFC) on a Diacel® 3×25 Chiralcel OJ-H column using a mobile phase with 30% MeOH in carbon dioxide, 5-(5-Chloro-1H benzimidazol-1-yl)-3-{[(1R)-1-(2-chloro-3-{[(2S)-2-morpholimylmethyl]oxy}phenyl)-ethyl]oxy}-2-thiophenecarboxamide eluted first with a retention time of 9.64 min at a flow rate of 2 mL/min on the analytical instrument. The title compound eluted second with a retention time of 12.40 min. $^1$H NMR (400 MHz, d$_6$-DMSO) δ 8.61 (s, 1H), 7.83 (m, 1H), 7.81 (br s, 1H), 7.48 (d, J=8.8 Hz, 1H), 7.39-7.32 (m, 2H), 7.21 (d, J=7.6 Hz, 1H), 7.12-7.10 (m, 3H), 5.96 (m, 1H), 4.12-3.94 (m, 3H), 3.84-3.81 (m, 1H), 3.70-3.67 (m, 2H), 3.44-3.39 (m, 1H), 2.84 (m, 2H), 1.68 (d, J=6.0 Hz, 3H), 1.36 (s, 9H).

Step C—5-(5-Chloro-1H-benzimidazol-1-yl)-3-{[(1R)-1-(2-chloro-3-{[(2R)-2-morpholinylmethyl]oxy}phenyl)ethyl]oxy}-2-thiophenecarboxamide (Title Compound)

1,1-Dimethylethyl (2R)-2-({[3-((1R)-1-{[2-(aminocarbonyl)-5-(5-chloro-1H-benzimidazol-1-yl)-3-thienyl]oxy}ethyl)-2-chlorophenyl]oxy}methyl)-4-morpholinecarboxylate (90 mg. 0.14 mmol) was deprotected using a procedure analogous to Example 5, Step C to give 60 mg of the title compound (79%). $^1$H NMR (400 MHz, d$_6$-DMSO) δ 8.62 (s, 1H), 7.84-7.82 (m, 2H), 7.49-7.31 (m, 3H), 7.20 (d, J=7.6 Hz, 1H), 7.13-7.09 (m, 3H), 5.96 (m, 1H), 4.03-3.95 (m, 2H), 3.73-3.64 (m, 2H), 3.46-3.40 (m, 1H), 2.87-2.84 (m, 1H), 2.65-2.51 (m, 3H), 1.69 (d, J=6.4 Hz, 3H). HRMS calculated [M+H]$^+$ C$_{25}$H$_{25}$Cl$_2$N$_4$O$_4$S 547.0974, found 547.0968.

EXAMPLE 28

5-(5-Chloro-1H-benzimidazol-1-yl)-3-{[(1R)-1-(2-chloro-3-{[(2S)-2-morpholinylmethyl]oxy}phenyl)ethyl]oxy}-2-thiophenecarboxamide

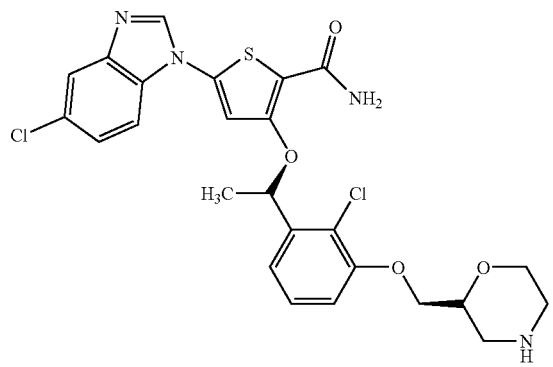

5-(5-Chloro-1H-benzimidazol-1-yl)-3-{[(1R)-1-(2-chloro-3-{[(2S)-2-morpholinylmethyl]oxy}phenyl)ethyl]oxy}-2-thiophenecarboxamide (Intermediate 2, 40 mg, 0.06 mmol) was deprotected using a procedure analogous to Example 5, Step C to give 23 mg of the title compound (82%). $^1$H NMR (400 MHz, $d_6$-DMSO) δ 8.61 (s, 1H), 7.83 (s, 1H), 7.80 (br s, 1H), 7.46-7.31 (m, 3H), 7.20 (d, J=7.6 Hz, 1H), 7.11-7.08 (m, 3H), 5.96 (m, 1H), 4.05-3.95 (m, 2H), 3.78-3.75 (m, 2H), 3.50-3.44 (m, 1H), 2.95-2.91 (m, 1H), 2.74-2.66 (m, 2H), 2.60-2.54 (m, 1H), 1.68 (d, J=6.0 Hz, 3H). HRMS calculated [M+H]$^+$ $C_{25}H_{25}Cl_2N_4O_4S$ 547.09681, found 547.09655.

EXAMPLE 29

3-{[(1R)-1-(2-Chloro-3-{[1-(2-fluoroethyl)-4-piperidinyl]oxy}phenyl)ethyl]oxy}-5-[5-(1-methyl-1H-pyrazol-4-yl)-1H-benzimidazol-1-yl]-2-thiophenecarboxamide

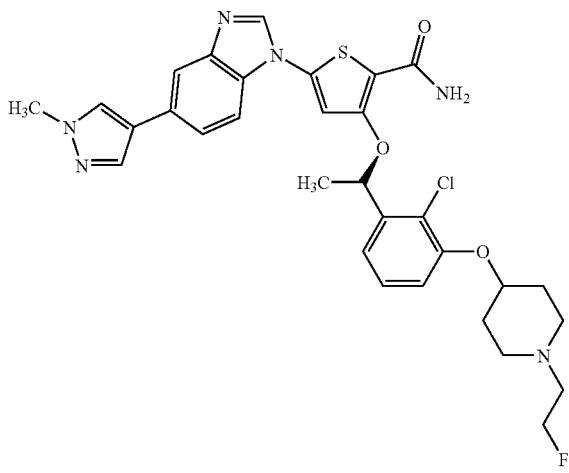

Step A—Methyl 3-{[(1R)-1-(2-chloro-3-{[1-(2-fluoroethyl)-4-piperidinyl]oxy}phenyl)ethyl]oxy}-5-[5-(1-methyl-1H-pyrazol-4-yl)-1H-benzimidazol-1-yl]-2-thiophenecarboxylate

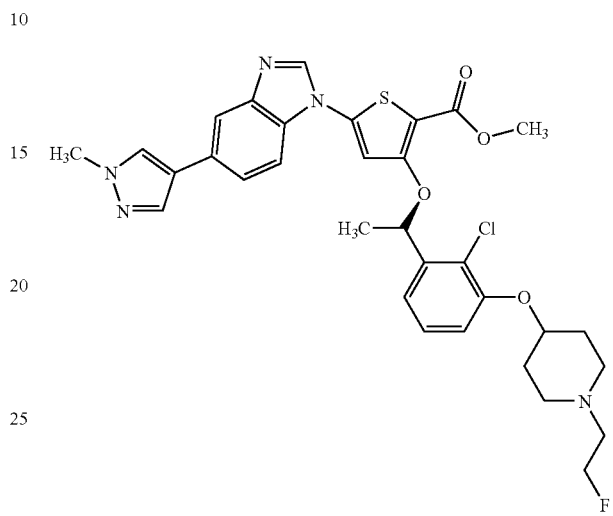

Methyl 3-({(1R)-1-[2-chloro-3-(4-piperidinyloxy)phenyl]oxy}-5-[5-(1-methyl-1H-pyrazol-4-yl)-1H-benzimidazol-1-yl]-2-thiophenecarboxylate (Intermediate 13, 150 mg, 0.25 mmol) and 1-bromo-2-fluoroethane (37 mL, 0.50 mmol) were coupled using a procedure analogous to Example 19, Step A to give 78 mg of the desired product (49%). MS (ESI) m/z=638.54 [M+H]$^+$.

Step B—3-{[(1R)-1-(2-Chloro-3-{[1-(2-fluoroethyl)-4-piperidinyl]oxy}phenyl)ethyl]oxy}-5-[5-(1-methyl-1H-pyrazol-4-yl)-1H-benzimidazol-1-yl]-2-thiophenecarboxamide (Title Compound)

Methyl 3-{[(1R)-1-(2-chloro-3-{[1-(2-fluoroethyl)-4-piperidinyl]oxy}phenyl)ethyl]oxy}-5-[5-(1-methyl-1H-pyrazol-4-yl)-1H-benzimidazol-1-yl]-2-thiophenecarboxylate (78 mg, 0.12 mmol) was subjected to aminolysis using a procedure analogous to Example 4, Step B to give 50 mg of the title compound (67%). $^1$H NMR (400 MHz, $d_6$-DMSO) δ 8.51 (s, 1H), 8.15 (s, 1H), 7.93 (s, 1H), 7.89 (s, 1H), 7.78 (br s, 1H), 7.53 (d, J=8.8 Hz, 1H), 7.45 (d, J=8.8 Hz, 1H), 7.32 (t, J=8.0 Hz, 1H), 7.20-7.14 (m, 2H), 7.09 (m, 2H), 5.97 (m, 1H), 4.51-4.47 (m, 2H), 4.40-4.37 (m, 1H), 3.84 (s, 3H), 2.63-2.56 (m, 3H), 2.51-2.46 (m, 1H), 2.31-2.24 (m, 2H), 1.86 (m, 2H), 1.70-1.62 (m, 5H). HRMS calculated [M+H]$^+$ $C_{31}H_{33}ClFN_6O_3S$ 623.20019, found 623.20020.

EXAMPLE 30

3-{[(1R)-1-(2-chloro-3-{[1-(3,3,3-trifluoropropyl)-4-piperidinyl]oxy}phenyl)ethyl]oxy}-5-[5-(1-methyl-1H-pyrazol-4-yl)-1H-benzimidazol-1-yl]-2-thiophenecarboxamide

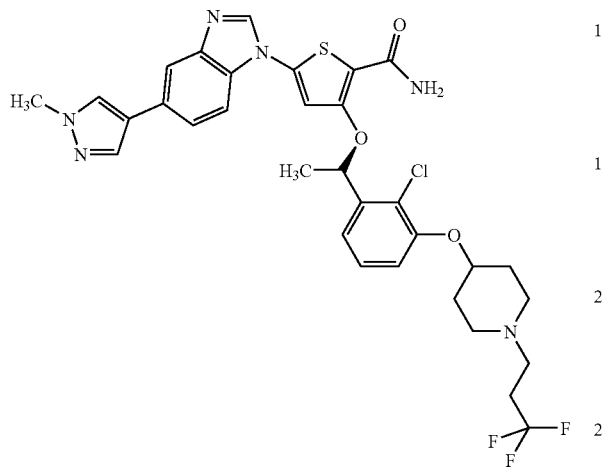

Step A—Methyl 3-{[(1R)-1-(2-chloro-3-{[1-(3,3,3-trifluoropropyl)-4-piperidinyl]oxy}phenyl)ethyl]oxy}-5-[5-(1-methyl-1H-pyrazol-4-yl)-1H-benzimidazol-1-yl]-2-thiophenecarboxylate

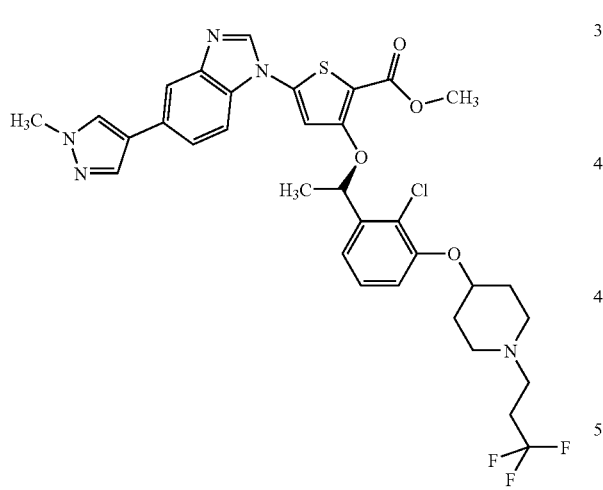

Methyl 3-({(1R)-1-[2-chloro-3-(4-piperidinyloxy)phenyl]ethyl}oxy)-5-[5-(1-methyl-1H-pyrazol-4-yl)-1H-benzimidazol-1-yl]-2-thiophenecarboxylate (Intermediate 13, 150 mg, 0.25 mmol) and 3-bromo-1,1,1-trifluoropropane (53 µl, 0.50 mmol) were coupled using a procedure analogous to Example 19, Step A to give 107 mg of the desired product (62%). $^1$H NMR (400 MHz, d$_6$-DMSO) δ 8.62 (s, 1H), 8.17 (s, 1H), 7.95 (s, 1H), 7.90 (s, 1H), 7.58 (m, 2H), 7.35-7.27 (m, 3H), 7.14 (d, J=7.6 Hz, 1H), 5.96 (m, 1H), 4.48 (m, 1H), 3.85 (s, 3H), 3.81 (s, 3H), 2.65-2.58 (m, 2H), 2.48-2.38 (m under DMSO peak, 4H), 2.31-2.23 (m, 2H), 1.87 (m, 2H), 1.66-1.60 (m, 5H).

Step B—3-{[(1R)-1-(2-chloro-3-{[1-(3,3,3-trifluoropropyl)-4-piperidinyl]oxy}phenyl)ethyl]oxy}-5-[5-(1-methyl-1H-pyrazol-4-yl)-1H-benzimidazol-1-yl]-2-thiopenecarboxamide (Title Compound)

Methyl 3-{[(1R)-1-(2-chloro-3-{[1-(3,3,3-trifluoropropyl)-4-piperidinyl]oxy}phenyl)ethyl]oxy}-5-[5-(1-methyl-1H-pyrazol-4-yl)-1H-benzimidazol-1-yl]-2-thiophenecarboxylate (103 mg, 0.15 mmol) was subjected to aminolysis using a procedure analogous to Example 4, Step B to give 74 mg of the title compound (73%). $^1$H NMR (400 MHz, d$_6$-DMSO) δ 8.51 (s, 1H), 8.15 (s, 1H), 7.92 (s, 1H), 7.89 (s, 1H), 7.79 (br s, 1H), 7.53 (d, J=8.4 Hz, 1H), 7.45 (d, J=8.4 Hz, 1H), 7.32 (t, J=8.2 Hz, 1H), 7.20-7.14 (m, 2H), 7.09 (m, 2H), 5.99-5.94 (m, 1H), 4.47 (m, 1H), 3.84 (s, 3H), 2.61-2.55 (m, 2H), 2.47-2.35 (m under DMSO peak, 4H), 2.28-2.17 (m, 2H), 1.85-1.72 (m, 2H), 1.70-1.59 (m, 5H). HRMS calculated [M+H]$^+$ C$_{32}$H$_{33}$ClF3N$_6$O$_3$S 873.19700, found 673.19712.

EXAMPLE 31

3-({(1R)-1-[2-Chloro-3-({1-[2-(methylsulfonyl)ethyl]-4-piperldinyl}oxy)phenyl]ethyl}oxy)-5-[5-(1-methyl-1H-pyrazol-4-yl)-1H-benzimidazol-1-yl]-2-thiophenecarboxamide

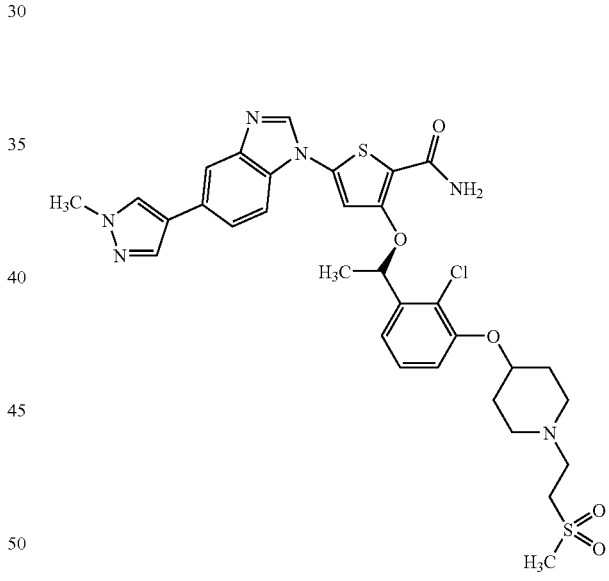

3-({(1R)-1-[2-chloro-3-(4-piperidinyloxy)phenyl]ethyl}oxy)-5-[5-(1-methyl-1H-pyrazol-4-yl)-1H-benzimidazol-1-yl]-2-thiophenecarboxamide (Intermediate 13, 144 mg, 0.25 mmol) and methyl vinyl sulfone (26 µL, 0.30 mmol) were coupled using a procedure analogous to Example 23 to give 74 mg of the title compound (43%). $^1$H NMR (400 MHz, d$_6$-DMSO) δ 8.51 (s, 1H), 8.16 (s, 1H), 7.93 (s, 1H), 7.89 (s, 1H), 7.79 (br s, 1H), 7.53 (d, J=8.8 Hz, 1H), 7.45 (d, J=8.4 Hz, 1H), 7.32 (t, J=8.0 Hz, 1H), 7.20-7 14 (m, 2H), 7.09 (m, 2H), 5.99-5.94 (m, 1H), 4.48 (m, 1H), 3.84 (s, 3H), 3.20 (t, J=6.6 Hz, 2H), 2.97 (s, 3H), 2.65-2.59 (m, 4H), 2.29-2.21 (M, 2H), 1.86-1.72 (m, 2H), 1.69 (d, J=6.4 Hz, 3H), 1.64-1.60 (m, 2H). HRMS calculated [M+H]$^+$ C$_{32}$H$_{36}$ClN$_6$O$_5$S$_2$ 683,18716, found 683.18702.

EXAMPLE 32

5-(5-Chloro-1H-benzimidazol-1-yl)-3-[((1R)-1-{2-chloro-4-fluoro-3-[(1-methyl-4-piperidinyl)oxy]phenyl}ethyl)oxy]-2-thiophenecarboxamide

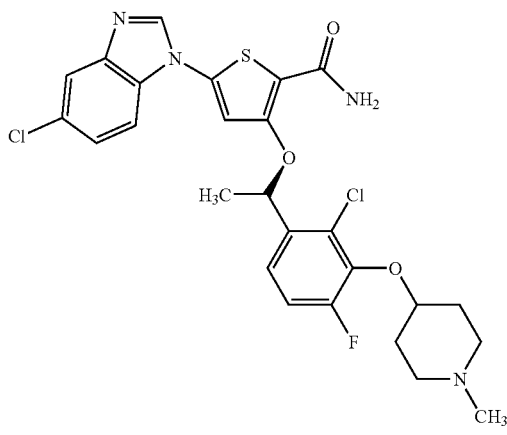

Step A—Methyl 5-(5-chloro-1H-benzimidazol-1-yl)-3-{[(1R)-1-(2-chloro-4-fluoro-3-hydroxyphenyl)ethyl]oxy}-2-thiophenecarboxylate

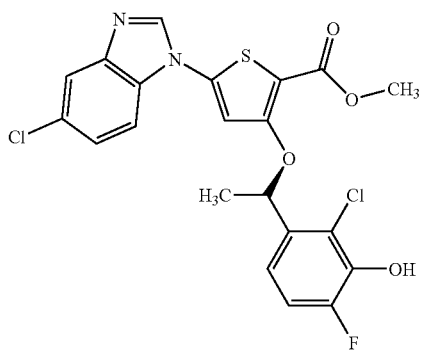

Methyl 5-(5-chloro-1H-benzimidazol-1-yl)-3-hydroxy-2-thiophene-carboxylate (Intermediate 2, Step B, 153 mg, 0.50 mmol) and (1S)-1-(2-chloro-3-{[(1,1-dimethylethyl)(diphenyl)silyl]oxy}-4-fluorophenyl)ethanol (Intermediate 14, 257 mg, 0.60 mmol) were coupled using a procedure analogous to Intermediate 2, Step C to give 200 mg of the desired product (83%). $^1$H NMR (400 MHz, $d_6$-DMSO) δ 10.47 (s, 1H), 8.72 (s, 1H), 7.87 (d, J=2.0 Hz, 1H), 7.67 (d, J=8.8 Hz, 1H), 7.43-7.40 (m, 2H), 7.27-7.23 (m, 1H), 7.18-7.14 (m, 1H), 5.91-5.86 (m, 1H), 3.80 (s, 3H), 1.59-1.58 (m, 3H).

Step B—Methyl 5-(5-chloro-1H-benzimidazol-1-yl)-3-[((1R)-1-{2-chloro-4-fluoro-3-[(1-methyl-4-piperidinyl)oxy]phenyl}ethyl)oxy]-2-thiophenecarboxylate

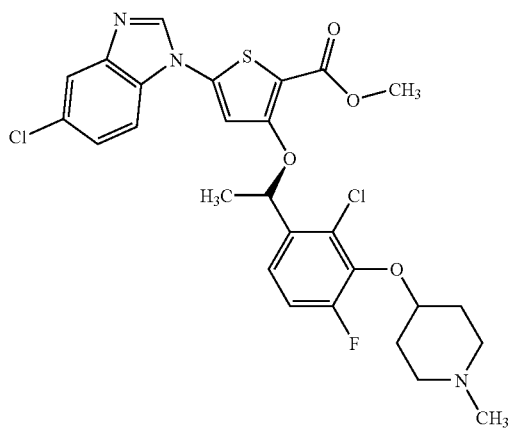

Methyl 5-(5-chloro-1H-benzimidazol-1-yl)-3-{[(1R)-1-(2-chloro-4-fluoro-3-hydroxyphenyl)ethyl]oxy}-2-thiophenecarboxylate (110 mg, 0.23 mmol) and 1-methyl-4-piperidinol (32 µL, 0.27 mmol) were coupled using a procedure analogous to Example 4, Step A to give 68 mg of the desired product (51%).

$^1$H NMR (400 MHz, $d_6$-DMSO) δ 8.72 (s, 1H), 7.87 (m, 1H), 7.73 (d, J=8.8 Hz, 1H), 7.50-7.35 (m, 4H), 5.91 (m, 1H), 4.12 (m, 1H), 3.81 (s, 3H), 2.65-2.58 (m, 2H), 2.13 (s, 3H), 2.04 (m, 2H), 1.83-1.79 (m, 2H), 1.72-1.66 (m, 2H), 1.60 (d, J=6.4 Hz, 3H).

Step C—5-(5-Chloro-1H-benzimidazol-1-yl)-3-[((1R)-1-{2-chloro-4-fluoro-3-[(1-methyl-4-piperidinyl)oxy]phenyl}ethyl)oxy]-2-thiophenecarboxamide (Title Compound)

Methyl 5-(5-chloro-1H-benzimidazol-1-yl)-3-[((1R)-1-(2-chloro-4-fluoro-3-[(1-methyl-4-piperidinyl)oxy]phenyl}ethyl)oxy]-2-thiophenecarboxylate (65 mg, 0.11 mmol) was subjected to aminolysis according to the procedure analogous to Example 4, Step B to give 45 mg of the title compound (69%).

$^1$H NMR (400 MHz, $d_6$-DMSO) δ 8.60 (s, 1H), 7.84 (s, 1H), 7.79 (br s, 1H), 7.60 (d, J=8.8 Hz, 1H), 7.43-7.32 (m, 3H), 7.14 (s, 1H), 7.08 (br s, 1H), 5.91 (m, 1H), 4.09 (m, 1H), 2.57 (m, 1H), 2.08 (s, 3H), 1.93-1.60 (m, 10H).

EXAMPLE 33

3-({(1R)-1-[2-Chloro-4-fluoro-3-(4-piperidinyloxy)phenyl]ethyl}oxy)-5-[5-(1-methyl-1H-pyrazol-4-yl)-1H-benzimidazol-1-yl]-2-thiophenecarboxamide

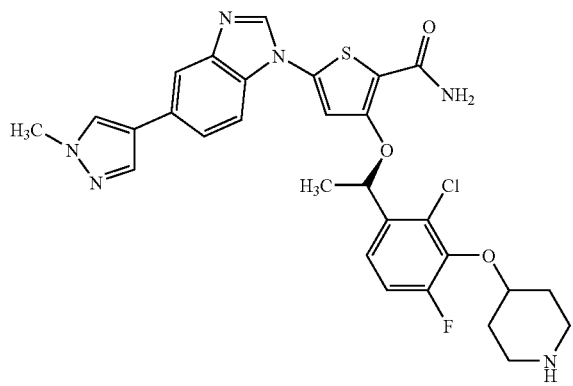

Step A—Methyl 3-{[(1R)-1-(2-chloro-4-fluoro-3-hydroxyphenyl)ethyl]oxy}-5-[5-(1-methyl-1H-pyrazol-4-yl)-1H-benzimidazol-1-yl]-2-thiophenecarboxylate

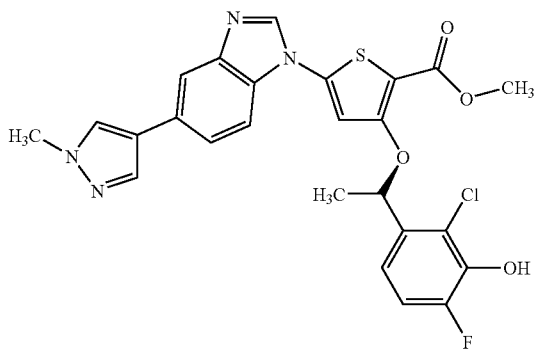

Methyl 3-hydroxy-5-[5-(1-methyl-1H-pyrazol-4-yl)-1H-benzimidazol-1-yl]-2-thiophenecarboxylate (Intermediate 16, 710 mg, 2.0 mmol) and (1S)-1-(2-chloro-3-{[(1,1-dimethylethyl)(diphenyl)silyl]oxy}-4-fluorophenyl)ethanol (Intermediate 14, 1.03 g, 2.4 mmol) were coupled and deprotected using a procedure analogous to Intermediate 2, Step C to give 802 mg of the desired product (76% over 2 steps). $^1$H NMR (400 MHz, $d_6$-DMSO) δ 10.48 (s, 1H), 8.63 (s, 1H), 8.19 (s, 1H), 7.96 (s, 1H), 7.92 (s, 1H), 7.65-7.58 (m, 2H), 7.39 (s, 1H), 7.28-7.23 (m, 1H), 7.18-7.15 (m, 1H), 5.93-5.89 (m, 1H), 3.86 (s, 3H), 3.81 (s, 3H), 1.59 (d, J=6.4 Hz, 3H).

Step B—1,1-Dimethylethyl 4-({2-chloro-6-fluoro-3-[(1R)-1-({2-[(methyloxy)carbonyl]-5-[5-(1-methyl-1H-pyrazol-4-yl)-1H-benzimidazol-1-yl]-3-thienyl}oxy)ethyl]phenyl}oxy)-1-piperidinecarboxylate

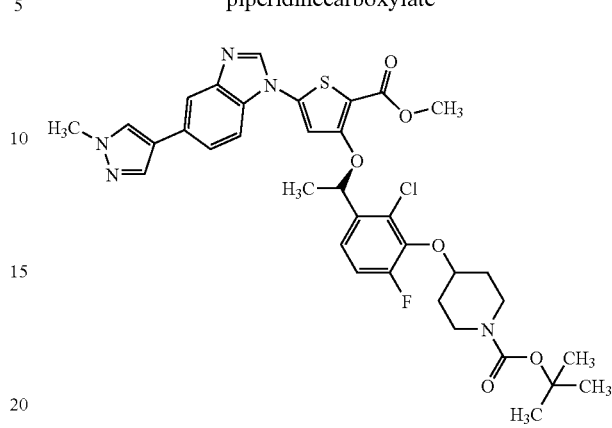

Methyl 3-{[(1R)-1-(2-chloro-4-fluoro-3-hydroxyphenyl)ethyl]oxy}-5-[5-(1-methyl-1H-pyrazol-4-yl)-1H-benzimidazol-1-yl]-2-thiophenecarboxylate (490 mg, 0.93 mmol) and 1,1-dimethylethyl 4-hydroxy-1-piperidinecarboxylate (221 mg, 1.1 mmol) were coupled using a procedure analogous to Example 5, Step A to give the desired product. MS (ESI) m/z=710.56 [M+H]$^+$.

Step C—Methyl 3-({(1R)-1-[2-chloro-4-fluoro-3-(4-piperidinyloxy)phenyl]ethyl}oxy)-5-[5-(1-methyl-1H-pyrazol-4-yl)-1H-benzimidazol-1-yl]-2-thiophenecarboxylate

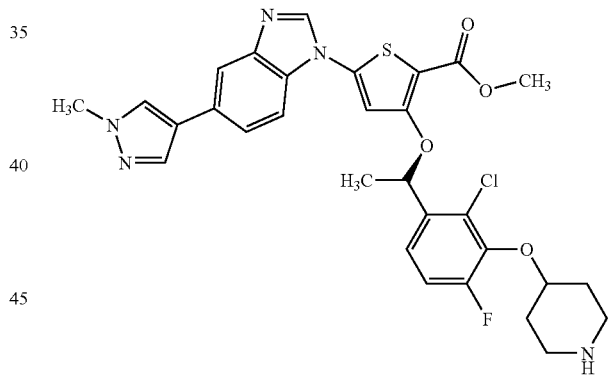

1,1-Dimethylethyl 4-({2-chloro-6-fluoro-3-[(1R)-1-({2-[(methyloxy)carbonyl]-5-[5-(1-methyl-1H-pyrazol-4-yl)-1H-benzimidazol-1-yl]-3-thienyl}oxy)ethyl]phenyl}oxy)-1-piperidinecarboxylate (crude from above) was deprotected using a procedure analogous to Example 5, Step C to give 298 mg of the desired product (53% over 2 steps). $^1$H NMR (400 MHz, $d_6$-DMSO) δ 8.63 (s, 1H), 8.19 (s, 1H), 7.96 (s, 1H), 7.92 (s, 1H), 7.68 (d, J=8.2 Hz, 1H), 7.61-7.58 (m, 1H), 7.50-7.47 (m, 1H), 7.43-7.35 (m, 2H), 5.93 (m, 1H), 4.19-4.15 (m, 1H), 3.86 (s, 3H), 3.81 (s, 3H), 2.95-2.87 (m, 2H), 2.43-2.38 (m, 2H), 1.86-1.79 (m, 2H), 4.61 (d, J=6.4 Hz, 3H), 1.56-1.51 (m, 2H).

Step D—3-({(1R)-1-[2-Chloro-4-fluoro-3-(4-piperidinyloxy)phenyl]ethyl}oxy)-5-[5-(1-methyl-1H-pyrazol-4-yl)-1H-benzimidazol-1-yl]-2-thiophenecarboxamide (Title Compound)

Methyl 3-({(1R)-1-[2-chloro-4-fluoro-3-(4-piperidinyloxy)phenyl]ethyl}oxy)-5-[5-(1-methyl-1H-pyrazol-4-yl)-

1H-benzimidazol-1-yl]-2-thiophenecarboxylate (195 mg, 0.32 mmol) was subjected to aminolysis according to a procedure analogous to Example 5, Step B to give 126 mg of the title compound (66%). $^1$H NMR (400 MHz, d$_6$-DMSO) δ 8.52 (s, 1H), 8.18 (s, 1H), 7.95 (s, 1H), 7.91 (s, 1H), 7.78 (br s, 1H), 7.56 (m, 2H), 7.45-7.34 (m, 2H), 7.15 (s, 1H), 7.08 (br s, 1H), 5.94 (m, 1H), 4.17-4.12 (m, 1H), 3.85 (s, 3H), 2.93-2.80 (m, 2H), 2.39-2.29 (m, 2H), 2.12 (br s, 1H), 1.83-1.74 (m, 2H), 1.70 (d, J=6.0 Hz, 3H), 1.55-1.43 (m, 2H). HRMS calculated [M+H]$^+$ C$_{29}$H$_{29}$ClFN$_6$O$_3$S 595.16889, found 595, 16893.

EXAMPLE 34

3-[((1R)-1-{2-Chloro-4-fluoro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide trifluoroacetate

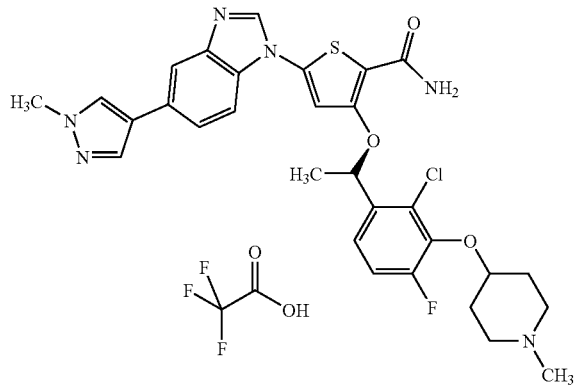

Step A—Methyl 3-[((1R)-1-{2-chloro-4-fluoro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxylate

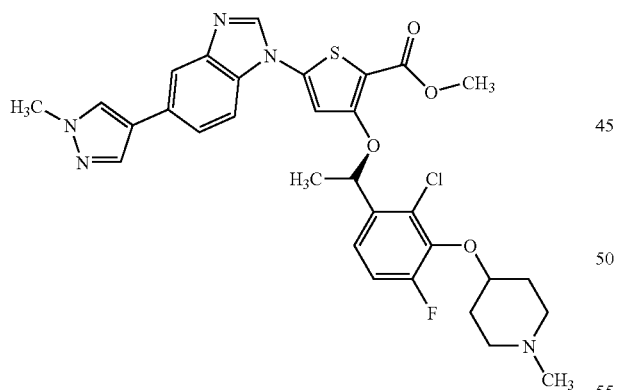

Methyl 3-{[(1R)-1-(2-chloro-4-fluoro-3-hydroxyphenyl)ethyl]oxy}-5-[5-(1-methyl-1H-pyrazol-4-yl)-1H-benzimidazol-1-yl]-2-thiophenecarboxylate (Example 33, Step A, 125 mg, 0.24 mmol) and 1-methyl-4-piperidinol (34 μl, 0.29 mmol) were coupled using a procedure analogous to Example 4, Step A to give 95 mg of the desired product (63%). $^1$H NMR (400 MHz, d$_6$-DMSO) δ 8.63 (s, 1H), 8.19 (s, 1H), 7.96 (s, 1H), 7.92 (s, 1H), 7.67 (d, J=8.8 Hz, 1H), 7.59 (m, 1H), 7.49-7.46 (m, 1H), 7.40-7.35 (m, 2H), 5.93 (m, 1H), 4.11 (m, 1H), 3.86 (s, 3H), 3.81 (s, 3H), 2.58-2.50 (m, 2H), 2.07 (s, 3H), 1.95 (m, 2H), 1.80 (m, 2H), 1.69 (m, 2H), 1.61 (d, J=6.0 Hz, 3H).

Step B—3-[((1R)-1-{2-Chloro-4-fluoro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide trifluoroacetate (Title Compound)

Methyl 3-[((1R)-1-{2-chloro-4-fluoro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxylate (95 mg, 0.15 mmol) was subjected to aminolysis according to a procedure analogous to Example 4, Step B. The crude material was purified by reverse-phase liquid chromatography to give 40 mg of the title compound (44%). $^1$H NMR (400 MHz, d4-CD$_3$OD) δ 8.42 (s, 1H), 8.01 (s, 1H), 7.88 (s, 1H), 7.85 (s, 1H), 7.62-7.53 (m, 2H), 7.45-7.41 (m, 1H), 7.31-7.26 (m, 1H), 7.03-7.01 (m, 1H), 6.02 (m, 1H), 7.37 (m, 1H), 3.93 (s, 3H), 3.52-3.33 (m, 2H), 3.01-2.80 (m, 5H), 2.30-2.19 (m, 2H), 2.01-1.94 (m, 2H), 1.79 (m, 3H). HRMS calculated [M+H]$^+$ C$_{30}$C$_{31}$ClFN$_6$O$_3$S 609.18454, found 609.18425.

EXAMPLE 35

3-{[(1R)-1-(2-Chloro-4-fluoro-3-{[1-(2-fluoroethyl)-4-piperidinyl]oxy}phenyl)ethyl]oxy}-5-[5-(1-methyl-1H-pyrazol-4-yl)-1H-benzimidazol-1-yl]-2-thiophenecarboxamide

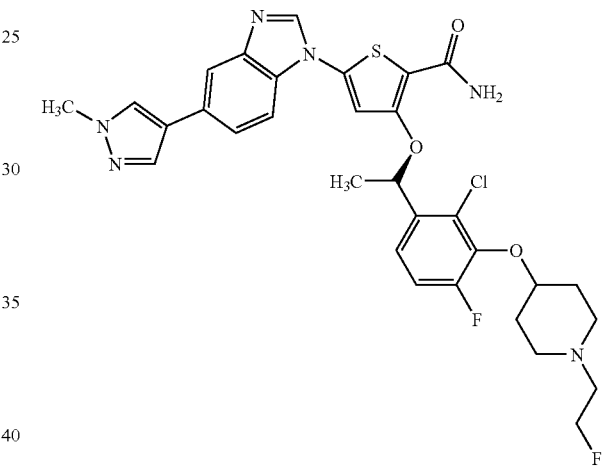

Step A—Methyl 3-{[(1R)-1-(2-chloro-4-fluoro-3-{[1-(2-fluoroethyl)-4-piperidinyl]oxy}phenyl)ethyl]oxy}-5-[5-(1-methyl-1H-pyrazol-4-yl)-1H-benzimidazol-1-yl]-2-thiophenecarboxylate

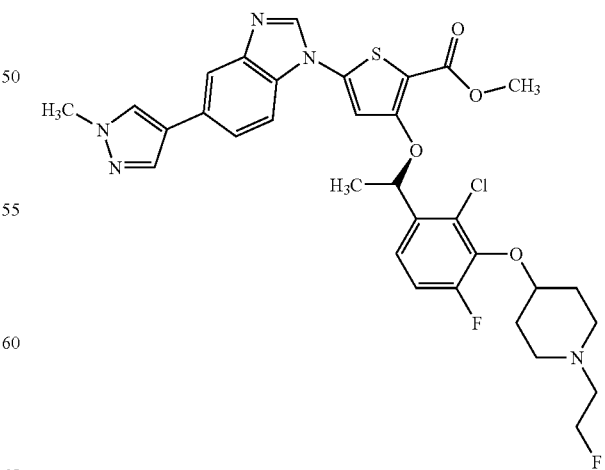

Methyl 3-({(1R)-1-[2-chloro-4-fluoro-3-(4-piperidinyloxy)phenyl]ethyl}oxy)-5-[5-(1-methyl-1H -pyrazol-4-yl)-

1H-benzimidazol-1-yl]-2-thiophenecarboxylate (Example 33, Step A, 90 mg, 0.15 mmol) and 1-bromo-2-fluoroethane (22 µL, 0.30 mmol) were coupled using a procedure analogous to Example 19, Step A to give 92 mg of the desired product (94%). $^1$H NMR (400 MHz, $d_6$-DMSO) δ 8.63 (s, 1H), 8.18 (s, 1H), 7.96 (s, 1H), 7.92 (s, 1H), 7.68 (d, J=8.4 Hz, 1H), 7.60 (m, 1H), 7.50-7.46 (m, 1H), 7.41-7.35 (m, 2H), 5.93 (m, 1H), 4.50 (t, J=5.0 Hz, 1H), 4.38 (t, J=5.0 Hz, 1H), 3.86 (s, 3H), 3.81 (s, 3H), 2.74-2.65 (m, 2H), 2.56 (t, J=5.0 Hz, 1H), 2.48 (m under DMSO peak, 1H), 2.13 (m, 2H), 2.11 (m, 2H), 1.82 (m, 2H), 1.67 (m, 2H), 1.61 (d, J=6.0 Hz, 3H).

Step B—3-{[(1R)-1-(2-Chloro-4-fluoro-3-{[1-(2-fluoroethyl)-4-piperidinyl]oxy}phenyl)ethyl]oxy}-5-[5-(1-methyl-1H-pyrazol-4-yl)-1H-benzimidazol-1-yl]-2-thiophenecarboxamide (Title Compound)

Methyl 3-{[(1R)-1-(2-chloro-4-fluoro-3-{[1-(2-fluoroethyl)-4-piperidinyl]oxy}phenyl)ethyl]oxy}-5-[5-(1-methyl-1H-pyrazol-4-yl)-1H-benzimidazol-1-yl]-2-thiophenecarboxylate (89 mg, 0.14 mmol) was subjected to aminolysis according to a procedure analogous to Example 4, Step B to give 46 mg of the title compound (55%). $^1$H NMR (400 MHz, $d_6$-DMSO) δ 8.52 (s, 1H), 8.18 (s, 1H), 7.95 (s, 1H), 7.91 (s, 1H), 7.80 (br s, 1H), 7.56 (m, 2H), 7.45-7.35 (m, 2H), 7.13 (s, 1H), 7.09 (br s, 1H), 5.97-5.92 (m, 1H), 4.47 (t, J=4.8 Hz, 1H), 4.35 (t, J=5.0 Hz, 1H), 4.14-4.12 (m, 1H), 3.85 (s, 3H), 2.71-2.68 (m, 1H), 2.61-2.58 (m, 1H), 2.51 (t, J=4.8 Hz, 1H), 2.44 ft, J=5.0 Hz, 1H), 2.13-2.02 (m, 2H), 1.82-1.61 (m, 7H). HRMS calculated [M+H]$^+$ $C_{31}H_{32}ClF_2N_6O_3S$ 641.19077, found 641.19054.

EXAMPLE 36

3-({(1R)-1-[2-Chloro-4-fluoro-3-({1-[2-(methylsulfonyl)ethyl]-4-piperidinyl}oxy)phenyl]ethyl}oxy)-5-[5-(1-methyl-1H-pyrazol-4-yl)-1H-benzimidazol-1-yl]-2-thiophenecarboxamide

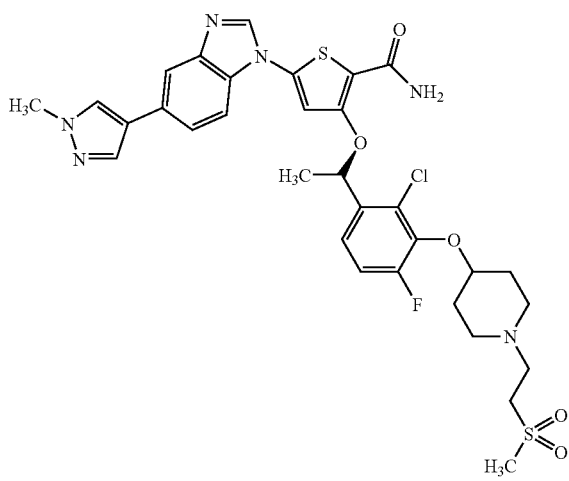

3-({(1R)-1-[2-chloro-4-fluoro-3-(4-piperidinyloxy)phenyl]ethyl}oxy)-5-[5-(1-methyl-1H-pyrazol-4-yl)-1H-benzimidazol-1-yl]-2-thiophenecarboxamide (Example 33, Step A, 80 mg, 0.13 mmol) and methyl vinyl sulfone (13 µL, 0.15 mmol) were coupled using a procedure analogous to Example 23 to give 72 mg of the title compound (79%). $^1$H NMR (400 MHz, $d_6$-DMSO) δ 8.52 (s, 1H), 8.17 (s, 1H), 7.95 (s, 1H), 7.91 (s, 1H), 7.79 (br s, 1H), 7.56 (m, 2H), 7.45-7.35 (m, 2H), 7.13 (s, 1H), 7.08 (br s, 1H), 5.94 (m, 1H), 4.13 (m, 1H), 3.85 (s, 3H), 3.17 (t, J=6.2 Hz, 2H), 2.97 (s, 3H), 2.69-2.58 (m, 4H), 2.07 (m, 2H), 1.81-1.66 (m, 7H). HRMS calculated [M+H]$^+$ $C_{32}H_{35}ClFN_6O_5S_2$ 701.17774, found 701.17740.

EXAMPLE 37

3-({(1R)-1-[2-Chloro-3-(4-piperidinyloxy)phenyl]ethyl}oxy)-5-[5-(1-oxido-4-pyridinyl)-1H-benzimidazol-1-yl]-2-thiophenecarboxamide

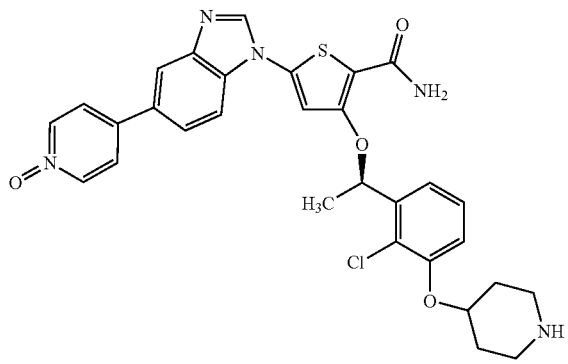

Step A—1,1-Dimethylethyl 4-({2-Chloro-[(1R)-1-({2-[(methyloxy)carbonyl]-5-[5-(4-pyridinyl)-1H-benzimidazol-1-yl]-3-thienyl}oxy)ethyl]phenyl}oxy)-1-piperidinecarboxylate

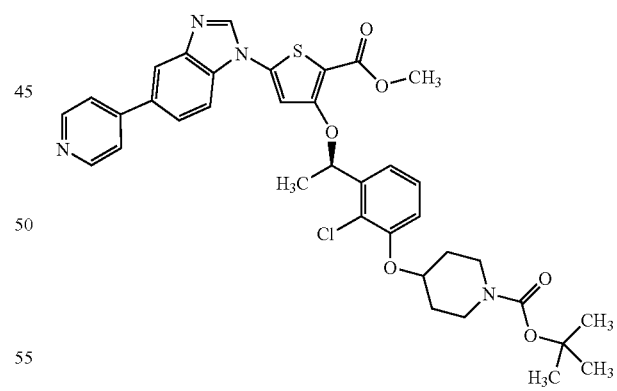

The title compound was prepared from 1,1-dimethylethyl 4-({3-[(1R)-1-({5-(5-bromo-1H-benzimidazol-1-yl)-2-[(methyloxy)carbonyl]-3-thienyl}oxy)ethyl]-2-chlorophenyl}oxy)-1-piperidinecarboxylate (400 mg, 0.58 mmol) and pyridine-4-boronic acid (92 mg, 0.75 mmol) using a procedure analogous to Intermediate 9 to give 135 mg of the desired product. MS (ESI): 689.6 [M+H]$^+$.

Step B—1,1-Dimethylethyl 4-({3-[(1R)-1-({2-(aminocarbonyl)-5-[5-(4-pyridinyl)-1H-benzimidazol-1-yl]-3-thieoyl}oxy)ethyl]-2-chlorophenyl}oxy)-1-piperidinecarboxylate

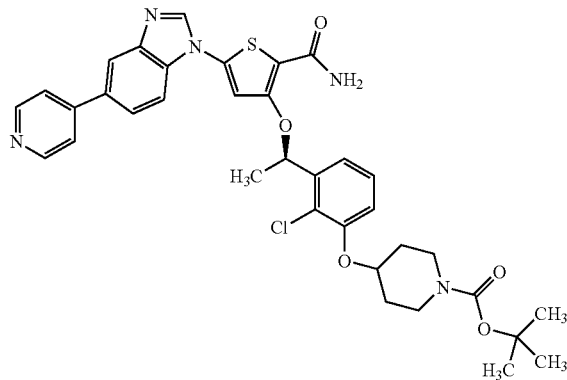

The title compound was prepared from 1, 1-dimethylethyl 4-({2-chloro-3-[(1R)-1-({2-[(methyloxy)carbonyl]-5-[5-(4-pyridinyl)-1H-benzimidazol-1-yl]-3-thienyl}oxy)ethyl]phenyl}oxy)-1-piperidinecarboxylate (135 mg, 0.196 mmol) using a procedure analogous to Example 5S Step 3 to give 109 mg of the desired product. MS (AP); 674.3 [M+H]$^+$.

Step C—1,1-Dimethylethyl 4-({3-[(1R)-1-({2-(aminocarbonyl)-5-[5-(1-oxido-4-pyridinyl)-1H-benzimidazol-1-yl]-3-thienyl}oxy)ethyl]-2-chlorophenyl}oxy)-1-piperidinecarboxylate

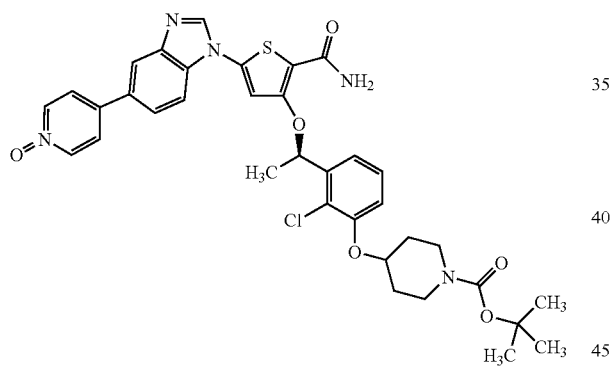

1,1-Dimethylethyl 4-({3-[(1R)-1-({2-(aminocarbonyl)-5-[5-(4-pyridinyl)-1H-benzimidazol-1-yl]-3-thienyl}oxy)ethyl]-2-chlorophenyl}oxy)-1-piperidinecarboxylate (0.109 g, 0.16 mmol) and 50% m-chloroperoxybenzoic acid (0.44 g, 1.3 mmol) were combined in DCM (8 mL) at 0° C. The reaction mixture was stirred overnight, warming to rt, after which time the reaction was quenched with aqueous saturated NaHCO$_3$ and extracted three times with DCM. The organics were combined, dried over MgSO$_4$, filtered and concentrated. The resulting yellow oil was used directly in the next step without purification. MS (ESI): 692.4 [M+H]$^+$.

Step D—3-({(1R)-1-[2-Chloro-3-(4-piperidinyloxy)phenyl]ethyl}oxy)-5-[5-(1-oxido-4-pyridinyl)-1H-benzimidazol-1-yl]-2-thiophenecarboxamide (Title Compound)

The title compound was prepared from 1,1-dimethylethyl 4-({3-[(1R)-1-({2-(aminocarbonyl)-5-[5-(1-oxido-4-pyridinyl)-1H-benzimidazol-1-yl]-3-thienyl}oxy)ethyl]-2-chlorophenyl}oxy)-1-piperidinecarboxylate (crude material from Example 37, Step C) using a procedure analogous to Example 5, Step C to give 0.012 g of the desired product. $^1$H NMR (400 MHz, CD$_3$OD): δ 8.44 (s, 1H), 8.36 (d, J=6.8 Hz, 2H), 8.11 (s, 1H), 7.90 (d, J=6.8 Hz, 2H), 7.75 (d, J=8.2 Hz, 1H), 7.61 (d, J=8.6 Hz, 1H), 7.35 (t, J=8.0 Hz, 1H), 7.23 (d, J=7.5 Hz, 1H), 7.16 (d, J=8.1 Hz, 1H), 7.02 (s, 1H), 6.06 (q, J=6.4 Hz, 1H), 4.79 (m, 1H), 3.41-3.31 (m, 2H), 3.25-3.13 (m, 2H), 2.18-1.97 (m, 4H), 1.78 (d, J=6.2 Hz, 3H); MS (ESI): 590,3 [M+H]$^+$.

EXAMPLE 38

3-[((1R)-1-{2-Chloro-6-fluoro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide

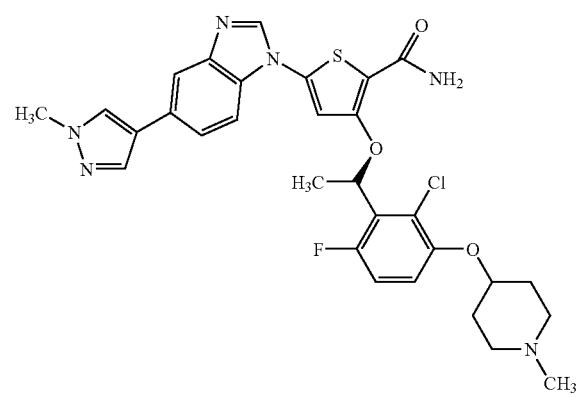

Step A—Methyl 3-{[1-(2-chloro-3-{[(1,1-dimethylethyl)(diphenyl)silyl]oxy}-6-fluorophenyl)ethyl]oxy}-5-[5-(1-methyl-1H-pyrazol-4-yl)-1H-benzimidazol-1-yl]-2-thiophenecarboxylate

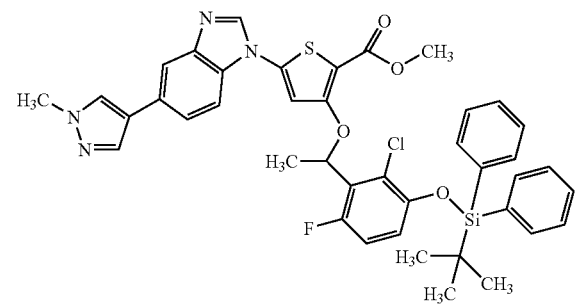

Methyl 3-hydroxy-5-[5-(1-methyl-1H-pyrazol-4-yl)-1H-benzimidazol-1-yl]-2-thiophenecarboxylate (Intermediate 18, 450 mg, 1.3 mmol) and 1-(2-chloro-3-{[(1,1-dimethylethyl)(diphenyl)silyl]oxy}-6-fluorophenyl)ethanol (Intermediate 15, 686 mg, 1.6 mmol) were coupled using a procedure analogous to Intermediate 3, Step B to give the desired product, which was not separated from the triphenylphosphine oxide.

Step B—Methyl 3-{[1-(2-chloro-6-fluoro-3-hydroxyphenyl)ethyl]oxy}-5-[5-(1-methyl-1H-pyrazol-4-yl)-1H-benzimidazol-1-yl]-2-thiophenecarboxylate

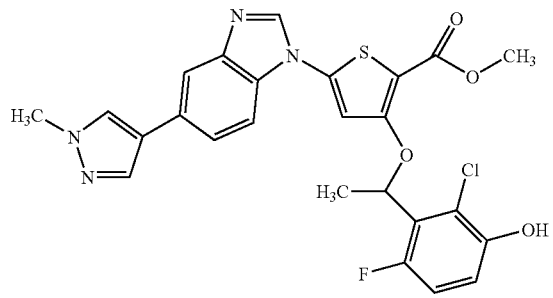

Methyl 3-{[1-(2-chloro-3-{[(1,1-dimethylethyl)(diphenyl)silyl]oxy}-6-fluorophenyl)ethyl]oxy}-5-[5-(1-methyl-1H-pyrazol-4-yl)-1H-benzimidazol-1-yl]-2-thiophenecarboxylate was deprotected using a procedure analogous to Intermediate 3, Step F to give 288 mg of the desired product. $^1$H NMR (400 MHz, d$_6$-DMSO) δ 10.29 (s, 1H), 8.60 (s, 1H), 8.19 (s, 1H), 7.97 (s, 1H), 7.93 (s, 1H), 7.60 (dd, J=8.4 and 1.2 Hz, 1H), 7.51 (d, J=8.8 Hz, 1H), 7.20 (s, 1H), 7.10-7.05 (m, 1H), 6.97-6.93 (m, 1H), 6.10-6.05 (m, 1H), 3.86 (s, 3H), 3.76 (s, 3H), 1.75 (d, J=6.4 Hz, 3H).

Step C—Methyl 3-[(1-{2-chloro-6-fluoro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxylate

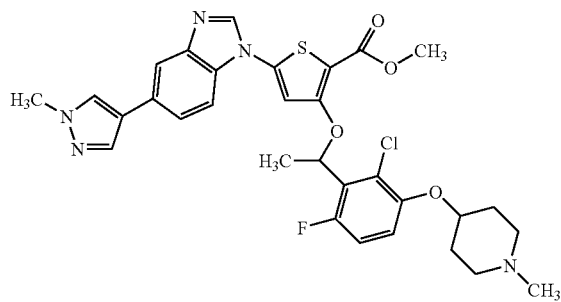

Methyl 3-{[1-(2-chloro-6-fluoro-3-hydroxyphenyl)ethyl]oxy}-5-[5-(1-methyl-1H-pyrazol-4-yl)-1H-benzimidazol-1-yl]-2-thiophenecarboxylate (288 mg, 0.55 mmol) and 1-methyl-4-piperidinol (76 mg, 0.66 mmol) were coupled using a procedure analogous to Example 4, Step A to give 297 mg of the desired product (87%). $^1$H NMR (400 MHz, d$_6$-DMSO) δ 8.59 (s, 1H), 8.19 (s, 1H), 7.97 (s, 1H), 7.92 (s, 1H), 7.60-7.52 (m, 2H), 7.22-7.17 (m, 3H), 6.12-6.07 (m, 1H), 4.38 (m, 1H), 3.86 (s, 3H), 3.76 (s, 3H), 2.48-2.43 (m under DMSO peak, 2H, 2.13-2.08 (m, 5H), 1.81-1.75 (m, 5H), 1.63-1.56 (m, 2H).

Step D—3-[((1R)-1-{2-Chloro-6-fluoro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide (Title Compound)

Methyl 3-[(1-{2-chloro-6-fluoro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxylate (297 mg, 0.48 mmol) was subjected to aminolysis using a procedure analogous to Example 4, Step B to give 268 mg of the racemic compound (92%). NMR (400 MHz, d$_6$-DMSO) δ 8.54 (s, 1H), 8.17 (s, 1H), 7.95 (s, 1H), 7.90 (s, 1H), 7.83 (bs, 1H), 7.59-7.55 (m, 2H), 7.31 (s, 1H), 7.24-7.22 (m, 2H), 6.97 (bs, 1H), 6.19-6.14 (m, 1H), 4.41-4.37 (m, 1H), 3.84 (s, 3H), 2.47-2.41 (m under DMSO peak, 2H), 2.12-2.02 (m, 5H), 1.81-1.77 (m, 5H), 1.63-1.56 (m, 2H). MS (ESI): 609 [M+H]$^+$.

EXAMPLE 39

1,1-Dimethylethyl 4-[({3-[(1R)-1-({2-(aminocarbonyl)-5-[5,6-bis(methyloxy)-1H-benzimidazol-1-yl]-3-thienyl}oxy)ethyl]-2-chlorophenyl}oxy)methyl]-1-piperidinecarboxylate

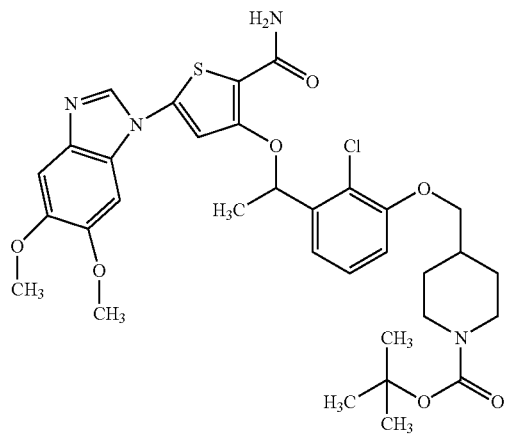

Step A—1,1-Dimethylethyl 4-[({3-[(1R)-1-({5-[5,6-bis(methyloxy)-1H-benzimidazol-1-yl]-2-[(methyloxy)carbonyl]-3-thienyl}oxy)ethyl]-2-chlorophenyl}oxy)methyl]-1-piperidinecarboxylate

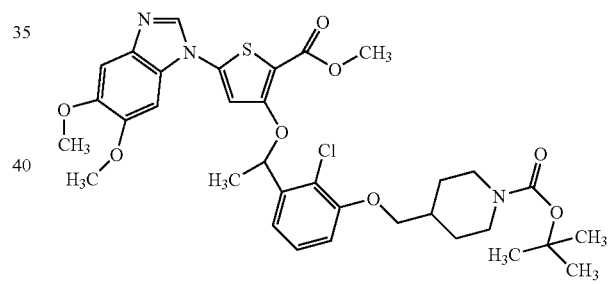

Methyl 5-[5,6-bis(methyloxy)-1H-benzimidazol-1-yl]-3-{[(1R)-1-(2-chloro-3-hydroxyphenyl)ethyl]oxy}-2-thiophenecarboxylate (Intermediate 19, 150 mg, 0.31 mmol) and 1,1-dimethylethyl 4-(hydroxymethyl)-1-piperidinecarboxylate (73 mg, 0.47 mmol) were coupled using a procedure analogous to Example 5, Step A to give 170 mg of the desired product (80%). $^1$H NMR (400 MHz, CDCl$_3$) δ 7.86 (s, 1H), 7.28-7.22 (m, 3H), 6.93 (s, 1H), 6.82 (dd, J=6.0, 4.01 Hz, 1H), 6.65 (s, 1H) 5.83 (q, J=6.4 Hz, 1H), 4.23-4.12 (m, 2H), 3.94 (s, 3H), 3.92 (s, 3H), 3.88 (s, 3H), 3.87-3.78 (m, 2H), 2.82-2.69 (m, 2H), 2.06-1.97 (m, 1H) 1.92-1.79 (m, 2H), 1.71 (d, J=6.4 Hz, 3H), 1.47 (s, 9H), 1.36-1.24 (m, 2H). MS (ESI): 686 [M+H]$^+$.

Step B—1,1-Dimethylethyl 4-[({3-[(1R)-1-({2-(aminocarbonyl)-5-[5,6-bis(methyloxy)-1H-benzimidazol-1-yl]-3-thienyl}oxy)ethyl]-2-chlorophenyl}oxy)methyl]-1-piperidinecarboxylate (Title Compound)

1,1-Dimethylethyl 4-[({3-[(1R)-1-({5-[5,6-bis(methyloxy)-1H-benzimidazol -yl]-2-[(methyloxy)carbonyl]-3-thienyl}oxy)ethyl]-2-chlorophenyl}oxy)methyl]-1-piperidinecarboxylate (206 mg, 0.30 mmol) was subjected to aminolysis using a procedure analogous to Example 4, Step B to give 200 mg of the title compound, ¹H NMR (400 MHz, CDCl₃) δ 7.81 (s, 1H), 7.25-7.19 (m, 3H) 7.02 (dd, J=7.8, 1.1 Hz, 1H), 6.90 (s, 1H), 6.82 (dd, J=8.4, 1.1 Hz, 1H), 6.74 (bs, 1H), 6.54 (s, 1H) 5.84 (q, J=6.4 Hz, 1H), 4.25-4.05 (m, 2H), 3.90 (s, 3H), 3.82 (S, 3H), 3.82-3.75 (m, 2H), 2.76-2.69 (m, 2H), 2.06-1.92 (m, 1H) 1.87-1.77 (m, 2H), 1.71 (d, J=6.4 Hz, 3H), 1.43 (s, 9H), 1.32-1.20 (m, 2H). MS (ESI): 671 [M+H]⁺.

EXAMPLE 40

5-[5.6-Bis(methyloxy)-1H-benzimidazol-1-yl]-3-[((1R)-1-{2-chloro-3-[(4-piperidinylmethyl)oxy]phenyl}ethyl)oxy]-2-thiophenecarboxamide

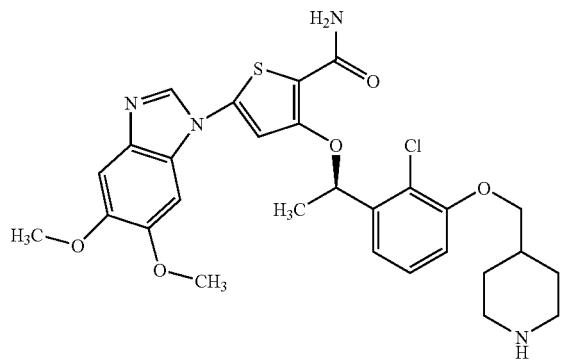

1,1-Dimethylethyl 4-[({3-[(1R)-1-({2-(aminocarbonyl)-5-[5,6-bis(methyloxy)-1H-benzimidazol-1-yl]-3-thienyl}oxy)ethyl]-2-chlorophenyl}oxy)mwthyl]-1-piperidinecarboxylate (Example 39, 180 mg, 0.27 mmol) was deprotected using a procedure analogous to Example 5. Step C to give 120 mg of the title compound. ¹H NMR (400 MHz, CDCl₃) δ 8.20-7.80 (m, 2H), 7.85 (s, 1H), 7.34-7.22 (m, 2H) 7.14-6.99 (m, 2H), 6.96 (s, 1H), 6.86 (d, J=7.3 Hz, 1H), 6.58 (s, 1H), 5.87 (q, J=6.4 Hz, 1H), 3.99-3.83 (m, 2H), 3.93 (s, 3H), 3.87 (s, 3H), 3.52 (d, J=12.2 Hz, 2H), 2.97 (dd, J=12.2, 10.8 Hz, 2H), 2.25-2.01 (m, 3H) 1.82-1.69 (m, 2H), 1.75 (d, J=6.4 Hz, 3H). MS (ESI): 571 [M+H]⁺.

EXAMPLE 41

5-[5,6-Bis(methyloxy)-1H-benzimidazol-1-yl]-3-{[(1R)-1-(2-chloro-3-{[(1-methyl-4-piperidinyl)methyl]oxy}phenyl)ethyl]oxy}-2-thiophenecarboxamide

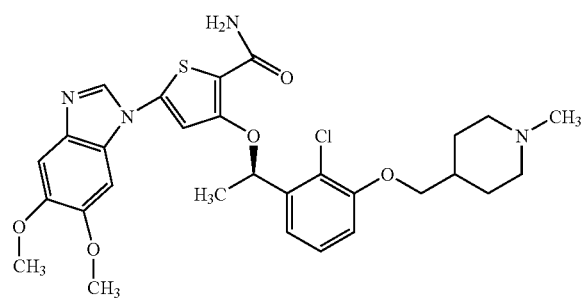

5-[5,6-bis(methyloxy)-1H-benzimidazol-1-yl]-3-[((1R)-1-{2-chloro-3-[(4-piperidinylmethyl)oxy]phenyl}ethyl)oxy]-2-thiophenecarboxamide (Example 40, 70 mg, 0.12 mmol) was reductively methylated using a procedure analogous to Example 48 to give 50 mg of the title compound (71%). ¹H NMR (400 MHz, CDCl₃) δ 7.84 (s, 1H), 7.29-7.21 (m, 3H) 7.05 (d, J=7.4 Hz, 1H), 6.95 (s, 1H), 6.86 (d, J=7.4 Hz, 1H), 6.58 (s, 1H), 6.33 (bs, 1H), 5.89 (q, J=6.4 Hz, 1H), 3.94 (s, 3H), 3.91-3.79 (m, 2H), 3.87 (s, 3H), 2.92 (d, J=11.3 Hz, 2H), 2.30 (s, 3H), 2.10-1.80 (m, 5H) 1.75 (d, J=6.4 Hz, 3H), 1.54-1.40 (m, 2H). MS (ESI): 585 [M+H]+.

EXAMPLE 42

5-[5,6-Bis(methyloxy)-1H-benzimidazol-1-yl]-3-{[(1R)-1-(2-chloro-3-{[2-(4-methyl-1-piperazinyl)ethyl]oxy}phenyl)ethyl]oxy}-2-thiophenecarboxamide

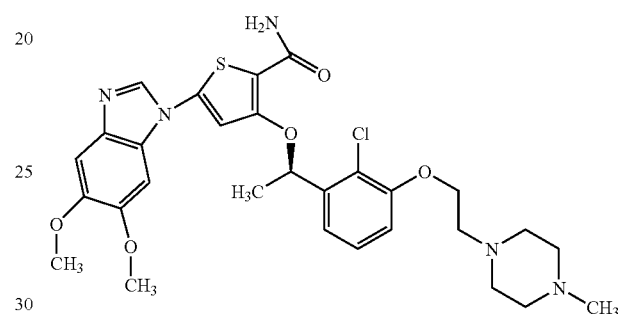

Step A—Methyl 5-[5,6-bis(methyloxy)-1H-benzimidazol-1-yl]-3-[((1R)-1-{3-[(2-bromoethyl)oxy]-2-chlorophenyl}ethyl)oxy]-2-thiophenecarboxylate

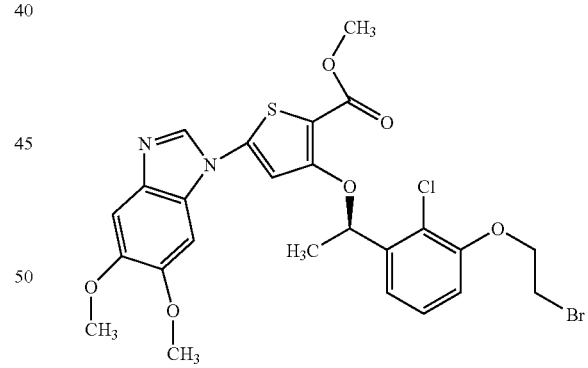

Methyl 5-[5,6-bis(methyloxy)-1H-benzimidazol-1-yl]-3-{[(1R)-1-(2-chloro-3-hydroxyphenyl)ethyl]oxy}-2-thiophenecarboxylate (Intermediate 19, 980 mg, 2.0 mmol) and 2-bromoethanol (350 μL, 5.0 mmol) were coupled using a procedure analogous to Example 4, Step A to give 520 mg of the desired product (44%). ¹H NMR (400 MHz, CDCl₃) δ 7.86 (s, 1H), 7.32-7.22 (m, 3H), 6.95 (s, 1H), 6.86 (dd, J=8.0, 2.4 Hz, 1H), 6.65 (s, 1H), 5.84 (q, J=6.4 Hz, 1H), 4.33 (t, J=6.4, 2H) 3.95 (s, 3H), 3.92 (s, 3H), 3.90 is, 3H), 3.68 (t, J=6.4 Hz, 2H), 1.73 (d, J=6.4 Hz, 3H).

Step B—Methyl 5-[5,6-bis(methyloxy)-1H-benzimidazol-1-yl]-3-{[(1R)-1-(2-chloro-3-{[2-(4-methyl-1-piperazinyl)ethyl]oxy}phenyl)ethyl]oxy}-2-thiophenecarboxylate

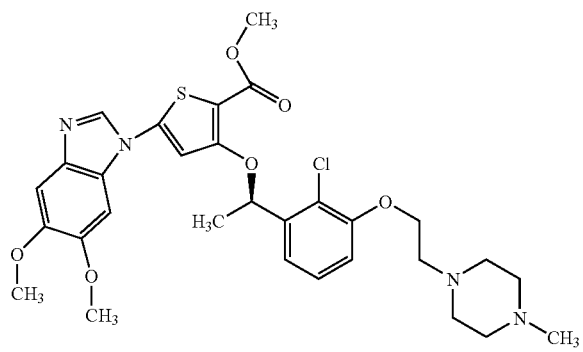

Methyl 5-[5,6-bis(methyloxy)-1H-benzimidazol-1-yl]-3-[((1R)-1-{3-[(2-bromoethyl)oxy]-2-chlorophenyl}ethyl)oxy]-2-thiophenecarboxylate (100 mg, 0.17 mmol) and 1-methylpiperazine (52 μL, 0.51 mmol) were coupled using a procedure analogous to Example 15, Step A to give 54 mg of the desired product (53%). MS (ESI): 615 [M+H]⁺.

Step C—5-[5,6-Bis(methyloxy)-1H-benzimidazol-1-yl]-3-{[(1B)-1-(2-chloro-3-{[2-(4-methyl-1-piperazinyl)ethyl]oxy}phenyl)ethyl]oxy}-2-thiophenecarboxamide (Title Compound)

Methyl 5-[5,6-bis(methyloxy)-1H-benzimidazol-1-yl]-3-{[(1R)-1-(2-chloro-3-{[2-(4-methyl-1-piperazinyl)ethyl]oxy}phenyl)ethyl]oxy}-2-thiophenecarboxylate (54 mg, was subjected to aminolysis using a procedure analogous to Example 4, Step B to give 50 mg of the title compound. ¹H NMR (400 MHz, CDCl₃) δ 7.84 (s, 1H), 7.29-7.23 (m, 3H), 7.07 (d, J=7.4 Hz, 1H), 6.96 (s, 1H), 6.89 (d, J=7.4 Hz, 1H), 6.58 (s, 1H), 6.57 (bs, 1H), 5.89 (q, J=6.4 Hz, 1H), 4.15 (dd, J=6.8, 5.8, 2H) 3.94 (s, 3H), 3.88 (s, 3H), 2.90 (ddd, J=7.8, 5.8, 2.0 Hz, 2H), 2.76-2.36 (m, 8H), 2.29 (s, 3H), 1.75 (d, J=6.4 Hz, 3H). MS (ESI): 600 [M+H]⁺.

EXAMPLE 43

1,1-Dimethylethyl 4-[({3-[(1R)-1-({2-(aminocarbonyl)-5-[5-(1-methyl-1H-pyrazol-4-yl)-1H-benzimidazol-1-yl]-3-thienyl}oxy)ethyl]-2-chlorophenyl}oxy)methyl]-1-piperidinecarboxylate

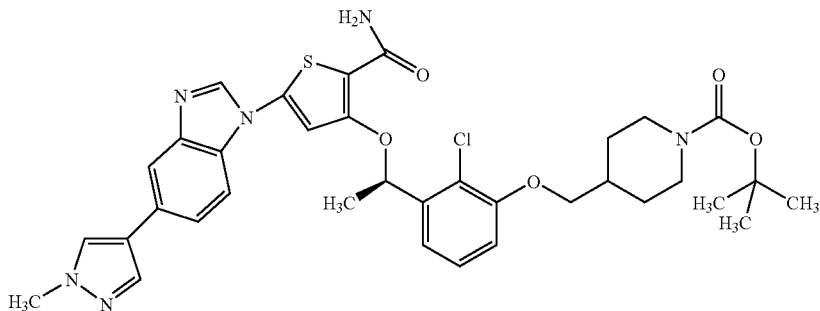

Step A—1,1-Dimethylethyl 4-[({2-chloro-3-[(1R)-1-({2-[(methyloxy)carbonyl]-5-[5-(1-methyl-1H-pyrazol-4-yl)-1H-benzimidazol-1-yl]-3-thienyl}oxy)ethyl]phenyl}oxy)methyl]-1-piperidinecarboxylate

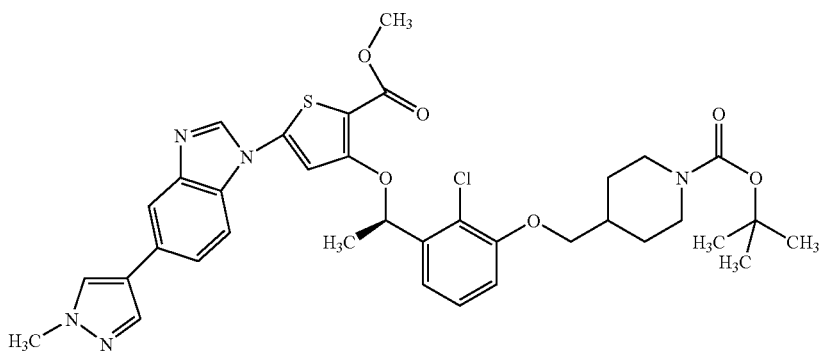

Methyl 3-hydroxy-5-[5-(1-methyl-1H-pyrazol-4-yl)-1H-benzimidazol-1-yl]-2-thiophenecarboxylate (Intermediate 16, 250 mg, 0.50 mmol) and 1,1-dimethylethyl 4-(hydroxymethyl)-1-piperidinecarboxylate (129 mg, 0.60 mmol) were coupled using a procedure analogous to Example 5, Step A to give the desired product (275 mg, 78 %). MS (ESI); 706 [M+H]$^+$.

Step B—1,1-Dimethylethyl 4-[({3-[(1R)-1-({2-(aminocarbonyl)-5-[5-(1-methyl-1H-pyrazol-4-yl)-1H-benzimidazol-1-yl]-3-thienyl}oxy)ethyl]-2-chlorophenyl}oxy)methyl]-1-piperidinecarboxylate (Title Compound)

1,1-Dimethylethyl 4-[({2-chloro-3-[(1R)-1-({2-[(methyloxy)carbonyl]-5-[5-(1-methyl-1H-pyrazol-4-yl)-1H-benzimidazol-1-yl]-3-thienyl}oxy)ethyl]phenyl}oxy)methyl]-1-piperidinecarboxylate) (275 mg, 0.39 mmol) was subjected to aminolysis using a procedure analogous to Example 4, Step B to give 200 mg of the title compound (74%). $^1$H NMR (400 MHz, CDCl$_3$) δ 7.95 (s, 1H), 7.88 (s, 1H), 7.79 (s, 1H), 7.65 (s, 1H) 7.50-7.42 (m, 2H), 7.26 (dd, J=7.9. 8.1 Hz, 1H), 7.22 (bs, 1H), 7.05 (dd, J=7.9, 1.3 Hz, 1H), 6.87 (dd, J=8.1, 1.3 Hz, 1H), 6.60 (s, 1H), 6.13 (bs, 1H), 5.90 (q, J=6.4 Hz, 1H), 4.25-4.05 (m, 2H) 3.96 (s, 3H), 3.91-3.80 (m, 2H), 2.83-2.68 (m, 2H), 2.09-1.98 (m, 1H), 1.91-1.79 (m, 2H), 1.75 (d, J=6.4 Hz, 3H), 1.45 (s, 9H), 1.37-1.23 (m, 2H). MS (ESI): 692 [M+H]$^+$.

EXAMPLE 44

3-[((1R)-1-{2-Chloro-3-[(4-piperidinylmethyl)oxy]phenyl}ethyl)oxy]-5-[5-(1-methyl-1H-pyrazol-4-yl)-1H-benzimidazol-1-yl]-2-thiophenecarboxamide trifluoroacetate

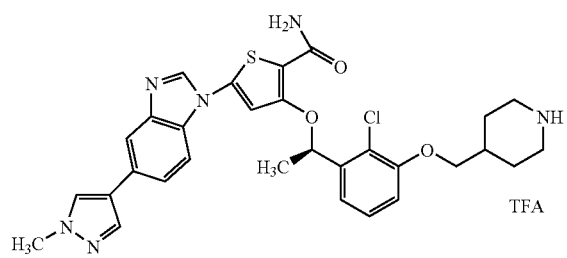

1,1-Dimethylethyl 4-[({3-[(1R)-1-({2-(aminocarbonyl)-5-[5-(1-methyl-1H-pyrazol-4-yl)-1H-benzimidazol-1-yl]-3-thienyl}oxy)ethyl]-2-chlorophenyl}oxy)methyl]-1-piperidinecarboxylate (Example 43, 180 mg, 0.26 mmol) was deprotected using a procedure analogous to Example 5, Step C to give 155 mg of the title compound. $^1$H NMR (400 MHz, CDCl$_3$) δ 8.97-8.87 (m, 1H), 8.77 (s, 1H), 8.66-8.53 (m, 1H), 8.00 (s, 1H), 7.90 (s, 1H), 7.78 (s, 1H), 7.65-7.58 (m, 2H), 7.44 (bs, 1H), 7.32-7.24 (m, 3H), 7.06 (d, J=6.9 Hz, 1H), 6.89 (d, J=8.6 Hz, 1H), 6.87 (s, 1H), 5.94 (q, J=6.4 Hz, 1H), 4.02 (s, 3H), 3.97-3.91 (m, 2H), 3.06-2.94 (m, 2H), 2.21-2.04 (m, 3H), 1.87-1.73 (m, 2H), 1.79 (d, J=6.4 Hz, 3H), 1.27-1.19 (m, 2H).

EXAMPLE 45

3-{[(1R)-1-(2-Chloro--3-{[(1-methyl-4-piperidinyl)methyl]oxy}phenyl)ethyl]oxy}-5-[5-(1-methyl-1H-pyrazol-4-yl)-1H-benzimidazol-1-yl]-2-thiopnenecarboxamide

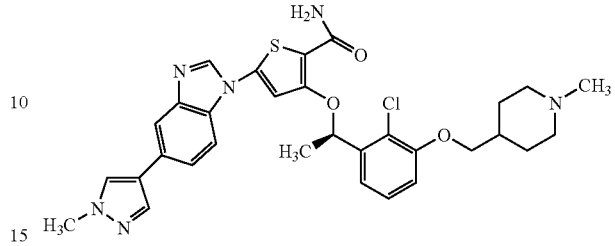

3-[((1R)-1-{2-chloro-3-[(4-piperidinylmethyl)oxy]phenyl}ethyl)oxy]-5-[5-(1-methyl-1H-pyrazol-4-yl)-1H-benzimidazol-1-yl]-2-thiophenecarboxamide trifluoroacetate (Example 44, 124 mg, 0.18 mmol) was reductively methylated using a procedure analogous to Example 48 to give 65 mg of the title compound, $^1$H NMR (400 MHz, CDCl$_3$) δ 7.97 (s, 1H), 7.88 (s, 1H), 7.79 (s, 1H), 7.65 (s, 1H), 7.49-7.42 (m, 2H), 7.28-7.22 (m, 2H), 7.06 (d, J=7.9 Hz, 1H), 6.88 (d, J=8.3 Hz, 1H), 6.63 (bs, 1H), 6.63 (s, 1H), 5.91 (q, J=6.4 Hz, 1H), 3.97 (s, 3H), 3.92-3.81 (m, 2H), 2.90 (d, J=11.6, 2H), 2.29 (s, 3H), 2.02-1.82 (m, 5H), 1.76 (d, J=6.4 Hz, 3H), 1.53-1.42 (m, 2H). MS (ESI): 605 [M+H]$^+$.

EXAMPLE 46

1,1-Dimethylethyl 4-({3-[(1R)-1-({2-(aminocarbonyl)-5-[5-(1-methyl-1H-pyrazol-4-yl)-1H-benzimidazol-1-yl]-3-thienyl}oxy)ethyl]-2-chlorophenyl}oxy)-1-piperidinecarboxylate

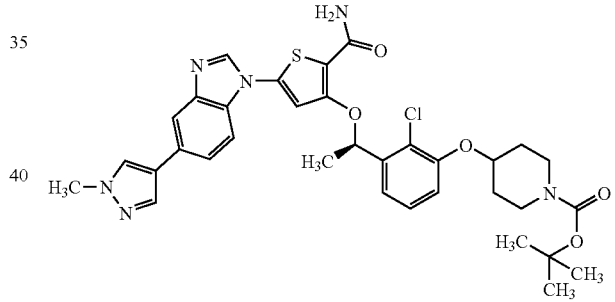

Step A—1,1-Dimethylethyl 4-({2-chloro-3-[(1R)-1-({2-[(methyloxy)carbonyl]-5-[5-(1-methyl-1H-pyrazol-4-yl)-1H-benzimidazol-1-yl]-3-thienyl}oxy)ethyl]phenyl}oxy)-1-piperidinecarboxylate

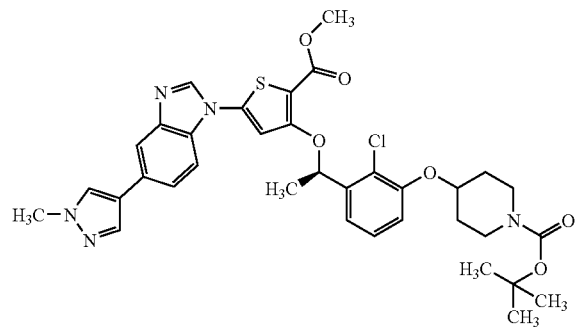

Methyl 3-{[(1R)-1-(2-chloro-3-hydroxyphenyl)ethyl]oxy}-5-[5-(1-methyl-1H-pyrazol-4-yl)-1H-benzimidazol-1-yl]-2-thiophenecarboxylate (Intermediate 18, 650 mg, 1.3 mmol) and tert-butyl 4-hydroxypiperidine-1-carboxylate (402 mg, 2.0 mmol) were coupled using a procedure analogous to Example 5, Step A to give 680 mg of the desired product (75%). MS (ESI): 605 [M+H]+.

Step B—1,1-Dimethylethyl 4-({3-[(1R)-1-({2-(aminocarbonyl)-5-[5-(1-methyl-1H-pyrazol-4-yl)-1H-benzimidazol-1-yl]-3-thienyl}oxy)ethyl]-2-chlorophenyl}oxy)-1-piperidinecarboxylate (Title Compound)

1,1-Dimethylethyl 4-({2-chloro-3-[(1R)-1-({2-[(methyloxy)carbonyl]-5-[5-(1-methyl-1H-pyrazol-4-yl)-1H-benzimidazol-1-yl]-3-thienyl}oxy)ethyl]phenyl}oxy)-1-piperidinecarboxylate) (680 mg, 0.98 mmol) was subjected to aminolysis using a procedure analogous to Example 4, Step B to give 500 mg of the title compound (75%). 1H NMR (400 MHz, CDCl3) δ 7.97 (s, 1H), 7.89 (s, 1H), 7.79 (s, 1H), 7.67 (s, 1H) 7.49-7.43 (m, 2H), 7.30-7.21 (m, 1H), 7.08 (dd, J=7.8, 1.1 Hz, 1H), 6.93 (dd, J=8.4, 1.1 Hz, 1H), 6.63 (s, 1H), 6.59 (bs, 1H), 5.91 (q, J=6.4 Hz, 1H), 4.61-4.54 (m, 1H) 3.97 (s, 3H), 3.71-3.59 (m, 2H), 3.52-3.42 (m, 2H), 1.97-1.80 (m, 4H), 1.77 (d, J=6.4 Hz, 3H), 1.46 (s, 9H). MS (ESI): 677 [M+H]+.

EXAMPLE 47

3-({(1R)-1-[2-Chloro-3-(4-piperidinyloxy)phenyl]ethyl}oxy)-5-[5-(1-methyl-1H-pyrazol-4-yl)-1H-benzimidazol-1-yl]-2-thiophenecarboxamide

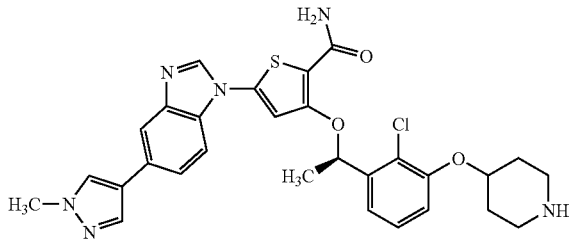

1,1-Dimethylethyl 4-({3-[(1R)-1-({2-(aminocarbonyl)-5-[5-(1-methyl-1H-pyrazol-4-yl)-1H-benzimidazol-1-yl]-3-thienyl}oxy)ethyl]-2-chlorophenyl}oxy)-1-piperidinecarboxylate (Example 46, 500 mg, 0.74 mmol) was deprotected using a procedure analogous to Example 5, Step C to give 290 mg of the title compound (68%). 1H NMR (400 MHz, CDCl3) δ 7.96 (s, 1H), 7.88 (s, 1H), 7.79 (s, 1H), 7.65 (s, 1H) 7.48-7.44 (m, 2H), 7.29-7.23 (m, 1H), 7.21 (bs, 1H) 7.06 (d, J=6.6 Hz, 1H), 6.93 (d, J=8.4 Hz, 1H), 6.62 (s, 1H), 5.92 (q, J=6.4 Hz, 1H), 5.73 (bs, 1H), 4.52-4.44 (m, 1H) 3.97 (s, 3H), 3.22-3.12 (m, 2H), 2.81-2.71 (m, 2H), 2.06-1.96 (m, 2H), 1.85-1.75 (m, 2H), 1.77 (d, J=6.4 Hz, 3H).

EXAMPLE 48

3-[((1R)-1-{2-Chloro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide

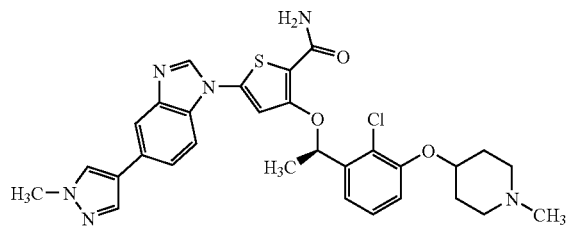

To a solution of 3-({(1R)-1-[2-chloro-3-(4-piperidinyloxy)phenyl]ethyl}oxy)-5-[5-(1-methyl-1H-pyrazol-4-yl)-1H-benzimidazol-1-yl]-2-thiophenecarboxamide (Example 47, 230 mg, 0.40 mmol) in DCM (4 mL) and MeOH (2 mL) was added formaldehyde (0.033 mL, 1.2 mmol) and acetic acid (0.046 mL, 0.80 mmol) followed by sodium triacetoxy borohydride (0.17 g, 0.80 mmol). The solution was stirred for 1 h. The solution was diluted with DCM (20 mL) and washed with sat'd NaHCO3 solution (10 mL). The organic layers were dried (MgSO4), filtered and the solvent removed on a rotovap. The residue was dissolved in DCM and loaded onto a 4 g ISCO chromatography column and eluted with a gradient of 100:0 to 30:70 DCM : (80:20:2 DCM:MeOH:ammonium hydroxide) over 20 min. The appropriate fractions were combined and the solvent removed to provide 0.20 g of the title compound as a white solid (85 %). 1H NMR (400 MHz, CDCl3) δ 7.97 (s, 1H), 7.88 (s, 1H), 7.79 (s, 1H), 7.65 (s, 1H), 7.45 (d, J=1.1 Hz, 2H), 7.30-7.22 (m, 2H), 7.06 (d, J=7.9 Hz, 1H), 6.93 (d, J=8.4 Hz, 1H), 6.74 (bs, 1H), 6.64 (s, 1H), 5.91 (q, J=6.4 Hz, 1H), 4.45-4.38 (m, 1H), 3.97 (s, 3H), 2.71-2.61 (m, 2H), 2.47-2.27 (m, 2H), 2.29 (s, 3H), 2.05-1.87 (m, 4H), 1.77 (d, J=6.4 Hz, 3H). MS (ESI): 591 [M+H]+.

EXAMPLE 49

3-({(1R)-1-[2-Chloro-3-(4-piperidinyloxy)phenyl]ethyl}oxy)-5-[5-(2-methyl-4-pyridinyl)-1H-benzimidazol-1-yl]-2-thiophenecarboxamide

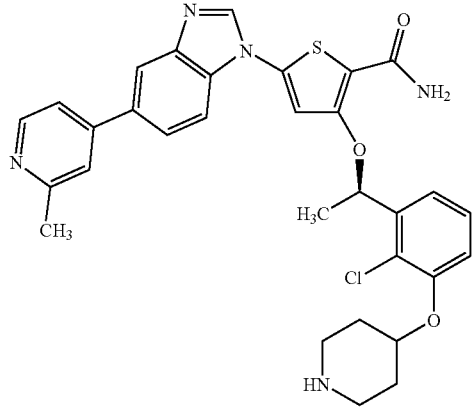

Step A—1,1-Dimethylethyl 4-({2-chloro-3-[(1R)-1-({2-[(methyloxy)carbonyl]-5-[5-(2-methyl-4-pyridinyl)-1H-benzimidazol-1-yl]-3-thienyl}oxy)ethyl]phenyl}oxy)-1-piperidinecarboxylate

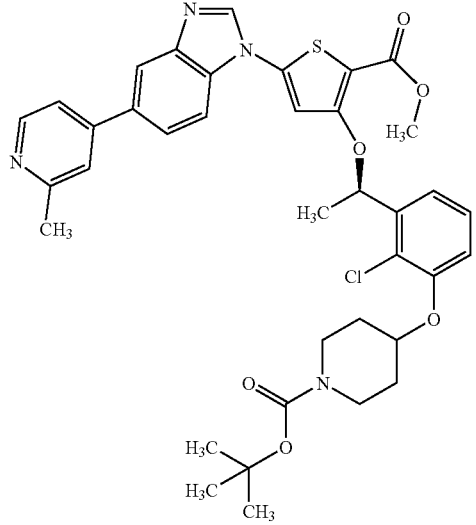

Methyl 3-{[(1R)-1-(2-chloro-3-hydroxyphenyl)ethyl]oxy}-5-[5-(2-methyl-4-pyridinyl)-1H-benzimidazol-1-yl]-2-thiophenecarboxylate (Intermediate 20, 126 mg, 0.24 mmol) and tert-butyl 4-hydroxypiperidine-1-carboxylate (97 mg, 0.48 mmol) were coupled using a procedure analogous to Example 5, Step A to give the desired product (120 mg, 71%) MS (ESI): 703 [M+H]⁺.

Step B—1,1-Dimethylethyl 4-({3-[(1R)-1-({2-(aminocarbonyl)-5-[5-(2-methyl-4-pyridinyl)-1H-benzimidazol-1-yl]-3-thienyl}oxy)ethyl]-2-chlorophenyl}oxy)-1-piperidinecarboxylate

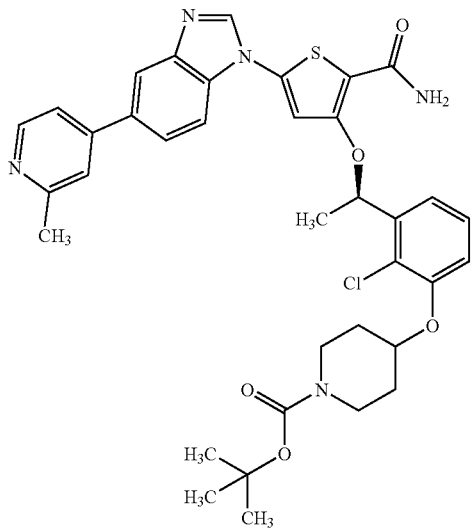

1,1-Dimethylethyl 4-({2-chloro-3-[(1R)-1-({2-[(methyloxy)carbonyl]-5-[5-(2-methyl-4-pyridinyl)-1H-benzimidazol-1-yl]-3-thienyl}oxy)ethyl]phenyl}oxy)-1-piperidinecarboxylate (120 mg, 0.17 mmol) was subjected to aminolysis using a procedure analogous to Example 4, Step B to give 100 mg of the title compound (85%). ¹H NMR (400 MHz, CDCl₃) δ 8.57 (d, J=5.1 Hz, 1H), 8.08 (s, 1H), 8.04 (s, 1H), 7.63-7.56 (m, 2H) 7.43 (s, 1H), 7.37 (d, J=5.1 Hz, 1H), 7.28 (dd, J=8.2, 7.8 Hz, 1H) 7.24 (bs, 1H), 7.08 (d, J=7.8 Hz, 1H), 6.94 (d, J=8.2 Hz, 1H), 6.67 (s, 1H), 6.47 (bs, 1H), 5.93 (q, J=6.4 Hz, 1H), 4.62-4.53 (m, 1H), 3.71-3.58 (m, 2H), 3.52-3.40 (m, 2H), 2.65 (s, 3H), 1.97-1.80 (m, 4H), 1.78 (d, J=6.4 Hz, 3H), 1.46 (s, 9H). MS (ESI): 688 [M+H]⁺.

Step C—3-({(1R)-1-[2-Chloro-3-(4-piperidinyloxy)phenyl]ethyl}oxy)-5-[5-(2-methyl-4-pyridinyl)-1H-benzimidazol-1-yl]-2-thiophenecarboxamide (Title Compound)

1,1-Dimethylethyl 4-({3-[(1R)-1-({2-(aminocarbonyl)-5-[5-(2-methyl-4-pyridinyl)-1H-benzimidazol-1-yl]-3-thienyl}oxy)ethyl]-2-chlorophenyl}oxy)-1-piperidinecarboxylate (100 mg, 0.14 mmol) was deprotected using a procedure analogous to Example 5, Step C to give 50 mg of the title compound (59%). ¹H NMR (400 MHz, DMSO) δ 8.63 (s, 1H), 8.47 (d, J=5.1, 1H), 8.19 (d, J=1.5 Hz, 1H), 7.82 (bs, 1H) 7.74 (dd, J=8.7, 1.5 Hz, 1H), 7.65 (s, 1H), 7.56 (d, J=8.3 Hz, 1H) 7.32 (dd, J=8.2, 7.7 Hz, 1H), 7.20-7.07 (ms 3H), 5.97 (q, J=6.4 Hz, 1H), 4.53-4.44 (m, 1H) 3.29 (s, 3H), 2.93-2.81 (m, 2H), 2.55-2.44 (m, 2H), 1.90-1.78 (m, 2H), 1.70 (d, J=6.4 Hz, 3H), 1.50-1.40 (m, 2H). MS (ESI): 587 [M+H]⁺.

EXAMPLE 50

3-[((1R)-1-{2-Chloro-3-[(1-methyl-4-piperidinyl)oxy]phenyl}ethyl)oxy]-5-[5-(2-methyl-4-pyridinyl)-1H-benzimidazol-1-yl]-2-thiophenecarboxamide

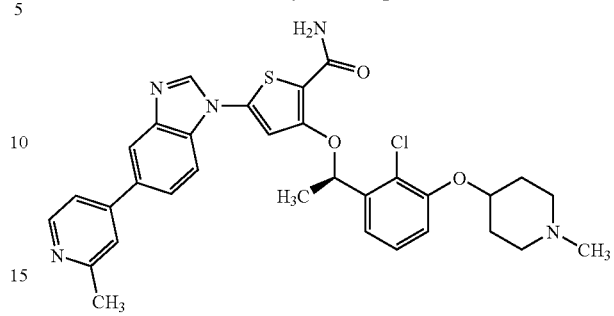

3-({(1R)-1-[2-chloro-3-(4-piperidinyloxy)phenyl]ethyl}oxy)-5-[5-(2-methyl-4-pyridinyl)-1H-benzimidazol-1-yl]-2-thiophenecarboxamide (Example 49, 30 mg, 0.050 mmol) was reductively methylated using a procedure analogous to Example 48 to give 20 mg of the title compound (65%). ¹H NMR (400 MHz, CDCl₃) δ 8.56 (d, J=5.2 Hz, 1H), 8.08 (d, J=1.4 Hz, 1H), 8.04 (s, 1H), 7.61 (dd, J=8.6, 1.7 Hz, 1H), 7.54 (d, J=8.6 Hz, 1H) 7.43 (s, 1H), 7.37 (dd, J=5.2, 1.8 Hz, 1H), 7.29-7.22 (m, 2H), 7.08 (dd, J=7.9, 1.4 Hz, 1H), 6.94 (dd, J=8.5, 1.2 Hz, 1H), 6.68 (s, 1H), 6.56 (bs, 1H), 5.93 (q, J=6.4 Hz, 1H), 4.46-4.38 (m, 1H), 2.71-2.61 (m, 2H), 2.65 (s, 3H), 2.39-2.26 (m, 2H), 2.29 (s, 3H), 2.06-1.87 (m, 4H), 1.78 (d, J=6.4 Hz, 3H). MS (ESI): 602 [M+H]⁺.

EXAMPLE 51

5-(5-Bromo-1H-benzimidazol-1-yl)-3-[((1R)-1-{2-chloro-3-[(1-methyl-4-piperidinyl)oxy]phenyl}ethyl)oxy]-2-thiophenecarboxamide

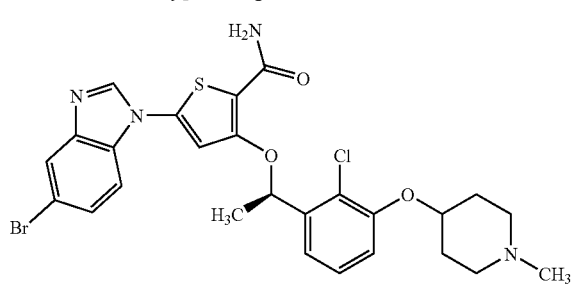

Step A—Methyl 5-(5-bromo-1H-benzimidazol-1-yl)-3-{[(1R)-1-(2-chloro-3-hydroxyphenyl)ethyl]oxy}-2-thiophenecarboxylate

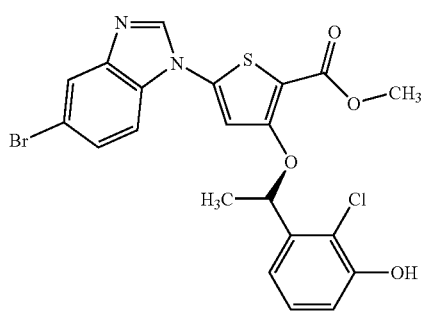

Methyl 5-(5-bromo-1H-benzimidazol-1-yl)-3-{[(1R)-1-(2-chloro-3-{[(1,1-dimethylethyl)(dimethyl)silyl]oxy}phenyl)ethyl]oxy}-2-thiophenecarboxylate (Intermediate 8, 9.0 g, 14 mmol) was deprotected using a procedure analogous to Intermediate 18, Step B to give 6.2 g of the desired product (85%). ¹H NMR (400 MHz, CDCl₃) δ 7.96 (s, 1H), 7.44 (d, J=8.8 Hz, 1H), 7.24-7.18 (m, 4H), 6.99 (dd, J=7.1, 2.5 Hz, 1H), 6.62 (s, 1H), 5.72 (q, J=6.4, 1H), 3.90 (s, 3H), 1.73 (d, J=6.4 Hz, 3H).

Step B—Methyl 5-(5-bromo-1H-benzimidazol-1-yl)-3-[((1R)-1-{2-chloro-3-[(1-methyl-4-piperidinyl)oxy]phenyl}ethyl)oxy]-2-thiophenecarboxylate

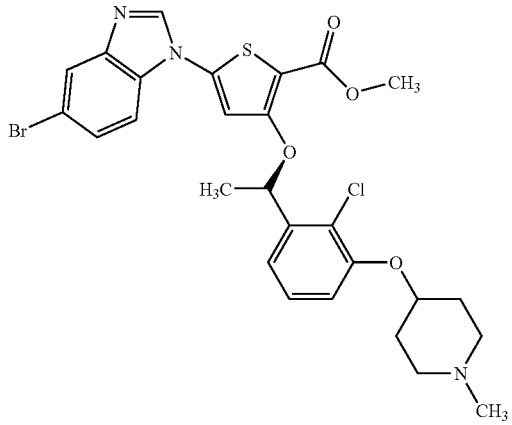

Methyl 5-(5-bromo-1H-benzimidazol-1-yl)-3-{[(1R)-1-(2-chloro-3-hydroxyphenyl)ethyl]oxy}-2-thiophenecarboxylate (6.2 g, 12 mmol) and 1-methylpiperidin-4-ol (2.1 g, 18 mmol) were coupled using a procedure analogous to Example 4, Step A to give 8.4 g of the desired product (85%).
$^1$H NMR (400 MHz, CDCl$_3$) δ 7.96 (s, 1H), 7.42 (d, J=8.7 Hz, 1H), 7.31-7.18 (m, 4H), 6.88 (dd, J=5.3, 4.2 Hz, 1H), 6.66 (s, 1H), 5.82 (q, J=6.4, 1H), 4.43-4.34 (m, 1H), 3.90 (s, 3H), 2.71-2.60 (m, 2H), 2.39-2.25 (m, 2H), 2.30 (s, 3H), 2.04-1.85 (m, 4H), 1.72 (d, J=6.4 Hz, 3H).

Step C—5-(5-Bromo-1H-benzimidazol-1-yl)-3-[((1R)-1-{2-chloro-3-[(1-methyl-4-piperidinyl)oxy]phenyl}ethyl)oxy]-2-thiophenecarboxamide (Title Compound)

Methyl 5-(5-bromo-1H-benzimidazol-1-yl)-3-[((1R)-1-{2-chloro-3-[(1-methyl-4-piperidinyl)oxy]phenyl}ethyl)oxy]-2-thiophenecarboxylate (6.0 g, 9.9 mmol) was subjected to an aminolysis reaction analogous to Example 4, Step B to give 3.9 g of the title compound (66%). $^1$H NMR (400 MHz, CDCl$_3$) δ 7.96 (d, J=7.5 Hz, 1H), 7.43 (d, J=8.8 Hz, 1H), 7.31-7.22 (m, 3H), 7.20 (bs, 1H), 7.04 (d, J=7.9 Hz, 1H), 6.93 (d, J=8.1 Hz, 1H), 6.60 (s, 1H), 5.89 (q, J=6.4Hz, 1H), 5.73 (bs, 1H), 4.46-4.38 (m, 1H), 2.71-2.61 (m, 2H), 2.38-2.27 (m, 2H), 2.32 (s, 3H), 2.05-1.87 (m, 4H), 1.77 (d, J=6.4 Hz, 3H). MS (ESI): 589 & 591 [M+H]$^+$.

EXAMPLE 52

5-(6-Chloro-1H-benzimidazol-1-yl)-3-({(1R)-1-[2-chloro-3-(4-piperidinyloxy)phenyl]ethyl}oxy)-2-thiophenecarboxamide

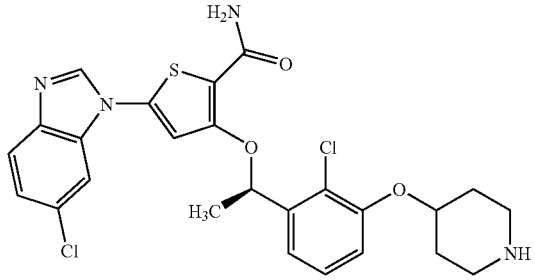

Step A—1,1-Dimethylethyl 4-({2-chloro-3-[(1R)-1-({5-(6-chloro-1H-benzimidazol-1-yl)-2-[(methyloxy)carbonyl]-3-thienyl}oxy)ethyl]phenyl}oxy)-1-piperidinecarboxylate

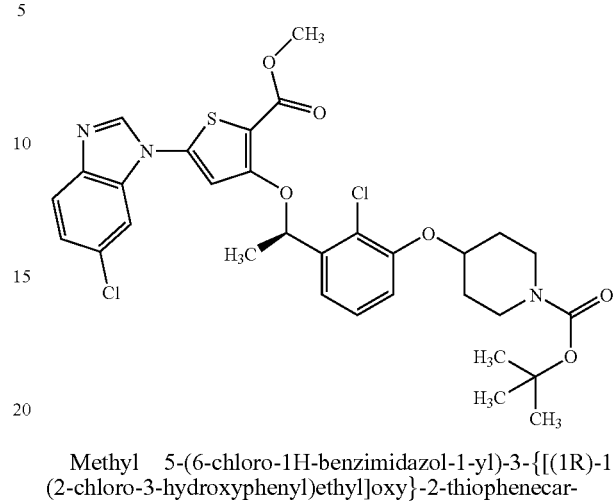

Methyl 5-(6-chloro-1H-benzimidazol-1-yl)-3-{[(1R)-1-(2-chloro-3-hydroxyphenyl)ethyl]oxy}-2-thiophenecarboxylate (Intermediate 21, 430 mg, 0.93 mmol) and tert-butyl 4-hydroxypiperidine-1-carboxylate (280 mg, 1.4 mmol) were coupled using a procedure analogous to Example 5, Step A to give the desired product (420 mg, 70%). MS (ESI): 646 [M+H]$^+$.

Step B—1,1-Dimethylethyl 4-{[3-((1R)-1-{[2-(aminocarbonyl)-5-(6-chloro-1H-benzimidazol-1-yl)-3-thienyl]oxy}ethyl)-2-chlorophenyl]oxy}-1-piperidinecarboxylate

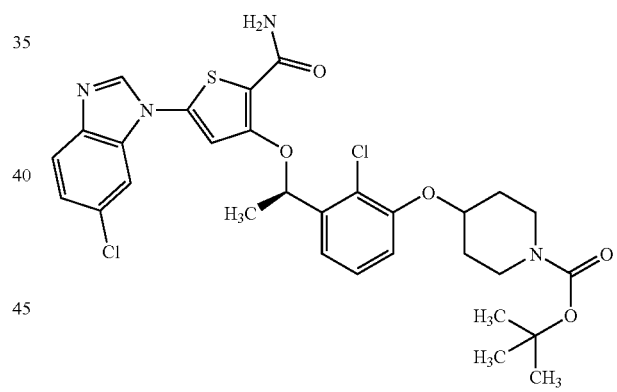

1,1-Dimethylethyl 4-({2-chloro-3-[(1R)-1-({5-(6-chloro-1H-benzimidazol-1-yl)-2-[(methyloxy)carbonyl]-3-thienyl}oxy)ethyl]phenyl}oxy)-1-piperidinecarboxylate (420 mg, 0.65 mmol) was subjected to aminolysis using a procedure analogous to Example 4, Step B to give 300 mg of the title compound (72%). $^1$H NMR (400 MHz, DMSO) δ 8.57 (s, 1H), 8.56 (s, 1H), 7.81 (bs, 1H), 7.75 (d, J=8.6 Hz, 1H), 7.53 (d, J=2.0 Hz, 1H), 7.34 (dd, J=8.6, 2.0 Hz, 1H), 7.32 (d, J=7.5 Hz, 1H), 7.23-7.14 (m, 3H), 7.10 (bs, 1H), 5.98 (q, J=6.4 Hz, 1H), 4.68-4.60 (m, 1H), 3.57-3.45 (m, 2H), 3.30-3.13 (m, 2H), 1.87-1.75 (m, 2H), 1.68 (d, J=6.4 Hz, 3H), 1.59-1.46 (m, 2H). MS (ESI): 631 [M+H]$^+$.

Step C—5-(6-Chloro-1H-benzimidazol-1-yl)-3-({(1R)-1-[2-chloro-3-(4-piperidinyloxy)phenyl]ethyl}oxy)-2-thiophenecarboxamide (Title Compound)

1,1-Dimethylethyl 4-({3-[(1R)-1-({2-(aminocarbonyl)-5-[5-(2-methyl-4-pyridinyl)-1H-benzimidazol-1-yl]-3- thienyl}oxy)ethyl]-2-chlorophenyl}oxy)-1-piperidinecarboxylate was deprotected using a procedure analogous to Example 5, Step G to give 150 mg of the title compound (59%). ¹H HMR (400 MHz, DMSO) δ 8.59 (s, 1H), 7.85 (bs, 1H), 7.77 (d, J=8.8 Hz, 1H), 7.55 (d, J=2.0 Hz, 1H), 7.36 (dd, J=8.6, 2.0 Hz, 1H), 7.33 (d, J=8.0 Hz, 1H), 7.23-7.15 (m, 3H), 7.13 (bs, 1H), 6.00 (q, J=6.4 Hz, 1H), 4.57-4.40 (m, 1H), 3.01-2.91 (m, 2H), 2.71-2.61 (m, 2H), 1.94-1.83 (m, 2H), 1.70 (d, J=6.4 Hz, 3H), 1.61-1.50 (m, 2H). MS (ESI): 531 [M+H]⁺.

EXAMPLE 53

5-(6-Chloro-1H-benzimidazol-1-yl)-3-[(1R)-1-{2-chloro-3-[(1-methyl-4-piperidinyl)oxy]phenyl}ethyl)oxy]-2-thiophenecarboxamide

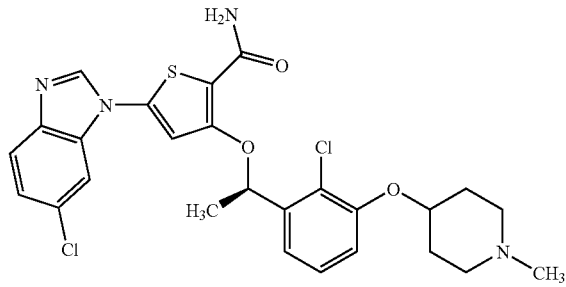

5-(6-Chloro-1H-benzimidazol-1-yl)-3-({(1R)-1-[2-chloro-3-(4-piperidinyloxy)phenyl]ethyl}oxy)-2-thiophenecarboxamide (Example 52, 100 mg, 0.19 mmol) was reductively methylated using a procedure analogous to Example 48 to give 55 mg of the title compound. ¹H MMR (400 MHz, DMSO) δ 8.59 (s, 1H), 7.85 (bs, 1H), 7.77 (d, J=8.6 Hz, 1H), 7.55 (d, J=2.0 Hz, 1H), 7.36 (dd, J=8.6, 2.0 Hz, 1H), 7.31 (d, J=8.0 Hz, 1H), 7.23-7.10 (m, 4H), 6.00 (q, J=6.4 Hz, 1H), 4.48-4.41 (m, 1H), 2.58-2.43 (m, 2H), 2.21-2.06 (m, 2H), 2.11 (s, 3H), 1.92-1.78 (m, 2H), 1.70 (d, J=6.4 Hz, 3H), 1.68-1.57 (m, 2H). MS (ESI): 545 [M+H]⁺.

EXAMPLE 54

3-({(1R)-1-[2-Chloro-3-(4-piperidinyloxy)phenyl]ethyl}oxy)-5-{6-[(methylsulfonyl)methyl]-1H-benzimidazol-1-yl}-2-thiophenecarboxamide

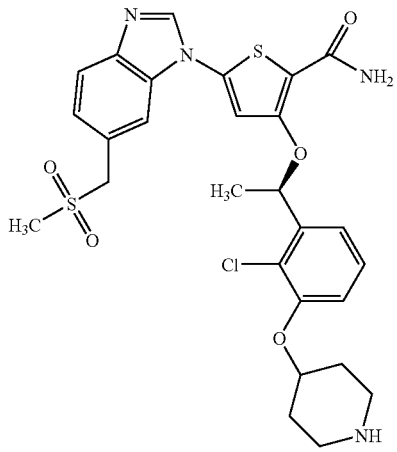

To a slurry of methyl 3-{[(1R)-1-(2-chloro-3-hydroxyphenyl)ethyl]oxy}-5-{6-[(methylsulfonyl)methyl]-1H-benzimidazol-1-yl}-2-thiophenecarboxylate (Intermediate 23, 0.050 g, 0.095 mmol) and 1,1-dimethylethyl 4-hydroxy-1-piperidinecarboxylate (0.058 g, 0.29 mmol) in THF (10 mL) was added 4-(diphenylphosphanyl)-N,N-dimethylaniline (0.088 g, 0.28 mmol) and di-tert-butylazodicarboxylate (0.066 g, 0.28 mmol). The clear, yellow solution was stirred for 24 h, and then silica gel (1 g) was added. The volatiles were evaporated under reduced pressure and the residue was purified by flash column chromatography (0 to 50% EtOAc:CH₂Cl₂) to give 1,1-dimethylethyl 4-[(2-chloro-3-{(1R)-1-[2-[(methyloxy)carbonyl]-5-{6--[(methylsulfonyl)methyl]-1H-benzimidazol-1-yl}-3-thienyl)oxy]ethyl}phenyl)oxy]-1-piperidinecarboxylate 0.06 g (0.085 mmol) which was then was added to a solution of 7 N ammonia in MeOH (10 mL). The mixture was heated in a sealed tube to 80° C. for 40 h and then cooled to rt and the volatiles were evaporated under reduced pressure. The residue was then dissolved in DCM (5 mL) and TFA (1 mL, 5.9 mmol) was added. After 1 h the volatiles were evaporated under reduced pressure and the residue was dissolved in 10 mL of DCM and 1 g of MP-Carbonate resin was added to remove excess TFA. After 30 min the resin was removed by filtration and the volatiles were evaporated under reduced pressure to afford 0.04 g (70%) of the title compound as a light yellow solid.

¹H NMR (400 MHz, CD₃OD): δ 8.40 (s, 1H), 7.74 (d, J=8.42 Hz, 1H), 7.54 (s, 1H), 7.45 (d, J=8.42 Hz, 1H), 7.30 (t, J=7.97 Hz, 1H), 7.16 (d, J=7.87 Hz, 1H), 7.09 (d, J=7.87 Hz, 1H), 6.99 (s, 1H), 6.05 (q, J=6.29 Hz, 1H) 4.56 (m, 3H), 2.85 (s, 3H), 1.94 (br m, 2H), 1.86 (br m, 4H), 1.76 (d, J=6.23 Hz, 3H), 170 (br m, 2H); MS (ESI): 589 [M+H]⁺.

EXAMPLE 55

3-[((1R)-1-{2-chloro-3-[(1-methyl-4-piperidinyl)oxy]phenyl}ethyl)oxy]-5,6-{6-[(methylsulfonyl)methyl]-1H-benzimidazol-1-yl}-2-thiophenecarboxamide

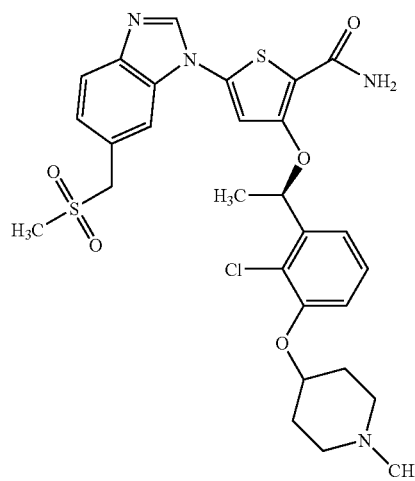

To a solution of 3-({(1R)-1-[2-chloro-3-(4-piperidinyloxy)phenyl]ethyl}oxy)-5-{6-[(methylsulfonyl)methyl]-1H-benzimidazol-1-yl}-2-thiophenecarboxamide (Example 54, 0.03 g, 0.05 mmol) in DCM/MeOH (3:2) (5 mL) was added formaldehyde (0.037 g, 1.23 mmol), followed by sodium triacetoxy borohydride (0.025 g, 0.122 mmol) and the mixture stirred at rt for 30 min. Silica (1 g) was added, the volatiles were evaporated under reduced pressure and the residue was purified by flash column chromatography (0 to 100% 80/20/1 DCM/MeOH/ammonium hydroxide:DCM) to afford 0.026 g (86%) of the title compound as a light yellow solid. ¹H NMR (400 MHz, CD₃OD): δ 8.42 (s, 1H), 7.77 (d, J=8.23 Hz, 1H), 7.56 (s, 1H), 7.47 (d, J=8.42 Hz, 1H), 7.32 (t, J=7.96 Hz, 1H), 7.17 (d, J=7.87 Hz, 1H), 7.11 (d, J=8.23 Hz, 1H), 7.01 (s, 1H), 6.07 (q, J=6.34 Hz, 1H) 4.55 (m, 3H), 2.85 (s, 3H), 2.66 (br m, 2H), 2.35 (br m, 2H), 2.27 (s, 3H), 1.96 (br m, 2H), 1.86 (br m, 2H), 1.78 (d, J=6.22 Hz, 3H); MS (ESI): 603 [M+H]⁺.

EXAMPLE 56

3-[((1R)-1-{2-chloro-3-[(4-piperidinylmethyl)oxy]phenyl}ethyl)oxy]-5-{6-[(methylsulfonyl)methyl]-1H-benzimidazol-1-yl}-2-thiophenecarboxamide

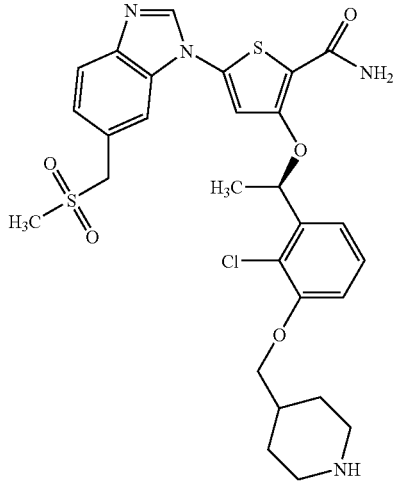

The title compound was prepared by a procedure analogous to Example 54 using methyl 3-{[(1R)-1-(2-chloro-3-hydroxyphenyl)ethyl]oxy}-5-{6-[(methylsulfonyl)methyl]-1H-benzimidazol-1-yl}-2-thiophenecarboxylate (Intermediate 23, 0.1 g, 0.2 mmol) and 1,1-dimethylethyl 4-(hydroxymethyl)-1-piperidinecarboxylate (0.124 g, 0.57 mmol) to afford 0.05 g (43%) of the title compound. $^1$H NMR (400 MHz, CD$_3$OD): δ 8.39 (s, 1H), 7.73 (d, J=8.24 Hz, 1H), 7.51 (s, 1H), 7.43 (d, J=8.43 Hz, 1H), 7.30 (t, J=7.97 Hz, 1H), 7.14 (d, J=7.87 Hz, 1H), 7.01 (m, 2H), 6.05 (q, J=6.35 Hz, 1H), 4.47 (q, J=13.92 Hz, 2H,), 3.99 (m, 1H), 3.85 (m, 1H), 3.15 (d, J=12.82 Hz, 2H), 2.81 (s, 3H), 2.73 (t, J=11.99 Hz, 2H), 2.05 (br s, 1H,), 1.91 (q, J=13.28 Hz, 2H), 1.75 (d, 3H), 1.41 (m, 2H); MS (ESI): 603 [M+H]$^+$.

EXAMPLE 57

3-({(1R)-1-[2-Chloro-3-({[(2S)-1-methyl-2-pyrrolidinyl]metliyl}oxy)phenyl]ethyl}oxy)-5-{6-[(methylsulfonyl)methyl]-1H-benzimidazol-1-yl}-2-thiophenecarboxamide

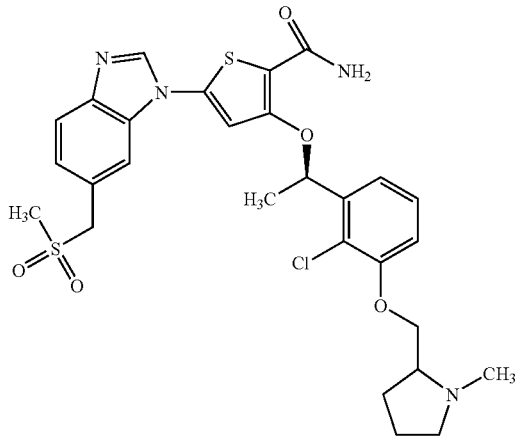

To methyl 3-{[(1R)-1-(2-chloro-3-hydroxyphenyl)ethyl]oxy}-5-{6-[(methylsulfonyl)methyl]-1H-benzimidazol-1-yl}-2-thiophenecarboxylate (Intermediate 23, 0.050 g, 0.095 mmol) in dimethylformamide (5 mL) was added 1,1-dimethylethyl (2S)-2-({[(4-methylphenyl)sulfonyl]oxy}methyl)-1-pyrrolidinecarboxylate (which may be prepared using literature reference: *Tetrahedron Lett*, 1991, 47, 7179-7184) (0.053 g, 0.14 mmol), and Cs$_2$CO$_3$ (0.046 g, 0.14 mmol). The mixture was heated in a sealed tube to 60° C. for 24 h and then cooled to rt. The DMF was evaporated under reduced pressure and the residue was purified by flash column chromatography (0 to 50% EtOAc:DCM) to afford 0.050 g (0.071 mmol) of 1,1-dimethylethyl (2S)-2-{[(2-chloro-3-{(1R)-1-[(2-[(methyloxy)carbonyl]-5-{6-[(methylsulfonyl)methyl]-1H-benzimidazol-1-yl}-3-thienyl)oxy]ethyl}phenyl)oxy]methyl}-1-pyrrolidinecarboxylate which was then dissolved in DCM (5 mL) and TFA (1.0 mL, 5.9 mmol) was added. After 1 h the volatiles were evaporated under reduced pressure and the residue was dissolved in 10 mL of DCM and 1 g of MP-Carbonate resin was added to remove excess TFA. After 30 min the resin was removed by filtration and the volatiles were evaporated under reduced pressure to afford 0.040 g (0.068 mmol) of methyl 3-{[(1R)-1-(2-chloro-3-{[(2S)-2-pyrrolidinylmethyl]oxy}phenyl)ethyl]oxy}-5-{6-[(methylsulfonyl)methyl]-1H-benzimidazol-1-yl}-2-thiophenecarboxylate which was then dissolved in DCM/MeOH (3:2) (5 mL). Formaldehyde was added (0.037 g, 1.23 mmol), followed by sodium triacetoxy borohydride (0.025 g, 0.122 mmol) and the mixture stirred at rt for 30 min. The volatiles were evaporated under reduced pressure and the residue was dissolved in 7 N ammonia In MeOH (10 mL). The mixture was heated in a sealed tube to 80° C. for 40 h and then cooled to rt. Silica (1 g) was added, the volatiles were evaporated under reduced pressure and the residue was purified by flash column chromatography (0 to 100% 80/20/1 DCM/MeOH/ammonium hydroxide:DCM) to give 0.024 g (0.04 mmol) of the title compound as a yellow solid. $^1$H NMR (400 MHz, DMSO): δ 8.60 (s, 1H), 7.84 (s, 1H), 7.78 (d, J=8.23 Hz, 1H), 7.73 (s, 1H), 7.36 (m, 2H), 7.20 (t, J=3.93 Hz, 2H), 7.10 (m, 2H), 5.95 (q, J=6.22 Hz, 1H), 4.61 (m, 2H), 4.00-3.85 (m, 2H), 2.87 (br s, 4H), 2.58 (m, 1H), 2.34 (s, 3H), 2.15 (m, 1H), 1.92 (m, 1H), 1.71 (d, 3H) 1.67-1.52 (m, 3H); MS (ESI): 603 [M+H]$^+$.

EXAMPLE 58

3-({(1R)-1-[2-chloro-3-({[(2S)-1-methyl-2-pyrrolidinyl]methyl}oxy)phenyl]ethyl}oxy)-5-{6-[(methylsulfonyl)methyl]-1H-benzimidazol-1-yl}-2-thiophenecarboxamide

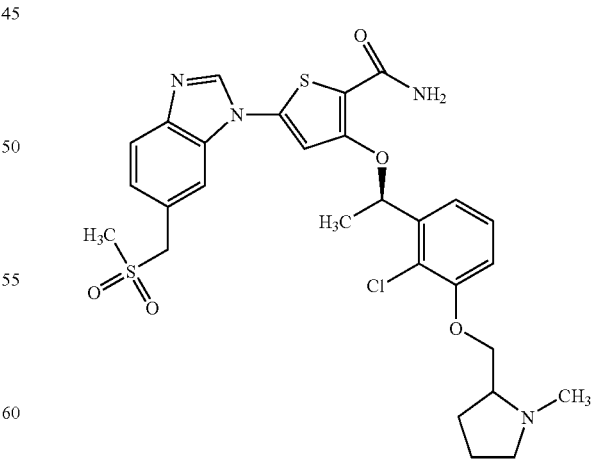

The title compound was prepared using a procedure analogous to Example 57 from methyl 3-{[(1R)-1-(2-chloro-3-hydroxyphenyl)ethyl]oxy}-5-{6-[(methylsulfonyl)methyl]-1H-benzimidazol-1-yl}-2-thiophenecarboxylate (Intermediate 23, 0.050 g, 0.095 mmol) and 1,1-dimethylethyl (2R)-2-({[(4-methylphenyl)sulfonyl]oxy}methyl)-1-pyrrolidinecarboxylate (which may be prepared using procedures similarly described for the (S)-enantiomer in *Tetrahedron Lett*, 1991, 47, 7179-7184) (0.053 g, 0.14 mmol). ¹H NMR (400 MHz, CD₃OD): δ 8.42 (s, 1H), 7.76 (d, J=8.23 Hz, 1H), 7.61 (s, 1H), 7.55 (s, 1H), 7.46 (d, J=8.42 Hz, 1H), 7.34 (t, J=8.05 Hz, 1H), 7.18 (d, J=7.87 Hz, 1H) 7.07 (d, J=7.32 Hz, 1H), 7.00 (s, 1H), 6.08 (q, J=6.40 Hz, 1H), 4.53 (m, J=14.00 Hz, 2H), 4.17 (dd, J=3.84, 9.70 Hz, 1H,), 3.97 (m, 1H), 3.07 (m, 1H), 2.83 (m, 4H), 2.37 (m, 1H), 2.09 (m, 1H), 1.8 (m, 5H) 1.8 (s, 1H); MS (ESI): 603[M+H]⁺.

EXAMPLE 59

3-({(1R)-1-[2-chloro-3-(4-piperidineloxy)phenyl]ethyl}oxy)-5-[5-(methylsulfonyl)-1H-benzimidazol-1-yl]-2-thiophenecarboxamide; and

EXAMPLE 60

3-({(1R)-1-[2-chloro-3-(4-piperidineloxy)phenyl]ethyl}oxy)-5-[6-(methylsulfonyl)-1H-benzimidazol-1-yl]-2-thiophenecarboxamide

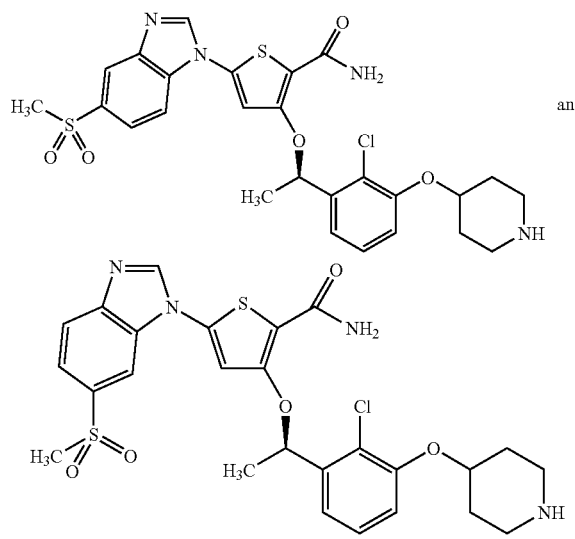

and

Step A—5-(Methylthio)-2-nitroaniline

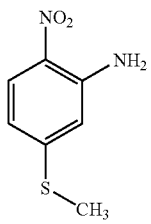

5-Chloro-2-nitroaniline (15 g, 87.2 mmol) was dissolved in 250 mL of DMF with stirring. Sodium thiomethoxide (9.8 g, 140 mmol) was added and the reaction stirred at 65° C. for 20 h. The reaction was cooled to rt and diluted with EtOAc. then washed with water (5×), brine (1×), dried over MgSO₄, filtered, and concentrated in vacuo. The residue was purified by flash chromatography to afford 12.9 g (81%) of 5-(methylthio)-2-nitroaniline as a red-orange solid. ¹H NMR (400 MHz, DMSO-d₆) δ 7.85 (d, J=8.97 Hz, 1H), 7.45 (br s, 2H), 6.78 (d, J=1.83 Hz, 1H), 6.47 (dd, J=1.83 and 9.16 Hz, 1H), 2.47 (s, 3H).

Step B—4-(Methylthio)benzene-1,2-diamine

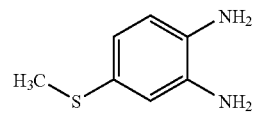

5-(Methylthio)-2-nitroaniline (12.9 g, 70.1 mmol) was dissolved In 475 mL of EtOH with stirring. Tin (II) Chloride (74.0 g, 392 mmol) was added and the reaction was refluxed for 20 h. The reaction was cooled to rt and concentrated in vacuo to a volume of 150 mL. The pH of the solution was adjusted to approximately 10 using concentrated aqueous 3N NaOH. EtOAc (1.5 L) was added and the reaction was filtered through Celite, washing with water and EtOAc. The aqueous layer was separated, then extracted with EtOAc (2×). The combined organic layers were washed with brine, dried over MgSO₄, filtered, and concentrated in vacuo to give 10.7 g (99%) of the crude 4-(methylthio)benzene-1,2-diamine as a dark oil. ¹H NMR (400 MHz, DMSO-d₆) δ 6.52 (m, 1H), 6.44 (m, 1H), 6.37 (m, 1H), 4.49 (br s, 4H), 2.29 (s, 3H).

Step C—8-(Methylthio)-1H-benzimidazole

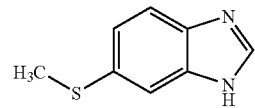

4-(Methylthio)benzene-1,2-diamine (10.7 g, 69.2 mmol) was dissolved in 230 mL of aqueous 4N HCl with stirring. Formic acid (7.85 mL, 208 mmol) was added and the reaction was refluxed for 1 h. The reaction was cooled to rt then concentrated in vacuo to a dark solid. The dark solid was dissolved In 500 mL of MeOH with stirring, NaHCO₃ (51.0 g, 607 mmol) was added and the reaction was stirred for 1 h. The reaction was then filtered, and the filtrate concentrated in vacuo to a solid. The solid was stirred in 400 mL of EtOAc and heated to reflux, then filtered. The filtrate was concentrated in vacuo to a solid. The solid dissolved in 400 mL of DCM with stirring, then dried over MgSO₄, and filtered. The filtrate was concentrated in vacuo to give 11.3 g (99%) of the crude 6-(methylthio)-1H-benzimidazole as a dark oil. ¹H NMR (400 MHz, CD₃OD) δ 8.12 (s, 1H), 7.52 (m, 2H), 7.24 (m, 1H), 2.50 (s, 3H). MS m/z 165 (M+1).

Step D—Methyl 3-hydroxy-5-[5-(methylthio)-1H-benzimidazol-1-yl]thiophene-2-carboxylate and Methyl 3-hydroxy-5-[6-(methylthio)-1H-benzimidazol-1-yl]thiophene-2-carboxylate

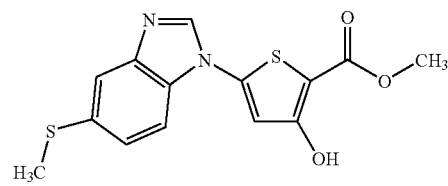

-continued

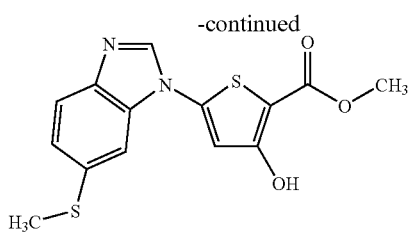

Methyl 2-chloro-3-oxo-2,3-dihydro-2-thiophenecarboxylate (1.69 g, 8.80 mmol) was added to a stirred solution of 6-(methylthio)-1H-benzimidazole (2.71 g, 17.6 mmol) in 35 mL of CHCl$_3$, and the mixture was allowed to stir at 45° C. for 24 h. The reaction was diluted with CHCl$_3$ (700 mL) and water (250 mL). The aqueous layer was extracted with CHCl$_3$ (2×150 mL). The combined organic layers were dried over MgSO$_4$. filtered, and concentrated in vacuo. Purification by flash chromatography afforded 1.84 g (65%) of a regioisomeric mixture of Methyl 3-hydroxy-5-[5-(methylthio)-1H-benzimidazol-1-yl]thiophene-2-carboxylate and Methyl 3-hydroxy-5-[6-(methylthio)-1H-benzimidazol-1-yl]thiophene-2-carboxylate. MS (ESI): 321 [M+H]$^+$.

Step E—Methyl 5-[5-(methylthio)-1H-benzimidazol-1-yl]-3-[(phenylmethyl)oxy]-2-thiophenecarboxylate and Methyl 5-[6-(methylthio)-1H-benzimidazol-1-yl]-3-[(phenylmethyl)oxy]-2-thiophenecarboxylate

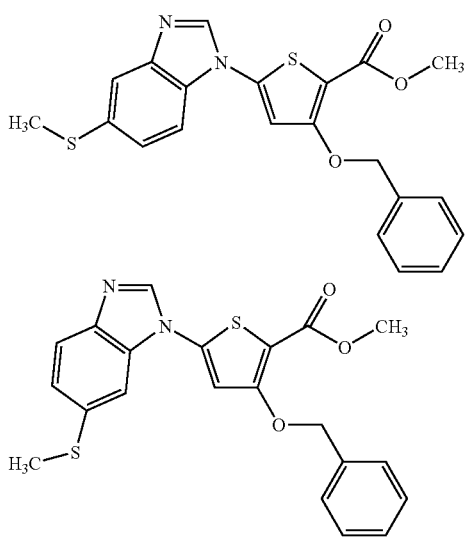

To a solution of a regioisomeric mixture of methyl 3-hydroxy-5-[5-(methylthio)-1H-benzimidazol-1-yl]thiophene-2-carboxylate and methyl 3-hydroxy-5-[6-(methylthio)-1H-benzimidazol-1-yl]thiophene-2-carboxylate which was prepared using a procedure analogous to Example 59, Step D (8.81 g, 27.5 mmol) in 150 mL of DMF was added K$_2$CO$_3$ (11.4 g, 82.5 mmol) and benzyl bromide (3.90 mL, 33.0 mmol). The reaction stirred for 16 h and was then poured into water and extracted with EtOAc (3×). Combined organics were dried over anhydrous MgSO$_4$, filtered, concentrated onto silica gel and purified by flash chromatography to give 8.75 g (78%) of a mixture of 5 and 6-regioisomers which was carried on to the next step without further purification. MS (ESI): 411 [M+H]$^+$.

Step F—Methyl 5-[5-(methylsulfonyl)-1H-benzimidazol-1-yl]-3-[(phenylmethyl)oxy]-2-thiophenecarboxylate and Methyl 5-[6-(methylsulfonyl)-1H-benzimidazol-1-yl]-3-[(phenylmethyl)oxy]-2-thiophenecarboxylate

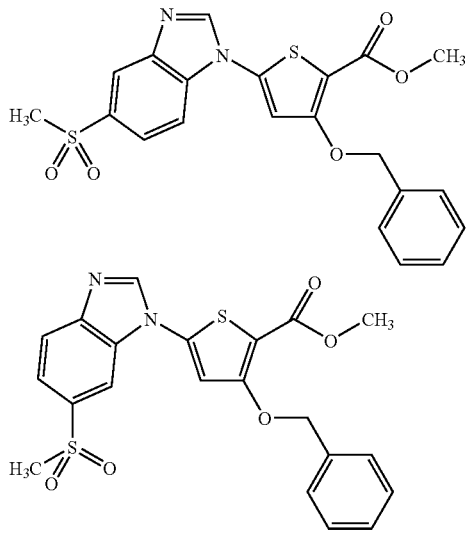

To a solution of a regioisomeric mixture of methyl 5-[5-(methylthio)-1H-benzimidazol-1-yl]-3-[(phenylmethyl)oxy]-2-thiophenecarboxylate and methyl 5-[6-(methylthio)-1H-benzimidazol-1-yl]-3-[(phenylmethyl)oxy]-2-thiophenecarboxylate (8.75 g, 21.3 mmol) in 200 mL of DCM was added 3-chloroperoxybenzoic acid (70%) (11.6 g, 46.9 mmol). The reaction stirred for 16 h and was then poured into saturated aqueous NaHCO$_3$ solution and extracted with DCM (1×) and EtOAc (2×). Combined organics were dried over anhydrous MgSO$_4$, filtered, concentrated onto silica gel and purified by flash chromatography to give 9.0 g (95%) of a mixture of 5 and 6-regioisomers which was carried on to the next step without further purification. MS (ESI): 443 [M+H]$^+$.

Step G—Methyl 3-hydroxy-5-[5--(methylsulfonyl)-1H-benzimidazol-1-yl]-2-thiophenecarboxylate and Methyl 3-hydroxy-5-[6-(methylsufonyl)-1H-benzimidazol-1-yl]-2-thiophenecarboxylate

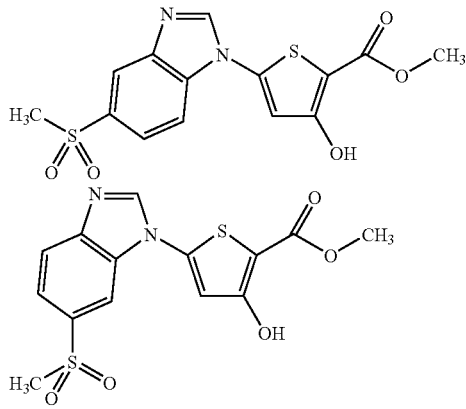

A regioisomeric mixture of methyl 5-[5-(methylsulfonyl)-1H-benzimidazol-1-yl]-3-[(phenylmethyl)oxy]-2-thiophenecarboxylate and methyl 5-[8-(methylsulfonyl)-1H-benzimidazol-1-yl]-3-[(phenylmethyl)oxy]-2-thiophenecarboxylate (9.00 g, 21.3 mmol) was dissolved in 50 mL of neat TFA. The reaction stirred for 16 h and was then heated to 50° C. for 2 h at which time most of the TFA was removed in vacuo. The remaining mixture was quenched with saturated aqueous NaHCO₃ solution and extracted with EtOAc (3×). Combined organics were dried over anhydrous MgSO₄, filtered and concentrated. The crude product was triturated with ether filtered and air dried to give 4.5 g (60%) of a mixture of 5 and 6-regioisomers which was carried on to the next step without further purification. MS (ESI): 353 [M+H]⁺.

Step H—Methyl 3-{[(1R)-1-(2-chloro-3-{[(1,1-dimethylethyl)(dimethyl)silyl]oxy}phenyl)ethyl]oxy}-5-[5-(methylsulfonyl)-1H-benzimidazol-1-yl]-2-thiophenecarboxylate; and Methyl 3-{[(1R)-1-(2-chloro-3-{[(1,1-dimethylethyl)(dimethyl)silyl]oxy}phenyl) ethyl]oxy}-5-[6-(methylsulfonyl)-1H-benzimidazol-1-yl]-2-thiophenecarboxylate

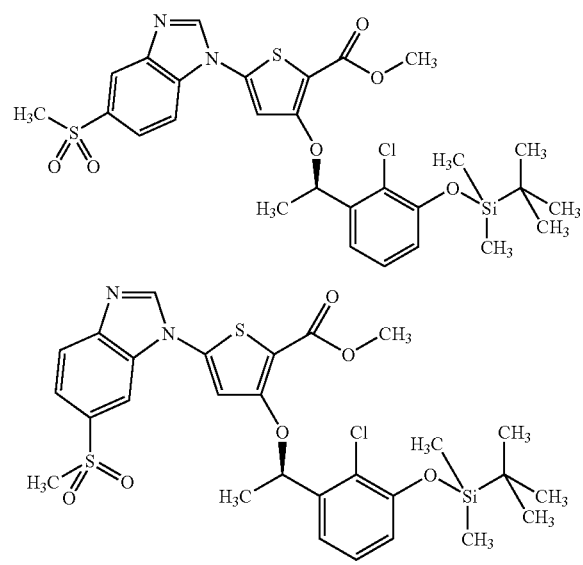

Title compounds were prepared from a regioisomeric mixture of methyl 3-hydroxy-5-[5-(methylsulfonyl)-1H-benzimidazol-1-yl]-2-thiophenecarboxylate and methyl 3-hydroxy-5-[6-(methylsulfonyl)-1H-benzimidazol-1-yl]-2-thiophenecarboxylate (783 mg) using a procedure analogous to Intermediate 3, Step E to give 800 mg (58%) of a mixture of 5 and 6-regioisomers which was carried on to the next step without further purification. MS (ESI): 622 [M+H]⁺.

Step I—Methyl 3-{[(1R)-1-(2-chloro-3-hydroxyphenyl)ethyl]oxy}-5-[6-(methylsulfonyl)-1H-benzimidazol-1-yl]-2-thiophenecarboxylate; and Methyl 3-{[(1R)-1-(2-chloro-3-hydroxyphenyl)ethyl]oxy}-5-[5-(methylsulfonyl)-1H-benzimidazol-1-yl]-2-thiophenecarboxylate

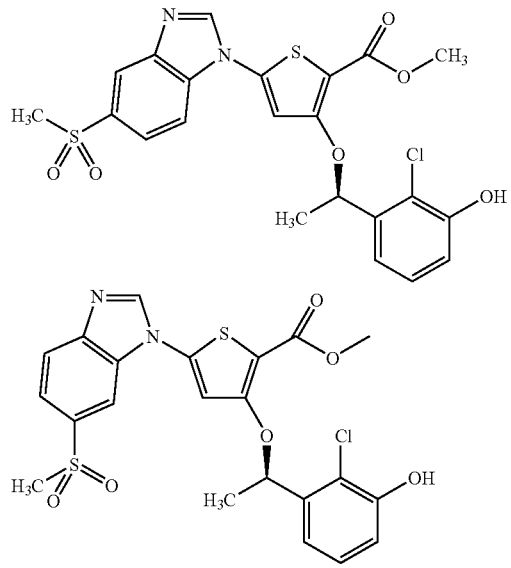

Title compounds were prepared from a regioisomeric mixture of methyl 3-{[(1R)-1-(2-chloro-3-{[(1,1-dimethylethyl)(dimethyl)silyl]oxy}phenyl)ethyl]oxy}-5-[5-(methylsulfonyl)-1H-benzimidazol-1-yl]-2-thiophenecarboxylate and methyl 3-{[(1R)-1-(2-chloro-3-{[(1,1-dimethylethyl)(dimethyl)silyl]oxy}phenyl)ethyl]oxy}-5-[6-(methylsulfonyl)-1H-benzimidazol-1-yl]-2-thiophenecarboxylate (800 mg) using a procedure analogous to Intermediate 3, Step F to give 650 mg (100%) of a mixture of 5 and 6-regioisomers which was carried on to the next step without further purification. MS (ESI): 507 [M+H]⁺.

Step J—1,1-Dimethylethyl 4-({2-chloro-3-[(1R)-1-({2-[(methyloxy)carbonyl]-5-[5-(methylsulfonyl)-1H-benzimidazol-1-yl]-3-thienyl}oxy)ethyl]phenyl}oxy)-1-piperidinecarboxylate; and 1,1-Dimethylethyl 4-({2-chloro-3-[(1R)-1-({2-[(methyloxy)carbonyl]-5-[8-(methylsulfonyl)-1H-benzimidazol-1-yl]-3-thienyl}oxy)ethyl]phenyl}oxy)-1-piperidinecarboxylate

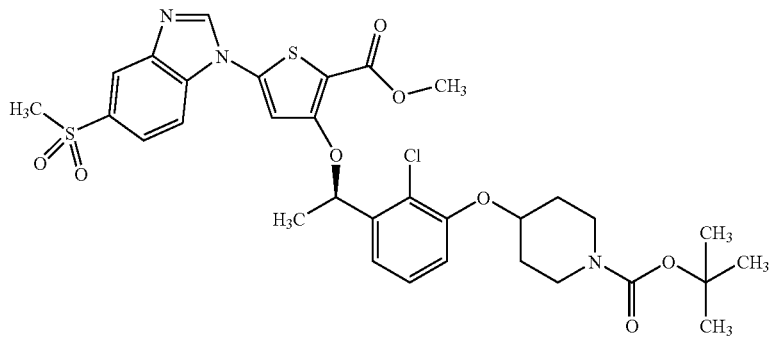

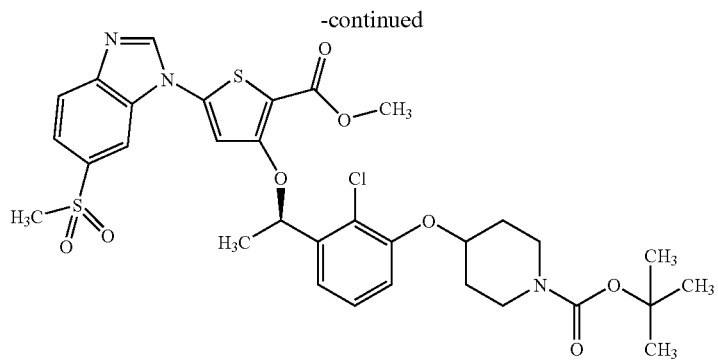

Title compounds were prepared from a regioisomeric mixture of methyl 3-{[(1R)-1-(2-chloro-3-hydroxyphenyl)ethyl]oxy}-5-[6-(methylsulfonyl)-1H-benzimidazol-1-yl]-2-thiophenecarboxylate and methyl 3-{[(1R)-1-(2-chloro-3-hydroxyphenyl)ethyl]oxy}-5-[5-(methylsulfonyl)-1H-benzimidazol-1-yl]-2-thiophenecarboxylate (650 mg) using a procedure analogous to Example 5, Step A to give 800 mg (90%) of a mixture of 5 and 6-regioisomers which was carried on to the next step without further purification. MS (ESI): 691 [M+H]$^+$.

Step K—1,1-Dimethylethyl 4-({3-[(1R)-1-({2-(aminocarbonyl)-5-[5-(methylsulfonyl)-1H-benzimidazol-1-yl]-3-thienyl}oxy)ethyl]-2-chlorophenyl}oxy)-1-piperidinecarboxylate; and 1,1-Dimethylethyl 4-({3-[(1R)-1-({2-(aminocarbonyl)-5-[6-(methylsulfonyl)-1H-benzimidazol-1-yl]-3-thienyl}oxy)ethyl]-2-chlorophenyl}oxy)-1-piperidinecarboxylate piperidinecarboxylate and 1,1-dimethylethyl 4-({2-chloro-3-[(1R)-1-({2-[(methyloxy)carbonyl]-5-[6-(methylsulfonyl)-1H-benzimidazol-1-yl]-3-thienyl}oxy)ethyl]phenyl}oxy)-1-piperidinecarboxylate (800 mg) using a procedure analogous to Example 5, Step B to give 750 mg (96%) of a mixture of 5 and 8-regioisomers which was carried on to the next step without further purification. US (ESI): 676 [M+H]$^+$.

Step L—3-({(1R)-1-[2-chloro-3-(4-piperidineloxy)phenyl]ethyl}oxy)-5-[5-(methylsulfonyl)-1H-benzimidazol-1-yl]-2-thiophenecarboxamide; and 3-({(1R)-1-[2-chloro-3-(4-piperidineloxy)phenyl]ethyl}oxy)-5-[6-(methylsulfonyl)-1H-benzimidazol-1-yl]-2-thiophenecarboxamide (Title Compounds)

Title compounds were prepared from a regioisomeric mixture of 1,1-dimethylethyl 4-({3-[(1R)-1-({2-(aminocarbonyl)-5-[5-(methylsulfonyl)-1H-benzimidazol-1-yl]-3-

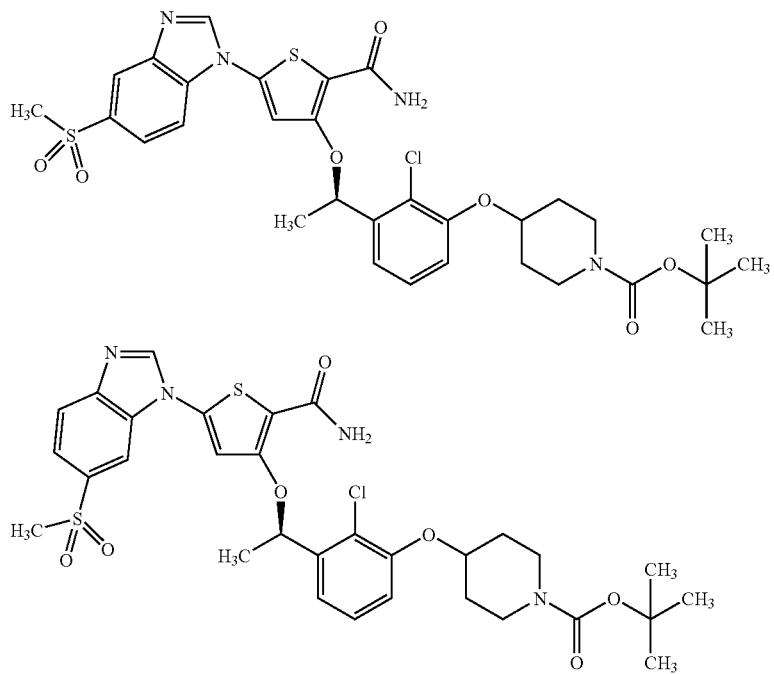

Title compounds were prepared from a regioisomeric mixture of 1,1-dimethylethyl 4-({2-chloro-3-[(1R)-1-({2-[(methyloxy)carbonyl]-5-[5-(methylsulfonyl)-1H-benzimidazol-1-yl]-3-thienyl}oxy)ethyl]phenyl}oxy)-1- thienyl}oxy)ethyl]-2-chlorophenyl}oxy)-1-piperidinecarboxylate and 1,1-dimethylethyl 4-({3-[(1R)-1-({2-(aminocarbonyl)-5-[6-(methylsulfonyl)-1H-benzimidazol-1-yl]-3-thienyl}oxy)ethyl]-2- chlorophenyl}oxy)-1-piperidinecarboxylate (750 mg) using a procedure analogous to Example 5, Step C and then the regioisomers were separated using packed column supercritical fluid chromatography (SFC) on a Diacel® 3×25 Chiralcel OJ-H column at 103 bar, 27° C. using a mobile phase of 75% Carbon Dioxide/25% (89.5% MeOH/10% CHCl₃/0.5% Diethylamine). The 6-regioisomer title compound, 3-({(1R)-1-[2-chloro-3-(4-piperidinyloxy)phenyl]ethyl}oxy)-5-[6-(methylsulfonyl)-1H-benzimidazol-1-yl]-2-thiophenecarboxamide (246 mg) eluted first with a retention time of 5.32 min at a flow rate of 2 mL/min on the analytical instrument ¹H NMR (400 MHz, DMSO-d₆) δ 8.81 (s, 1H), 8.11 (s, 1H), 7.98 (d, J=8.5 Hz, 1H), 7.86 (dd. J=8.6, 1.6 Hz, 2H), 7.34-7.29 (m, 2H), 7.22 (d, J=7.7 Hz, 1H), 7.15 (d, J=8.2 Hz, 1H), 7.11 (s, 1H), 5.94 (q, J=6.2 Hz, 1H), 4.57 (m, 1H), 3.23 (s, 3H), 3.00 (m, 2H), 2.78 (m, 2H), 1.93 (m, 2H), 1.68 (d, J=6.3 Hz, 3H), 1.65 (m, 2H). MS (ESI): 576 [M+H]⁺. The 5-regioisomer title compound, 3-({(1R)-1-[2-chloro-3-(4-piperidinyloxy)phenyl]ethyl}oxy)-5-[5-(methylsulfonyl)-1H-benzimidazol-1-yl]-2-thiophenecarboxamide (134 mg) eluted second with a retention time of 8.89 min at a flow rate of 2 mL/min. ¹H NMR (400 MHz, DMSO-d₆) δ 8.78 (s, 1H), 8.29 (s, 1H), 7.87-7.82 (m, 2H), 7.68 (d, J=8.6 Hz, 1H), 7.38-7.31 (m, 1H), 7.25-7.18 (m, 3H), 7.11 (s, 1H), 5.95 (q, J=6.3 Hz, 1H), 4.73 (m, 1H), 3.23 (s, 3H), 3.13 (m, 2H), 3.03 (m, 2H), 2.06 (m, 2H), 1.84 (m, 2H), 1.68 (d, J=6.5 Hz, 3H). MS (ESS): 576 [M+H]⁺.

EXAMPLE 61

3-({(1R)-1-[2-chloro-3-(4-piperidinyloxy)phenyl]ethyl}oxy)-5-{5-[(trifluoromethyl)oxy]-1H-benzimidazol-1-yl}-2-thiophenecarboxamide

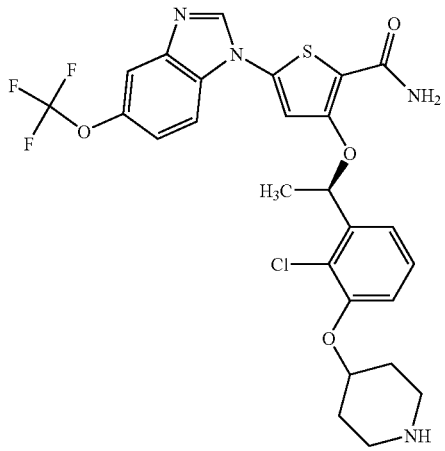

To a slurry of methyl 3-{[(1R)-1-(2-chloro-3-hydroxyphenyl)ethyl]oxy}-5-{5-[(trifluoromethyl)oxy]-1H-benzimidazol-1-yl}-2-thiophenecarboxylate (Intermediate 25, 0.18 g, 0.35 mmol) and 1,1-dimethylethyl 4-hydroxy-1-piperidinecarboxylate (0.21 g, 1.0 mmol) in DCM (10 mL) was added triphenylphosphine (0.18 g, 0.70 mmol) and di-tert-butylazodicarboxylate (0.16 g, 0.70 mmol). The clear, yellow solution was stirred for 1 h, and then silica gel (3 g) was added. The volatiles were evaporated under reduced pressure and the residue was purified by flash column chromatography (0 to 50% EtOAc:CH₂Cl₂) to give 0.20 g (0.29 mmol) of 1,1-dimethylethyl 4-[(2-chloro-3-{(1R)-1-[(2-[(methyloxy)carbonyl]-5-{5-[(trifluoromethyl)oxy]-1H-benzimidazol-1-yl}-3-thienyl)oxy]ethyl}phenyl)oxy]-1-piperidinecarboxylate which was then dissolved in 5 mL of DCM and TFA (1 mL, 5.9 mmol) was added. After 1 h the volatiles were evaporated under reduced pressure and the residue was dissolved in a solution of 7 N ammonia in MeOH (10 mL). The mixture was heated in a sealed tube to 80° C for 40 h and then cooled to rt. Silica (1 g) was added, the volatiles were evaporated under reduced pressure and the residue was purified by flash column chromatography (0 to 100% 80/20/1 DCM/MeOH/ammonium hydroxide; DCM) to afford 0.14 g (69%) of the title compound as a light yellow solid. ¹H NMR (400 MHz, CD₃OD): δ 8.45 (s, 1H), 7.63 (s, 1H), 7.42 (d, J=8.79 Hz, 1H), 7.30 (m, 2H), 7.15 (d, J=7.87 Hz, 1H), 7.10 (d, J=7.87 Hz, 1H), 6.97 (s, 1H), 6.05 (q, J=6.29 Hz, 1H), 4.56 (m, 3H), 3.06 (m, 2H), 2.69 (m, 2H), 1.95 (m, 2H), 1.77 (d, J=6.23 Hz, 3H), 1.71 (br m, 2H); MS (ESI): 581 [M+H]⁺.

EXAMPLE 62

3-[((1R)-1-{2-chloro-3-[(1-methyl-4-piperidinyl)oxy]phenyl}ethyl)oxy]-5-{5-[(trifluoromethyl)oxy]-1H-benzimidazol-1-yl}-2-thiophenecarboxamide

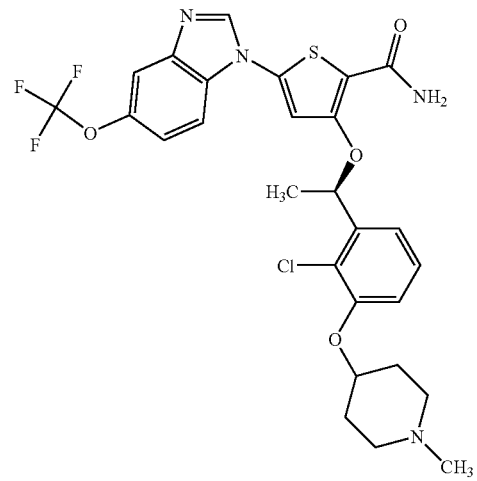

To a slurry of methyl 3-{[(1R)-1-(2-chloro-3-hydroxyphenyl)ethyl]oxy}-5-{5-[(trifluoromethyl)oxy]-1H-benzimidazol-1-yl}-2-thiophenecarboxylate (Intermediate 25, 0.18 g, 0.35 mmol) and 1-methyl-4-piperidinol (0.12 g, 1.1 mmol) in DCM (10 mL) was added triphenylphosphine (0.18 g, 0.70 mmol) and di-tert-butyl azodicarboxylate (0.16 g, 0.70 mmol). The clear, yellow solution was stirred for 1 h, and then silica gel (3 g) was added. The volatiles were evaporated under reduced pressure and the residue was purified by flash column chromatography (0 to 100% 80/20/1 DCM/MeOH/ammonium hydroxide:DCM) to give 0.20 g (0.34 mmol) of methyl 3-[((1R)-1-{2-chloro-3-[(1-methyl-4-piperidinyl)oxy]phenyl}ethyl)oxy]-5-{5-[(trifluoromethyl)oxy]-1H-benzimidazol-1-yl}-2-thiophenecarboxylate which was then dissolved in a solution of 7 N ammonia in MeOH (10 mL). The mixture was heated in a sealed tube to 80° C. for 40 h and then cooled to rt. Silica (1 g) was added, the volatiles were evaporated under reduced pressure and the residue was purified by flash column chromatography (0 to 100% 80/20/1 DCM/MeOH/ammonium hydroxide:DCM) to afford 0.18 g (86%) of the title compound as a light yellow solid. ¹H NMR (400 MHz, CD₃OD): δ 8.45 (s, 1H), 7.63 (s, 1H), 7.45 (d, J=8.79 Hz, 1H), 7.31 (m, 2H), 7.17 (d, J=7.51 Hz, 1H), 7.10 (d, J=8.24 Hz, 1H), 6.97 (s, 1H), 6.05 (q, J=6.29 Hz, 1H), 4.56 (m, 3H), 2.72 (br m, 2H), 2.47 (br m, 2H), 2.33 (s, 3H), 1.95 (br m, 4H), 1.77 (d, J=6.41 Hz, 3H): MS (ESI): 595 [M+H]⁺.

EXAMPLE 63

3-({(1R)-1-[2-chloro-3-(4-piperidinyloxy)phenyl]ethyl}oxy)-5-{6-[(trifluoromethyl)oxy]-1H-benzimidazol-1-yl}-2-thiophenecarboxamide

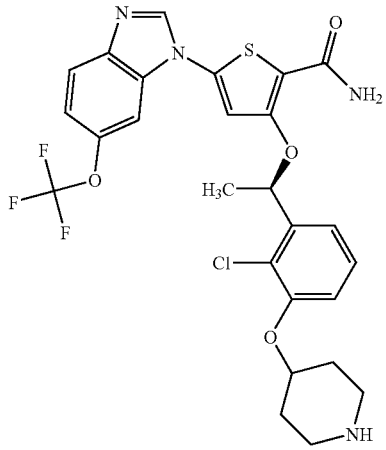

The title compound was prepared from methyl 3-{[(1R)-1-(2-chloro-3-hydroxyphenyl)ethyl]oxy}-5-{6-[(trifluoromethyl)oxy]-1H-benzimidazol-1-yl}-2-thiophenecarboxylate (Intermediate 26, 0.350 g, 0.682 mmol) and 1,1-dimethylethyl 4-hydroxy-1-piperidinecarboxylate (0.314 g, 1.36 mmol) using a procedure analogous to Example 61 to give 0.119 g (30%) of the desired product. $^1$H NMR (400 MHz, CD$_3$OD): δ 8.43 (s, 1H), 7.78 (d, J=8.61 Hz, 1H), 7.30 (m, 3H), 7.15 (d, J=7.51 Hz, 1H), 7.07 (d, J=7.87 Hz, 1H), 6.94 (s, 1H), 6.04 (q, J=6.29 Hz, 1H), 4.54 (m, 3H), 3.03 (m, 2H), 2.67 (m, 2H), 1.94 (m, 2H), 1.76 (d, J=6.23 Hz, 3H), 1.69 (br m, 2H); MS (ESI): 581 [M+H]$^+$.

EXAMPLE 64

3-[((1R)-1-{2-chloro-3-[(1-methyl-4-piperidinyl)oxy]phenyl}ethyl)oxy]-5-{6-[(trifluoromethyl)oxy]-1H-benzimidazol-1-yl}-2-thiophenecarboxamide

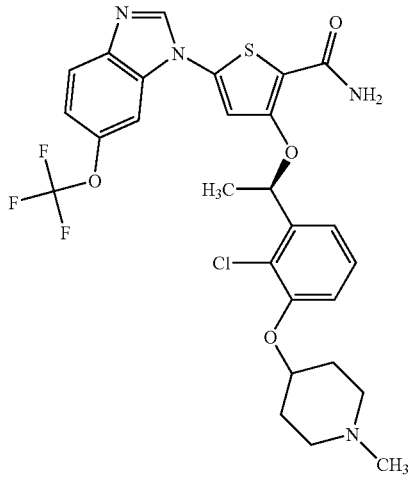

The title compound was prepared from methyl 3-{[(1R)-1-(2-chloro-3-hydroxyphenyl)ethyl]oxy}-5-{6-[(trifluoromethyl)oxy]-1H-benzimidazol-1-yl}-2-thiophenecarboxylate (Intermediate 26, 0.350 g, 0.682 mmol) and 1-methyl-4-piperidinol (0.314 g, 1.36 mmol) using a procedure analogous to Example 62 to give 0.119 g (29%) of the desired product. $^1$H NMR (400 MHz, CD$_3$OD): δ 8.44 (s, 1H), 7.80 (d, J=8.61 Hz, 1H), 7.31 (m, 3H), 7.16 (d, J=7.69 Hz, 1H), 7.07 (d, J=8.24 Hz, 1H), 6.95 (s, 1H), 6.04 (q, J=6.17 Hz, 1H), 4.52 (m, 3H), 2.66 (br m, 2H), 2.39 (br m, 2H), 2.27 (s, 3H), 1.89 (br m, 4H), 1.77 (d, J=6.23 Hz, 3H): MS (ESI): 595 [M+H]$^+$.

EXAMPLE 65

3-({(1R)-1-[2-chloro-3-(4-piperidinyloxy)phenyl]ethyl}oxy)-5-(5,6-difluoro-1H-benzimidazol-1-yl)-2-thiophenecarboxamide

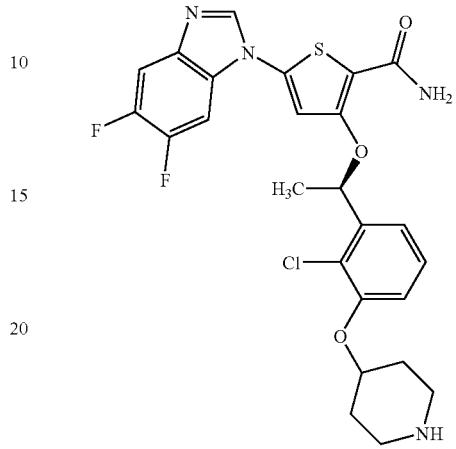

The title compound was prepared from methyl 3-{[(1R)-1-(2-chloro-3-hydroxyphenyl)ethyl]oxy}-5-(5,6-difluoro-1H-benzimidazol-1-yl)-2-thiophenecarboxylate (Intermediate 27, 0.20 g, 0.43 mmol) and 1,1-dimethylethyl 4-hydroxy-1-piperidinecarboxylate (0.26 g, 1.3 mmol) using a procedure analogous to Example 61 to give 0.1 g (43%) of the desired product. $^1$H NMR (400 MHz, DMSO-d$_6$): δ 8.59 (s, 1H), 7.85 (m, 2H), 7.59 (m, 1H), 7.30 (t, J=7.97 Hz, 1H), 7.14 (m, 4H), 5.99 (q. J=6.17 Hz, 1H), 4.44 (m, 1H), 2.87 (m, 2H), 2.50 (m, 2H), 1.82 (m, 2H), 1.68 (d, J=6.04 Hz, 3H), 1.44 (br m, 2H); MS (ESI): 533 [M+H]$^+$.

EXAMPLE 66

3-[((1R)-1-{2-chloro-3-[(1-methyl-4-piperidinyl)oxy]phenyl}ethyl)-oxy]-5-(5,6-difluoro-1H-benzimidazol-1-yl)-2-thiophenecarboxamide

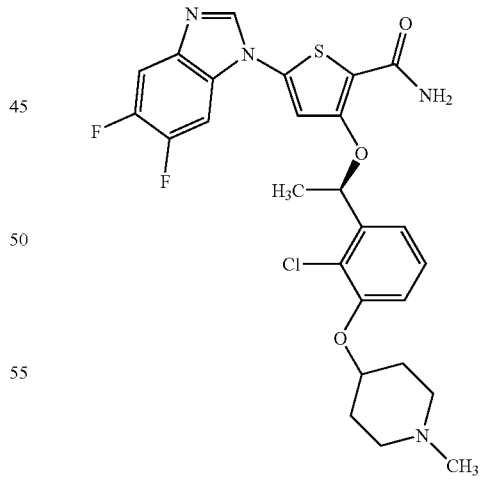

The title compound was prepared from methyl 3-{[(1R)-1-(2-chloro-3-hydroxyphenyl)ethyl]oxy}-5-(5,6-difluoro-1H-benzimidazol-1-yl)-2-thiophenecarboxylate (Intermediate 27, 0.20 g, 0.43 mmol) and 1-methyl-4-piperidinol (0.15 g, 1.3 mmol) using a procedure analogous to Example 62 to give 0.165 g (70%) of the desired product. $^1$H NMR (400 MHz, CD$_3$OD): δ 8.40 (s, 1H), 7.63 (m, 1H), 7.32 (t, J=7.96 Hz, 3H), 7.25 (m, 1H), 7.16 (d, J=7.50 Hz, 1H), 7.10 (d, J=8.05 Hz, 1H), 6.93 (s, 1H), 6.07 (q, J=6.34 Hz, 1H), 4.52 (br m, 1H), 2.65 (br m, 2H), 2.38 (br m, 2H), 2.27 (s, 3H), 1.91 (br m, 4H), 1.77 (d, J=6.40 Hz, 3H): MS (ESI): 547 [M+H]⁺.

EXAMPLE 67

5-(5-Chloro-6-fluoro-1H-benzimidazol-1-yl)-3-({(1R)-1-[2-chloro-3-(4-piperidinyloxy)phenyl]ethyl}oxy)-2-thiophenecarboxamide

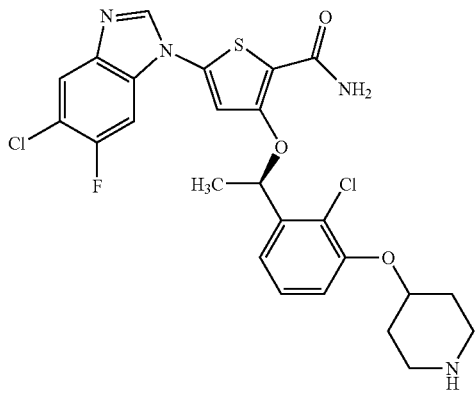

Step A—1-Bromo-4-chloro-5-fluoro-2-nitrobenzene

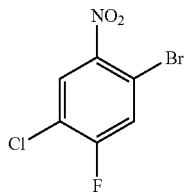

To a solution of 4-bromo-1-chloro-2-fluorobenzene (8.4 g, 40 mmol) and ammonium nitrate in DCM (335 mL) at 0° C. was added TFA anhydride (41.3 mL) via addition funnel over 15 min. The reaction mixture was stirred at 0° C. for 15 min and then at rt for 2 h. The reaction was quenched with 560 mL saturated MaHCO₃ solution and the layers separated. The aqueous layer was extracted with DCM and then EtOAc. The combined organic layer was dried over Na₂SO₄, filtered and silica gel was added. The volatiles were evaporated under reduced pressure, and the residue was purified by flash column chromatography (0 to 15% EtOAc:hexane) to give 3.7 g (36%) of the title compound. ¹H NMR (400 MHz, DMSO-d₆): δ 8.46 (d, J=6.9 Hz, 1H), 8.18 (d, J=8.8 Hz, 1H).

Step B—Methyl 5-(5-chloro-6-fluoro-1H-benzimidazol-1-yl)-3-{[(1R)-1-(2-chlorophenyl)ethyl]oxy}-2-thiophenecarboxylate

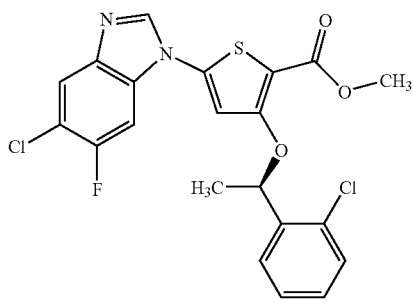

To a solution of 1-bromo-4-chloro-5-fluoro-2-nitrobenzene (6.0 g, from a different batch prepared analogous to Example 67, Step A, 23.0 mmol) and methyl 5-amino-3-{[(1R)-1-(2-chlorophenyl)ethyl]oxy}-2-thiophenecarboxylate (Intermediate 30, 11.0 g, 35.0 mmol) in toluene (70 mL) was added tris(dibenzylideneacetone)dipalladium (0) chloroform complex (595 mg, 0.58 mmol), 9,9-dimethyl-4,5-bis(diphenylphosphino)xantphos (665 mg, 1.20 mmol) and Cs₂CO₃ (22.5 g, 69.0 mmol)) with vigorous stirring. The reaction flask was sealed and carefully evacuated and refilled with N₂ three times and the reaction mixture was stirred at 60° C. for 15 h. The reaction mixture was filtered through a pad of silica gel washing with copious amounts of 20% EtOAc in hexanes. The volatiles were evaporated under reduced pressure to give methyl 5-[(4-chloro-5-fluoro-2-nitrophenyl)amino]-3-{[(1R)-1-(2-chlorophenyl)ethyl]oxy}-2-thiophenecarboxylate 7.24 g (64%). This intermediate was dissolved in acetic acid (25 mL) and added via an addition funnel to a solution of iron power (4.0 g, 75 mmol) and acetic acid (20 mL) at 55° C. with vigorous stirring. The reaction mixture was then cooled to rt, diluted with EtOAc and filtered through celite and the resulting filtrate was neutralized with 6N MaOH solution and saturated NaHCO₃ solution. The layers were separated and the aqueous layer was extracted three times with EtOAc. The combined organic layer was dried over Na₂SO₄ and the volatiles were evaporated under reduced pressure to give methyl 5-[(2-amino-4-chloro-5-fluorophenyl)amino]-3-{[(1R)-1-(2-chlorophenyl)ethyl]oxy}-2-thiophenecarboxylate. To this material was added trimethylorthoformate (150 mL) and formic acid (10 mL) and the resulting reaction mixture was stirred at 40° C. for 1 h. Silica gel was added and the volatiles were evaporated under reduced pressure and the residue was purified by flash chromatography (0 to 15% EtOAc:hexane) to afford 4.7 g (67%) of the title compound. ¹H NMR (400 MHz, DMSO-d₆): δ 8.70 (s, 1H), 8.03 (d, J=6.8 Hz, 1H), 7.58-7.83 (m, 2H), 7.38-7.50 (m, 2H), 7.44 (s, 1H), 7.25-7.37 (m, 1H), 5.99 (q, J=8.2 Hz, 1H), 3.82 (s, 3H), 1.62 (d, J=6.2 Hz, 3H), MS (ESI): 467 [M+H]⁺.

Step C—Methyl 5-(5-chloro-6-fluoro-1H-benzimidazol-1-yl)-3-hydroxy-2-thiophenecarboxylate

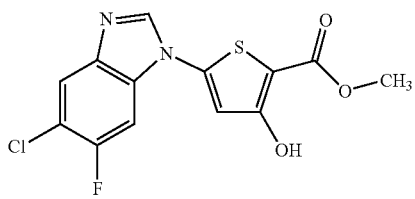

To a solution of methyl 5-(5-chloro-6-fluoro-1H-benzimidazol-1-yl)-3-{[(1R)-1-(2-chlorophenyl)ethyl]oxy}-2-thiophenecarboxylate (2.5 g, 5.4 mmol) in dichloroethane (10 mL) was added TFA (10 mL) and the reaction mixture was stirred at 60° C. for 1 h. The reaction mixture was cooled to rt, diluted with EtOAc and neutralized with saturated NaHCO₃ solution. The layers were separated and the aqueous layer extracted two times with EtOAc. The combined organic layer was dried over Na₂SO₄ and the volatiles were evaporated under reduced pressure. The residue was washed with 10% EtOAc:hexane and filtered to afford 1.5 g (84%) of the title compound. ¹H NMR (400 MHz, DMSO-d₆) δ 11.13 (s, 1H), 8.72 (s, 1H), 8.03 (d, J=6.8 Hz, 1H), 7.80 (d, J=9.1 Hz, 1H), 7.20 (s, 1H), 3.77 (s, 3H), MS (ESI): 326 [M+H]⁺.

Step D—Methyl 5-(5-chloro-6-fluoro-1H-benzimidazol-1-yl)-3-({(1R)-1-[2-chloro-3-(4-piperidinyloxy)phenyl]ethyl}oxy)-2-thiophenecarboxylate

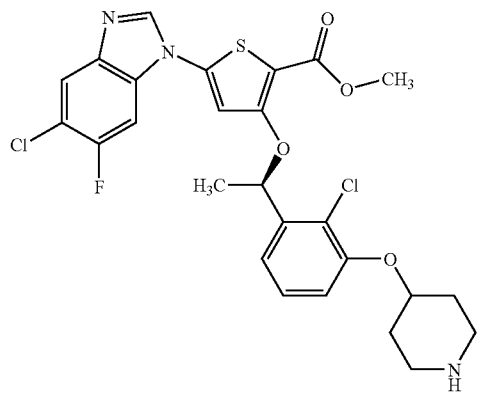

To a solution of methyl 5-(5-chloro-6-fluoro-1H-benzimidazol-1-yl)-3-hydroxy-2-thiophenecarboxylate (0.25 g, 0.77 mmol) and 1,1-dimethylethyl 4-({2-chloro-3-[(1S)-1-hydroxyethyl]phenyl}oxy)-1-piperidinecarboxylate (0.33 g, 0.93 mmol) in $CH_2Cl_2$ (8 mL) was added polymer-supported triphenylphosphine (0.45 g, 1.5 mmol) and di-tert-butylazodicarboxylate (0.36 g, 1.4 mmol) and the reaction mixture stirred at rt overnight. The reaction mixture was filtered with DCM washings and the volatiles evaporated under reduced pressure. The residue was dissolved in DCM (1 mL) and TFA (1 mL) was added. After 1 h, silica was added and the volatiles evaporated under reduced pressure and the residue was purified by flash chromatography (0 to 100% 89/10/1 DCM/MeOH/ammonium hydroxide:DCM) to afford 0.27 g, (62%) of the title compound. MS (ESI): 564 $[M+H]^+$.

Step E—5-(5-Chloro-6-fluoro-1H-benzimidazol-1-yl)-3-({(1R)-1-[2-chloro-3-(4-piperidinyloxy)phenyl]ethyl}oxy)-2-thiophenecarboxamide (Title Compound)

To methyl 5-(5-chloro-8-fluoro-1H-benzimidazol-1-yl)-3-({(1R)-1-[2-chloro-3-(4-piperidinyloxy)phenyl]ethyl}oxy)-2-thiophenecarboxylate (0.26 g, 0.46 mmol) was added a solution of 7 N ammonia in MeOH (10 mL). The mixture was heated In a sealed tube to 70° C. for 40 h and then cooled to rt. Silica was added and the volatiles evaporated under reduced pressure and the residue was purified by flash chromatography (0 to 100% 89/10/1 DCM/MeOH/ammonium hydroxide:DCM) to afford 0.20 g (80%) of the title compound. $^1H$ NMR (400 MHz, DMSO-$d_6$) δ 8.64 (s, 1H), 8.47 (br. s, 1H), 8.05 (d, J=6.6 Hz, 1H), 7.85 (s, 1H), 7.61 (d, J=9.3 Hz, 1H), 7.37 (t, J=8.0 Hz, 1H), 7.07-7.31 (m, 4H), 6.03 (q, J=6.6 Hz, 1H), 4.64-4.88 (m, 1H), 3.14-3.26 (m, 2H), 3.00-3.14 (m, 2H), 1.99-2.18 (m, 2H), 1.78-1.92 (m, 2H), 1.72 (d, J=6.2 Hz, 3H). MS (ESI): 549 $[M+H]^+$.

EXAMPLE 68

5-(5-Chloro-6-fluoro-1H-benzimidazol-1-yl)-3-[((1R)-1-{2-chloro-3-[(1-methyl-4-piperidinyl)oxy]phenyl}ethyl)oxy]-2-thiophenecarboxamide

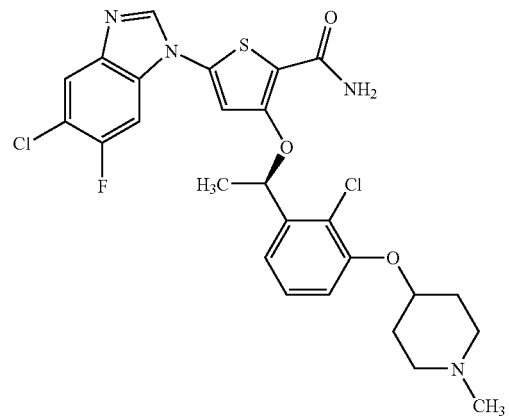

Step A—Methyl 5-(5-chloro-6-fluoro-1H-benzimidazol-1-yl)-3-{[(1R)-1-(2-chloro-3-hydroxyphenyl)ethyl]oxy}-2-thiophenecarboxylate

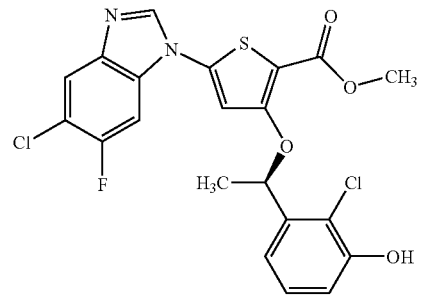

To a solution of methyl 5-(5-chloro-6-fluoro-1H-benzimidazol-1-yl)-3-hydroxy-2-thiophenecarboxylate (Example 67, Step C, 0.33 g, 1.0 mmol) and (1S)-1-(2-chloro-3-{[(1,1-dimethylethyl)(dimethyl)silyl]-oxy}phenyl)ethanol (Intermediate 17, 0.34 g, 1.2 mmol) in DCM (10 mL) was added polymer-supported triphenylphosphine (0.91 g, 2.0 mmol), di-tert-butylazodicarboxylate (0.46 g, 4.0 mmol). The reaction mixture was stirred overnight. The reaction was filtered with DCM washings and the volatiles evaporated under reduced pressure. The residues was dissolved in THF (10 mL) and a solution of 1 N tetrabutylammonium fluoride in THF (1 mL, 1 mmol) was added. After 10 min, silica was added, the volatiles were evaporated under reduced pressure and the residue was purified by flash column chromatography (0 to 100% 84/15/1 DCM/MeOH/ammonium hydroxide:DCM) to give 0.34 g (71%) of the title compound. MS (ESI): 481 $[M+H]^+$.

Step B—5-(5-Chloro-6-fluoro-1H-benzimidazol-1-yl)-3-[((1R)-1-{2-chloro-3-[(1-methyl-4-piperidinyl)oxy]phenyl}ethyl)oxy]-2-thiophenecarboxamide

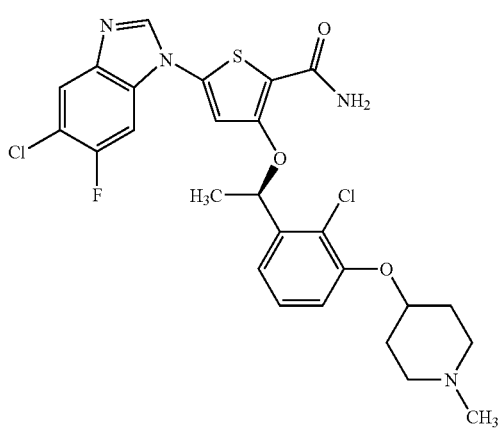

To a solution of methyl 5-(5-chloro-6-fluoro-1H-benzimidazol-1-yl)-3-{[(1R)-1-(2-chloro-3-hydroxyphenyl)ethyl]oxy}-2-thiophenecarboxylate (0.30 g, 0.62 mmol) and 1-methyl-4-piperidinol (0.11 g, 0.95 mmol) in DCM was added polymer-supported triphenylphosphine (0.56 g, 1.2 mmol), di-tert-butylazodicarboxylate (0.29 g, 1.2 mmol). The reaction mixture was stirred overnight. The reaction mixture was filtered with DCM washings and the volatiles evaporated under reduced pressure. To the residue was added a solution of 7 N ammonia in MeOH (10 mL). The mixture was heated in a sealed tube to 70° C. for 48 h and then cooled to rt. Silica was added and the volatiles evaporated under reduced pressure and the residue was purified by flash chromatography ((0 to 100% 89/10/1 DCM/MeOH/ammonium hydroxide:DCM) to afford 0.12 g (34%) of the title compound. $^1$H NMR (300 MHz, DMSO-$d_6$) δ 8.64 (s, 1H), 8.05 (d, J=6.7 Hz, 1H), 7.85 (s, 1H), 7.60 (d, J=9.3 Hz, 1H), 7.33 (t, J=7.9 Hz, 1H), 7.05-7.26 (m, 4H), 6.02 (q, J=6.4 Hz, 1H), 4.45 (s, 1H), 2.54 (s, 2H), 2.02-2.26 (m, 5H), 1.88 (s, 1H), 1.56-1.74 (m, 4H), 1.31-1.46 (m, 2H). MS (ESI): 563 [M+H]$^+$.

EXAMPLE 69

5-(6-Chloro-5-fluoro-1H-benzimidazol-1-yl)-3-({(1R)-1-[2-chloro-3-(4-piperidinyloxy)phenyl]ethyl}oxy)-2-thiophenecarboxamide

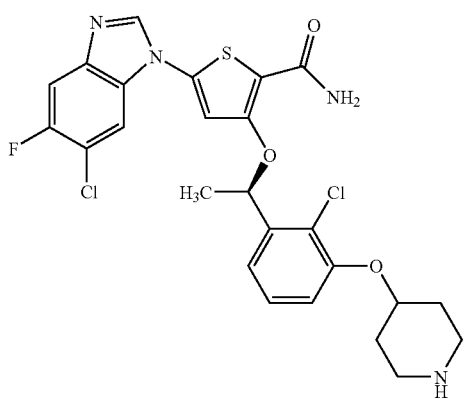

Step A—1-Bromo-5-chloro-4-fluoro-2-nitrobenzene

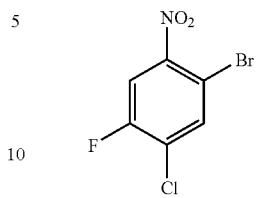

A solution of 5-chloro-4-fluoro-2-nitroaniline (3.62 g, 19.0 mmol) in acetonitrile (60 mL) was slowly added via an addition funnel to a mixture or copper (II) bromide (6.37 g,. 28.5 mmol), tert-butyl nitrile (4.33 g, 42.0 mmol) in acetonitrile (40 mL) at 60° C. The reaction mixture was stirred for 10 min, cooled to rt and poured into a solution of 2 N HCl (400 mL). EtOAc was added and the layers separated. The aqueous layer was extracted three times with EtOAc. The combine organic layer was washed with brine and dried over Na$_2$SO$_4$. The volatiles were evaporated under reduced pressure and the residue dissolved in 5% EtOAc:hexane and passed through a pad of silica with copious hexane washings to afford 4.53 g (94%) of the title compound. $^1$H NMR (300 MHz, DMSO-$d_6$) δ 8.3 (m, 2H).

Step B—Methyl 5-[(5-chloro-4-fluoro-2-nitrophenyl)amino]-3-[(phenylmethyl)oxy]-2-thiophenecarboxylate

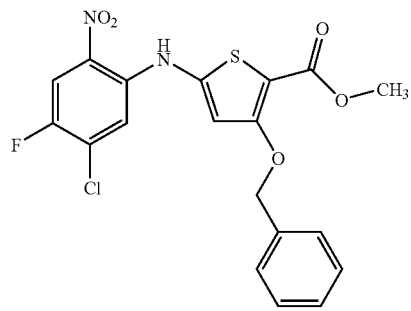

To a solution of bromo-5-chloro-4-fluoro-2-nitrobenzene and methyl 5-amino-3-[(phenylmethyl)oxy]-2-thiophenecarboxylate (1.0 g, 4.0 mmol) in toluene (11 mL) was added tris(dibenzylideneacetone)dipalladium (0) chloroform complex (100 mg, 0.10 mmol), XANTPHOS (110 mg, 0.20 mmol) and Cs$_2$CO$_3$ (3.8 g, 12 mmol)). The reaction flask was sealed and carefully evacuated and refilled with N$_2$ three times and the reaction mixture was stirred at 60° C. overnight. Silica gel was added and the volatiles evaporated under reduced pressure, the residue was purified by flash chromatography (0 to 50% EtOAc:hexane) to give 1.2 g (68%) of the title compound. $^1$H NMR (300 MHz, DMSO-$d_6$) δ 9.73 (s, 1H) 8.19 (d, J=9.3 Hz, 1H) 7.57 (d, J=6.6 Hz, 1H) 7.26-7.49 (m, 5H) 6.94 (s, 1H) 5.23 (s, 2H) 3.71 (s, 3H). MS (ESI): 436 [M+H]$^+$.

Step C—Methyl 5-(6-chloro-5-fluoro-1H-benzimidazol-1-yl)-3-[(phenylmethyl)oxy]-2-thiophenecarboxylate

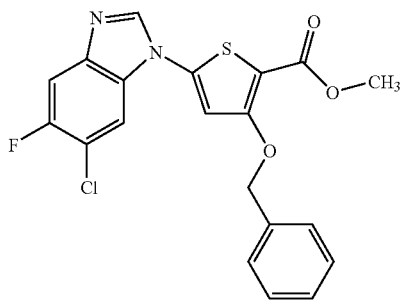

To a solution of methyl 5-[(5-chloro-4-fluoro-2-nitrophenyl)amino]-3-[(phenylmethyl)oxy]-2-thiophenecarboxylate (1.0 g, 2.3 mmol) in acetic acid (7 mL) at 55° C. was added iron power (0.64, 12 mmol) and the reaction mixture stirred 1 h. The reaction mixture was cooled to rt, diluted with EtOAc and filtered and the resulting filtrate was neutralized with saturated NaHCO$_3$ and separated. The aqueous layer was extracted two times with EtOAc. The combined organic layer was dried over Na$_2$SO$_4$ and the volatiles were evaporated under reduced pressure. To this material was added trimethylorthoformate (50 mL) and formic acid (1 mL) and the resulting reaction mixture was stirred at rt overnight. Silica was added and the volatiles were evaporated under reduced pressure and the residue was purified by flash chromatography (0 to 60% EtOAc:hexane) to afford 0.82 g (82%) of the title compound. $^1$H NMR (300 MHz, DMSO-d$_6$) δ 8.75 (s, 1H) 7.93 (d, J=6.5 Hz, 1H), 7.87 (d, J=9.7 Hz, 1H), 7.66 (s, 1H), 7.47-7.53 (m, 2H), 7.30-7.46 (m, 3H), 5.38 (s, 2H), 3.77 (s, 3H). MS (ESI): 416 [M+H]$^+$.

Step D—Methyl 5-(6-chloro-5-fluoro-1H-benzimidazol-1-yl)-3-hydroxy-2-thiophenecarboxylate

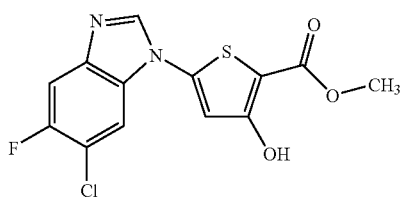

To a solution of methyl 5-(6-chloro-5-fluoro-1H-benzimidazol-1-yl)-3-[(phenylmethyl)oxy]-2-thiophenecarboxylate (0.80 g, 1.9 mmol) In 95% EtOH (12 mL) was added 10% palladium on carbon (0.16 g, 1.5 mmol) and stirred under H$_2$ balloon for 48 h. The reaction mixture was filtered through a pad of silica with copious EtOAc washings to give 0.34 g (54%) of the title compound. MS (ESI): 326 [M+H]$^+$.

Step E—Methyl 5-(6-chloro-5-fluoro-1H-benzimidazol-1-yl)-3-{[(1R)-1-(2-chloro-3-hydroxyphenyl)ethyl]oxy}-2-thiophenecarboxylate

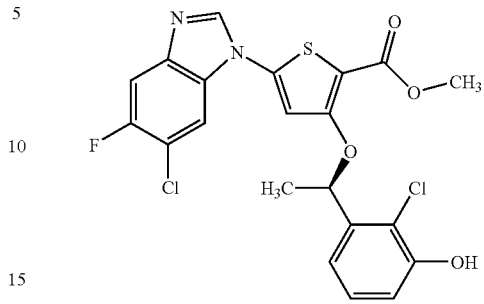

To a solution of methyl 5-(6-chloro-5-fluoro-1H-benzimidazol-1-yl)-3-hydroxy-2-thiophenecarboxylate (0.33 g, 1.0 mmol) and (1S)-1-(2-chloro-3-{[(1,1-dimethylethyl)(dimethyl)sliyl]-oxy}phenyl)ethanol (0.34 g, 1.2 mmol) in DCM (10 mL) was added polymer-supported triphenylphosphine (0.91 g, 2.0 mmol), di-tert-butylazodicarboxylate (0.46 g, 4.0 mmol). The reaction mixture was stirred overnight. The reaction was filtered with DCM washings and the volatiles were evaporated under reduced pressure. The residue was dissolved in THF (10 mL) and a solution of 1 N tetrabutylammonium fluoride in THF (1 mL, 1 mmol) was added. After 10 min, silica was added, the volatiles were evaporated under reduced pressure and the residue was purified by flash column chromatography (0 to 100% EfOAc:hexane) to give 0.30 g (60%) of the title compound. $^1$H NMR (400 MHz, DMSO-d$_6$) δ 10.25 (s, 1H), 8.72 (s, 1H), 7.87 (d, J=9.5 Hz, 1H), 7.79 (d, J=6.6 Hz, 1H), 7.36 (s, 1H), 7.06-7.25 (m, 2H), 6.91 (d, J=7.7 Hz, 1H), 5.96 (q, J=6.1 Hz, 1H), 3.82 (s, 3H), 1.60 (d, J=6.2 Hz, 3H). MS (ESI): 481 [M+H]$^+$.

Step F—Methyl 5-(6-chloro-5-fluoro-1H-benzimidazol-1-yl)-3-({(1R)-1-[2-chloro-3-(4-piperidinyloxy)phenyl]ethyl}oxy)-2-thiophenecarboxylate

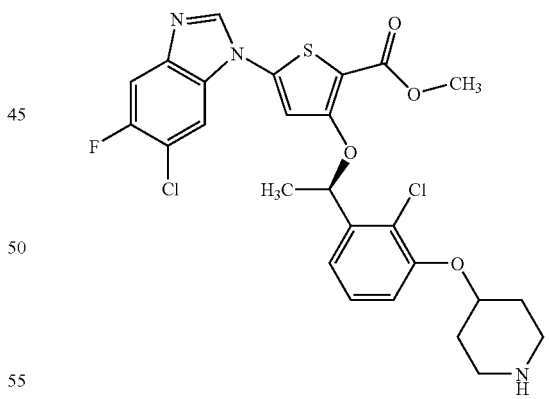

To a solution of methyl 5-(6-chloro-5-fluoro-1H-benzimidazol-1-yl)-3-{[(1R)-1-(2-chloro-3-hydroxyphenyl)ethyl]oxy}-2-thiophenecarboxylate (0.16 g, 0.33 mmol) and 1,1-dimethylethyl 4-hydroxy-1-piperidinecarboxylate (0.13 g, 0.66 mmol) in DCM (4 mL) was added polymer-supported triphenylphosphine (0.30 g, 0.66 mmol), di-tert-butylazodicarboxylate (0.15 g, 0.66 mmol). The reaction mixture was stirred for 8 h. The reaction mixture was filtered with DCM washings and the volatiles were evaporated under reduced pressure. The residue was dissolved in THF (3 mL) and a solution of 1 N tetrabutylammonium fluoride in THF (1 mL, 1 mmol) was added. After 10 min, silica was added, the volatiles were evaporated under reduced pressure and the residue was purified by flash column chromatography (0 to 100% 89/10/1 DCM/MeOH/ammonium hydroxide:DCM) to give 0.18 g (97%) of the title compound. MS (ESI): 564 [M+H]$^+$.

Step G—5-(6-Chloro-5-fluoro-1H-benzimidazol-1-yl)-3-({(1R)-1-[2-chloro-3-(4-piperidinyloxy)phenyl]ethyl}oxy)-2-thiophenecarboxamide (Title Compound)

To methyl 5-(6-chloro-5-fluoro-1 H-benzimidazol-1-yl)-3-({(1R)-1-[2-chloro-3-(4-piperidinyloxy)phenyl]ethyl}oxy)-2-thiophenecarboxylate (0.18 g, 0.32 mmol) was added a solution of 7 N ammonia in MeOH (10 mL). The mixture was heated in a sealed tube to 70° C. for 48 h and then cooled to rt. Silica was added and the volatiles evaporated under reduced pressure and the residue was purified by flash chromatography ((0 to 100% 89/10/1 DCM/MeOH/ammonium hydroxide:DCM) to afford 0.13 (76%) of the title compound. $^1$H NMR (400 MHz, DMSO-d$_6$) δ 8.67 (s, 1H), 8.52 (s, 1H), 7.77-7.99 (m, 1H), 7.72 (d, J=6.4 Hz, 1H), 7.39 (t, J=8.0 Hz, 1H), 7.14 (s, 1H), 7.03-7.35 (m, 4H), 6.03 (q, J=6.6 Hz, 1H), 4.64-4.88 (m, 1H), 3.14-3.26 (m, 2H), 3.00-3.14 (m, 2H), 1.99-2.18 (m, 2H), 1.78-1.92 (m, 2H), 1.72 (d, J=6.2 Hz, 3H). MS (ESI): 549 [M+H]$^+$.

EXAMPLE 70

5-(6-Chloro-5-fluoro-1H-benzimidazol-1-yl)-3-[((1R)-1-{2-chloro-3-[(1-methyl-4-piperidinyl)oxy]phenyl}ethyl)oxy]-2-thiophenecarboxamide

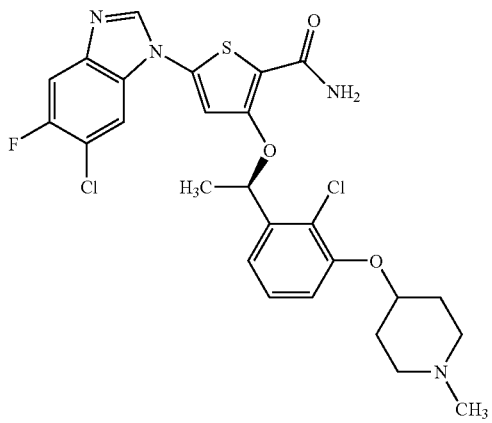

To a solution of methyl 5-(6-chloro-5-fluoro-1H-benzimidazol-1-yl)-3-{[(1R)-1-(2-chloro-3-hydroxyphenyl)ethyl]oxy}-2-thiophenecarboxylate (Example 69, Step E, 0.10 g, 0.21 mmol) and 1-methyl-4-piperidinol (0.05 g, 0.42 mmol) in DCM (2 mL) was added polymer-supported triphenylphosphine (0.19 g, 0.42 mmol), di-tert-butylazodicarboxylate (0.10 g, 0.42 mmol). The reaction mixture was stirred for 8 h. The reaction was filtered with DCM washings and the volatiles were evaporated under reduced pressure. To the residue was added a solution of 7 N ammonia in MeOH (8 mL). The mixture was heated in a sealed tube to 70° C. for 48 h and then cooled to rt. Silica; was added and the volatiles evaporated under reduced pressure and the residue was purified by flash chromatography ((0 to 100% 89/10/1 DCM/MeOH/ammonium hydroxide:DCM) to afford 0.72 g (61%) of the title compound. $^1$H NMR (400 MHz, DMSO-d$_6$) δ 8.65 (s, 1H), 7.86 (d, J=9.7 Hz, 1H), 7.84 (s, 1H), 7.72 (d, J=6.4 Hz, 1H), 7.33 (t, J=8.0 Hz, 1H), 7.20 (d, J=7.5 Hz, 1H), 7.17 (s, 1H), 7.15 (d, J=8.2 Hz, 1H), 7.13 (s, 1H), 6.00 (q, J=6.0 Hz, 1H), 4.45 (s, 1H), 2.51-2.62 (m, 2H), 2.15-2.25 (m, 2H), 2.13 (s, 3H), 1.78-1.93 (m, 2H), 1.70 (d, J=6.4 Hz, 3H), 1.56-1.67 (m, 2H). MS (ESI): 564 [M+H]$^+$.

EXAMPLE 71

3-({(1R)-1-[2-Chloro-3-(4-piperidinyloxy)phenyl]ethyl}oxy)-5-(5,6-dichloro-1H-benzimidazol-1-yl)-2-thiophenecarboxamide

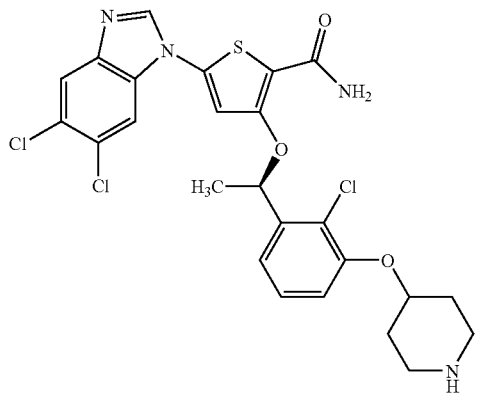

Step A—5,6-Dichloro-1H-benzimidazole

To 4,5-dichloro-1,2-benzenediamine (15 g, 85 mmol) was added trimethylorthoformate (850 mL) and formic acid (0.32 mL) and the reaction mixture heated to 70° C. overnight. Silica was added and the volatiles evaporated under reduced pressure and the residue was purified by flash column chromatography (0 to 15% MeOH:DCM) to give 12 g (76%) of the title compound. $^1$H NMR (400 MHz, DMSO-d$_6$) δ 12.73 (s, 1H), 8.34 (s, 1H), 7.87 (s, 2H). MS (ESI): 187 [M+H]$^+$.

Step B—Methyl 5-(5,6-dichloro-1H-benzimidazol-1-yl)-3-hydroxy-2-thiophenecarboxylate

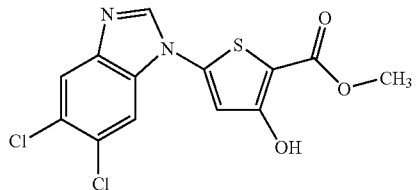

To a solution of 5,6-dichloro-1H-benzimidazole (1.26 g, 6.72 mmol) and methyl 2-chloro-3-oxo-23-dihydro-2-thiophenecarboxylate (1.49 g, 7.73 mmol) in DCM (34 mL) was added NaHCO$_3$ (1.70 g, 20.2 mmol) and N-methylimidazole (0.830 g, 10.1 mmol) and heated at 40° C. overnight. The reaction mixture was cooled to rt and DCM and water were added. The layers were separated and the aqueous layer was extracted with DCM. The combined organic layers were dried over Na₂SO₄ and filtered. Silica was added to the filtrate and the volatiles were evaporated under reduced pressure and the residue was purified by flash column chromatography (0 to 100% EtOAc:hexane) to afford 1.5 g (65%) of the title compound. ¹H NMR (300 MHz, DMSO-d₆) δ 10.88 (s, 1H), 8.76 (s, 1H), 8.10 (s, 1H), 7.99 (s, 1H), 7.17 (s, 1H), 3.79 (s, 3H). MS (ESI): 343 (M+H)⁺.

Step C—Methyl 3-({(1R)-1-[2-chloro-3-(4-piperidinyloxy)phenyl]ethyl}oxy)-5-(5,6-dichloro-1-benzimidazol-1-yl)-2-thiophenecarboxylate

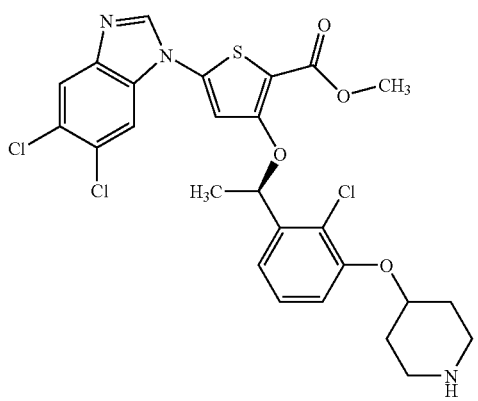

To a solution of methyl 5-(5,6-dichloro-1H-benzimidazol-1-yl)-3-hydroxy-2-thiophenecarboxylate (0.34 g, 1.0 mmol) and 1,1-dimethylethyl 4-({2-chloro-3-[(1S)-1-hydroxyethyl]phenyl}oxy)-1-piperidinecarboxylate (0.43 g, 1.2 mmol) in DCM (4 mL) was added polymer-supported triphenylphosphine (0.36 g, 0.80 mmol) and di-tert-butylazodicarboxylate (0.18 g, 0.80 mmol) and the reaction mixture stirred at rt overnight. The reaction mixture was filtered with DCM washings and the volatiles removed. The residue was dissolved in DCM (10 mL) and TFA (5 mL) was added. After 1 h, silica was added and the volatiles evaporated under reduced pressure and the residue was purified by flash chromatography (0 to 100% 89/10/1 DCM/MeOH/ammonium hydroxide:DCM) to afford 0.40 g (68%) of the title compound. MS (ESI): 580 (M+H)⁺.

Step D—3-({(1R)-1-[2-Chloro-3-(4-piperidinyloxy)phenyl]ethyl}oxy)-5-(5,6-dichloro-1H-benzimidazol-1-yl)-2-thiophenecarboxamide (Title Compound)

To methyl 3-({(1R)-1-[2-chloro-3-(4-piperidinyloxy)phenyl]ethyl}oxy)-5-(5,6-dichloro-1H-benzimidazol-1-yl)-2-thiophenecarboxylate (0.38 g, 0.65 mmol) was added a solution of 7 N ammonia in MeOH (10 mL). The mixture was heated in a sealed tube to 70° C. for 48 h and then cooled to rt. Silica was added and the volatiles evaporated under reduced pressure and the residue was purified by flash chromatography ((0 to 100% 89/10/1 DCM/MeOH/ammonium hydroxide:DCM to afford 0.13 g (36%) of the title compound. ¹H HMR (400 MHz, DMSO-d₆) δ 8.67 (s, 1H), 8.09 (s, 1H), 7.87 (s, 1H), 7.76 (s, 1H), 7.33 (t, J=8.0 Hz, 1H), 7.12-7.24 (m, 4H), 6.00 (q, J=6.1 Hz, 1H), 4.57-4.37 (m, 1H), 3.25 (s, 1H), 2.79-3.02 (m, 2H), 2.35-2.65 (m, 2H), 1.76-1.96 (m, 2H), 1.71 (d, J=6.2 Hz, 3H), 1.39-1.57 (m, 2H). MS (ESI): 565 (M+H)⁺.

EXAMPLE 72

3-[((1R)-1-{2-chloro-3-[(1-methyl-4-piperidinyl)oxy]phenyl}ethyl)oxy]-5-(5,6-dichloro-1H-benzimidazol-1-yl)-2-thiophenecarboxamide

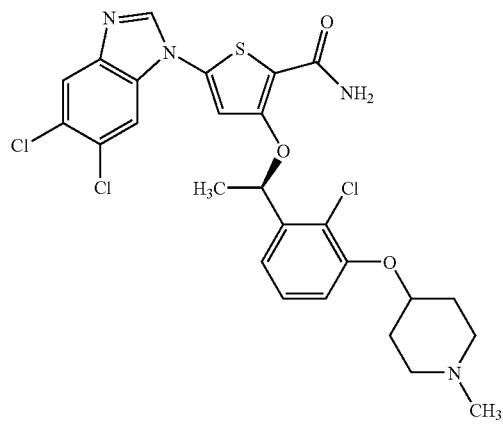

Step A—Methyl 3-{[(1R)-1-(2-chloro-3-hydroxyphenyl)ethyl]oxy}-5-(5,8-dichloro-1H-benzimidazol-1-yl)-2-thiophenecarboxylate

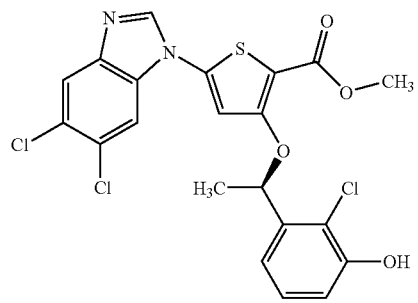

Methyl 5-(5,6-dichloro-1H-benzimidazol-yl)-3-hydroxy-2-thiophenecarboxylate (Example 71, Step B, 0.32 g, 0.93 mmol) and (1S)-1-(2-chloro-3-{[(1,1-dimethylethyl)(dimethyl)silyl]-oxy}phenyl)ethanol (Intermediate 17, 0.32 g, 1.1 mmol) in DCM (9 mL) was added polymer-supported triphenylphosphine (0.82 g, 1.9 mmol), di-tert-butylazodicarboxylate (0.43 g, 1.9 mmol). The reaction mixture was stirred overnight. Filtered, washed with DCM and concentrated under reduced pressure. The residuce was dissolved in THF (9 mL) and a solution of 1 N tetrabutylammonium fluoride in THF (1 mL, 1.0 mmol) was added. After 10 min, silica was added, the volatiles were evaporated under reduced pressure and the residue was purified by flash column chromatography (0 to 100% EtOAc:hexane) to give 0.17 g (37%) of the title compound. MS (ESI): 497 (M+H)⁺

Step B—3-[((1R)-1-{2-chloro-3-[(1-methyl-4-piperidinyl)oxy]phenyl}ethyl)oxy]-5-(5,6-dichloro-1H-benzimidazol-1-yl)-2-thiophenecarboxamide (Title Compound)

To a solution of methyl 3-{[(1R)-1-(2-chloro-3-hydroxyphenyl)ethyl]oxy}-5-(5,6-dichloro-1H-benzimidazol-1-yl)-thiophenecarboxylate (0.12 g, 0.24 mmol) and 1-methyl-4-piperidinol (0.042 g, 0.36 mmol) in DCM (3 mL) was added polymer-supported triphenylphosphine (0.22 g, 0.48 mmol), di-tert-butylazodicarboxylate (0.11 g, 0.48 mmol).

The reaction mixture was stirred overnight. The reaction mixture was then filtered, washed with DCM and concentrated under reduced pressure. To the residue was added a solution of 7 N ammonia in MeOH (10 mL). The mixture was heated in a sealed tube to 75° C. for 48 h and then cooled to rt Silica was added and the volatiles evaporated under reduced pressure and the residue was purified by flash chromatography (0 to 100% 89/10/1 DCM/MeOH/ammonium hydroxide:DCM) to afford 0.70 g (50%) of the title compound, $^1$H NMR (400 MHz, DMSO-$d_6$) δ 8.66 (s, 1H), 8.08 (s, 1H), 7.85 (s, 1H), 7.77 (s, 1H), 7.32 (t, J=8.1 Hz, 1H), 7.20 (d, J=7.7 Hz, 1H), 7.17 (s, 1H), 7.15 (d, J=8.4 Hz, 1H), 7.12 (s, 1H), 6.00 (q, J=6.0 Hz, 1H), 4.33-4.55 (m, 1H), 2.50-2.63 (m, 2H), 2.12-2.25 (m, 2H), 2.11 (s, 3H), 1.84 (s, 2H), 1.70 (d, J=6.4 Hz, 3H), 1.62 (s, 2H). MS (ESI): 579 [M+H]$^+$.

EXAMPLE 73

(+/−)-5-[5-(1-Methyl-1H-pyrazol-4-yl)-1H-benzimidazol-1-yl]-3-({1-[3-(4-piperidinyloxy)phenyl]ethyl}oxy)-2-thiophenecarboxamide

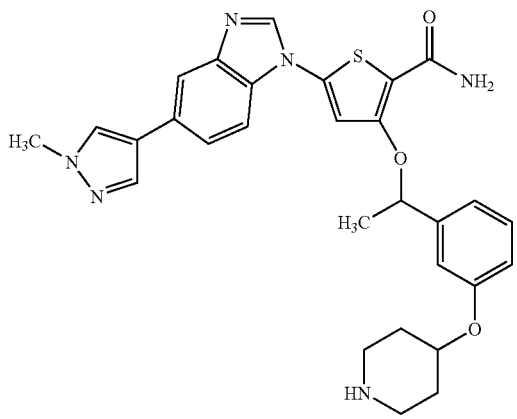

Step A—(3-Hydroxyphenyl)methyl 2,2-dimethylpropanoate

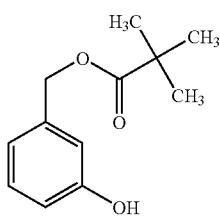

3-Hydroxybenzyl alcohol (3.00 g, 24.2 mmol) and 3-(2,2-dimethylpropanoyl)-1,3-thiazolidine-2-thione (Yamada. S. *J. Org. Chem* 1992, 57, 1591) (5.41 g, 26.6 mmol) were dissolved in 80 mL of toluene and heated to reflux for 18 h. The reaction was cooled to rt and concentrated onto silica gel. Purification by flash chromatography afforded 2.71 g (54%) of the title compound. $^1$H NMR (400 MHz, DMSO-$d_6$) δ 9.42 (s, 1H), 7.12 (m, 1H), 6.73-6.63 (m, 3H), 4.97 (s, 2H), 1.14 (s, 9H).

Step B—1,1-Dimethylethyl 4-[(3-{[(2,2-dimethylpropanoyl)oxy]-methyl}phenyl)oxy]-1-piperidinecarboxylate

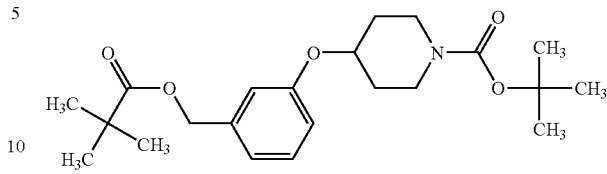

(3-Hydroxyphenyl)methyl 2,2-dimethylpropanoate (2.71 g, 13.0 mmol), triphenylphosphine (10.2 g, 39.0 mmol), and t-butyl 4 hydroxy-1-piperidinecarboxylate (5.23 g, 26.0 mmol) were dissolved in 80 mL of DCM with stirring and cooled to 0° C. Diisopropyl azodicarboxylate (3.9 mL, 20 mmol) was added dropwise via syringe over 5 min. The reaction was warmed to rt and stirred for 18 h. The solution was concentrated onto silica gel. Purification by flash chromatography afforded 3.68 g (72%) of the title compound. $^1$H NMR (400 MHz, DMSO-$d_6$) δ 7.25 (m, 1H), 6.93-6.83 (m, 3H), 5.01 (s, 2H), 4.51 (m, 1H), 3.67-3.57 (m, 2H), 3.20-3.06 (m, 2H), 1.91-1.81 (m, 2H), 1.54-1.42 (m, 2H), 1.37 (s, 9H), 1.14 (s, 9H).

Step C—1,1-Dimethylethyl 4-{[3-(hydroxyethyl)phenyl]oxy}-1-piperidinecarboxylate

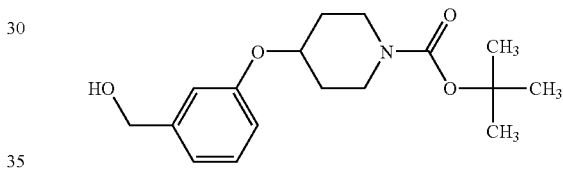

1,1-Dimethylethyl 4-[(3-{[(2,2-dimethylpropanoyl)oxy]methyl}phenyl)oxy]-1-piperidinecarboxylate (3.68 g, 9.40 mmol) was dissolved in 50 mL of dioxane with stirring. Aqueous lithium hydroxide solution (50 mL, 1N, 50 mmol) was added and the solution was stirred for 1.5 h. The reaction was placed in a 50° C. oil bath and heated at that temperature for 2 h. The reaction was cooled to rt and poured into water and EtOAc. The layers were separated, and the organic layer was washed with brine. The combined aqueous layers were washed with EtOAc. The combined organic layers were dried over MgSO$_4$, filtered, and concentrated in vacuo to provide 3.14 g (>90% pure, >90%) of the title compound. $^1$H NMR (400 MHz, DMSO-$d_6$) δ 7.18 (m, 1H), 6.93-6.75 (m, 3H), 5.12 (t, J=5.8 Hz, 1H), 4.50 (m, 1H), 4.42 (d, J=5.8 Hz, 2H), 3.66-3.56 (m, 2H), 3.22-3.08 (m, 2H), 1.91-1.80 (m, 2H), 1.54-1.41 (m, 2H), 1.37 (s, 9H).

Step D—1,1-Dimethylethyl 4-[(3-formylphenyl)oxy]-1-piperidinecarboxylate

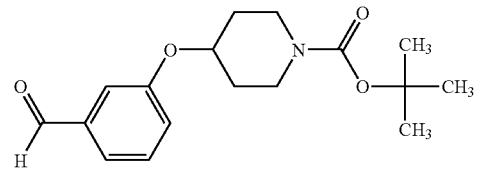

1,1-Dimethylethyl 4-{[3-(hydroxymethyl)phenyl]oxy}-1-piperidinecarboxylate (0.590 g, 1.82 mmol) was dissolved in 20 mL of DCM with stirring. Manganese dioxide (1.67 g, 19.2 mmol) was added in a single portion. The mixture was stirred for 4 h and filtered through a celite pad, washing with DCM. The filtrate was concentrated. Purification by flash chromatography afforded 0.320 g (55%) of the tie compound. $^1$H NMR (400 MHz, DMSO-d$_6$) δ 9.95 (s, 1H), 7.54-7.42 (m, 3H), 7.33-7.27 (m, 1H), 4.66 (m, 1H), 3.69-3.60 (m, 2H), 3.24-3.12 (m, 2H), 1.96-1.85 (m, 2H), 1.59-1.46 (m, 2H), 1.39 (s, 9H).

Step E—(+/−)-1,1-Dimethylethyl 4-{[3-(1-hydroxyethyl)phenyl]oxy}-1-piperidinecarboxylate

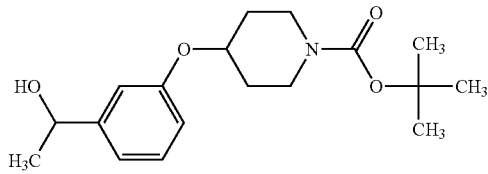

Methyl magnesium chloride (0.53 mL, 3M in THF, 1.6 mmol) was added to 6 mL of ether, and the solution was cooled to −15° C. with stirring. 1,1-Dimethylethyl 4-[(3-formylphenyl)oxy]-1-piperidinecarboxylate (0.319 g, 1.05 mmol) dissolved in 8 mL of ether was added slowly dropwise via syringe. After 15 min, an additional amount of methyl magnesium chloride (0.25 mL, 3M in THF, 0.75 mmol) was added. The reaction was stirred for 15 min more and quenched by the addition of aqueous saturated ammonium chloride. The mixture was poured into water and EtOAc, and the layers were separated. The aqueous layer was washed with EtOAc. The combined organic layers were dried over MgSO$_4$, filtered, and concentrated. Purification by flash chromatography gave 0.286 g (85%) of the title compound, $^1$H NMR (400 MHz, DMSO-d$_6$) δ 7.17 (dd, J=7.8, 7.8 Hz, 1H), 6.90-6.83 (m, 2H), 6.77 (dd, J=8.1, 2.6 Hz, 1H), 5.07 (d, J=4.4 Hz, 1H), 4.63 (m, 1H), 4.50 (m, 1H), 3.66-3.57 (m, 2H), 3.21-3.09 (m, 2H), 1.90-1.81 (m, 2H), 1.54-1.42 (m, 2H), 1.37 (s, 9H), 1.26 (d, J=6.4 Hz, 3H).

Step F—(+/−)-1,1-Dimethylethyl 4-({3-[1-({2-[(methyloxy)carbonyl]-5-[5-(1-methyl-1H-pyrazol-4-yl)-1H-benzimidazol-1-yl]-3-thienyl}oxy)ethyl]phenyl}oxy)-1-piperidinecarboxylate

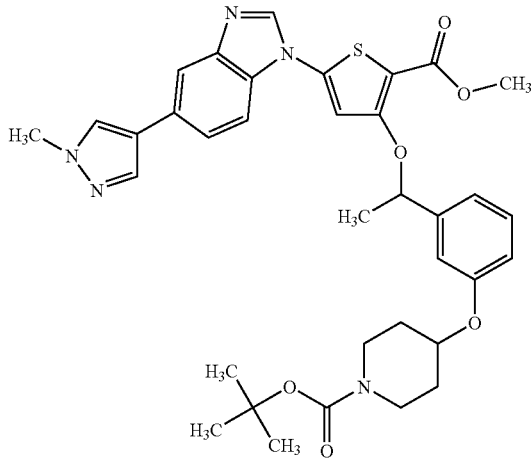

Methyl 3-hydroxy-5-[5-(1-methyl-1H-pyrazol-4-yl)-1H-benzimidazol-1-yl]-2-thiophenecarboxylate (0.300 g, 0.847 mmol), (+/−)-1,1-dimethylethyl 4-{[3-(1-hydroxyethyl)phenyl]oxy}-1-piperidinecarboxylate (0.285 mmol), and triphenylphosphine (0.667 g, 2.54 mmol) were dissolved in 25 mL of DCM with stirring. Diisopropyl azodicarboxylate was added slowly dropwise via syringe. The reaction was stirred overnight, and the mixture was adsorbed onto silica gel. Purification by flash chromatography afforded 0.467 g (84%) of the title compound. $^1$H NMR (400 MHz, DMSO-d$_6$) δ 8.68 (s, 1H), 8.17 (s, 1H), 7.94 (s, 1H), 7.90 (s, 1H), 7.56 (s, 2H), 7.48 (s, 1H), 7.26 (dd, J=8.1, 7.9 Hz, 1H), 7.08 (m, 1H), 7.01 (d, J=7.9 Hz, 1H), 6.87 (dd, J=8.1, 2.2 Hz, 1H), 5.69 (q, J=6.0 Hz, 1H), 4.50 (m, 1H), 3.84 (s, 3H), 3.78 (s, 3H), 3.65-3.56 (m, 2H), 3.18-3.05 (m, 2H), 1.91-1.78 (m, 2H), 1.58 (d, J=6.2 Hz, 3H), 1.53-1.40 (m, 2H), 1.35 (s, 9H).

Step G—(+/−)-1,1-Dimethylethyl 4-({3-[1-({2-(aminocarbonyl)-5-[5-(1-methyl-1H-pyrazol-4-yl)-1H-benzimidazol-1-yl]-3-thienyl}oxy)ethyl]phenyl}oxy)-1-piperidinecarboxylate

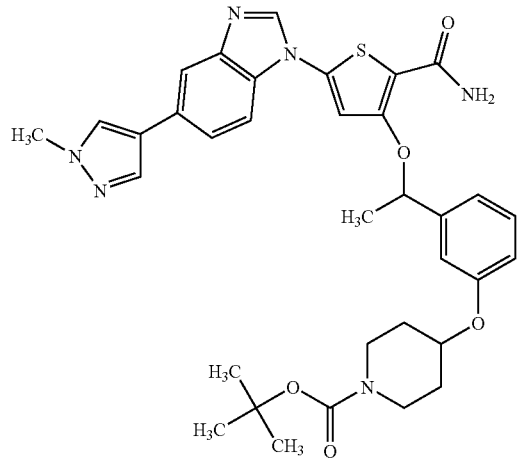

(+/−)-1,1-Dimethylethyl 4-({3-[1-({2-[(methyloxy)carbonyl]-5-[5-(1-methyl-1H-pyrazol-4-yl)-1H-benzimidazol-1-yl]-3-thienyl}oxy)ethyl]phenyl}oxy)-1-piperidinecarboxylate (0.466 g, 0.708 mmol) was placed in a pressure vessel. Ammonia solution (20 mL, 7.0N in MeOH, 140 mmol) was added and the vessel was sealed and placed in an 80° C. oil bath. The reaction was stirred at this temperature for 2.5 days and cooled to rt. The mixture was adsorbed onto silica gel. Purification by flash chromatography gave 0.379 g (83%) of the title compound. $^1$H NMR (400 MHz, DMSO-d$_6$) δ 8.52 (s, 1H), 8.17 (s, 1H), 7.93 (m, 1H), 7.90 (s, 1H), 7.77 (br s, 1H), 7.57-7.48 (m, 2H), 7.43 (s, 1H), 7.27 (dd, J=8.1, 7.9 Hz, 1H), 7.15-7.08 (m, 2H), 7.06 (d, J=7.9 Hz, 1H), 6.88 (dd, J=8.1, 2.2 Hz, 1H), 5.69 (q, J=6.2 Hz, 1H), 4.51 (m, 1H), 3.84 (s, 3H), 3.67-3.57 (m, 2H), 3.15-3.03 (m, 2H), 1.92-1.77 (m, 2H), 1.67 (d, J=6.2 Hz, 3H), 1.64-1.35 (m, 2H), 1.35 (s, 9H).

Step H—(+/−)-5-[5-(1-Methyl-1H-pyrazol-4-yl)-1H-benzimidazol-1-yl]-3-({1-[3-(4-piperidinyloxy)phenyl]ethyl}oxy)-2-thiophenecarboxamide (Title Compound)

(+/−)-1,1-Dimethylethyl 4-({3-[1-({2-(aminocarbonyl)-5-[5-(1-methyl-1H-pyrazol-4-yl)-1H-benzimidazol-1-yl]-3-thienyl}oxy)ethyl]phenyl}oxy)-1-piperidinecarboxylate (0.378 g, 0.588 mmol) was dissolved in 12 mL of DCM with stirring and cooled to 0° C. TFA (3.0 mL, 39 mmol) was added, and the reaction was stirred for 1.5 h. The solution was pipeted onto 80 mL of aqueous 2N NaOH solution, rinsing with DCM. The mixture was extracted three times with 4:1 DCM/i-PrOH. The combined organic layers were dried over MgSO$_4$, filtered, and concentrated in vacuo. Purification by flash chromatography afforded 0.218 g (68%) of the title compound. $^1$H NMR (400 MHz, DMSO-$d_6$) δ 8.51 (s, 1H), 8.17 (s, 1H), 7.93 (m, 1H), 7.90 (s, 1H), 7.75 (br s, 1H), 7.55 (dd, J=8.4, 1.4 Hz, 1H), 7.49 (d, J=8.4 Hz, 1H), 7.42 (s, 1H), 7.26 (dd, J=8.1, 7.9 Hz, 1H), 7.11-7.06 (m, 2H), 7.04 (d, J=7.9 Hz, 1H), 6.84 (dd, J=8.1, 2.2 Hz, 1H), 5.69 (q, J=6.4 Hz, 1H), 4.34 (m, 1H), 3.84 (s, 3H), 2.90-2.81 (m, 2H), 2.53-2.43 (m, 2H), 1.88-1.76 (m, 2H), 1.67 (d, J=6.4 Hz, 3H), 1.42-1.26 (m, 2H). MS (APCI): 543 [M+H]$^+$.

EXAMPLE 74

(+/−)-3-[(1-{3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide

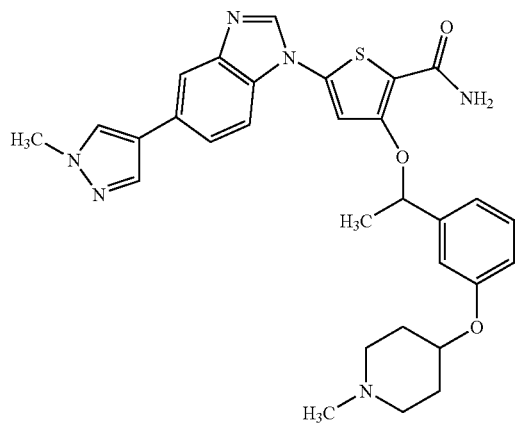

(+/−)-5-[5-(1-Methyl-1H-pyrazol-4-yl)-1H-benzimidazol-1-yl]-3-({1-[3-(4-piperidinyloxy)phenyl]ethyl}oxy)-2-thiophenecarboxamide (0.108 g, 0.199 mmol) was dissolved in 9 mL of DCM and 4.5 mL of MeOH with stirring. Acetic acid solution (0.24 mL, 1.0M in DCM, 0.24 mmol) and formaldehyde solution (0.030 mL, 37% in water, 0.40 mmol) were added. Sodium triacetoxyborohydride (0.0633 g, 0.299 mmol) was added in a single portion. The reaction was stirred for 1.5 h and poured into 1N aqueous NaOH solution. The mixture was extracted three times with 4:1 DCM/i-PrOH. The combined organic layers were dried over MgSO$_4$, filtered, and concentrated in vacuo. The solid was triturated with 1:1 ether/hexanes, filtered, and washed with hexanes. The solid was dried and collected to afford 0.099 g (90%) of the title compound. $^1$H NMR (400 MHz, DMSO-$d_6$) δ 8.51 (s, 1H), 8.17 (s, 1H), 7.93 (m, 1H), 7.90 (s, 1H), 7.75 (br s, 1H), 7.55 (dd, J=8.6, 1.5 Hz, 1H), 7.49 (d, J=8.6 Hz, 1H), 7.42 (s, 1H), 7.26 (dd, J=7.9, 7.9 Hz, 1H), 7.12-7.07 (m, 2H), 7.05 (d, J=7.9 Hz, 1H), 6.85 (dd, J=7.9, 2.2 Hz, 1H), 5.69 (q, J=6.4 Hz, 1H), 4.30 (m, 1H), 3.84 (s, 3H), 2.57-2.43 (m, 2H), 2.09 (s, 3H), 2.10-2.00 (m, 2H), 1.88-1.78 (m, 2H), 1.67 (d, J=8.4 Hz, 3H), 1.60-1.47 (m, 2H). MS (ESI): 557 [M+H]$^+$.

EXAMPLE 75

(+/−)-3-({1-[2-Fluoro-3-(4-piperidinyloxy)phenyl]ethyl}oxy)-5-[5-(1-methyl-1H-pyrazol-4-yl)-1H-benzimidazol-1-yl]-2-thiophenecarboxamide

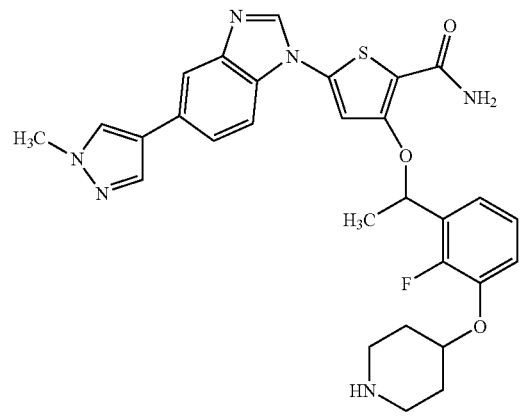

Step A—2-Fluoro-3-(hydroxymethyl)phenol

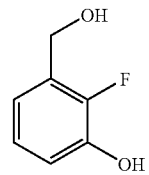

Reduction of 2-fluoro-3-hydroxybenzaldehyde (Kirk, K. L., et. al. *J. Med. Chem.* 1986, 29, 1982) with sodium borohydride would provide the title compound.

Step B—3-({[(1,1-Dimethylethyl)(diphenyl)silyl]oxy}methyl)-2-fluorophenol

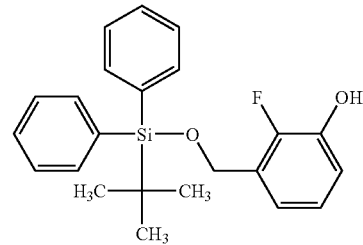

2-Fluoro-3-(hydroxymethyl)phenol (2.87 g, 20.2 mmol) was dissolved in 100 mL of DCM and 10 mL of N,N-DMF with stirring and cooled to 0° C. Triethylamine (6.20 mL, 44.5 mmol) and 4-(dimethylamino)pyridine (5.43 g, 44.4 mmol) were added and the mixture was stirred for 10 min. Tert-butylchlorodiphenylsilane (5.25 mL, 20.2 mmol) was added and the solution was allowed to reach rt slowly. The mixture was stirred for 4 h and poured into 1N HCl solution. The layers were separated, and the aqueous layer was washed with EtOAc. The combined organic layers were dried over MgSO$_4$, filtered, and concentrated in vacuo. Purification by flash chromatography afforded 5.31 g (69%) of the title compound. $^1$H NMR (400 MHz, DMSO-$d_6$) δ 9.74 (s, 1H), 7.63-7.58 (m, 4H), 7.46-7.37 (m, 8H), 7.00-6.81 (m, 3H), 4.73 (s, 2H), 0.99 (s, 9H).

Step C—1,1-Dimethylethyl 4-{[3-({[(1,1-dimethylethyl)(diphenyl)silyl]-oxy}methyl)-2-fluorophenyl]oxy}-1-piperidinecarboxylate

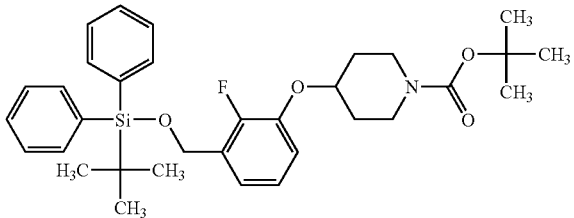

Title compound was prepared from 3-({[(1,1-Dimethylethyl)(diphenyl)silyl]-oxy}methyl)-2-fluorophenol (5.31 g, 14.0 mmol) using a procedure analogous to Example 73, Step B (6.34 g, 80%). ¹H NMR (300 MHz, DMSO-d₆) δ 7.70-7.63 (m, 4H), 7.55-7.43 (m, 8H), 7.25-7.11 (m, 3H), 4.81 (s, 2H), 4.56 (m, 1H), 3.73-3.62 (m, 2H), 3.26-3.13 (m, 2H), 1.97-1.86 (m, 2H), 1.63-1.48 (m, 2H), 1.43 (s, 9H), 1.05 (s, 9H).

Step D—1,1-Dimethylethyl 4-{[2-fluoro-3-(hydroxymethyl)phenyl]oxy}-1-piperidinecarboxylate

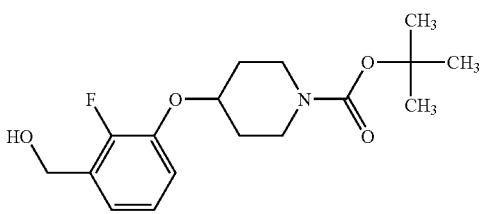

1,1-Dimethylethyl 4-{[3-({[(1,1-dimethylethyl)(diphenyl)silyl]-oxy}methyl)-2-fluorophenyl]oxy}-1-piperidinecarboxylate (6.34 g, 11.2 mmol) was dissolved in 80 mL of THF with stirring. Tetrabutylammonium fluoride (13.4 mL, 1M in THF, 13.4 mmol) was added via syringe. The reaction was stirred for 2 h and poured into 0.5 M sodium hydrogensulfate solution and EtOAc. The layers were separated and the organic layer was washed with brine. The combined organic layers were washed with EtOAc. The combined organic layers were dried over MgSO₄, filtered, and concentrated in vacuo. Purification by flash chromatography afforded 3.42 g (94%) of the title compound. ¹H NMR (400 MHz, DMSO-d₆) δ 7.13-6.96 (m, 3H), 5.19 (t, J=5.7 Hz, 1H), 4.49 (m, 1H), 4.49 (d, J=5.7 Hz, 2H), 3.66-3.56 (m, 2H), 3.20-3.08 (m, 2H), 1.90-1.80 (m, 2H), 1.56-1.44 (m, 2H), 1.37 (s, 9H).

Step E—1,1-Dimethylethyl 4-[(2-fluoro-3-formylphenyl)oxy]-1-piperidinecarboxylate

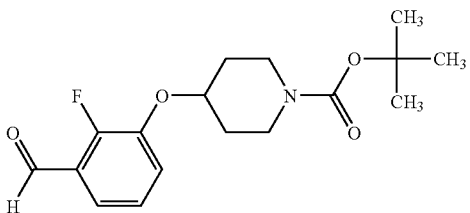

Oxalyl chloride (2.06 mL, 2M in DCM, 4.12 mmol) was added to 10 mL of DCM and cooled to −78° C. Dimethyl sulfoxide (0.59 mL, 8.31 mmol) was added slowly dropwise via syringe. The reaction was stirred for 5 min. 1,1-Dimethylethyl 4-{[2-fluoro-3-(hydroxymethyl)phenyl]oxy}-1-piperidinecarboxylate (0.895 g, 2.75 mmol) was dissolved in 10 mL of DCM and added slowly via syringe. The reaction was stirred for 30 min. Triethylamine (1.92 mL, 13.8 mmol) was added dropwise via syringe, and the cold bath was taken away. The reaction was allowed to reach rt slowly. The mixture was poured Into half-saturated NaHCO₃ solution and 1:1EtOAc/ether. The layers were separated, and the organic layer was washed with brine. The combined aqueous layers were extracted with EtOAc. The combined organic layers were dried over MgSO₄, filtered, and concentrated in vacuo. Purification by flash chromatography gave 0.827 g (93%) of the title compound. ¹H NMR (400 MHz, DMSO-d₆ δ 10.18 (s, 1H), 7.57 (m, 1H), 7.36 (m, 1H), 7.26 (m, 1H), 4.61 (m, 1H), 3.67-3.57 (m, 2H), 3.21-3.10 (m, 2H), 1.94-1.84 (m, 2H), 1.59-1.48 (m, 2H), 1.37 (s, 9H).

Step F—(+/−)-1,1-Dimethylethyl 4-{[2-fluoro-3-(1-hydroxyethyl)phenyl]-oxy}-1-piperidinecarboxylate

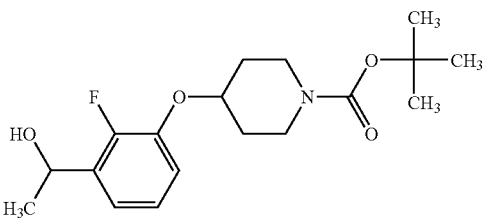

Title compound was prepared from 1,1-dimethylethyl 4-[(2-fluoro-3-formylphenyl)oxy]-1-piperidinecarboxylate (0.826 g, 2.55 mmol) using a procedure analogous to Example 73, Step E (0.820 g, 95%). ¹H NMR (400 MHz, DMSO-d₆) δ 7.09-7.01 (m, 3H), 5.22 (d, J=4.4 Hz, 1H), 4.93 (m, 1H), 4.48 (m, 1H), 3.66-3.56 (m, 2H), 3.21-3.07 (m, 2H), 1.91-1.81 (m, 2H), 1.56-1.44 (m, 2H), 1.37 (s, 9H), 1.28 (d, J=6.4 Hz, 3H).

Step G—(+/−)-1,1-Dimethylethyl 4-({2-fluoro-3-[1-({2-[(methyloxy)carbonyl]-5-[5-(1-methyl-1H-pyrazol-4-yl)-1H-benzimidazol-1-yl]-3-thienyl}oxy)ethyl]phenyl}oxy)-1-piperidinecarboxylate

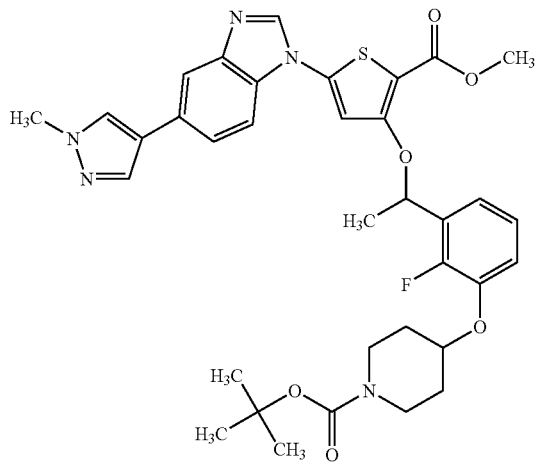

Reaction of (+/−)-1,1-dimethylethyl 4-{[2-fluoro-3-(1-hydroxyethyl)phenyl]-oxy}-1-piperidinecarboxylate (0.819 g, 2.41 mmol) and methyl 3-hydroxy-5-[5-(1-methyl-1H-pyrazol-4-yl)-1H-benzimidazol-1-yl]-2-thiophenecarboxylate (0.750 g, 2.12 mmol) using a procedure analogous to that described In Example 73, Step F afforded 1.36 g (95%) of the title compound. ¹H NMR (400 MHz, OMSO-d₆) δ 8.64 (s, 1H), 8.19 (s, 1H), 7.96 (s, 1H), 7.92 (s, 1H), 7.66 (d, J=8.4 Hz, 1H), 7.59 (dd, J=8.6, 1.5 Hz, 1H), 7.53 (s, 1H), 7.22-7.13 (m, 3H), 5.94 (q, J=6.4 Hz, 1H), 4.64 (m, 1H), 3.86 (s, 3H), 3.80 (s, 3H), 3.67-3.56 (m, 2H), 3.20-3.07 (m, 2H), 1.94-1.79 (m, 2H), 1.63 (d, J=6.4 Hz, 3H), 1.57-1.44 (m, 2H), 1.37 (s, 9H).

Step H—(+/−)-1,1-Dimethylethyl 4-({3-[1-({2-(aminocarbonyl)-5-[5-(1-methyl-1H-pyrazol-4-yl)-1H-benzimidazol-1-yl]-3-thienyl}oxy)ethyl]-2-fluorophenyl}oxy)-1-piperidinecarboxylate

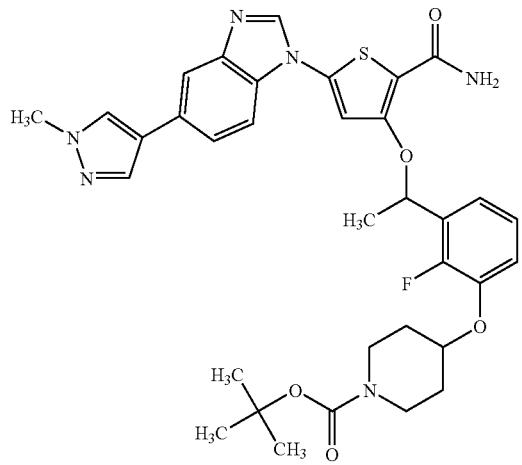

Reaction of (+/−)-1,1-Dimethylethyl 4-({2-fluoro-3-[1-({2-[(methyloxy)carbonyl]-5-[5-(1-methyl-1H-pyrazol-4-yl)-1H-benzimidazol-1-yl]-3-thienyl}oxy)ethyl]phenyl}oxy)-1-piperidinecarboxylate (1.36 g, 2.01 mmol) using a procedure analogous to that described in Example 73, Step G afforded 0.904 g (68%) of the title compound. $^1$H NMR (400 MHz, DMSO-$d_6$) δ 8.54 (s, 1H), 8.17 (s, 1H), 7.94 (s, 1H), 7.90 (s, 1H), 7.78 (br s, 1H), 7.58-7.54 (m, 2H), 7.42 (s, 1H), 7.25-7.10 (m, 3H), 7.02 (br s, 1H), 5.92 (q, J=6.4 Hz, 1H), 4.52 (m, 1H), 3.84 (s, 3H), 3.66-3.54 (m, 2H), 3.18-3.04 (m, 2H), 1.92-1.79 (m, 2H), 1.71 (d, J=6.4 Hz, 3H), 1.56-1.43 (m, 2H), 1.35 (s, 9H).

Step I—(+/−)-3-({1-[2-Fluoro-3-(4-piperidinyloxy)phenyl]ethyl}oxy)-5-[5-(1-methyl-1H-pyrazol-4-yl)-1H-benzimidazol-1-yl]-2-thiophenecarboxamide (Title Compound)

Reaction of (+/−)-1,1-dimethylethyl 4-({3-[1-({2-(aminocarbonyl)-5-[5-(1-methyl-1H-pyrazol-4-yl)-1H-benzimidazol-1-yl]-3-thienyl}oxy)ethyl]-2-fluorophenyl}oxy)-1-piperidinecarboxylate (0.903 g, 1.37 mmol) using a procedure analogous to that described in Example 73, Step H afforded 0.656 g (85%) of the title compound. $^1$H NMR (400 MHz, DMSO-$d_6$) δ 8.56 (s, 1H), 8.19 (s, 1H), 7.96 (s, 1H), 7.92 (s, 1H), 7.80 (br s, 1H), 7.68 (s, 2H), 7.43 (s, 1H), 7.21-7.10 (m, 3H), 7.04 (br s, 1H), 5.93 (q, J=6.2 Hz, 1H), 4.37 (m, 1H), 3.86 (s, 3H), 2.95-2.82 (m, 2H), 2.55-2.43 (m, 2H), 1.92-1.80 (m, 2H), 1.72 (d, J=6.2 Hz, 3H), 1.50-1.35 (m, 2H). MS (ESI): 561 [M+H]$^+$.

EXAMPLE 76

(+/−)-3-[(1-{2-Fluoro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide

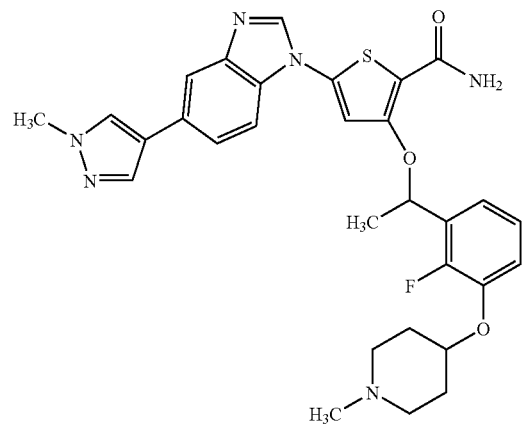

Reaction of (+/−)-3-({1-[2-fluoro-3-(4-piperidinyloxy)phenyl]ethyl}oxy)-5-[5-(1-methyl-1H -pyrazol-4-yl)-1H-benzimidazol-1-yl]-2-thiophenecarboxamide (Example 75, 0.362 g, 0.646 mmol) using a procedure analogous to that described In Example 74 afforded 0.311 g (84%) of the title compound. $^1$H NMR (400 MHz, DMSO-$d_6$) δ 8.53 (s, 1H), 8.16 (s, 1H), 7.93 (s, 1H), 7.90 (s, 1H), 7.77 (s, 1H), 7.56 (s, 2H), 7.40 (s, 1H), 7.19-7.09 (m, 3H), 7.02 (br s, 1H), 5.91 (q, J=6.2 Hz, 1H), 4.32 (m, 1H), 3.84 (s, 3H), 2.57-2.42 (m, 2H), 2.12-1.98 (m, 2H), 2.08 (s, 3H), 1.90-1.77 (m, 2H), 1.70 (d, J=6.2 Hz, 3H), 1.65-1.51 (m, 2H). MS (ESI): 575 [M+H]$^+$.

EXAMPLE 77

(+/−)-5-[5-(1-Methyl-1H -pyrazol-4-yl)-1H-benzimidazol-1-yl]-3-({1-[2-(4-piperidinyloxy)-4-pyrimidinyl]ethyl}oxy)-2-thiophenecarboxamide

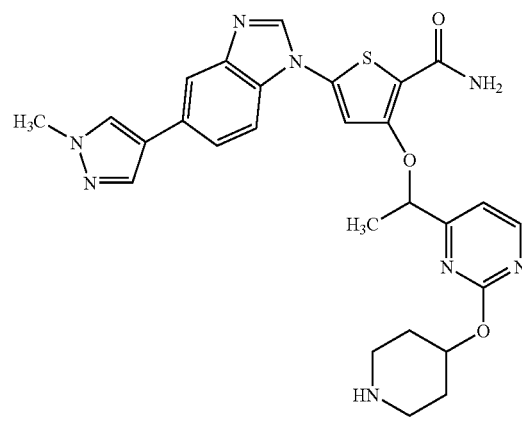

Step A—4-[Bis(methyloxy)methyl]-2-(methylsulfonyl)pyrimidine

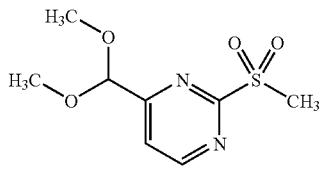

4-[Bis(methyloxy)methyl]-2-(methylthio)pyrimidine (U.S. Pat. No. 6,218,537, 2001) (9.24 g, 46.1 mmol) was dissolved in 150 mL of DCM and cooled to 0° C. with stirring. 3-Chloroperoxybenzoic acid (23.87 g, 70%, 96.8 mmol) was added in a single portion. The reaction was allowed to reach rt slowly. The reaction was stirred 2 h and quenched by the addition of 150 mL of 10% sodium sulfite solution. The mixture was poured into a separatory funnel and the layers were separated. The organic layer was washed with 150 mL of 10% Na$_2$CO$_3$ solution (2×) and brine (1×). The organic layer was dried over MgSO$_4$, filtered, and concentrated in vacuo. Purification by flash chromatography afforded 10.25 g (96%) of the title compound. $^1$H NMR (400 MHz, CDCl$_3$) δ 8.96 (d, J=4.9 Hz, 1H), 7.78 (d, J=4.9 Hz, 1H), 5.34 (s, 1H), 3.46 (s, 6H), 3.38 (s, 3H).

Step B—2-Propen-1-yl 4-hydroxy-1-piperidinecarboxylate

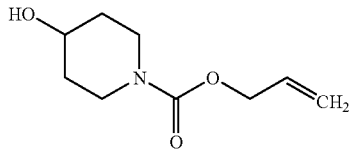

4-Hydroxypiperidine (5.00 g, 49.4 mmol) was dissolved in 150 mL of DCM with stirring. Triethylamine (10.3 mL, 73.9 mmol) was added, and the solution was cooled to 0° C. Allyl chloroformate (8.30 mL, 59.4 mmol) was added dropwise via addition funnel over 20 min. The reaction was stirred for an additional 30 min and poured into 1N HCl solution. The layers were separated, and the aqueous layer was washed with EtOAc. The combined organic layers were dried over MgSO$_4$, filtered, and concentrated in vacuo. Purification by flash chromatography gave 7.81 g (85%) of the title compound.

$^1$H NMR (400 MHz, DMSO-d$_6$) δ 5.90 (m, 1H), 5.28-5.13 (m, 2H), 4.72 (d, J=4.0 Hz, 1H), 4.51-4.46 (m, 2H), 3.73-3.64 (m, 2H), 3.62 (m, 1H), 3.15-2.94 (m, 2H), 1.72-1.63 (m, 2H), 1.30-1.19 (m, 2H).

Step C—2-Propen-1-yl 4-({4-[bis(methyloxy)methyl]-2-pyrimidinyl}oxy)-1-piperidinecarboxylate

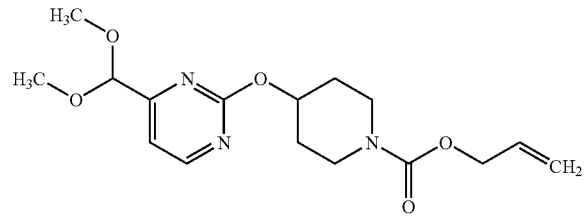

Sodium hydride (1.69 g, 60% dispersion in mineral oil, 42.3 mmol) was washed with hexanes (2×), and 40 mL of dry THF was added, 2-Propen-1-yl 4-hydroxy-1-piperidinecarboxylate (7.81 g, 42.2 mmol) was dissolved in 20 mL of THF and added dropwise via addition funnel, The addition funnel was rinsed with 10 mL of THF. The mixture was stirred for 45 min, 4-[Bis(methyloxy)methyl]-2-(methylsulfonyl)pyrimidine (6.53 g, 28.1 mmol) was dissolved in 20 mL of THF and added via addition funnel. The addition funnel was rinsed with 10 mL of THF. The reaction was stirred for 3 h and quenched by the addition of water. The mixture was poured into water and EtOAc, and the layers were separated. The organic layer was washed with brine, and the combined aqueous layers were extracted with EtOAc. The combined organic layers were dried over MgSO$_4$, filtered, and concentrated in vacuo. Purification by flash chromatography provided 8.39 g (89%) of the title compound. $^1$H NMR (400 MHz, DMSO-d$_6$) δ 8.63 (d, J=4.9 Hz, 1H), 7.15 (d, J=4.9 Hz, 1H), 5.93 (m, 1H), 5.30-5.15 (m, 2H), 5.16 (s, 1H), 5.14 (m, 1H), 4.54-4.50 (m, 2H), 3.75-3.65 (m, 2H), 3.39-3.21 (m, 2H), 3.31 (s, 6H), 2.03-1.92 (m, 2H), 1.69-1.57 (m, 2H).

Step D—2-Propen-1-yl 4-{[4-(hydroxymethyl)-2-pyrimidinyl]oxy}-1-piperidinecarboxylate

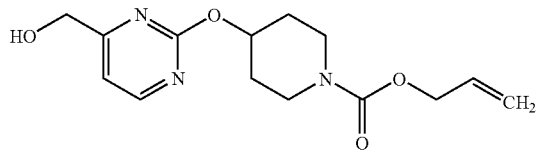

2-Propen-1-yl 4-({4-[bis(methyloxy)methyl]-2-pyrimidinyl}oxy)-1-piperidinecarboxylate (8.39 g, 24.9 mmol) was dissolved in 100 mL of THF with stirring. 100 mL of 2N HCl was added. The mixture was stirred for 4 h and then placed in a 50° C. oil bath. The reaction was stirred at that temperature for 8 h and cooled to rt. The reaction was stirred an additional 12 h at rt. The mixture was cooled to 0° C., and quenched by portionwise addition of solid NaHCO$_3$ until the pH was basic. The mixture was poured into water and EtOAc, and the layers were separated. The organic layer was washed with brine, and the combined aqueous layers were extracted with EtOAc. The combined organic layers were dried over MgSO$_4$, filtered, and concentrated in vacuo. The residue was dissolved in 60 mL of THF and 60 mL of EtOH with stirring. Sodium borohydride (1.88 g, 49.7 mmol) was added in a single portion. The reaction was stirred for 1 h and quenched with 2N NaOH solution. The mixture was poured into water and EtOAc, and the layers were separated. The organic layer was washed with brine, and the combined aqueous layers were extracted with EtOAc. The combined organic layers were dried over MgSO$_4$, filtered, and concentrated in vacuo. Purification by flash chromatography afforded 2.63 g (36%) of the title compound. $^1$H NMR (400 MHz, DMSO-d$_6$) δ 8.54 (d, J=4.9 Hz, 1H), 7.15 (d, J=4.9 Hz, 1H), 5.92 (m, 1H), 5.58 (t, J=6.0 Hz, 1H), 5.31-5.14 (m, 2H), 5.12 (m, 1H), 4.55-4.49 (m, 2H), 4.44 (d, J=6.0 Hz, 2H), 3.76-3.64 (m, 2H), 3.38-3.19 (m, 2H), 2.01-1.90 (m, 2H), 1.66-1.53 (m, 2H).

Step E—1,1-Dimethylethyl 4-{[4-(hydroxymethyl)-2-pyrimidinyl]oxy}-1-piperidinecarboxylate

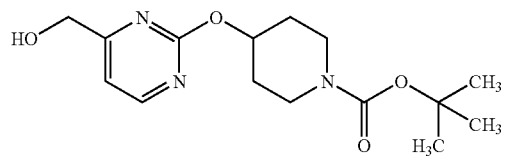

2-Propen-1-yl 4-{[4-(hydroxymethyl)-2-pyrimidinyl]oxy}-1-piperidinecarboxylate (0.768 g, 2.62 mmol) and di-tert-butyl-dicarbonate (1.43 g, 6.55 mmol) were dissolved in 20 mL of DCM with stirring. The solution was degassed with $N_2$ for 10 min. Tributyltin hydride (1.06 mL, 3.94 mmol) was added via syringe. Tetrakis(triphenylphosphine)palladium (0) (0.151 g, 0.131 mmol) was added in a single portion. The reaction was stirred for 2 h and adsorbed onto silica gel. Purification by flash chromatography gave 0.573 g (71%) of the title compound. $^1$H NMR (400 MHz, DMSO-$d_6$) δ 8.52 (d, J=5.0 Hz, 1H), 7.14 (d, J=5.0 Hz, 1H), 5.56 (t, J=5.9 Hz, 1H), 5.09 (m, 1H), 4.42 (d, J=5.9 Hz, 2H), 3.67-3.58 (m, 2H), 3.23-3.08 (m, 2H), 1.97-1.85 (m, 2H), 1.60-1.47 (m, 2H), 1.37 (s, 9H).

Step F—1,1-Dimethylethyl 4-[(4-formyl-2-pyrimidinyl)oxy]-1-piperidinecarboxylate

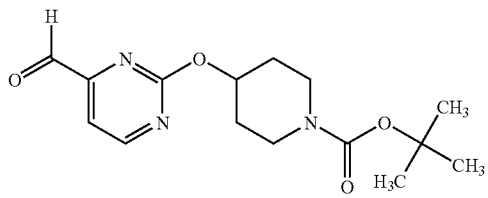

Reaction of 1,1-dimethylethyl 4-{[4-(hydroxymethyl)-2-pyrimidinyl]oxy}-1-piperidinecarboxylate (0.572 g, 1.85 mmol) using a procedure analogous to that described in Example 75, Step E afforded 0.545 g (96%) of the title compound. $^1$H NMR (400 MHz, DMSO-$d_6$) δ 9.80 (s, 1H), 8.88 (d, J=5.0 Hz, 1H), 7.47 (d, J=5.0 Hz, 1H), 5.20 (m, 1H), 3.70-3.60 (m, 2H), 3.27-3.10 (m, 2H), 2.02-1.88 (m, 2H), 1.67-1.52 (m, 2H), 1.38 (s, 9H).

Step G—(+/−)-1,1-Dimethylethyl 4-{[4-(1-hydroxyethyl)-2-pyrimidinyl]oxy}-1-piperidinecarboxylate

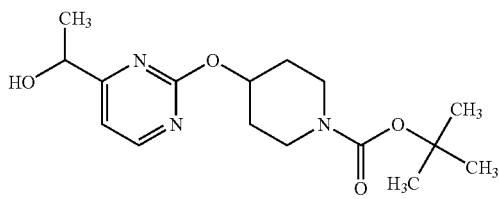

Reaction of 1,1-dimethylethyl 4-[(4-formyl-2-pyrimidinyl)oxy]-1-piperidinecarboxylate (0.544 g, 1.77 mmol) using a procedure analogous to that described in Example 73, Step E afforded 0.391 g (68%) of the title compound. $^1$H NMR (400 MHz, DMSO-$d_6$) δ 8.61 (d, J=5.1 Hz, 1H), 7.16 (d, J=5.1 Hz, 1H), 5.51 (d, J=4.8 Hz, 1H), 5.08 (m, 1H), 4.53 (m, 1H), 3.70-3.60 (m, 2H), 3.21-3.09 (m, 2H), 1.97-1.87 (m, 2H), 1.60-1.48 (m, 2H), 1.37 (s, 9H), 1.31 (d, J=6.8 Hz, 3H).

Step H—(+/−)-1,1-Dimethylethyl 4-({4-[1-({2-[(methyloxy)carbonyl]-5-[5-(1-methyl-1H-pyrazol-4-yl)-1H-benzimidazol-yl]-3-thienyl}oxy)ethyl]-2-pyrimidinyl}oxy)-1-piperidinecarboxylate

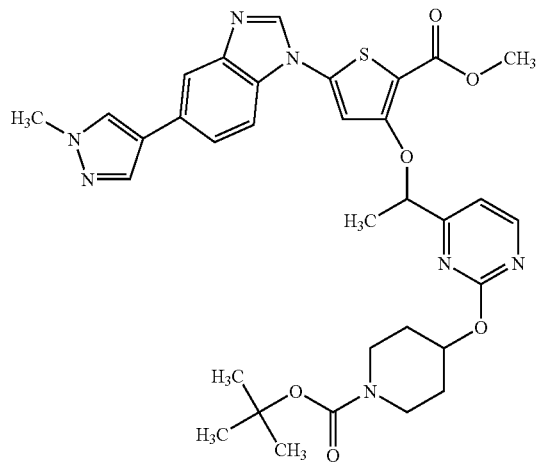

Reaction of (+/−)-1,1-dimethylethyl 4-{[4-(1-hydroxyethyl)-2-pyrimidinyl]oxy}-1-piperidinecarboxylate (0.390 g, 1.21 mmol) and methyl 3-hydroxy-5-[5-(1-methyl-1H-pyrazol-4-yl)-1H-benzimidazol-1-yl]-2-thiophenecarboxylate (0.390 g, 1.10 mmol) using a procedure analogous to that described in Example 73, Step F afforded 0.654 g (90%) of the title compound, $^1$H NMR (400 MHz, DMSO-$d_6$) δ 8.67-8.64 (m, 2H), 8.19 (s, 1H), 7.97 (d, J=1.6 Hz, 1H), 7.92 (s, 1H), 7.74 (d, J=8.4 Hz, 1H), 7.62-7.58 (m, 2H), 7.37 (d, J=5.1 Hz, 1H), 5.65 (q, J=6.5 Hz, 1H), 5.10 (m, 1H), 3.86 (s, 3H), 3.82 (s, 3H), 3.71-3.61 (m, 2H), 3.20-3.08 (m, 2H), 1.99-1.86 (m, 2H), 1.65 (d, J=6.5 Hz, 3H), 1.62-1.50 (m, 2H), 1.38 (s, 9H).

Step I—1,1-Dimethylethyl 4-({4-[1-({2-(aminocarbonyl)-5-[5-(1-methyl-1H-pyrazol-4-yl)-1H-benzimidazol-1-yl]-3-thienyl}oxy)ethyl]-2-pyrimidinyl}oxy)-1-piperidinecarboxylate

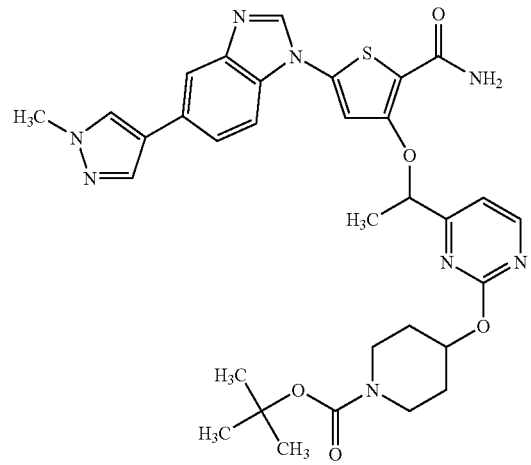

Reaction of (+/−)-1,1-dimethylethyl 4-({4-[1-({2-[(methyloxy)carbonyl]-5-[5-(1-methyl-1H-pyrazol-4-yl)-1H-benzimidazol-1-yl]-3-thienyl}oxy)ethyl]-2-pyrimidinyl}oxy)-1-piperidinecarboxylate (0.653 g, 0.990 mmol) using a procedure analogous to that described in Example 73, Step G afforded 0.610 g (96%) of the title compound. $^1$H NMR (400 MHz, DMSO-d$_6$) δ 8.61 (d, J=5.0 Hz, 1H), 8.54 (s, 1H), 8.17 (s, 1H), 7.93 (m, 1H), 7.90 (s, 1H), 7.84 (br s, 1H), 7.62 (d, J=8.4 Hz, 1H), 7.56 (dd, J=8.4, 1.4 Hz, 1H), 7.45 (s, 1H), 7.23 (d, J=5.0 Hz, 1H), 7.20 (br s, 1H), 5.71 (q, J=6.4 Hz, 1H), 5.07 (m, 1H), 3.84 (s, 3H), 3.68-3.58 (m, 2H), 3.19-3.05 (m, 2H), 1.97-1.81 (m, 2H), 1.67 (d, J=6.4 Hz, 3H), 1.61-1.44 (m, 2H), 1.36 (s, 9H).

Step J—(+/−)-5-[5-(1-Methyl-1H -pyrazol-4-yl)-1H-benzimidazol-1-yl]-3-({1-[2-(4-piperidinyloxy)-4-pyrimidinyl]ethyl}oxy)-2-thiophenecarboxamide (Title Compound)

Reaction of (+/−)-1,1-dimethylethyl 4-({4-[1-({2-(aminocarbonyl)-5-[5-(1-methyl-1H-pyrazol-4-yl)-1H-benzimidazol-1-yl]-3-thienyr}oxy)ethyl]-2-pyrimldinyl}oxy)-1-piperidinecarboxylate (0.609 g, 0.945 mmol) using a procedure analogous to that described in Example 73, Step H afforded 0.455 g (88%) of the title compound. $^1$H NMR (400 MHz, DMSO-d6) δ 8.61 (d, J=5.1 Hz, 1H), 8.55 (s, 1H), 8.19 (s, 1H), 7.95 (d, J=1.3 Hz, 1H), 7.92 (d, J=0.6 Hz, 1H), 7.84 (br s, 1H), 7.64 (d, J=8.5 Hz, 1H), 7.58 (dd, J=8.5 Hz, 1.3 Hz, 1H), 7.46 (s, 1H), 7.23 (d, J=5.1 Hz, 1H), 7.18 (br s, 1H), 5.71 (q, J=6.4 Hz, 1H), 4.97 (m, 1H), 3.86 (s, 3H), 2.97-2.89 (m, 2H), 2.62-2.52 (m, 2H), 1.98-1.83 (m, 2H), 1.70 (d, J=6.4 Hz, 3H), 1.58-1.41 (m, 2H). MS (ESI): 545 [M+H]$^+$.

EXAMPLE 78

(+/−)-3-[(1-{2-[(1-methyl-4-piperidinyl)oxy]-4-pyrimidinyl}ethyl)oxy]-5-[5-(1-methyl-1H-pyrazol-4-yl)-1H-benzimidazol-1-yl]-2-thiophenecarboxamide

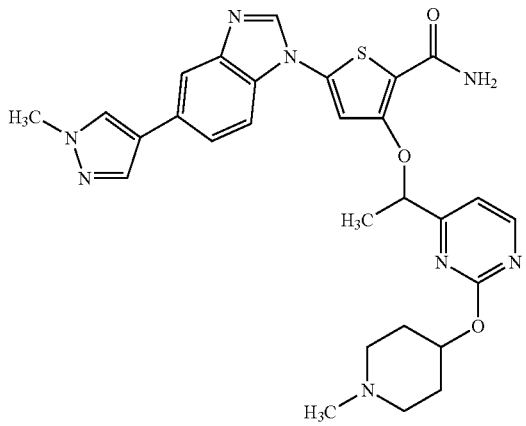

Reaction of (+/−)-5-[5-(1-methyl-1H-pyrazol-4-yl)-1H-benzimidazol-1-yl]-3-({1-[2-(4-piperidinyloxy)-4-pyrimidinyl]ethyl}oxy)-2-thiophenecarboxamide (Example 77, 0.236 g, 0.433 mmol) using a procedure analogous to that described in Example 74 afforded 0.231 g (95%) of the title compound. $^1$H NMR (400 MHz, DMSO-d$_6$) δ 8.63 (d, J=4.9 Hz, 1H), 8.56 (s, 1H), 8.19 (s, 1H), 7.96 (d, J=1.4 Hz, 1H), 7.92 (s, 1H), 7.84 (br s, 1H), 7.65 (d, J=8.6 Hz, 1H), 7.59 (dd, J=8.6, 1.4 Hz, 1H), 7.46 (s, 1H), 7.24 (d, J=4.9 Hz, 1H), 7.17 (br s, 1H), 5.71 (q, J=6.4 Hz, 1H), 4.90 (m, 1H), 3.86 (s, 3H), 2.66-2.51 (m, 2H), 2.21-2.06 (m, 2H), 2.15 (s, 3H), 1.99-1.84 (m, 2H), 1.74-1.58 (m, 2H), 1.70 (d, J=6.4 Hz, 3H). MS (ESI): 559 [M+H]$^+$.

EXAMPLE 79

(+/−)-5-[5-(1-Methyl-1H-pyrazol-4-yl)-1H-benzimidazol-1-yl]-3-({1-[2-(4-piperidinyloxy)-4-pyridinyl]ethyl}oxy)-2-thiophenecarboxamide

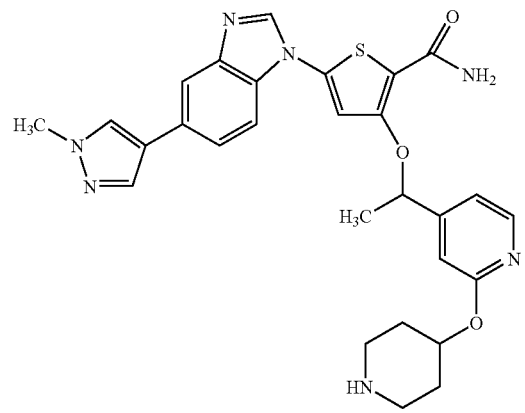

Step A—2-Fluoro-4-({[tris(1-methylethyl)silyl]oxy}methyl)pyridine

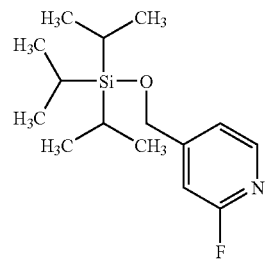

(2-Fluoro-4-pyridinyl)methanol (Pesti, J. A., et. al. *J. Org. Chem.* 2000, 65, 7718) (2.59 g, 20.4 mmol) was dissolved in 100 mL of DCM with stirring. Imidazole (3.06 g, 44.9 mmol) was added in a single portion. Triisopropylsilyl chloride (4.80 mL, 22.4 mmol) was added via syringe. The reaction was stirred for 2 h, and imidazole (1.00 g, 14.7 mmol) and triisopropylsilyl chloride (0.50 mL, 2.3 mmol) were added. The reaction was stirred an additional 1 h and poured Into water. The layers were separated, and the aqueous layer was washed with EtOAc, The DCM layer was washed with brine, and the combined aqueous layers were extracted with EtOAc. The combined organic layers were dried over MgSO$_4$, filtered, and concentrated in vacua Purification by flash chromatography afforded 6.07 g (>90 % pure) of the title compound. $^1$H NMR (400 MHz, DMSO-d$_6$ δ 8.17 (d, 75.1 Hz, 1H), 7.28 (m, 1H), 7.03 (s, 1H), 4.87 (s, 2H), 1.20-1.06 (m, 3H), 1.02 (d, J=7.1 Hz, 18H).

Step B—1,1-Dimethylethyl 4-{[4-({[tris(1-methylethyl)silyl]oxy}methyl)-2-pyridinyl]oxy}-1-piperidinecarboxylate

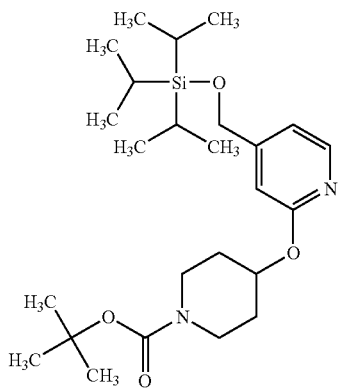

Sodium hydride (1.63 g, 60% dispersion in mineral oil, 40.8 mmol) was washed with hexanes (2×), and 60 mL of dry THF was added, t-Butyl 4-hydroxy-1-piperidinecarboxylate (8.21 g, 40.8 mmol) was dissolved in 30 mL of THF and added dropwise via addition funnel. The addition funnel was rinsed with 10 mL of THF. The mixture was stirred for 45 min. 2-Fluoro-4-({[tris(1-methylethyl)silyl]oxy}methyl)pyridine (5.78 g, 20.4 mmol) was dissolved in 15 mL of THF and added via addition funnel. The addition funnel was rinsed with 5 mL of THF. The reaction was stirred for 24 h and quenched by the addition of water. The mixture was poured into water and EtOAc, and the layers were separated. The organic layer was washed with brine, and the combined aqueous layers were extracted with EtOAc. The combined organic layers were dried over MgSO$_4$, filtered, and concentrated in vacuo, Purification by flash chromatography provided 8.16 g (86%, over 2 steps) of the title compound. $^1$H NMR (400 MHz, DMSO-d$_6$) δ 8.07 (d, J=5.3 Hz, 1H), 6.90 (d, J=5.3 Hz, 1H), 6.69 (s, 1H), 5.13 (m, 1H), 4.76 (s, 2H), 3.74-3.64 (m, 2H), 3.18-3.04 (m, 2H), 1.97-1.87 (m, 2H), 1.57-1.45 (m, 2H), 1.38 (s, 9H), 1.19-1.08 (m, 3H), 1.03 (d, J=6.8 Hz, 18H).

Step C—1,1-Dimethylethyl 4-{[4-(hydroxymethyl)-2-pyridinyl]oxy}-1-piperidinecarboxylate

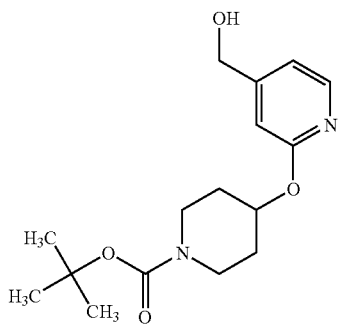

1,1-Dimethylethyl 4-{[4-({[tris(1-methylethyl)silyl]oxy}methyl)-2-pyridinyl]oxy}-1-piperidinecarboxylate (8.16 g, 17.6 mmol) was dissolved in 60 ml of THF with stirring. Tetrabutyammonium fluoride (23.0 ml, 1M in THF, 23.0 mmol) was added via syringe. The reaction was stirred for 2 h and poured into water and EtOAc. The layers were separated, and the organic layer was washed with brine. The combined aqueous layers were extracted with EtOAc. The combined organic layers were dried over MgSO$_4$, filtered, and concentrated in vacuo. Purification by flash chromatography gave 5.20 g (96%) of the title compound. $^1$H NMR (400 MHz, DMSO-d$_6$) δ 8.04 (d, J=5.3 Hz, 1H), 6.87 (m, 1H), 6.68 (s, 1H), 5.33 (t, J=5.9 Hz, 1H), 5.14 (m, 1H), 4.46 (d, J=5.9 Hz, 2H), 3.71-3.62 (m, 2H), 3.21-3.09 (m, 2H), 1.95-1.86 (m, 2H), 1.57-1.46 (m, 2H), 1.39 (s, 9H).

Step D—1,1-Dimethylethyl 4-[(4-formyl-2-pyridinyl)oxy]-1-piperidinecarboxylate

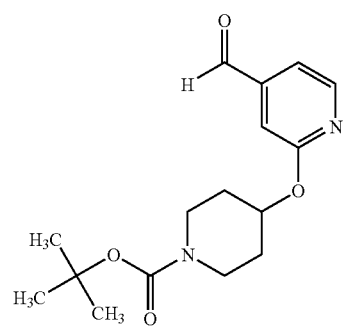

Reaction of 1,1-dimethylethyl 4-{[4-(hydroxymethyl)-2-pyridtnyl]oxy}-1-piperidinecarboxylate (0.700 g, 2.27 mmol) using a procedure analogous to that described In Example 75, Step E afforded 0.712 g (>90% pure) of the title compound. $^1$H NMR (400 MHz, DMSO-d$_6$) δ 10.00 (s, 1H), 8.88 (d, J=5.1 Hz, 1H), 7.34 (dd, J=5.1, 1.3 Hz, 1H), 7.25 (m, 1H), 5.21 (m, 1H), 3.72-3.64 (m, 2H), 3.25-3.11 (m, 2H), 1.99-1.90 (m, 2H), 1.63-1.51 (m, 2H), 1.39 (s, 9H).

Step E—(+/−)-1,1-Dimethylethyl 4-{[4-(1-hydroxyethyl)-2-pyridinyl]oxy}-1-piperidinecarboxylate

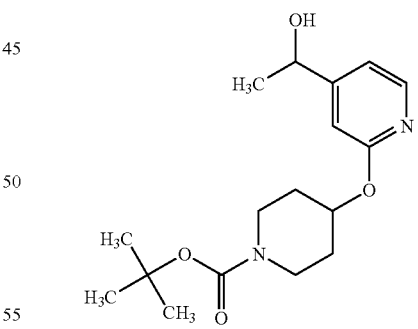

Reaction of 1,1-dimethylethyl 4-[(4-formyl-2-pyridinyl)oxy]-1-piperidinecarboxylate (0.695 g, 2.27 mmol) using a procedure analogous to that described in Example 73, Step E afforded 0.708 g (97%, over 2 steps) of the title compound. $^1$H NMR (400 MHz, DMSO-d$_6$) δ 8.01 (d, J=5.3 Hz, 1H), 6.89 (m, 1H), 6.68 (m, 1H), 5.28 (d, J=4.6 Hz, 1H), 5.12 (m, 1H), 4.62 (m, 1H), 3.69-3.60 (m, 2H), 3.20-3.05 (m, 2H), 1.94-1.84 (m, 2H), 1.55-1.44 (m, 2H), 1.37 (s, 9H), 1.26 (d, J=6.4 Hz, 3H).

Step F—(+/−)-1,1-Dimethylethyl 4-({4-[1-({2-[(methyloxy)carbonyl]-5-[5-(1-methyl-1H-pyrazol-4-yl)-1H-benzimidazol-1-yl]-3-thienyl}oxy)ethyl]-2-pyridinyl}oxy)-1-piperidinecarboxylate

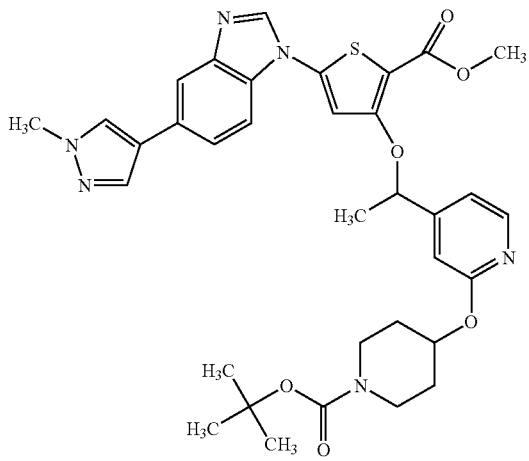

Reaction of (+/−)-1,1-dimethylethyl 4-{[4-(1-hydroxyethyl)-2-pyridinyl]oxy}-1-piperidinecarboxylate (0.705 g, 2.19 mmol) and methyl 3-hydroxy-5-[5-(1-methyl-1H-pyrazol-4-yl)-1H-benzimidazol-1-yl]-2-thiophenecarboxylate (Intermediate 16, 0.517 g, 1.46 mmol) using a procedure analogous to that described In Example 73, Step F afforded 0.759 g (79%) of the title compound. $^1$H NMR (400 MHz, DMSO-$d_6$) δ 8.62 (s, 1H), 8.19 (s, 1H), 8.15 (d, J=5.5 Hz, 1H), 7.96 (d, J=1.5 Hz, 1H), 7.92 (s, 1H), 7.67 (d, J=8.5 Hz, 1H), 7.59 (dd, J=8.5, 1.6 Hz, 1H), 7.53 (s, 1H), 7.06 (dd, J=5.3, 1.5 Hz, 1H), 6.89 (s, 1H), 5.73 (q, J=6.4 Hz, 1H), 5.14 (m, 1H), 3.86 (s, 3H), 3.81 (s, 3H), 3.72-3.63 (m, 2H), 3.20-3.06 (m, 2H), 1.96-1.86 (m, 2H), 1.59 (d, J=6.4 Hz, 3H), 1.56-1.45 (m, 2H), 1.38 (s, 9H).

Step G—(+/−)-1,1-Dimethylethyl 4-({4-[1-({2-(aminocarbonyl)-5-[5-(1-methyl-1H-pyrazol-4-yl)-1H-benzimidazol-1-yl]-3-thienyl}oxy)ethyl]-2-pyodinyl}oxy)-1-piperidinecarboxylate

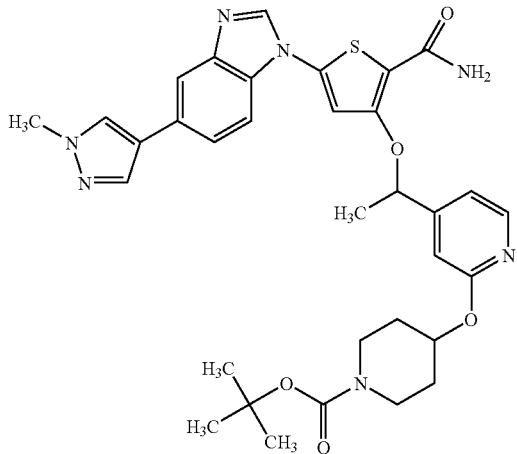

Reaction of (+/−)-1,1-dimethylethyl 4-({4-[1-({2-[(methyloxy)carbonyl]-5-[5-(1-methyl-1H-pyrazol-4-yl)-1H-benzimidazol-1-yl]-3-thienyl}oxy)ethyl]-2-pyridinyl}oxy)-1-piperidinecarboxylate (0.758 g, 1.15 mmol) using a procedure analogous to that described in Example 73, Step G afforded 0.696 g (94%) of the title compound. $^1$H NMR (400 MHz, DMSO-$d_6$) δ 8.52 (s, 1H), 8.16 (s, 1H), 8.14 (d, J=5.3 Hz, 1H), 7.93 (s, 1H), 7.90 (d, J=0.7 Hz, 1H), 7.77 (br s, 1H), 7.554 (s, 1H), 7.552 (s, 1H), 7.41 (s, 1H), 7.10 (br s, 1H), 7.09 (dd, J=5.3. 1.3 Hz, 1H), 6.92 (s, 1H), 5.69 (q, J=6.4 Hz, 1H), 5.12 (m, 1H), 3.84 (s, 3H), 3.71-3.62 (m, 2H), 3.15-3.02 (m, 2H), 1.96-1.85 (m, 2H), 1.66 (d, J=6.4 Hz, 3H), 1.55-1.43 (m, 2H), 1.36 (s, 9H).

Step H—(+/−)-5-[5-(1-Methyl-1H-pyrazol-4-yl)-1H-benzimidazol-1-yl]-3-({1-[2-(4-piperidinyloxy)-4-pyridinyl]ethyl}oxy)-2-thiophenecarboxamide (Title Compound)

Reaction of (+/−)-1,1-dimethylethyl 4-({4-[1-({2-(aminocarbonyl)-5-[5-(1-methyl-1H-pyrazol-4-yl)-1H-benzimidazol-1-yl]-3-thienyl}oxy)ethyl]-2-pyridinyl}oxy)-1-piperidinecarboxylate (0.695 g, 1.08 mmol) using a procedure analogous to that described in Example 73, Step H afforded 0.542 g (92%) of the title compound. $^1$H NMR (400 MHz, DMSO-$d_6$) δ 8.54 (s, 1H), 8.18 (s, 1H), 8.14 (d, J=5.1 Hz, 1H), 7.95 (s, 1H), 7.91 (s, J=1H), 7.80 (br s, 1H), 7.57 (s, 2H), 7.43 (s, 1H), 7.12 (br s, 1H), 7.08 (dd, J=5.4, 1.4 Hz, 1H), 6.91 (s, 1H), 5.70 (q, J=6.4 Hz, 1H), 5.00 (m, 1H), 3.85 (s, 3H), 2.96-2.88 (m, 2H), 2.60-2.50 (m, 2H), 1.96-1.86 (m, 2H), 1.67 (d, J=6.4 Hz, 3H), 1.52-1.38 (m, 2H). MS (ESI): 544 [M+H]$^+$.

EXAMPLE 80

3-[(1-{2-[(1-Methyl-4-piperidinyl)oxy]-4-pyridinyl}ethyl)oxy]-5-[5-(1-methyl-1H-pyrazol-4-yl)-1H-benzimidazol-1-yl]-2-thiophenecarboxamide

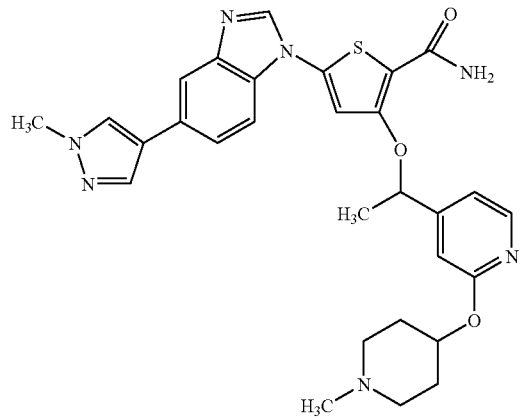

Reaction of (+/−)-5-[5-(1-methyl-1H-pyrazol-4-yl)-1H-benzimidazol-1-yl]-3-({1-[2-(4-piperidinyloxy)-4-pyridinyl]ethyl}oxy)-2-thiophenecarboxamide (Example 79, 0.322 g, 0.592 mmol) using a procedure analogous to that described in Example 74 afforded 0.313 g (95%) of the title compound. $^1$H NMR (400 MHz, DMSO-$d_6$) δ 8.53 (s, 1H), 8.18 (s, 1H), 8.15 (d, J=5.2 Hz, 1H), 7.95 (m, 1H), 7.91 (m, 1H), 7.79 (br s, 1H), 7.569 (s, 1H), 7.567 (s, 1H), 7.43 (s, 1H), 7.12 (br s, 1H), 7.08 (dd, J=5.2, 1.3 Hz, 1H), 6.92 (s, 1H), 5.70 (q, J=6.4 Hz, 1H), 4.93 (m, 1H), 3.85 (s, 3H), 2.64-2.53 (m, 2H), 2.13 (s, 3H), 2.15-2.03 (m, 2H), 1.97-1.87 (m, 2H), 1.67 (d, J=6.4 Hz, 3H), 1.67-1.55 (m, 2H). MS (ESI): 558 [M+H]$^+$.

EXAMPLE 81

(+/−)-5-[5-(1-Methyl-1H-pyrazol-4-yl)-1H-benzimidazol-1-yl]-3-({1-[6-(4-piperidinyloxy)-2-pyridinyl]ethyl}oxy)-2-thiophenecarboxamide

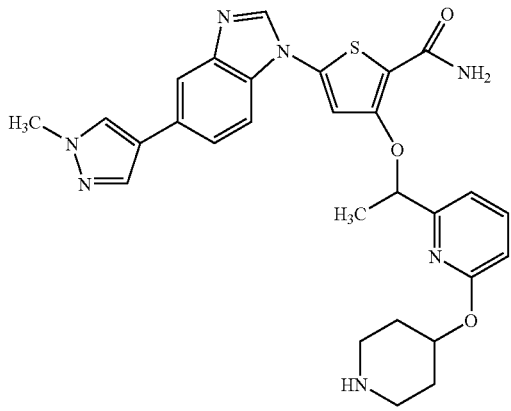

Step A—6-Fluoro-N-methyl-M-(methyloxy)-2-pyridinecarboxamide

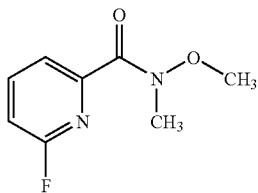

2-Fluoropyridine-6-carboxylic acid (1.00 g, 7.09 mmol) was dissolved in 50 mL of DCM with stirring. DMF (3 drops) was added. Oxalyl chloride (4.3 mL, 2M in DCM, 8.6 mmol) was added dropwise via syringe. The reaction was stirred for 1 h and cooled to 0° C. N,O-Dimethylhydroxylamine hydrochloride (0.761 g, 7.80 mmol) was added in a single portion. Pyridine (1.26 mL, 15.6 mmol) was added via syringe, and the reaction was allowed to warm to room temperature. The reaction was stirred for 16 h and poured into half-saturated NaHCO$_3$ solution and DCM. The layers were separated, and the aqueous layer was washed with EtOAc, The combined organic layers were dried over MgSO$_4$, filtered, and concentrated in vacuo. Purification by flash chromatography provided 1.10 g (84%) of the title compound. $^1$H NMR (400 MHz, DMSO-d$_6$) δ 8.11 (m, 1H), 7.56 (m, 1H), 7.32 (dd, J=8.2, 2.4 Hz, 1H), 3.65 (s, 3H), 3.25 (s, 3H).

Step B—1-(6-Fluoro-2-pyridinyl)ethanone

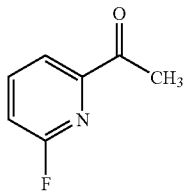

6-Fluoro-N-methyl-N-(methyloxy)-2-pyridinecarboxamide (1.10 g, 5.97 mmol) was dissolved in 40 mL of THF with stirring and cooled to 0° C. Methyl magnesium chloride (8.0 mL, 3.0M in THF, 24 mmol) was added via syringe. The reaction was stirred for 30 min and quenched by the addition of saturated ammonium chloride solution. The mixture was poured into water and ether. The layers were separated, and the organic layer was washed with brine. The combined aqueous layers were washed with ether. The combined organic layers were dried over MgSO$_4$, filtered, and concentrated in vacuo to afford 0.746 g (90%) of the title compound. $^1$H NMR (300 MHz, DMSO-d$_6$) δ 8.24 (m, 1H), 7.94 (ddd, J=7.4, 2.5, 0.7 Hz, IB), 7.54 (odd, J=8.2, 2.7, 0.7 Hz, 1H), 2.62 (s, 3H).

Step C—(+/−)-1-(6-Fluoro-2-pyridinyl)ethanol

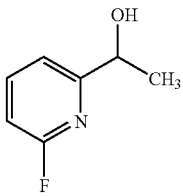

1-(6-Fluoro-2-pyridinyl)ethanone (0.745 g, 5.35 mmol) was dissolved in 40 mL of THF with stirring and cooled to −78° C. Diisobutylaluminum hydride (16.0 mL, 1.0M in cyclohexane, 16.0 mmol) was added dropwise via addition funnel over 10 min. The addition funnel was rinsed with 10 mL of THF. The reaction was stirred for 45 min and quenched by the dropwise addition of 10 mL of i-PrOH. 60 mL of saturated sodium/potassium tartrate solution was added, and the mixture was stirred at rt for 1.5 h. The mixture was poured into water and EtOAc, and the layers were separated. The organic layer was washed with brine, and the combined aqueous layers were extracted with EtOAc. The combined organic layers were dried over MgSO$_4$, filtered, and concentrated in vacuo to afford 0.708 g (94%) of the title compound. $^1$H NMR (400 MHz, DMSO-d$_6$) δ 7.95 (m, 1H), 7.42 (ddd, J=7.5, 2.7, 0.6 Hz, 1H), 6.98 (dd, J=8.1, 2.5 Hz, 1H), 5.47 (d, J=4.9 Hz, 1H), 4.62 (m, 1H), 1.32 (d, J=6.6 Hz, 3H).

Step D—(+/−)-2-(1-{[(1,1-Dimethylethyl)(dimethyl)silyl]oxy}ethyl)-6-fluoropyridine

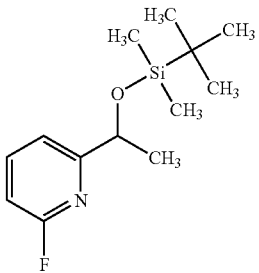

(+/−)-1-(6-Fluoro-2-pyridinyl)ethanol (0.707 g, 5.01 mmol) was dissolved in 50 mL of DCM with stirring, imidazole (0.750 g, 11.0 mmol) and tert-butyldimethylsilyl chloride (0.831 g, 5.51 mmol) were added. The reaction was stirred for 16 h and poured into water. The layers were separated, and the aqueous layer was washed with 1:1 EtOAc/hexanes. The combined organic layers were dried over MgSO$_4$, filtered, and concentrated in vacuo to provide 1.10 g (86%) of the title compound, $^1$H NMR (400 MHz, DMSO-d$_6$) δ 7.97 (m, 1H), 7.37 (m, 1H), 7.00 (m, 1H), 4.79 (q, J=6.4 Hz, 1H), 1.34 (d, 6.4 Hz, 3H), 0.85 (s, 9H), 0.04 (s, 3H), 0.03 (s, 3H).

Step E—(+/−)-1,1-Dimethylethyl 4-{[6-(1-{[(1,1-dimethylethyl)(dimethyl)silyl]oxy}ethyl)-2-pyridinyl]oxy}-1-piperidinecarboxylate

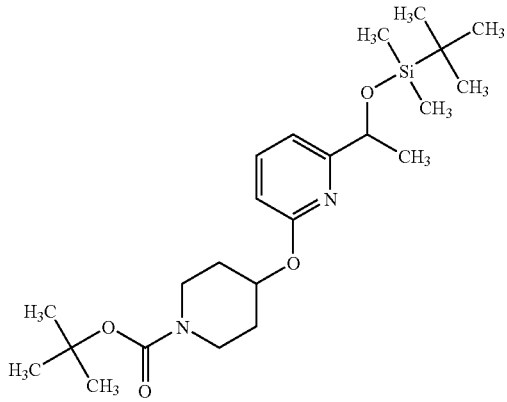

Sodium hydride (0.310 g, 60% dispersion in mineral oil, 7.75 mmol) was washed with hexanes (2×), and 15 mL of dry THF was added. t-Butyl 4-hydroxy-1-piperidinecarboxylate (1.56 g, 7.75 mmol) was dissolved in 10 mL of THF and added dropwise via syringe, The mixture was stirred for 30 min. (+/−)-2-(1-{[(1,1-Dimethylethyl)(dimethyl)silyl]oxy}ethyl)-6-fluoropyridine (1.10 g, 4.31 mmol) was dissolved in 10 mL of THF and added via syringe. After 2 h, the reaction was heated to 50° C. using an oil bath. The reaction was stirred for 2 days more at this temperature and quenched by the addition of saturated ammonium chloride solution. The mixture was poured into saturated ammonium chloride solution and EtOAc, and the layers were separated. The organic layer was washed with brine, and the combined aqueous layers were extracted with 1:1 EtOAc/hexanes. The combined organic layers were dried over magnesium sulfate, filtered, and concentrated in vacuo. Purification by flash chromatography provided 1.16 g (62%) of the title compound. $^1$H NMR (400 MHz, DMSO-$d_6$) δ 7.67 (dd, J=8.2, 7.3 Hz, 1H), 7.00 (d, J=7.3 Hz, 1H), 6.61 (d, J=8.2 Hz, 1H), 5.11 (m, 1H), 4.74 (q, J=6.2 Hz, 1H), 3.69-3.59 (m, 2H), 3.23-3.10 (m, 2H), 1.98-1.85 (m, 2H), 1.59-1.45 (m, 2H), 1.38 (s, 9H), 1.36 (d, J=6.2 Hz, 3H), 0.87 (s, 9H), 0.05 (s, 3H), −0.01 (s, 3H).

Step F—(+/−)-1,1-Dimethylethyl 4-{[6-(1-hydroxyethyl)-2-pyridinyl]oxy}-1-piperidinecarboxylate

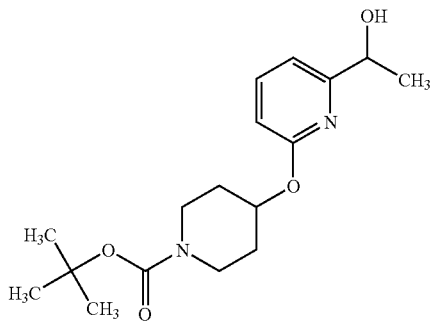

(+/−)-1,1-Dimethylethyl 4-{[6-(1-{[(1,1-dimethylethyl)(dimethyl)silyl]oxy}ethyl)-2-pyridinyl]oxy}-1-piperidinecarboxylate (1.16 g, 2.66 mmol) was dissolved in 25 mL of THF with stirring, Tetrabutyammonium fluoride (3.20 mL, 1M in THF, 3.20 mmol) was added via syringe. The reaction was stirred for 1 h and poured Into saturated ammonium chloride solution and EtOAc. The layers were separated, and the organic layer was washed with brine. The combined aqueous layers were extracted with EtOAc. The combined organic layers were dried over MgSC$_4$, filtered, and concentrated in vacuo. Purification by flash chromatography gave 0.810 g (94%) of the title compound. $^1$H MMR (300 MHz, DMSO-$d_6$) δ 7.69 (dd, J=8.1, 7.3 Hz, 1H), 7.08 (d, J=7.3 Hz, 1H), 6.64 (d, J=8.1 Hz, 1H), 5.28 (d, J=4.9 Hz, 1H), 5.18 (m, 1H), 4.62 (m, 1H), 3.75-3.63 (m, 2H), 3.29-3.15 (m, 2H), 2.03-1.91 (m, 2H), 1.66-1.50 (m, 2H), 1.44 (s, 9H), 1.87 (d, J=6.5 Hz, 3H).

Step G—(+/−)-1,1-Dimethylethyl 4-({6-[1-({2-[(methyloxy)carbonyl]-5-[5-(1-methyl-1H-pyrazol-4-yl)-1H-benzimidazol-1-yl]-3-thienyl}oxy)ethyl]-2-pyridinyl}oxy)-1-piperidinecarboxylate

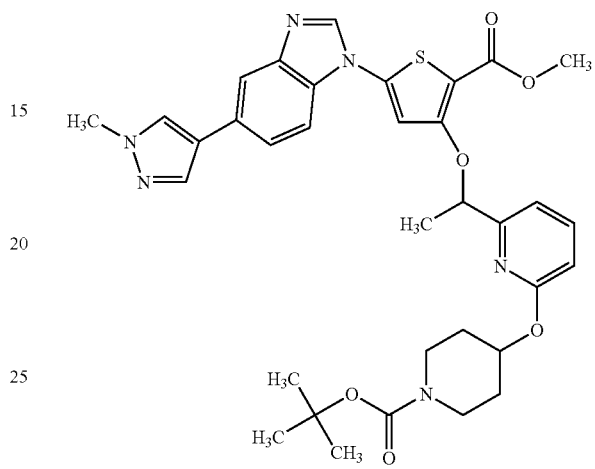

Reaction of (+/−)-1,1-dimethylethyl 4-{[6-(1-hydroxyethyl)-2-pyridlnyl]oxy}-1-piperidinecarboxylate (0.808 g, 2.51 mmol) and methyl 3-hydroxy-5-[5-(1-methyl-1H-pyrazol-4-yl)-1H-benzimidazol-1-yl]-2-thiophenecarboxylate (Intermediate 16, 0.593 g, 1.67 mmol) using a procedure analogous to that described in Example 73, Step F afforded 0.615 g (56%) of the title compound. $^1$H NMR (400 MHz, DMSO-$d_6$) δ 8.63 (s, 1H), 8.17 (s, 1H), 7.95 (m, 1H), 7.90 (s, 1H), 7.73 (dd, J=8.3, 7.4 Hz, 1H), 7.67-7.49 (m, 3H), 7.19 (d, J=7.4 Hz, 1H), 6.70 (d, J=8.3 Hz, 1H), 5.63 (q, J=6.4 Hz, 1H), 5.09 (m, 1H), 3.84 (s, 3H), 3.78 (s, 3H), 3.66-3.55 (m, 2H), 3.13-3.02 (m, 2H), 1.93-1.81 (m, 2H), 1.64 (d, J=6.4 Hz, 3H), 1.55-1.42 (m, 2H), 1.35 (s, 9H).

Step H—(+/−)-1,1-Dimethylethyl 4-({6-[1-({2-(aminocarbonyl)-5-[5-(1-methyl-1H-pyrazol-4-yl)-1H-benzimidazol-1-yl]-3-thienyl}oxy)ethyl]-2-pyridinyl}oxy)-1-piperidinecarboxylate

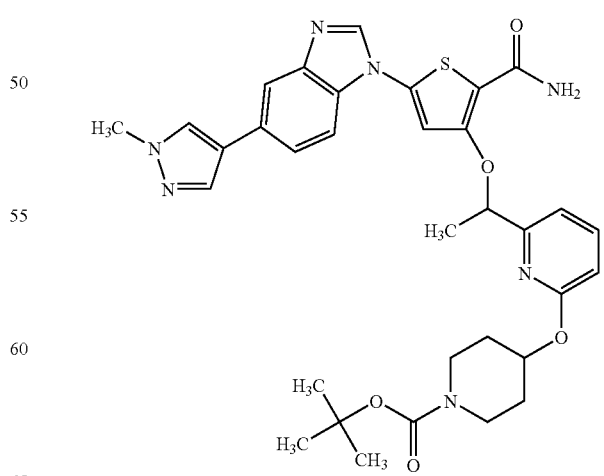

Reaction of (+/−)-1,1-dimethylethyl 4-({6-[1-({2-[(methyloxy)carbonyl]-5-[5-(1-methyl-1H-pyrazol-4-yl)-1H- benzimidazol-1-yl]-3-thienyl}oxy)ethyl]-2-pyridinyl}oxy)-1-piperidinecarboxylate (0.614 g, 0.932 mmol) using a procedure analogous to that described in Example 73, Step G afforded 0.509 g (85%) of the title compound. $^1$H NMR (400 MHz, DMSO-$d_6$) δ 8.54 (s, 1H), 8.17 (s, 1H), 7.94 (s, 1H), 7.90 (s, 1H), 7.86 (br s, 1H), 7.71 (dd, J=8.2, 7.1 Hz, 1H), 7.57 (s, 2H), 7.49 (s, 1H), 7.15 (br s, 1H), 7.10 (d, J=7.1 Hz, 1H), 6.71 (d, J=8.2 Hz, 1H), 5.72 (q, J=6.4 Hz, 1H), 5.08 (m, 1H), 3.84 (s, 3H), 3.67-3.55 (m, 2H), 3.17-3.02 (m, 2H), 1.95-1.76 (m, 2H), 1.67 (d, J=6.4 Hz, 3H), 1.56-1.37 (m, 2H), 1.36 (s, 9H).

Step I—(+/−)-5-[5-(1-Methyl-1H-pyrazol-4-yl)-1H-benzimidazol-1-yl]-3-({1-[6-(4-piperidinyloxy)-2-pyridinyl]ethyl}oxy)-2-thiophenecarboxamide (Title Compound)

Reaction of (+/−)-1,1-dimethylethyl 4-({6-[1-({2-(aminocarbonyl)-5-[5-(1-methyl-1H-pyrazol-4-yl)-1H-benzimidazol-1-yl]-3-thienyl}oxy)ethyl]-2-pyridinyl}oxy)-1-piperidinecarboxylate (0.508 g, 0.789 mmol) using a procedure analogous to that described in Example 73, Step H afforded 0.422 g (98%) of the title compound. $^1$H NMR (400 MHz, DMSO-$d_6$) δ 8.54 (s, 1H), 8.19 (s, 1H), 7.95 (m, 1H), 7.92 (m, 1H), 7.84 (br s, 1H), 7.71 (dd, J=8.1, 7.3 Hz, 1H), 7.59-7.57 (m, 2H), 7.48 (s, 1H), 7.13 (br s, 1H), 7.10 (d, J=7.3 Hz, 1H), 6.70 (d, J=8.1 Hz, 1H), 5.71 (q, J=6.4 Hz, 1H), 4.98 (m, 1H), 3.86 (s, 3H), 2.96-2.84 (m, 2H), 2.67-2.49 (m, 2H), 1.94-1.79 (m, 2H), 1.69 (d, J=6.4 Hz, 3H), 1.52-1.34 (m, 2H). MS (ESI): 544 [M+H]$^+$.

EXAMPLE 82

(+/−)-3-[(1-{6-[(1-Methyl-4-piperidinyl)oxy]-2-pyridinyl}ethyl)oxy]-5-[5-(1-methyl-1H-pyrazol-4-yl)-1H-benzimidazol-1-yl]-2-thiophenecarboxamide

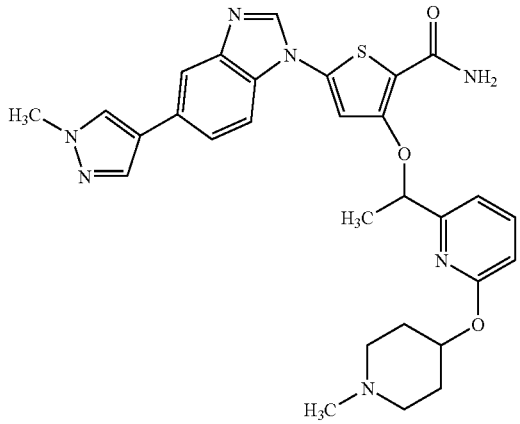

Reaction of (+/−)-5-[5-(1-methyl-1H-pyrazol-4-yl)-1H-benzimidazol-1-yl]-3-({1-[6-(4-piperidinyloxy)-2-pyridinyl]ethyl}oxy)-2-thiophenecarboxamide (Example 81, 0.222 g, 0.408 mmol) using a procedure analogous to that described in Example 74 afforded 0.170 g (75%) of the title compound. $^1$H NMR (400 MHz, DMSO-$d_6$) δ 8.55 (s, 1H), 8.19 (s, 1H), 7.95 (m, 1H), 7.92 (m, 1H), 7.82 (br s, 1H), 7.71 (dd, J=8.2, 7.1 Hz, 1H), 7.61-7.58 (m, 2H), 7.49 (s, 1H), 7.11 (br s, 1H), 7.11 (d, J=7.1 Hz, 1H), 6.70 (d, J=8.2 Hz, 1H), 5.71 (q, J=6.4 Hz, 1H), 4.89 (m, 1H), 3.85 (s, 3H), 2.58-2.40 (m, 2H), 2.12-1.94 (m, 2H), 2.08 (s, 3H), 1.91-1.79 (m, 2H), 1.69 (d, J=6.4 Hz, 3H), 1.63-1.48 (m, 2H). MS (ESI): 558 [M+H]$^+$.

EXAMPLE 83

5-[5-(1-Methyl-1H-pyrazol-4-yl)-1H-benzimidazol-1-yl]-3-({[3-(4-piperidinyloxy)phenyl]methyl}oxy)-2-thiophenecarboxamide

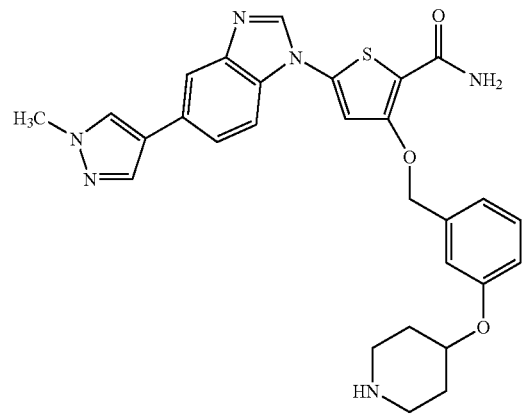

Step A—1,1-Dimethylethyl 4-({3-[({2-[(methyloxy)carbonyl]-5-[5-(1-methyl-1H-pyrazol-4-yl)-1H-benzimidazol-1-yl]-3-thienyl}oxy)methyl]phenyl}oxy)-1-piperidinecarboxylate

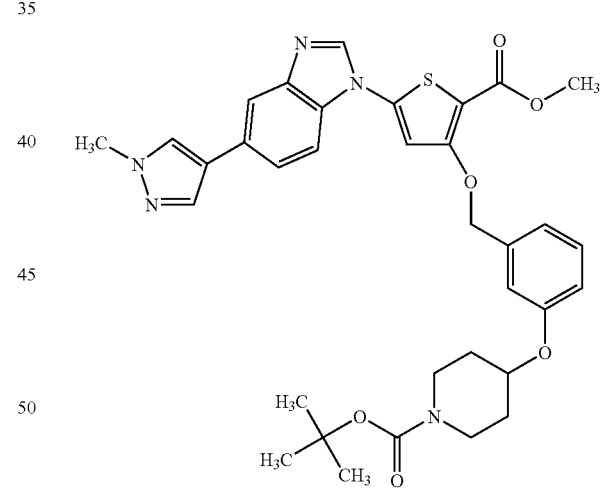

Reaction of 1,1-dimethylethyl 4-{[3-(hydroxymethyl)phenyl]oxy}-1-piperidinecarboxylate (0.386 g, 1.26 mmol) and methyl 3-hydroxy-5-[5-(1-methyl-1H-pyrazol-4-yl)-1H-benzimidazol-1-yl]-2-thiophenecarboxylate (Intermediate 16, 0.300 g, 0.847 mmol) using a procedure analogous to that described in Example 73, Step F afforded 0.501 g (92%) of the title compound. $^1$H NMR (400 MHz, DMSO-$d_6$) δ 8.67 (s, 1H), 8.20 (s, 1H), 7.98 (d, J=1.4 Hz, 1H), 7.93 (d, J=0.6 Hz, 1H), 7.75 (d, J=8.4 Hz, 1H), 7.64 (s, 1H), 7.61 (dd, J=8.6, 1.7 Hz, 1H), 7.32 (dd, J=8.1, 7.9 Hz, 1H), 7.12 (m, 1H), 7.04 (d, J=7.9 Hz, 1H), 6.94 (m, 1H), 5.35 (s, 2H), 4.55 (m, 1H), 3.86 (s, 3H), 3.77 (s, 3H), 3.69-3.60 (m, 2H), 3.21-3.09 (m, 2H), 1.95-1.85 (m, 2H), 1.56-1.44 (m, 2H), 1.38 (s, 9H).

Step B—1,1-Dimethylethyl 4-({3-[({2-(aminocarbonyl)-5-[5-(1-methyl-1H-pyrazol-4-yl)-1H-benzimidazol-1-yl]-3-thienyl}oxy)methyl]phenyl}oxy)-1-piperidinecarboxylate

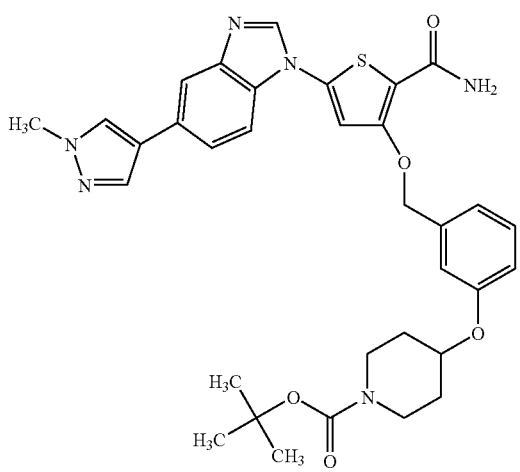

Reaction of 1-dimethylethyl 4-({3-[({2-[(methyloxy)carbonyl]-5-[5-(1-methyl-1H-pyrazol-4-yl)-1H-benzimidazol-1-yl]-3-thienyl}oxy)methyl]phenyl}oxy)-1-piperidinecarboxylate (0.500 g, 0.777 mmol) using a procedure analogous to that described in Example 73, Step G afforded 0.417 g (85%) of the title compound. $^1$H NMR (400 MHz, DMSO-$d_6$) δ 8.59 (s, 1H), 8.19 (s, 1H), 7.96 (m, 1H), 7.92 (s, 1H), 7.73 (br s, 1H), 7.68 (d, J=8.4 Hz, 1H), 7.61 (s, 1H), 7.60 (m, 1H), 7.31 (dd, J=8.1, 7.8 Hz, 1H), 7.17 (m, 1H), 7.11-7.03 (m, 2H), 6.94 (m, 1H), 5.36 (s, 2H), 4.53 (m, 1H), 3.86 (s, 3H), 3.77 (s, 3H), 3.69-3.59 (m, 2H), 3.18-3.07 (m, 2H), 1.92-1.82 (m, 2H), 1.55-1.42 (m, 2H), 1.37 (s, 9H).

Step C—5-[5-(1-Methyl-1H-pyrazol-4-yl)-1H-benzimidazol-1-yl]-3-({[3-(4-piperidinyloxy)phenyl]methyl}oxy)-2-thiophenecarboxamide (Title Compound)

Reaction of 1,1-dimethylethyl 4-({3-[({2-(aminocarbonyl)-5-[5-(1-methyl-1H-pyrazol-4-yl)-1H-benzimidazol-1-yl]-3-thienyl}oxy)methyl]phenyl}oxy)-1-piperidinecarboxylate (0.416 g, 0.662 mmol) using a procedure analogous to that described in Example 73, Step H afforded 0.263 g (75%) of the title compound. $^1$H NMR (400 MHz, DMSO-$d_6$) δ 8.57 (s, 1H), 8.18 (s, 1H), 7.95 (s, 1H), 7.91 (s, 1H), 7.70 (br s, 1H), 7.66 (d, J=8.2 Hz, 1H), 7.61-7.56 (m, 2H), 7.28 (dd, J=8.1, 7.7 Hz, 1H), 7.11 (s, 1H), 7.07-7.01 (m, 2H), 6.89 (m, 1H), 5.35 (s, 2H), 4.34 (m, 1H), 3.84 (s, 3H), 2.91-2.83 (m, 2H), 2.54-2.43 (m, 2H), 1.89-1.80 (m, 2H), 1.43-1.31 (m, 2H). MS (ESI): 529 [M+H]$^+$.

EXAMPLE 84

3-[({3-[(1-Methyl-4-piperidinyl)oxy]phenyl}methyl)oxy]-5-[5-(1-methyl-1H-pyrazol-4-yl)-1H-benzimidazol-1-yl]-2-thiophenecarboxamide

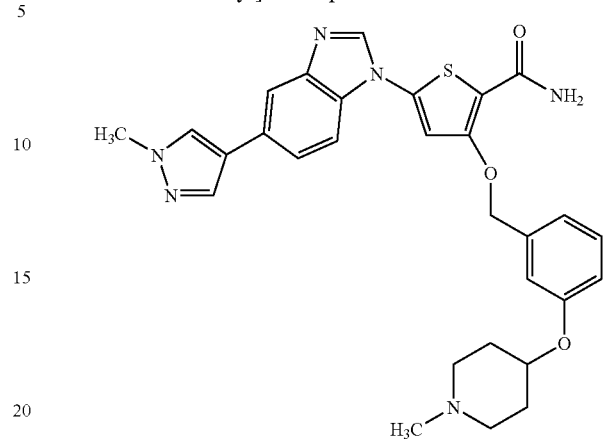

Reaction of 5-[5-(1-methyl-1H-pyrazol-4-yl)-1H-benzimidazol-1-yl]-3-({[3-(4-piperidinyloxy)phenyl]methyl}oxy)-2-thiophenecarboxamide (Example 83, 0.175 g, 0.330 mmol) using a procedure analogous to that described in Example 74 afforded 0.132 g (74%) of the title compound. 1H MMR (400 MHz, DMSO-$d_6$) δ 8.57 (s, 1H), 8.18 (s, 1H), 7.95 (s, 1H), 7.91 (s, 1H), 7.69 (br s, 1H), 7.67 (d, J=8.4 Hz, 1H), 7.61-7.56 (ms 2H), 7.28 (dd, J=8.2, 7.9 Hz, 1H), 7.12 (s, 1H), 7.08-7.01 (m, 2H), 6.90 (m, 1H), 5.35 (s, 2H), 4.31 (m, 1H), 3.85 (s, 3H), 2.57-2.44 (m, 2H), 2.10 (s, 3H), 2.10-2.02 (m, 2H), 1.90-1.81 (m, 2H), 1.61-1.50 (m, 2H). MS (ESI): 543 [M+H]$^+$.

EXAMPLE 85

5-[5-(1-Methyl-1H-pyrazol-4-yl)-1H-benzimidazol-1-yl]-3-({1-[4-(4-piperidinyloxy)-2-pyridinyl]ethyl}oxy)-2-thiophenecarboxamide

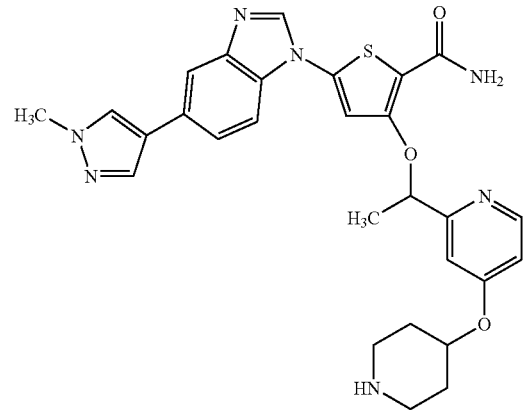

Step A: 1,1-Dimethylethyl 4-[(2-chloro-4-pyridinyl)oxy]-1-piperidinecarboxylate

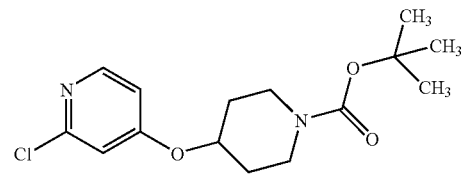

1,1-Dimethylethyl 4-hydroxy-1-piperidinecarboxylate (5.50 g, 27.4 mmol) was dissolved in 100.0 mL of THF and cooled to 0° C. Next, sodium hydride (1.19 g, 29.7 mmol, 60% dispersed in mineral oil) was added portion wise and the mixture stirred at rt for 1 h. The mixture was cooled to 0° C. again and 2-chloro-4-fluoropyridine (3.00 g, 22.8 mmol) was added dropwise as a THF solution. The reaction was allowed to stir at rt, and after 6 h TLC indicated that all of the 2-chloro-4-fluoropyridine had reacted. The mixture was again cooled to 0° C. and quenched with water. EtOAc was added and the organics separated. The organics were washed with brine and dried over anhydrous MgSO$_4$. The crude was purified via silica gel chromatography to give 6.14 g (86% yield) of a colorless oil. $^1$H NMR (400 MHz, DMSO-d$_6$) δ 8.16 (d, J=5.9 Hz, 1H), 7.12 (d, J=2.2 Hz, 1H), 6.99 (d, J=5.9 Hz, 1H), 4.62-4.87 (m, 1H), 3.51-3.69 (m, 2H), 2.96-3.22 (m, 2H), 1.78-1.93 (m, 2H), 1.41-1.57 (m, 2H), 1.36 (s, 9H).

Step B: 1,1-Dimethylethyl 4-[(2-acetyl-4-pyridinyl)oxy]-1-piperidinecarboxylate

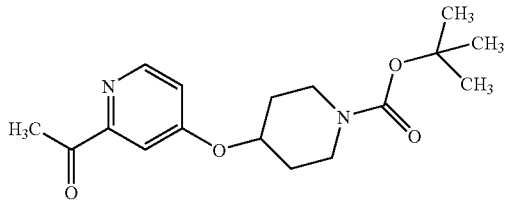

1,1-Dimethylethyl 4-[(2-chloro-4-pyridinyl)oxy]-1-piperidinecarboxylate (3.00 g, 9.59 mmol) was dissolved in 100 mL of acetonitrile. Next, tetraethylammonium-chloride (4.77, 28.7 mmol), dichlorobis(triphenylphosphine)palladium (II) (336 mg, 0.479 mmol), and tributyl(1-ethoxyvinyl)tin (3.96 g, 10.6 mmol) was added. The reaction was stirred at rt for 72 h. Water and EtOAc was added and the organics separated. The organics were concentrated to give the vinyl ether as a dark solid. This was re-dissolved in 50.0 mL of acetone, before addition of a speck of p-toluenesulfonic acid. The reaction was stirred for 4 h before TLC indicated complete consumption of the vinyl ether. The solvent was removed and the crude adsorbed onto silica gel and chromatographed to give 1.9 g (62% yield) of a white solid. $^1$H NMR (400 MHz, CDCl$_3$) δ 8.48 (d, J=5.7 Hz, 1H), 7.54 (d, J=2.6 Hz, 1H), 6.96 (dd, J=5.7, 2.6 Hz, 1H), 4.49-4.78 (m, 1H), 3.58-3.77 (m, 2H), 3.21-3.47 (m, 2H), 2.71 (s, 3H), 1.86-2.05 (m, 2H), 1.66-1.82 (m, 2H), 1.46 (s, 9H).

Step C: 1,1-Dimethylethyl 4-{[2-(1-hydroxyethyl)-4-pyridinyl]oxy}-1-piperidine carboxylate

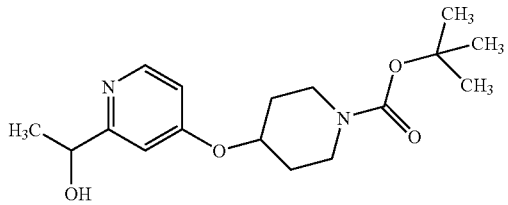

1,1-Dimethylethyl 4-[(2-acetyl-4-pyridinyl)oxy]-1-piperidinecarboxylate (1.62 g, 5.06 mmol) was dissolved in 50.0 mL of anhydrous DCM and the solution cooled to −78° C. Diisobutylaluminumhydride (15.2 ml, 15.2 mmol, 1.0M solution in hexanes) was added dropwise over 15 min and the reaction continued to be stirred at −78° C. for 1.5 h. The reaction was quenched with 50 mL of saturated sodium potassium tartrate solution, warmed to rt and stirred overnight. The organics were separated, washed with brine and dried over MgSO$_4$. The crude was purified via silica gel chromatography to give 0.962 g (59% yield) of the title compound, $^1$H NMR (300 MHz, Chloroform-d) δ 8.40 (d, J=5.8 Hz, 1H), 6.83 (d, J=2.4 Hz, 1H), 6.77 (dd, J=5.8, 2.4 Hz, 1H), 4.82-4.97 (m, J=6.5, 6.5 Hz, 1H), 4.51-4.74 (m, 1H), 3.62-3.83 (m, 2H), 3.29-3.53 (m, 2H), 1.90-2.08 (m, 2H), 1.66-1.90 (m, 2H), 1.55 (d, J=6.5 Hz, 3H), 1.52 (s, 9H).

Step D: 1,1-Dimethylethyl 4-({2-[1-({2-[(methyloxy)carbonyl]-5-[5-(1-methyl-1H-pyrazol-4-yl)-1H-benzimidazol-1-yl]-3-thienyl}oxy)ethyl]-4-pyridinyl}oxy)-1-piperidinecarboxylate

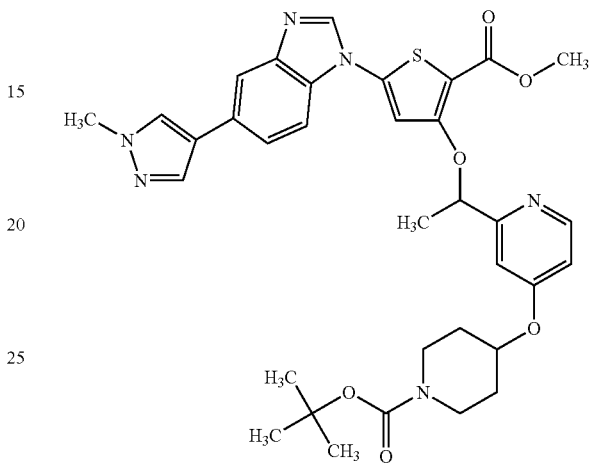

The title compound was prepared from methyl 3-hydroxy-5-[5-(1-methyl-1H-pyrazol-4-yl)-1H-benzimidazol-1-yl]-2-thiophenecarboxylate (Intermediate 16, 500 mg, 1.41 mmol) and 1,1-dimethylethyl 4-{[2-(1-hydroxyethyl)-4-pyridinyl]oxy}-1-piperidinecarboxylate (544 mg, 1.69 mmol) using a procedure analogous to Example 73, Step F to give 870 mg of the desired product. MS (ESI): 659 [M+H]$^+$.

Step E: 1,1-Dimethylethyl 4-({2-[1-({2-(aminocarbonyl)-5-[5-(1-methyl-1H-pyrazol-4-yl)-1H-benzimidazol-1-yl]-3-thienyl}oxy)ethyl]-4-pyridinyl}oxy)-1-piperidinecarboxylate

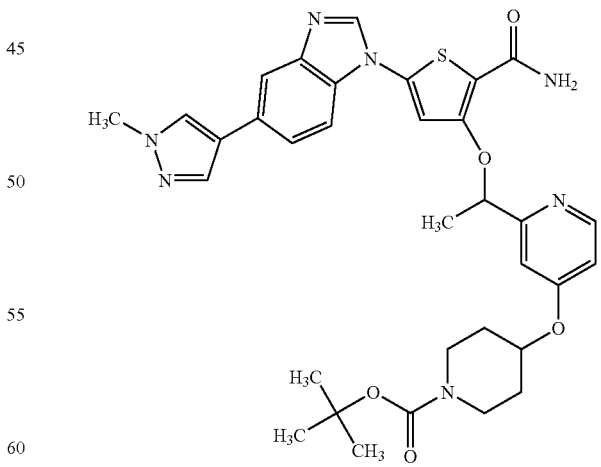

The title compound was prepared from 1,1-dimethylethyl 4-({2-[1-({2-[(methyloxy)carbonyl]-5-[5-(1-methyl-1H-pyrazol-4-yl)-1H-benzimidazol-1-yl]-3-thienyl}oxy)ethyl]-4-pyridinyl}oxy)-1-piperidinecarboxylate (870 mg, 1.32 mmol) using a procedure analogous to Example 73, Step G to give 765 mg of the desired product. MS (ESI): 644 [M+H]$^+$.

Step F: 5-[5-(1-Methyl-1H-pyrazol-4-yl)-1H-benzimidazol-1-yl]-3-({1-[4-(4-piperidinyloxy)-2-pyridinyl]ethyl}oxy)-2-thiophenecarboxamide (Title Compound)

The title compound was prepared from 1,1-dimethylethyl 4-({2-[1-({2-(aminocarbonyl)-5-[5-(1-methyl-1H-pyrazol-4-yl)-1H-benzimidazol-1-yl]-3-thienyl}oxy)ethyl]-4-pyridinyl}oxy)-1-piperidinecarboxylate (765 mg) using a procedure analogous to Example 73, Step H to give 542 mg of the desired product. $^1$H NMR (400 MHz, DMSO-d$_6$) δ 8.54 (s, 1H), 8.34 (d, J=5.9 Hz, 1H), 8.17 (s, 1H), 7.94 (s, 1H), 7.90 (s, 1H), 7.74 (br s, 1H), 7.56-7.60 (m, 2H), 7.46 (s, 1H), 7.38 (br s, 1H), 7.07-7.16 (m, 1H), 6.90 (dd, J=5.8, 2.5 Hz, 1H), 5.69 (q, J=6.3 Hz, 1H), 4.38-4.59 (m, 1H), 3.73-3.91 (m, 3H), 2.75-2.95 (m, 2H), 2.48-2.58 (m, 3H), 1.75-1.94 (m, 2H), 1.67 (d, J=6.4 Hz, 3H), 1.29-1.48 (m, 2H). MS: 544 [M+H]$^+$.

EXAMPLE 86

3-[(1-{4-[(1-Methyl-4-piperidinyl)oxy]-2-pyridinyl}ethyl)oxy]-5-[5-(1-methyl-1H-pyrazol-4-yl)-1H-benzimidazol-1-yl]-2-thiophenecarboxamide

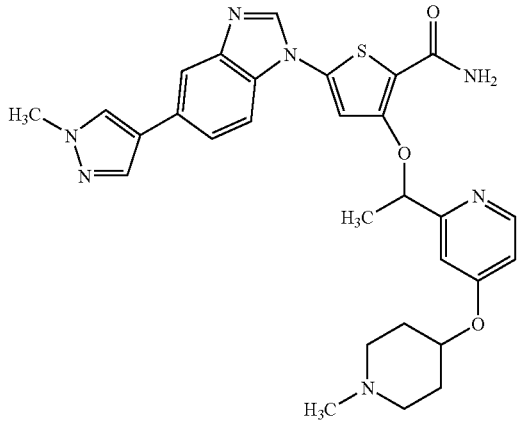

The title compound was prepared from 5-[5-(1-methyl-1H-pyrazol-4-yl)-1H-benzimidazol-1-yl]-3-({1-[4-(4-piperidinyloxy)-2-pyridinyl]ethyl}oxy)-2-thiophene carboxamide (Example 85, 212 mg) using a procedure analogous to Example 74 to give 187 mg of the desired product. $^1$H NMR (400 MHz, DMSO-d$_6$) δ 8.56 (s, 1H), 8.36 (d, J=5.7 Hz, 1H), 8.19 (s, 1H), 7.88-7.98 (m, 2H), 7.75 (br s, 1H), 7.58-7.62 (m, 2H), 7.47 (s, 1H), 7.39 (br s, 1H), 7.13 (d, J=2.4 Hz, 1H), 6.92 (dd, J=5.8, 2.5 Hz, 1H), 5.70 (q, J=6.4 Hz, 1H), 4.42-4.57 (m, 1H), 3.86 (s, 3H), 2.51-2.68 (m, 2H), 2.05-2.26 (m, 5H), 1.80-1.96 (m, 2H), 1.69 (d, J=6.4 Hz, 3H), 1.45-1.65 (m, 2H). MS (APCI): 558 [M+H]$^+$.

EXAMPLE 87

3-({(1R)-1-[2-Chloro-3-(4-piperidinyloxy)phenyl]ethyl}oxy)-5-[5-(5-methyl-1,3,4-oxadiazol-2-yl)-1H-benzimidazol-1-yl]-2-thiophenecarboxamide

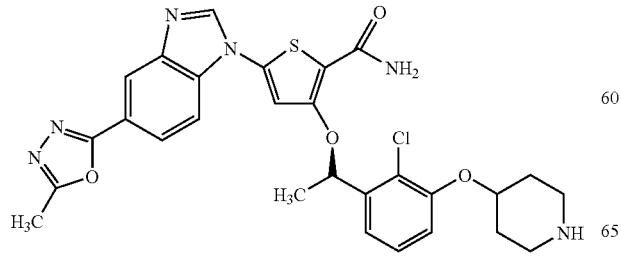

Step A: Methyl 5-{5-[(2-acetylhydrazino)carbonyl]-1H-benzimidazol-1-yl}-3-{[(1R)-1-(2-chlorophenyl)ethyl]oxy}-2-thiophenecarboxylate

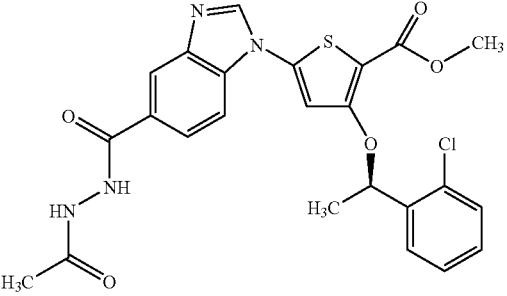

A 20.0 mL flask was charged with 150 mg (0.329 mmol) of 1-{4-{[(1R)-1-(2-chlorophenyl)ethyl]oxy}-5-[(methyloxy)carbonyl]-2-thienyl}-1H-benzimidazole-5-carboxylic acid (Intermediate 34, 0.120 mL, 0.658 mmol) of diisopropyl ethylamine, 24.4 mg (0.329 mmol) of acethydrazide and 2.00 ml of DMF. Next, 125 mg (0.329 mmol) of O-(7-Aza benzotriazole-1-yl)-N,N,N',N' tetramethyluranium hexafluoro phosphate was added and the reaction mixture stirred at rt for 30 min. 10 mL of water and 30 mL of DCM was added and the organic layer separated. The organic layer was adsorbed onto silica gel and chromatographed to give 154 mg (91% yield) of a tan solid. MS (APCI): 513 [M+H]$^+$.

Step B: Methyl 3-{[(1R)-1-(2-chlorophenyl)ethyl]oxy}-5-[5-(5-methyl-1,3,4-oxadiazol-2-yl)-1H-benzimidazol-1-yl]-2-thiophenecarboxylate

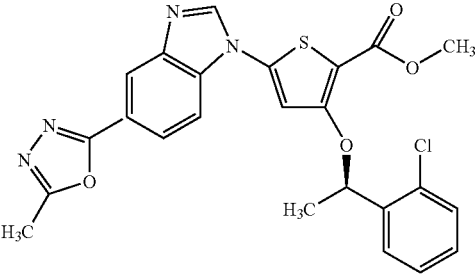

A 5.0 ml microwave vial was charged with 1.00 ml of THF, 286 mg (1.20 mmol) of methoxycarbonylsulfamoyl)triethylammonium hydroxide inner salt, and 154 mg (0.301 mmol) of methyl 5-{5-[(2-acetylhydrazino)carbonyl]-1H-benzimidazol-1-yl}-3-{[(1R)-1-(2-chlorophenyl)ethyl]oxy}-2-thiophene carboxylate. The reaction was heated in the microwave at 150° C. for 10 min. The crude was adsorbed onto silica gel and chromatographed to give 139 mg of a tan solid as the title compound, MS (APCI): 495 [M+H]$^+$.

Step C: Methyl 3-hydroxy-5-[5-(5-methyl-1,3,4-oxadiazol-2-yl)-1H-benzimidazol-1-yl]-2-thiophenecarboxylate

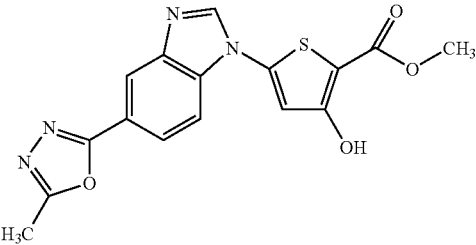

The title compound was prepared from methyl 3-{[(1R)-1-(2-chlorophenyl)ethyl]oxy}-5-[5-(5-methyl-1,3,4-oxadiazol-2-yl)-1H-benzimidazol-1-yl]-2-thiophenecarboxylate (139 mg) using a procedure analogous to Intermediate 3, Step D to give 82.0 mg of the desired product. MS (ESI): 357 [M+H]+.

Step D: Methyl 3-{[(1R)-1-(2-chloro-3-{[(1,1-dimethylethyl)(dimethyl)silyl]oxy}phenyl)ethyl]oxy}-5-[5-(5-methyl-1,3,4-oxadiazol-2-yl)-1H-benzimidazol-yl]-2-thiocarboxylate

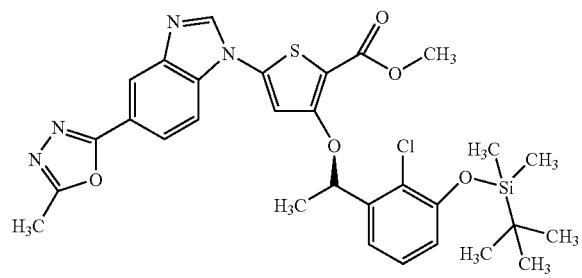

The title compound was prepared from methyl 3-hydroxy-5-[5-(5-methyl-1,3,4-oxadiazol-2-yl)-1H-benzimidazol-1-yl]-2-thiophenecarboxylate (65.0 mg, 0.183 mmol) using a procedure analogous to Intermediate 3, Step E to give 105 mg of the desired product. MS (ESI): 625 [M+H]+.

Step E: Methyl 3-{[(1R)-1-(2-chloro-3-hydroxyphenyl)ethyl]oxy}-5-[5-(5-methyl-1,3,4-oxadiazol-2-yl)-1H-benzimidazol-1-yl]-2-thiophenecarboxylate

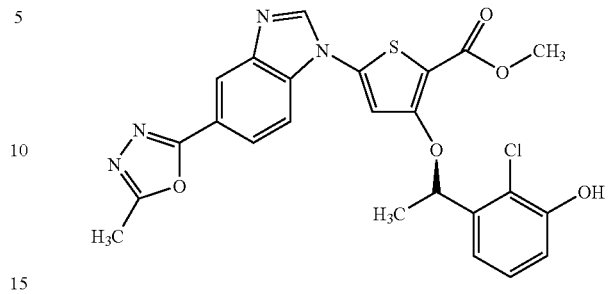

The title compound was prepared from methyl 3-{[(1R)-1-(2-chloro-3-{[(1,1-dimethylethyl)(dimethyl)silyl]oxy}phenyl)ethyl]oxy}-5-[5-(5-methyl-1,3,4-oxadiazol-2-yl)-1H-benzimidazol-1-yl]-2-thiophenecarboxylate (82.0 mg, 0.312 mmol) using a procedure analogous to Intermediate 3, Step F to give 55.9 mg of the desired product. MS (ESI): 511 [M+H]+.

Step F: 1,1-Dimethylethyl 4-({2-chloro-3-[(1R)-1-({5-[5-(5-methyl-1,3,4-oxadiazol-2-yl)-1H-benzimidazol-1-yl]-2-[(methyloxy)carbonyl]-thienyl}oxy)ethyl]phenyl}oxy)-1-piperidinecarboxylate

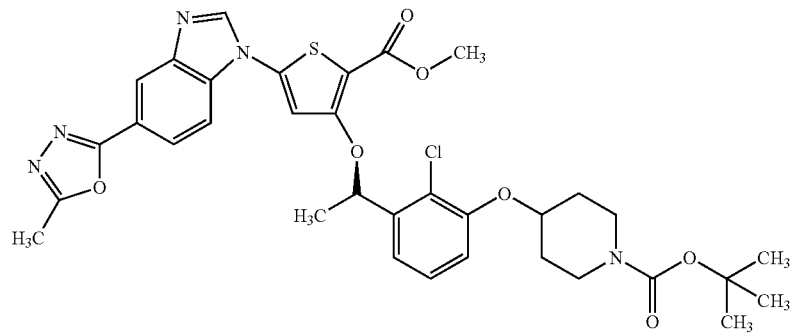

The title compound was prepared from methyl 3-{[(1R)-1-(2-chloro-3-hydroxyphenyl)ethyl]oxy}-5-[5-(5-methyl-1,3,4-oxadiazol-2-yl)-1H-benzimidazol-1-yl]-2-thiophenecarboxylate (58.2 mg, 0.114 mmol) using a procedure analogous to Example 5, Step A to give 72.0 mg of the desired product MS (ESI): 694 [M+H]+.

Step G: 1,1-Dimethylethyl 4-({3-[(1R)-1-({2-(aminocarbonyl)-5-[5-(5-methyl-1,3,4-oxadiazol-2-yl)-1H-benzimidazol-1-yl]-3-thienyl}oxy)ethyl]-2-chlorophenyl}oxy)-1-piperidinecarboxylate

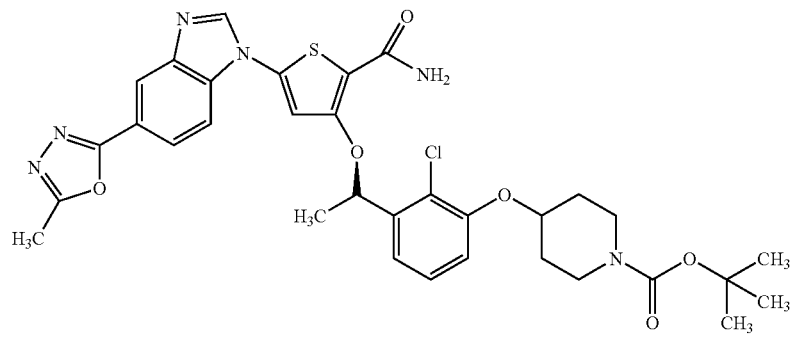

The title compound was prepared from 1,1-dimethylethyl 4-({2-chloro-3-[(1R)-1-({5-[5-(5-methyl-1,3,4-oxadiazol-2-yl)-1H-benzimidazol-1-yl]-2-[(methyloxy)carbonyl]-3-thienyl}oxy)ethyl]phenyl}oxy)-1-piperidinecarboxylate (70 mg, 0.101 mmol) using a procedure analogous to Example 5, Step δ to give 62.0 mg of the desired product. MS (ESI): 679 [M+H]$^+$.

Step H: 3-({(1R)-1-[2-chloro-3-(4-piperidinyloxy)phenyl]ethyl}oxy)-5-[5-(5-methyl-1,3,4-oxadiazol-2-yl)-1H-benzimidazol-1-yl]-2-thiophenecarboxamide (Title Compound)

The title compound was prepared from 1,1-dimethylethyl 4-({3-[(1R)-1-({2-(aminocarbonyl)-5-[5-(5-methyl-1,3,4-oxadiazol-2-yl)-1H-benzimidazol -yl]-3-thienyl}oxy)ethyl]-2-chlorophenyl}oxy)-1-piperidinecarboxylate [240 mg (62.0 mg from previous step plus 178 mg from a different batch using a procedure analogous to Example 87, Step G), 0.353 mmol] using a procedure analogous to Example 5, Step C) to give 187 mg of the title compound. $^1$H NMR (400 MHz, DMSO-d$_6$) δ ppm 8.73 (s, 1H), 8.30 (s, 1H), 7.97 (dd, J=8.6, 1.5 Hz, 1H), 7.86 (br s, 1H), 7.64 (d, J=8.6 Hz, 1H), 7.35 (t, J=8.1 Hz, 1H), 7.16-7.25 (m, 3H), 7.13 (br s, 1H), 5.99 (q, J=8.0 Hz, 1H), 4.44-4.62 (m, 1H), 2.84-3.00 (m, 2H), 2.60 (s, 3H), 2.51-2.59 (m, 3H), 1.82-1.97 (m, 2H), 1.72 (d, J=6.2 Hz, 3H), 1.41-1.59 (m, 2H). MS (ESI): 579 [M+H]$^+$.

EXAMPLE 88

3-[((1R)-1-{2-chloro-3-[(1-methyl-4-piperidinyl)oxy]phenyl}ethyl)-oxy]-5-[5-(5-methyl-1,3,4-oxadiazol-2-yl)-1H-benzimidazol-1-yl]-2-thiophenecarboxamide

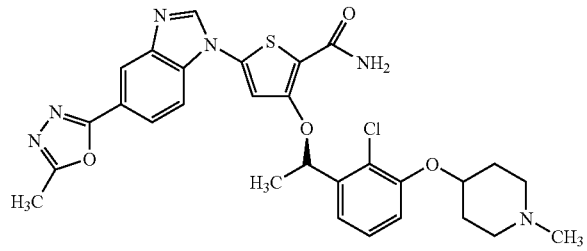

The title compound was prepared from 3-({(1R)-1-[2-chloro-3-(4-piperidinyloxy)phenyl]ethyl}oxy)-5-[5-(5-methyl-1,3,4-oxadiazol-2-yl)-1H-benzimidazol-1-yl]-2-thiophenecarboxamide (Example 87, 60.0 mg, 0.104 mmol) using a procedure analogous to Example 74 to give 61.0 mg of the desired product $^1$H NMR (400 MHz, DMSO-d$_6$) δ ppm 8.70 (s, 1H), 8.27 (s, 1H), 7.93 (d, J=7.3 Hz, 1H), 7.83 (br s, 1H), 7.61 (d, 8.6 Hz, 1H), 7.32 (t, J=8.0 Hz, 1H), 7.13-7.21 (m, 3H), 7.11 (br s, 1H), 5.96 (q, J=8.0 Hz, 1H), 4.35-4.53 (m, 1H), 2.57 (s, 3H), 2.49-2.55 (m, 2H), 2.12-2.22 (m, 2H), 2.11 (s, 3H), 1.79-1.94 (m, 2H), 1.69 (d, J=6.2 Hz, 3H), 1.57-1.67 (m, 2H). MS (ESI): 593 [M+H]$^+$

BIOLOGICAL EXAMPLES

I. Assay for Inhibition of PLK1

A. Preparation of 6× N-terminal His-tagged PLK Kinase Domain

6× N-terminal His-tagged PLK kinase domain (amino acids 21-346 preceded by MKKGHHHHHHD) SEQ ID: No. 1. was prepared from baculovirus infected T. ni cells under polyhedrin promoter control. All procedures were performed at 4° C. Cells were lysed In 50 mM HEPES, 200 mM NaCl, 50 mM imidazole, 5% glycerol; pH 7.5. The homogenate was centrifuged at 14K rpm in a SLA-1500 rotor for 1 hr and the supernatant filtered through a 1.2 micron filter. The supernatant was loaded onto a Nickel chelating Sepharose (Amersham Pharmacia) column and washed with lysis buffer. Protein was eluted using 20%, 30% and 100% buffer B steps where buffer B was 50 mM HEPES, 200 mM NaCl, 300 mM imidazole, 5% glycerol; pH 7.5. Fractions containing PLK were determined by SDS-PAGE. Fractions containing PLK were diluted five-fold with 50 mM HEPES, 1 mM DTT, 5% glycerol; pH 7.5, then loaded on an SP Sepharose (Amersham Pharmacia) column. After washing the column with 50 mM HEPES, 1 mM DTT, 5% glycerol; pH 7.5, PLK was step eluted with 50 mM HEPES, 1 mM DTT, 500 mM NaCl; 5% glycerol; pH 7.5. PLK was concentrated using a 10 kDa molecular weight cutoff membrane and then loaded onto a Superdex 200 gel filtration (Amersham Pharmacia) column equilibrated in 25 mM HEPES, 1 mM DTT, 500 mM NaCl, 5% glycerol; pH 7.5. Fractions containing PLK were determined by SDS-PAGE. PLK was pooled, aliquoted and stored at −80° C. Samples were quality controlled using mass spectrometry, N-terminal sequencing and amino acid analysis.

B. Enzyme Activity +/− Inhibitors was Determined as Follows:

All measurements were obtained under conditions where signal production increased linearly with time and enzyme. Test compounds were added to white 384-well assay plates (0.1 μL for 10 μL and some 20 μL assays, 1 μL for some 20 μL assays) at variable known concentrations in 100% DMSO. DMSO (1-5% final, as appropriate) and EDTA (65 mM in reaction) were used as controls. Reaction Mix was prepared as follows at 22° C.:

25 mM HEPES, pH 7.2
15 mM MgCl$_2$
1 μM ATP
0.05 μCi/well $^{33}$P-γ ATP (10 Ci/mMol)
1 μM substrate peptide (Biotin-Ahx-SFNDTLDFD) SEQ ID:No. 2.
0.15 mg/mL BSA
1 mM DTT
2 nM PLK1 kinase domain (added last)

Reaction Mix (10 or 20 μL) was quickly added to each well immediately following addition of enzyme via automated liquid handlers and incubated 1-1.5 h at 22° C. The 20 μL enzymatic reactions were stopped with 50 μL of stop mix (50 mM EDTA, 4.0 mg/mL Streptavidin SPA beads in Standard Dulbecco's PBS (without Mg$^{2+}$ and Ca$^{2+}$), 50 μM ATP) per well. The 10 μL reactions were stopped with 10 μL of stop mix (50 mM EDTA, 3.0 mg/mL Streptavidin-coupled SPA imaging Beads ("LeadSeeker") in Standard Dulbecco's PBS (without Mg$^{2+}$ and Ca$^{2+}$), 50 μM ATP) per well. Plates were sealed with clear plastic seals, spun at 500×g for 1 min or settled overnight, and counted in Packard TopCount for 30 seconds/well (regular SPA) or imaged using a Viewlux imager (LeadSeeker SPA). Signal above background (EDTA controls) was converted to percent Inhibition relative to that obtained in control (DMSO-only) wells.

C. Results

The data obtained is reported in Table 1 below, in Table 1, +=pIC$_{50}$<6; ++=pIC$_{50}$6-7; +++=pIC$_{50}$>7.

II. Inhibition of Cell Proliferation by PLK1 Inhibitors.

Exponentially growing cell lines of different tumor origins, cultured in appropriate media containing 10% fetal bovine serum at 37° C. In a 5% CO$_2$incubator were plated in 96 or 384-well plates. Twenty four hours post-plating, cells were treated with different concentrations of test compounds ranging from 20 μM to 0.04 nM. Several wells were Set untreated as a control. Seventy two hours post-treatment, cell numbers were determined using different techniques; 100 μl per well of methylene blue (Sigma M9140) (0.5% in 50:50 Ethanol: water), or 10-100 μl per well of CellTiter-Glo (Promega #G7573), depending on well size. For methylene blue staining, stain was incubated at room temperature for 30 minutes before plates were rinsed and dye solubilized in 1% N-lauroyl sarcosine, sodium salt, (Sigma L5125, In PBS). Plates were read on a microplate reader, measuring the OD at 620 nm. For CellTiter-Glo, plates were incubated at room temperature for 15 minutes and the chemiluminescent signal was read on the Victor V or Envison 2100 reader.

Percent inhibition of cell growth was expressed as percent proliferation relative to 100% proliferation (control). Concentration of test compound that inhibited 50% of cell growth ($IC_{50}$) was determined by 4 parameter fit of data using XLfit, (value of no cell control was substracted from all samples for background). The data are shown in Table 1 and Table 2 below and represent a compilation of several different experiments each performed using the general parameters outlined above, although minor variations may have been employed in some instances. In Table 1 and Table 2, +=$IC_{50}$>1 μM; ++=$IC_{50}$ 0.5-1 μM: +++=$IC_{50}$<0.5 μM.

TABLE 1

| Example | PLK1 $pIC_{50}$ | HCT116 $IC_{50}$ |
|---|---|---|
| 1 | +++ | ++ |
| 2 | +++ | +++ |
| 3 | +++ | +++ |
| 4 | +++ | +++ |
| 5 | +++ | +++ |
| 6 | +++ | +++ |
| 7 | +++ | +++ |
| 8 | +++ | +++ |
| 9 | +++ | +++ |
| 10 | +++ | +++ |
| 11 | +++ | +++ |
| 12 | +++ | +++ |
| 13 | +++ | +++ |
| 14 | +++ | +++ |
| 15 | +++ | +++ |
| 16 | +++ | +++ |
| 17 | +++ | +++ |
| 18 | +++ | +++ |
| 19 | +++ | +++ |
| 20 | +++ | +++ |
| 21 | +++ | +++ |
| 22 | +++ | +++ |
| 23 | +++ | +++ |
| 24 | +++ | +++ |
| 25 | +++ | +++ |
| 26 | +++ | +++ |
| 27 | +++ | +++ |
| 28 | +++ | +++ |
| 29 | +++ | +++ |
| 30 | +++ | +++ |
| 31 | +++ | +++ |
| 32 | +++ | +++ |
| 33 | +++ | +++ |
| 34 | +++ | +++ |
| 35 | +++ | +++ |
| 36 | +++ | +++ |
| 37 | +++ | + |
| 38 | +++ | +++ |
| 39 | +++ | ++ |
| 40 | +++ | +++ |
| 41 | +++ | +++ |
| 42 | +++ | +++ |
| 43 | ++ | + |
| 44 | +++ | +++ |
| 45 | +++ | +++ |
| 46 | +++ | +++ |
| 47 | +++ | +++ |
| 48 | +++ | +++ |
| 49 | +++ | +++ |
| 50 | +++ | +++ |
| 51 | +++ | +++ |
| 52 | +++ | +++ |
| 53 | +++ | +++ |
| 54 | +++ | + |
| 55 | +++ | + |
| 56 | +++ | + |
| 57 | +++ | + |
| 58 | +++ | + |
| 59 | +++ | + |
| 60 | +++ | + |
| 61 | +++ | +++ |
| 62 | +++ | +++ |
| 63 | +++ | +++ |
| 64 | +++ | +++ |
| 65 | +++ | +++ |
| 66 | +++ | +++ |
| 67 | +++ | +++ |
| 68 | +++ | +++ |
| 69 | +++ | +++ |
| 70 | +++ | +++ |
| 71 | +++ | +++ |
| 72 | +++ | +++ |
| 73 | +++ | + |
| 74 | +++ | +++ |
| 75 | +++ | +++ |
| 76 | +++ | +++ |
| 77 | ++ | + |
| 78 | ++ | + |
| 79 | +++ | + |
| 80 | +++ | + |
| 81 | +++ | + |
| 82 | +++ | + |
| 83 | +++ | + |
| 84 | +++ | ++ |
| 85 | +++ | + |
| 85 | +++ | + |
| 87 | +++ | +++ |
| 88 | +++ | +++ |

TABLE 2

| Cell Line | Tissue | Example 3 | Example 31 | Example 45 | Example 47 |
|---|---|---|---|---|---|
| A549-L $IC_{50}$ | lung | | | +++ | +++ |
| COLO205 $IC_{50}$ | Colon | +++ | +++ | +++ | +++ |
| HT29 $IC_{50}$ | Colon | +++ | +++ | +++ | +++ |
| MX-1 $IC_{50}$ | Breast | | +++ | +++ | +++ |
| SKOV-3 $IC_{50}$ | Ovarian | +++ | +++ | +++ | +++ |
| LNCaP $IC_{50}$ | Prostate | | ++ | | |
| P388 $IC_{50}$ | Mouse leukemia | +++ | | +++ | +++ |
| H1299 $IC_{50}$ | Lung | | +++ | | |
| Hela $IC_{50}$ | Endometrial | | +++ | | |
| HN5 $IC_{50}$ | Head and neck | | +++ | | |
| MCF7 $IC_{50}$ | Breast | | +++ | | |
| MV522 $IC_{50}$ | Lung | | | | |
| MDA-MB-468 $IC_{50}$ | Breast | | +++ | | |
| PANC-1 $IC_{50}$ | pancreatic | | | | |
| MiaPaca $IC_{50}$ | Pancreatic | | | | |
| ASPC3 $IC_{50}$ | Pancreatic | | | | |
| BXPC3 $IC_{50}$ | Pancreatic | | | | |
| RPMI 8226 $IC_{50}$ | leukemia | | +++ | | |
| Saos-2 | bone | | | | |
| U87-MG | brain | | | | |
| BT474 | breast | | | | |

TABLE 2-continued

| | | |
|---|---|---|
| BT549 | breast | |
| HCC1937 | breast | |
| HCC1954 | breast | |
| SK-BR-3 | breast | |
| T-47D | breast | |
| HCT-15 | colon | |
| LoVo | colon | |
| HT-1080 | connective tissue | |
| HN5 | head/neck | |
| A 704 | kidney | |
| A498 | kidney | |
| SW156 | kidney | |
| Hep3B | liver | |
| Calu1 | lung | |
| NCI-H358 | lung | |
| NCI-H727 | lung | |
| A2780 | ovary | |
| Capan-2 | pancreas | |
| Panc 02.03 | pancreas | |
| BC-1 | peripheral blood | |
| BC-2 | peripheral blood | |
| BDCM | peripheral blood | |
| CA46 | peripheral blood | |
| CEM/C1 | peripheral blood | |
| CRO-AP2 | peripheral blood | |
| EB-3 | peripheral blood | |
| A431 | skin | |
| SKMEL28 | skin | |
| SKMEL3 | skin | |
| SKMEL5 | skin | |
| MALME-3M | skin, derived from lung | |
| NCI-N87 | stomach | |
| T24 | urinary bladder | |

| Cell Line | Tissue | Example 48 | Example 49 | Example 66 |
|---|---|---|---|---|
| A549-L IC$_{50}$ | lung | +++ | | |
| COLO205 IC$_{50}$ | Colon | +++ | +++ | +++ |
| HT29 IC$_{50}$ | Colon | +++ | +++ | +++ |
| MX-1 IC$_{50}$ | Breast | +++ | +++ | +++ |
| SKOV-3 IC$_{50}$ | Ovarian | +++ | +++ | +++ |
| LNCaP IC$_{50}$ | Prostate | +++ | | |
| P388 IC$_{50}$ | Mouse leukemia | +++ | | +++ |
| H1299 IC$_{50}$ | Lung | +++ | | |
| Hela IC$_{50}$ | Endometrial | +++ | | |
| HN5 IC$_{50}$ | Head and neck | +++ | | |
| MCF7 IC$_{50}$ | Breast | +++ | | |
| MV522 IC$_{50}$ | Lung | +++ | | |
| MDA-MB-468 IC$_{50}$ | Breast | +++ | | |
| PANC-1 IC$_{50}$ | pancreatic | +++ | | |
| MiaPaca IC$_{50}$ | Pancreatic | +++ | | |
| ASPC3 IC$_{50}$ | Pancreatic | +++ | | |
| BXPC3 IC$_{50}$ | Pancreatic | +++ | | |
| RPMI 8226 IC$_{50}$ | leukemia | +++ | | |
| Saos-2 | bone | +++ | | |
| U87-MG | brain | +++ | | |
| BT474 | breast | + | | |
| BT549 | breast | +++ | | |
| HCC1937 | breast | + | | |
| HCC1954 | breast | +++ | | |
| SK-BR-3 | breast | +++ | | |
| T-47D | breast | + | | |
| HCT-15 | colon | +++ | | |
| LoVo | colon | +++ | | |
| HT-1080 | connective tissue | +++ | | |
| HN5 | head/neck | +++ | | |
| A 704 | kidney | +++ | | |
| A498 | kidney | +++ | | |
| SW156 | kidney | + | | |
| Hep3B | liver | +++ | | |
| Calu1 | lung | +++ | | |
| NCI-H358 | lung | +++ | | |
| NCI-H727 | lung | + | | |
| A2780 | ovary | +++ | | |
| Capan-2 | pancreas | + | | |
| Panc 02.03 | pancreas | +++ | | |
| BC-1 | peripheral blood | +++ | | |
| BC-2 | peripheral blood | + | | |
| BDCM | peripheral blood | +++ | | |
| CA46 | peripheral blood | +++ | | |
| CEM/C1 | peripheral blood | +++ | | |
| CRO-AP2 | peripheral blood | +++ | | |
| EB-3 | peripheral blood | +++ | | |
| A431 | skin | +++ | | |
| SKMEL28 | skin | + | | |
| SKMEL3 | skin | +++ | | |
| SKMEL5 | skin | +++ | | |
| MALME-3M | skin, derived from lung | + | | |
| NCI-N87 | stomach | +++ | | |
| T24 | urinary bladder | +++ | | |

That which is claimed is:

1. A compound of formula (I):

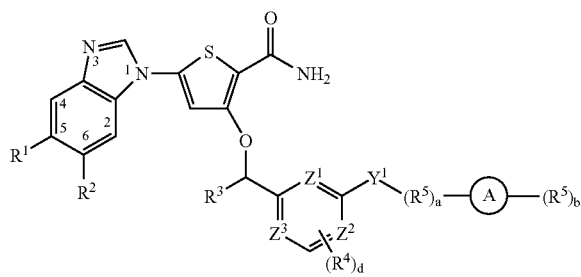

wherein:
- R$^1$ is selected from H, halo, alkyl, haloalkyl, —OR$^7$, —CN, —C(O)NR$^7$R$^8$, —S(O)$_2$R$^7$, —R$^5$—S(O)$_2$R$^7$, —NR$^7$R$^8$, —NR$^7$C(O)R$^8$, Ph, and Het$^1$;
- Ph is phenyl optionally substituted 1 or 2 times with halo, alkyl, haloalkyl, —OR$^7$, —CN, —S(O)$_2$R$^7$ or —NR$^7$R$^8$;
- Het$^1$ is a 5-6 membered heteroaryl having 1, 2 or 3 heteroatoms selected from N, O and S, optionally substituted 1 or 2 times with a substituent selected from halo, alkyl, haloalkyl, —OR$^7$, —CN, —S(O)$_2$R$^7$, —NR$^7$R$^8$, Het$^2$, —R$^5$-Het$^2$, and NR$^7$-Het$^2$;
- Het$^2$ is a 5-6 membered heterocycle having 1 or 2 heteroatoms selected from N, O and S, optionally substituted 1 or 2 times with a substituent selected from alkyl, —OR$^7$, —NR$^7$R$^8$, —C(O)NR$^7$R$^8$, —S(O)$_2$R$^7$, and oxo;
- R$^2$ is selected from H, halo, alkyl, haloalkyl, —OR$^7$, —CN, —C(O)NR$^7$R$^8$, —S(O)$_2$R$^7$, —R$^5$—S(O)$_2$R$^7$, —S(O)$_2$NR$^7$R$^8$, —R$^5$—S(O)$_2$NR$^7$R$^8$, —NR$^7$R$^8$, and —NR$^7$C(O)R$^8$;
- R$^3$ is H, alkyl or haloalkyl;
- Z$^1$, Z$^2$ and Z$^3$ are each the same or different and are independently C, CH or N, wherein at least one of Z$^1$, Z$^2$ and Z$^3$ is C or CH;
- d is 0, 1 or 2;
- each R$^4$ is the same or different and is independently halo, alkyl or haloalkyl;
- Y$^1$ is —O— or —N(R$^7$)—;
- a is 0 or 1;
- each R$^5$ is the same or different and is independently C$_{1-3}$alkylene;
- Ring A is a 5-6 membered heterocycle having 1 or 2 heteroatoms selected from N, O and S;
- b is 0, 1 or 2;
- each R$^6$ is the same or different and is independently selected from halo, alkyl, haloalkyl, alkenyl, —CN, —R$^5$—CN, —CO$_2$R$^7$, —R$^5$—CO$_2$R$^7$, —C(O)NR$^7$R$^8$, —R$^5$—C(O)NR$^7$R$^8$, —OR$^7$, —R$^5$—OR$^7$, —S(O)$_2$R$^7$, —R$^5$—S(O)$_2$R$^7$, —S(O)$_2$NR$^7$R$^8$, —R$^5$—S(O)$_2$NR$^7$R$^8$, —NR$^7$R$^8$, —R$^5$—NR$^7$R$^8$, —NR$^7$C(O)R$^8$, —NR$^7$S(O)$_2$R$^8$, —NR$^7$C(O)NR$^7$R$^8$, —NR$^7$C(O)$_2$R$^8$ and oxo;
- each R$^7$ and each R$^8$ are the same or different and are each independently selected from H, alkyl, haloalkyl, alkenyl, haloalkenyl, alkynyl, cycloalkyl and cycloalkenyl;

or a pharmaceutically acceptable salt thereof.

2. The compound according to claim 1, wherein R$^1$ is selected from H, halo, alkyl, haloalkyl, —OR$^7$, —S(O)$_2$R$^7$ and Het$^1$.

3. The compound according to claim 1, wherein R$^2$ is selected from H, halo, alkyl, haloalkyl, —OR$^7$, —CN, —S(O)$_2$R$^7$ and —R$^5$—S(O)$_2$R$^7$.

4. The compound according to claim 1, wherein R$^3$ is alkyl or haloalkyl.

5. The compound according to claim 1, wherein Z$^1$, Z$^2$ and Z$^3$ are each C or CH.

6. The compound according to claim 1, wherein d is 0 or 1.

7. The compound according to claim 1, wherein each R$^4$ is the same or different and is halo, C$_{1-3}$alkyl or C$_{1-3}$haloalkyl.

8. The compound according to claim 1, wherein Y$^1$ is —O— or —N(H)—.

9. The compound according to claim 1, wherein a is 0.

10. The compound according to claim 1, wherein Ring A is a 6 membered heterocycle having 1 N atom and optionally 1 more heteroatom selected from N, O and S.

11. The compound according to claim 1, wherein b is 0 or 1.

12. The compound according to claim 1, wherein each R$^6$ is the same or different and is independently selected from halo, alkyl, haloalkyl, —CN, —CO$_2$R$^7$, —R$^5$—CO$_2$R$^7$, —C(O)NR$^7$R$^8$, —OR$^7$, —R$^5$—OR$^7$, —S(O)$_2$R$^7$, —R$^5$—S(O)$_2$R$^7$, —NR$^7$R$^8$, —R$^5$—NR$^7$R$^8$, and oxo.

13. A compound according to claim 1, having the stereochemistry depicted in formula (I-1):

I-1

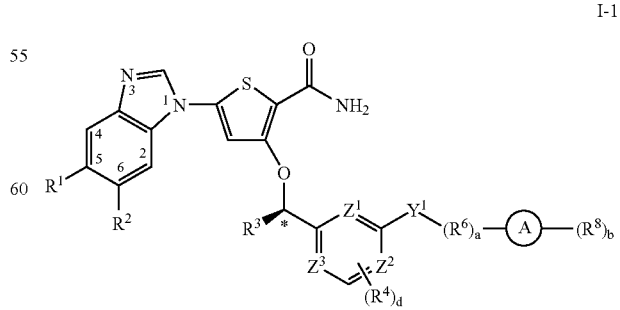

wherein * indicates a chiral carbon and all variables are as defined in claim 1.

14. A compound of formula (XL):

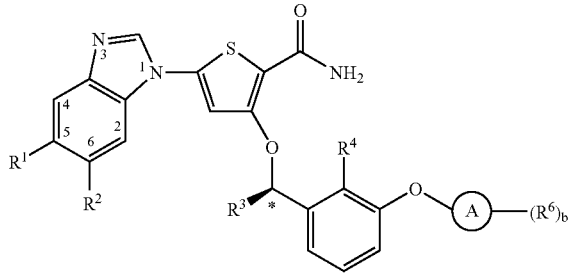

wherein:
- R¹ is selected from H, halo, alkyl, haloalkyl, —OR⁷, —CN, —C(O)NR⁷R⁸, —S(O)₂R⁷, —R⁵—S(O)₂R⁷ and Het¹;
- Het¹ is a 5-6 membered heteroaryl having 1, 2 or 3 heteroatoms selected from N, O and S, optionally substituted 1 or 2 times with a substituent selected from alkyl, haloalkyl, —OR⁷, —CN, —S(O)₂R⁷, and —NR⁷R⁸;
- R² is selected from H, halo, alkyl, haloalkyl, —OR⁷, —CN, —C(O)NR⁷R⁸, —S(O)₂R⁷, —R⁵—S(O)₂R⁷, —S(O)₂NR⁷R⁸, —R⁵—S(O)₂NR⁷R⁸, —NR⁷R⁸, and —NR⁷C(O)R⁸;
- R³ is alkyl;
- * indicates a chiral carbon;
- R⁴ is H or halo;
- each R⁵ is the same or different and is independently C₁₋₃alkylene;
- Ring A is a 5-6 membered heterocycle having 1 or 2 heteroatoms selected from N, O and S;
- b is 0 or 1;
- each R⁶ is the same or different and is independently selected from halo, alkyl, haloalkyl, —CO₂R⁷, —R⁵—CO₂R⁷, —OR⁷, —R⁵—OR⁷, —S(O)₂R⁷, —R⁵—S(O)₂R₇, —NR⁷R⁸, —R⁵—NR⁷R⁸ and oxo;
- each R⁷ and each R⁸ are the same or different and are each independently selected from H, alkyl and haloalkyl;

or a pharmaceutically acceptable salt thereof.

15. 3-[((1R)-1-{2-Chloro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide

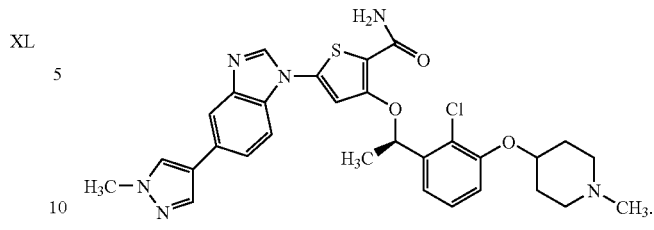

16. A pharmaceutical composition comprising a compound according to 1 claim and a pharmaceutically acceptable carrier, diluent or excipient.

17. The pharmaceutical composition according to claim 16 further comprising a chemotherapeutic agent.

18. A compound selected from the group consisting of
- 3-({(1R)-1-[2-Chloro-3-(4-piperidinyloxy)phenyl]ethyl}oxy)-5-[5-(1-methyl-1H-pyrazol-4-yl)-1H-benzimidazol-1-yl]-2-thiophenecarboxamide,
- 3-[((1R)-1-{2-Chloro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide, and
- 3-({(1R)-1-[2-Chloro-3-(4-piperidinyloxy)phenyl]ethyl}oxy)-5-[5-(2-methyl-4-pyridinyl)-1H-benzimidazol-1-yl]-2-thiophenecarboxamide, and pharmaceutically acceptable salts thereof.

19. 3-[((1R)-1-{2-Chloro-3-[(1-methyl-4-piperidinyl)oxy]phenyl}ethyl)oxy]-5-[5-(1-methyl-1H-pyrazol-4-yl)-1H-benzimidazol-1-yl]-2-thiophenecarboxamide

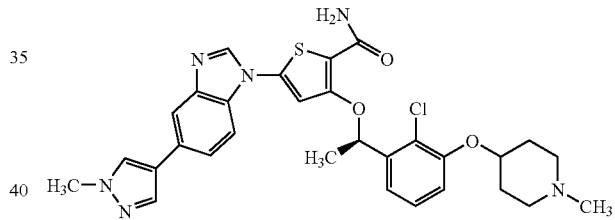

or a pharmaceutically acceptable salt thereof.

20. A pharmaceutical composition comprising a compound according to claim 15 and a pharmaceutically acceptable carrier, diluent or excipient.

21. A pharmaceutical composition comprising a compound according to claim 19 and a pharmaceutically acceptable carrier, diluent or excipient.

* * * * *